United States Patent
Savory et al.

(10) Patent No.: US 9,353,086 B2
(45) Date of Patent: May 31, 2016

(54) CXCR4 RECEPTOR ANTAGONISTS

(75) Inventors: Edward Daniel Savory, London (GB); Alison Stewart, London (GB); Allison Carley, London (GB); Giles Brown, London (GB); Iain Simpson, London (GB); Kathryn Oliver, London (GB); Lee Patient, London (GB); Michael Higginbottom, London (GB); Andrew Graham Cole, Cranbury, NJ (US)

(73) Assignee: Proximagen Limited, London (GB)

( * ) Notice: Subject to any disclaimer, the term of this patent is extended or adjusted under 35 U.S.C. 154(b) by 256 days.

(21) Appl. No.: 13/878,968

(22) PCT Filed: Oct. 13, 2011

(86) PCT No.: PCT/EP2011/067946
§ 371 (c)(1),
(2), (4) Date: Jun. 11, 2013

(87) PCT Pub. No.: WO2012/049277
PCT Pub. Date: Apr. 19, 2012

(65) Prior Publication Data
US 2013/0289020 A1    Oct. 31, 2013

(30) Foreign Application Priority Data

Oct. 14, 2010  (GB) .................................. 1017345.8

(51) Int. Cl.
| | | |
|---|---|---|
| A61K 31/55 | (2006.01) | |
| A61K 31/551 | (2006.01) | |
| A61K 31/439 | (2006.01) | |
| C07D 401/14 | (2006.01) | |
| C07D 405/14 | (2006.01) | |
| C07D 413/14 | (2006.01) | |
| C07D 417/14 | (2006.01) | |
| C07D 471/04 | (2006.01) | |
| C07D 471/08 | (2006.01) | |
| C07D 471/12 | (2006.01) | |
| A61K 45/06 | (2006.01) | |
| C07D 401/12 | (2006.01) | |

(52) U.S. Cl.
CPC .............. *C07D 401/14* (2013.01); *A61K 45/06* (2013.01); *C07D 401/12* (2013.01); *C07D 405/14* (2013.01); *C07D 413/14* (2013.01); *C07D 417/14* (2013.01); *C07D 471/04* (2013.01); *C07D 471/08* (2013.01)

(58) Field of Classification Search
CPC ... A61K 31/551; A61K 31/55; A61K 31/439; C07D 401/14; C07D 403/14; C07D 405/14; C07D 413/14; C07D 417/14; C07D 471/04; C07D 471/08; C07D 471/12
USPC ............. 514/218, 217.04, 215, 300; 540/575, 540/477, 580, 597; 546/113
See application file for complete search history.

(56) References Cited

U.S. PATENT DOCUMENTS

| | | | |
|---|---|---|---|
| 6,191,130 | B1 | 2/2001 | Patoiseau et al. |
| 2013/0210811 | A1* | 8/2013 | Ryu et al. ..................... 514/218 |

FOREIGN PATENT DOCUMENTS

| | | |
|---|---|---|
| EP | 0431580 A2 | 6/1991 |
| EP | 1571146 A1 | 9/2005 |
| EP | 1849781 A1 | 10/2007 |
| WO | 94/15928 | 7/1994 |
| WO | 98/25617 | 6/1998 |
| WO | 0114333 | 3/2001 |
| WO | 02/02539 A1 | 1/2002 |
| WO | 03/020716 A1 | 3/2003 |
| WO | 03/082855 A1 | 10/2003 |
| WO | 2004/089913 A1 | 10/2004 |
| WO | 2004/099176 A1 | 11/2004 |
| WO | 2005/059107 A2 | 6/2005 |
| WO | 2006/071958 A1 | 7/2006 |
| WO | 2006071875 | 7/2006 |
| WO | 2006/088836 A2 | 8/2006 |
| WO | 2006/088840 A1 | 8/2006 |
| WO | 2006/088919 A2 | 8/2006 |
| WO | 2006/088920 A1 | 8/2006 |
| WO | 2006/130426 A2 | 12/2006 |
| WO | 2006/138259 A2 | 12/2006 |
| WO | 2007/071952 A1 | 6/2007 |
| WO | 2007/109238 A1 | 9/2007 |
| WO | 2008/008453 A1 | 1/2008 |
| WO | 2008/060621 A2 | 1/2008 |
| WO | 2008/036379 A2 | 3/2008 |
| WO | 2008079279 | 7/2008 |
| WO | 2008/094992 A2 | 8/2008 |
| WO | 2008/121065 A1 | 10/2008 |
| WO | 2010054006 | 5/2010 |

OTHER PUBLICATIONS

Haas, Michael. "Two edges of sickle cell disease," SciBX, vol. 4, No. 3, pp. 1-16 (Jan. 20, 2011).
Benardi, Francesco et al. "Novel 4-(4-Aryl)cyclohexyl-1-(2-pyridyl)piperazines as Δ8-Δ7 Sterol Isomerase (Emopamil Binding Protein) Selective Ligands with Antiproliferative Activity," J. Med. Chem., vol. 51, pp. 7523-7531 (2008).
International Search Report dated Jan. 24, 2012 for PCT/EP2011/067946.

* cited by examiner

*Primary Examiner* — Brenda Coleman
(74) *Attorney, Agent, or Firm* — Sean B. Mahoney; Katherine A. Jackson Huebsch

(57) ABSTRACT

Disclosed are compounds that are antagonists of the CXCR4 receptor.

17 Claims, 2 Drawing Sheets

Figure 3:
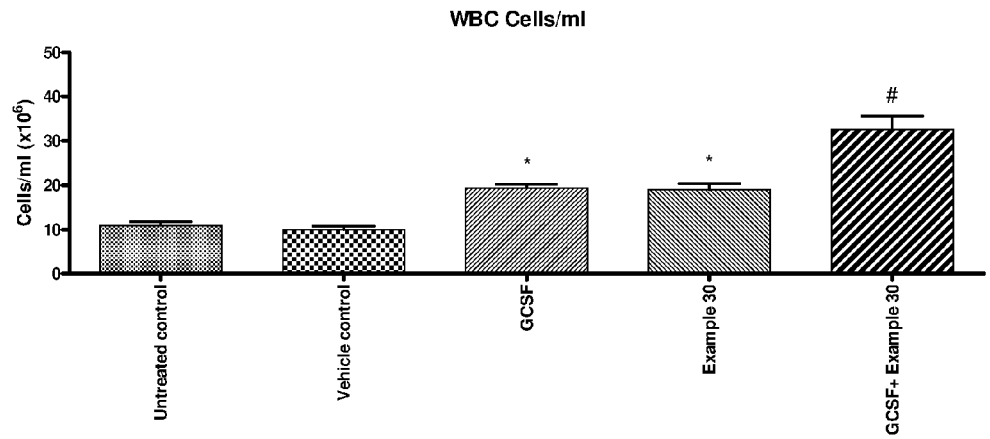

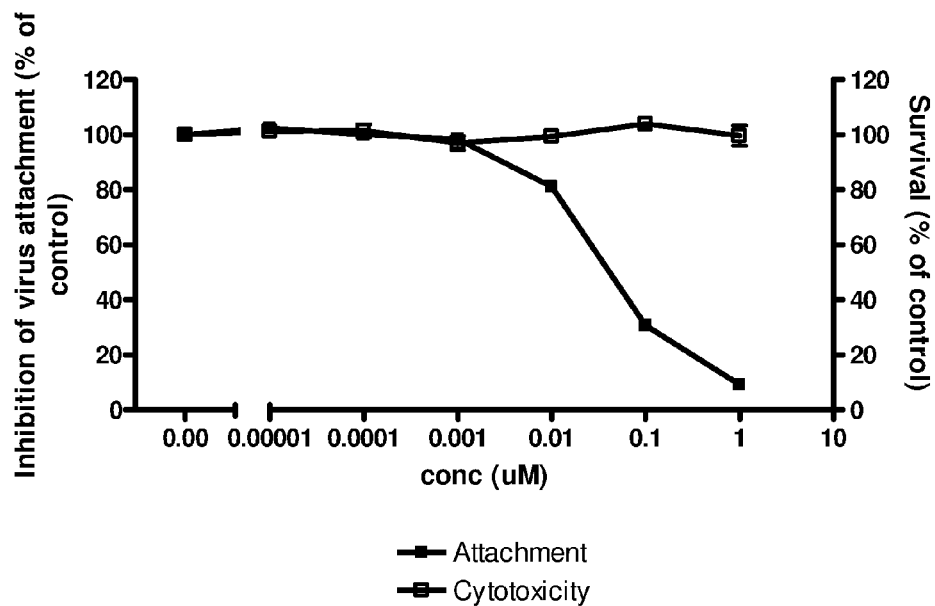
Figure 1: Effect of Example 30 in the attachment of CXCR4-tropic HIV-1 assay.
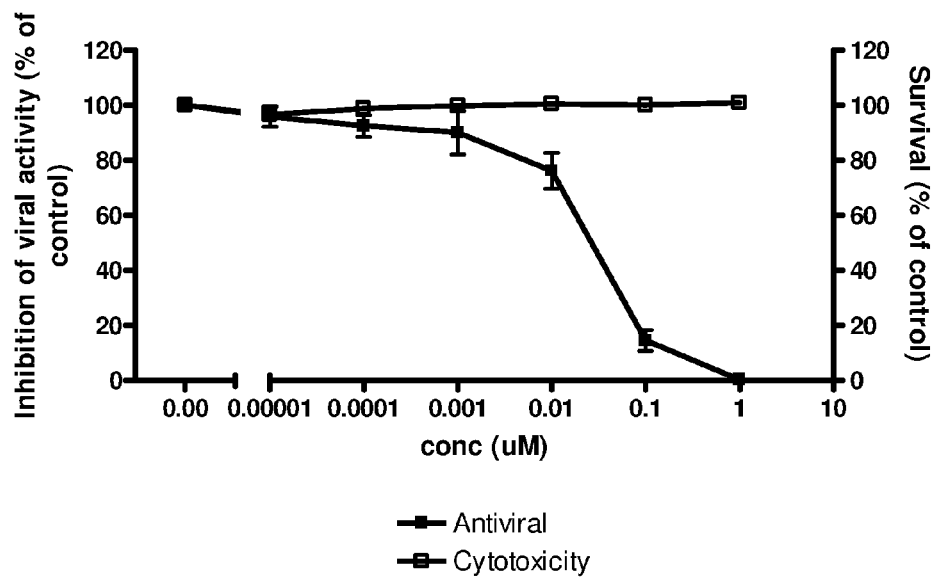
Figure 2: Effect of Example 30 in the HIV-1 antiviral assay \* p < 0.05 vs vehicle control (One way Anova with Dunnett's post test)
\# p < 0.05 vs GCSF (One way Anova with Dunnett's post test). Data are mean ± s.e.m, n=5

\* p < 0.05 vs vehicle control (One way Anova with Dunnett's post test)
\# p < 0.05 vs GCSF (One way Anova with Dunnett's post test). Data are mean ± s.e.m, n=5

CXCR4 RECEPTOR ANTAGONISTS

CROSS REFERENCE TO RELATED APPLICATION

The present application is the U.S. national stage of international Application PCT/EP2011/067946, filed Oct. 13, 2011, which international application was published on Apr. 18, 2012, as International Publication No. WO2012/049277. The International Application claims priority to British Patent Application No. 1017345.8, filed. Oct. 14, 2010, the contents of which are incorporated herein by reference in their entireties.

INTRODUCTION

This invention relates to compounds that are CXCR4 antagonists, to compositions containing them, to processes for their preparation, and to their use in medicine, in particular for the treatment of conditions which respond to antagonism of the CXCR4 receptor, such as cancer (including cancers of the haematopoietic system such as multiple myeloma and non-Hodgkin's lymphoma, non-small cell lung, breast and neuroblastoma), cancer metastasis, HIV/AIDS, neuropathy, HIV related neuropathy, brain inflammation, diabetic retinopathy, age related macular degeneration, and retinal neovascularisation and to methods of preventing, treating or ameliorating these conditions. This invention further relates to the use of compounds which are CXCR4 antagonists for use in stem cell apheresis procedures including, for example, promoting release and mobilisation of stem cells, including haematopoietic and non-haematopoietic stem cells and progenitor stem cells, prior to harvesting.

BACKGROUND TO THE INVENTION

CXCR4 is a G-protein coupled receptor whose natural endogenous ligand is the cytokine SDF-1 (stromal derived factor-1) or CXCL12. CXCR4 was first discovered as a co-receptor, with CD4, for the entry of T-cell line-tropic (X4) HIV-1 into T-cells. CXCR4 manipulation (in combination with granulocyte colony stimulating factor (G-CSF)) has proven to improve the outcome of haematopoietic (Broxmeyer et al., 2005) and endothelial progenitor cell (Pitchford et al., 2009) stem cell mobilization. The CXCR4-SDF-1 interaction is also a master regulator of cancer stem cell trafficking in the human body (Croker and Allan, 2008) and plays a key role in the progression and metastasis of various types of cancer cells in organs that highly express SDF-1 (Zlotnik, 2008). In view of these important biological functions mediated by CXCR4, small molecule antagonists of the CXCR4 receptor are promising as future therapeutics for stem cell transplantation and for the treatment of diseases such as diabetic retinopathy, cancer, HIV and AIDS.

Haematopoietic Stem Cell Mobilization

Haematopoietic stem cells or HSCs are widely used in the treatment of cancers of the haematopoietic system e.g. multiple myeloma and non-Hodgkin's lymphoma. Mobilisation and harvesting of HSCs allows the use of cytotoxic drugs to kill the tumour cells within the bone marrow. Subsequently the haematopoietic system can be re-introduced using the previously harvested stem cells.

Normally stem cells and progenitor cells are attracted to, and retained in, the bone marrow by the action of locally generated SDF-1 on CXCR4 expressed by such cells (see e.g. Lapidot et al., 2005). The stem cells used in transplantation can be mobilised from donors (allogeneic transplantation) or patients (autologous transplantation) after 4 or 5 days treatment with G-CSF. G-CSF is used in approximately 70 percent of the haematopoietic stem cell transplantations (the rest being bone marrow and umbilical cord transplants, Copelan, 2006) and acts by reducing the expression of CXCR4 in stem cells and reducing marrow SDF-1 levels (Levesque et al., 2003). Success in such treatments is based on the success of re-engraftment of the isolated stem cells. Should insufficient stem cells be isolated ($<5 \times 10^6$/kg) then the re-engraftment is unlikely to be successful and the patient will not be treated. Multiple days of treatment with G-CSF may only result in sufficient yield in approximately 50% of cases. The CXCR4 antagonist Mozobil is now used to increase the efficiency of mobilisation, resulting in an approximate success rate of 90%. A single administration of CXCR4 antagonist, with a mobilisation delay of only a few hours, we predict will generate sufficient stem cells for effective transplantation (Devine et al., 2008). Such stem cells are we expect to show increased re-engraftment efficiency as they will not have had the expression of this receptor reduced by G-CSF treatment.

Non-Haematopoietic Stem and Progenitor Cell Mobilisation

An increase in plasma SDF-1 has been seen in a variety of models including heart infarction (Kucia et al., 2004; Wojakowski et al., 2004), stroke (Kucia et al., 2006), liver damage (Hatch et al., 2002), kidney damage, (Togel et al., 2005), pancreatic damage (Hess et al., 2003), bone fractures (Sata et al., 2005) and lung damage (Gomperts et al., 2006). It is hypothesised that the increase in SDF-1 is caused by the tissue damage and that gradients of this cytokine act to attract the relevant stem cells to the site of injury. This suggests a practical application of stem cell therapeutics for a wide range of injuries, all of which are regulated by the CXCR4/SDF-1 pathway. Interestingly Pitchford et al (2009) showed that different growth factors (VEGF, GCSF) administered with CXCR4 antagonists resulted in the mobilisation of different populations of stem cells, suggesting that appropriate combinations of factors could be used to isolate stem cells for the repair of specific tissues.

HIV and HIV Associated Pain

There is a known relationship between CCR5 and HIV (Alkhatib et al., 1996). The CXCR4 and CCR5 receptors act as entry cofactors for HIV infection. In brief, binding of the HIV gp120 protein to CD4 on the surface of CD4+ lymphocytes or macrophages exposes a domain in the gp120 protein which then also binds to the CCR5 or CXCR4 receptor, prior to viral insertion into the plasma membrane. CXCR4 antagonists have been shown to reduce the infectivity of X4 strains of the virus (Fransen et al., 2008), thus suggesting that the use of CXR4 antagonists would be effective treatments of HIV infection, especially in combination with CCR5 antagonists such as Maraviroc. The X4 strain of HIV is the most pathogenic, and these strains tend to predominate in the later stages of infection when neuropathic pain becomes an increasing problem for patients. Painful peripheral neuropathy affects approximately 50% of HIV patients. The HIV gp120 protein binds to CXCR4 and/or CCR5 which are expressed on neuronal and glial cells (Pardo et al., 2001; Oh et al., 2001), causing peripheral axonal damage (Melli et al., 2006) and initiating a cytokine-driven neurotoxic cascade involving glia and immune cells (Herzberg and Sagen, 2001; Milligan et al., 2000, 2001). The highly active anti-retroviral therapy (HAART) can also cause painful neuropathy (Dalakas et al., 2001), but this is predicted to become less common as improved therapies are used.

Therefore we expect CXCR4 antagonists to show both anti-viral, cognition enhancing and neuropathic pain relieving properties, and could be administered with other anti-(retro)viral therapies as well as analgesics such as amitryptiline, duloxetine and opiates.

Pain and Inflammation

Since the penetration of the blood brain barrier by leukocytes and monocytes is also influenced by the CXCR4 receptor, forms of brain inflammation and neurodegeneration (Bachis et al., J. Neuroscience, 2006, 26, 6771) whether virally induced or not, we expect to be amenable to therapy by CXCR4 antagonists (Kohler et al., 2008; McAndless et al., 2008). Similarly the expression of CXCR4 on primary sensory neurons suggests that antagonists of this receptor could act as analgesics in the control of pain (Oh et al., J. Neurosci. 2001 21, 5027-35). In addition the potent chemotactic action of SDF-1 on inflammatory cells (Gouwy et al., Eur J Immunol. 2011 41, 963-73), suggests that CXCR4 antagonists could serve as anti-inflammatory therapeutics.

Retinal Neo-Vascularisation

Retinal neo-vascularisation is a major cause of blindness in patients with diabetes and age related macular degeneration. The SDF-1/CXCR4 axis is strongly implicated in ocular neo-vascularisation and has been suggested as a target for treating diabetic retinopathy. Blockade of the CXCR4 receptor prevents the recruitment of endothelial progenitor cells, essential for the formation of the new microvessels which are part of the pathology of diabetic retinopathy (Lima e Silva et al., 2009). We expect the effects of CXCR4 antagonists to be additive with those of VEGF antibodies such as avastin. Thus we expect topical or intravitreal administration of CXCR4 antagonist to be an effective treatment of retinal degeneration with diabetes and ageing.

Cancer and Cancer Metastasis

Several types of cancers (including non-small cell lung, breast and neuroblastoma) express CXCR4, and SDF-1 is highly expressed in internal organs that represent the primary metastatic destinations of the corresponding cancer cells (for review see Ben Baruch, 2008). CXCR4 and SDF-1 are also implicated in the maintenance of cancer stem cells (Wang et al., 2006; Croker and Allan, 2008) and in the recurrence of tumours after radiation therapy. The role of the SDF-1/CXCR4 axis in cancer and cancer stem cells metastasis is discussed in Gelmini S et al., 2008. Blockade of CXCR4 prevented both the vasculogenesis and recurrence of glioblastoma multiforme tumours (Kioi et al., 2010), after radiation treatment. This ability to inhibit tumour derived vasculogenesis leads us to expect that CXCR4 antagonists will be effective when dosed with other anti-angiogenic agents including those that inhibit VEGF (e.g. avastin and aflibercept) and inhibitors of VEGF and PDGFreceptors such as cediranib, sunitinib, sorafenib, pazopanib, tivozanib vatalanib, vandertanib, brivanib, dovitinib, motesanib, telatinib and axitinib (Bhargava and Robinson Curr Oncol Rep (2011) 13:103-111). Other anti-angiogenic agents for use in conjunction with CXCR4 antagonists include those which inhibit EGF, angiopioetins, MMP-9, TNF, bFGF, CXCL8, HGF and TF (Nozawa et al., Proc Natl Acad Sci USA. 103, 12493-12498, 2006; Murdoch et al., Nature Reviews Cancer 8, 618-631 2008). Therefore we expect CXCR4 antagonists to be useful in the prevention of metastasis, and in anti-angiogenic treatment, as well as in cancer stem cell protection and maintenance, and in the sensitization of tumours to radiotherapy.

BRIEF DESCRIPTION OF THE INVENTION

This invention makes available a class of compounds which are antagonists of the CXCR4 receptor, and their use in indications which respond to the antagonism of the CXCR4 receptor such as those mentioned above.

DETAILED DESCRIPTION OF THE INVENTION

According to the present invention there is provided a compound of formula (I) or a pharmaceutically acceptable salt thereof:

wherein:

$R^1$ is selected from hydrogen, $C_{1-4}$-alkyl, cyano, —$COR^3$, —$CONR^3R^4$ and heteroaryl, wherein (a) said heteroaryl is optionally substituted with one more substituents independently selected from halogen, hydroxy, cyano, nitro, $C_{1-6}$-alkyl, $C_{3-5}$-cycloalkyl, $C_{1-4}$-alkoxy, fluoro-$C_{1-6}$-alkyl, fluoro-$C_{1-4}$-alkoxy, $C_{1-4}$-alkoxy-$C_{1-4}$-alkyl, fluoro-$C_{1-4}$-alkoxy-$C_{1-4}$-alkyl, $C_{6-10}$-aryl, heteroaryl, —$NR^{5A}R^{5B}$, —$C_{1-4}$-alkyl-$NR^{5A}R^{5B}$, —$NR^4C(O)O$—$C_{1-4}$-alkyl, —$NR^4C(O)$—$C_{1-4}$-alkyl, —$NR^4C(O)O$-fluoro-$C_{1-4}$-alkyl, —$NR^4C(O)$-fluoro-$C_{1-4}$-alkyl, —$NR^4C(O)NR^{5A}R^{5B}$, —$C(O)NR^{5A}R^{5B}$, —$C(O)R^4$, —$C(O)OR^4$, —$NR^4S(O)_2$—$C_{1-4}$-alkyl and —$NR^4S(O)_2$-fluoro-$C_{1-4}$-alkyl, and (b) said $C_{1-4}$-alkyl is optionally substituted with one or more substituents independently selected from fluorine, hydroxyl and $C_{1-4}$-alkoxy;

X is selected from radicals of formulae (A)-(F) inclusive, any of which being optionally substituted with one more substituents independently selected from halogen, cyano, nitro, $C_{1-4}$-alkyl, $C_{1-4}$-alkoxy, fluoro-$C_{1-4}$-alkyl and fluoro-$C_{1-4}$-alkoxy, wherein the bond marked * is attached to $R^1$ and the bond marked ** is attached to Y:

(A)

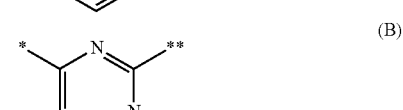

(B)

(C)

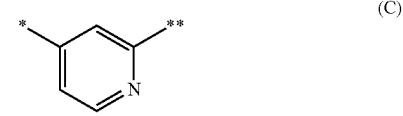

(D)

(E)

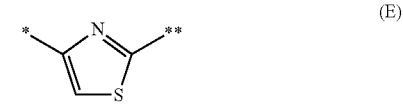

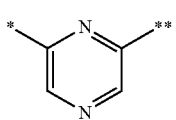

(F)

Y is selected from radicals of formulae (H), (J), (K), (L) and (M) any of which is optionally substituted with one more substituents independently selected from fluorine, hydroxyl, $C_{1-4}$-alkyl, a divalent $C_{1-4}$-alkylene radical which forms a bridge between ring carbons of said homopiperazine or piperazine, $C_{1-4}$-alkoxy, fluoro-$C_{1-4}$-alkyl, a divalent fluoro-$C_{1-4}$-alkylene radical which forms a bridge between ring carbons of said homopiperazine or piperazine and fluoro-$C_{1-4}$-alkoxy, wherein the bond marked * is attached to X and the bond marked ** is attached to $R^2$:

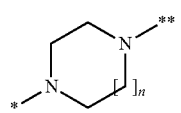

(H)

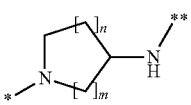

(J)

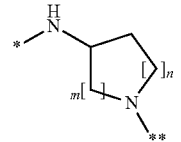

(K)

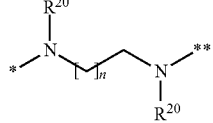

(L)

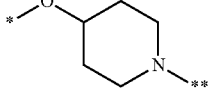

(M)

and n and m are each independently 1 or 2, and $R^{20}$ is hydrogen, or $C_{1-4}$-alkyl;

$R^2$ is selected from radicals of formulae (N)-(S) inclusive, any of which is optionally substituted with one more substituents independently selected from fluorine, hydroxyl, $C_{1-4}$-alkyl, $C_{1-4}$-alkoxy, fluoro-$C_{1-4}$-alkyl and fluoro-$C_{1-4}$-alkoxy, wherein the bond marked * is attached to Y:

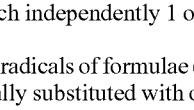

(N)

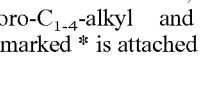

(O)

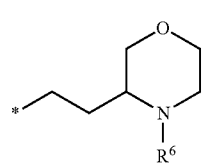

(P)

(Q)

(R)

(S)

and o and p are each independently 1 or 2, and W is O or $NR^9$;

$R^3$ is selected from hydrogen, $C_{1-6}$-alkyl, $C_{3-5}$-cycloalkyl, $C_{3-5}$-cycloalkyl-$C_{1-4}$-alkyl, heterocyclyl, heterocyclyl-$C_{1-4}$-alkyl, $C_{6-10}$-aryl, heteroaryl, $C_{6-10}$-aryl-$C_{1-4}$-alkyl and heteroaryl-$C_{1-4}$-alkyl, wherein (i) said $C_{1-6}$-alkyl, $C_{3-5}$-cycloalkyl, heterocyclyl or the heterocyclyl part of said heterocyclyl-$C_{1-4}$-alkyl, or the $C_{1-6}$-alkyl part of said heterocyclyl-$C_{1-4}$-alkyl, $C_{6-10}$-aryl-$C_{1-4}$-alkyl or heteroaryl-$C_{1-4}$-alkyl, is optionally substituted with one or more substituents independently selected from fluorine, hydroxy, $C_{1-4}$-alkoxy and $-NR^{5A}R^{5B}$, and (ii) said $C_{6-10}$-aryl or heteroaryl, or the $C_{6-10}$-aryl part of said $C_{6-10}$-aryl-$C_{1-4}$-alkyl or the heteroaryl part of said heteroaryl-$C_{1-4}$-alkyl, is optionally substituted with one more substituents independently selected from halogen, hydroxy, cyano, nitro, $C_{1-4}$-alkyl, $C_{1-4}$-alkoxy, fluoro-$C_{1-4}$-alkyl, fluoro-$C_{1-4}$-alkoxy, $C_{1-4}$-alkoxy-$C_{1-4}$-alkyl, fluoro-$C_{1-4}$-alkoxy-$C_{1-4}$-alkyl, $-NR^{5A}R^{5B}$, $-C_{1-4}$-alkyl-$NR^{5A}R^{5B}$, $-NR^4C(O)O-C_{1-4}$alkyl, $-NR^4C(O)-C_{1-4}$alkyl, $-NR^4C(O)O$-fluoro-$C_{1-4}$alkyl, $-NR^4C(O)$-fluoro-$C_{1-4}$alkyl, $-NR^4C(O)NR^{5A}R^{5B}$, $-C(O)NR^{5A}R^{5B}$, $-C(O)R^4$, $-C(O)OR^4$, $-NR^4S(O)_2-C_{1-4}$alkyl and $-NR^4S(O)_2$-fluoro-$C_{1-4}$alkyl;

$R^4$, $R^{5A}$ and $R^{5B}$ are each independently selected from hydrogen, $C_{1-4}$-alkyl and fluoro-$C_{1-4}$-alkyl, or $R^{5A}$ and $R^{5B}$ together with the nitrogen atom to which they are bound, form a 4- to 7-membered saturated heterocyclic ring or a heteroaryl ring, said ring being optionally substituted with one or more substituents independently selected from fluorine, hydroxyl, $C_{1-4}$-alkyl, fluoro-$C_{1-4}$-alkyl and $C_{1-4}$-alkoxy, or $R^3$ and $R^4$, together with the nitrogen atom to which they are bound, form a 4- to 7-membered saturated heterocyclic ring or a heteroaryl ring, said ring being optionally substituted with one or more substituents independently selected from fluorine, hydroxyl, $C_{1-4}$-alkyl, fluoro-$C_{1-4}$-alkyl and $C_{1-4}$-alkoxy; and $R^6$ is selected from $C_{1-6}$-alkyl, $C_{3-5}$-cycloalkyl, $C_{3-5}$-cycloalkyl-$C_{1-4}$-alkyl, heterocyclyl, heterocyclyl-$C_{1-4}$-alkyl, $C_{6-10}$-aryl-$C_{1-4}$-alkyl and $C_{6-10}$-aryl, wherein (iii) said $C_{1-6}$-alkyl, $C_{3-5}$-cycloalkyl, heterocyclyl, or the $C_{1-6}$-alkyl part of said heterocyclyl-$C_{1-4}$-alkyl or $C_{6-10}$-aryl-$C_{1-4}$-alkyl, or the heterocyclyl part of said heterocyclyl-$C_{1-4}$-alkyl is optionally substituted with one or more substituents independently selected from fluorine, hydroxyl and $C_{1-4}$-alkoxy, and (iv) said $C_{6-10}$-aryl or the $C_{6-10}$-aryl part of said $C_{6-10}$-aryl-$C_{1-4}$-alkyl is optionally substituted with one more substituents independently selected from halogen, hydroxy, cyano, nitro, $C_{1-4}$-alkyl, $C_{1-4}$-alkoxy, fluoro-$C_{1-4}$-alkyl, fluoro-$C_{1-4}$-alkoxy, $C_{1-4}$-alkoxy-$C_{1-4}$-alkyl and fluoro-$C_{1-4}$-alkoxy-$C_{1-4}$-alkyl;

$R^7$ is selected from $C_{1-6}$-alkyl, $C_{3-5}$-cycloalkyl, $C_{3-5}$-cycloalkyl-$C_{1-4}$-alkyl, heterocyclyl, heterocyclyl-$C_{1-4}$-alkyl, $C_{6-10}$-aryl-$C_{1-4}$-alkyl and $C_{6-10}$-aryl and —$NR^{10A}R^{10B}$, wherein (v) said $C_{1-6}$-alkyl, $C_{3-5}$-cycloalkyl, heterocyclyl, or the $C_{1-6}$-alkyl part of said heterocyclyl-$C_{1-4}$-alkyl or $C_{6-10}$-aryl-$C_{1-4}$-alkyl, or the heterocyclyl part of said heterocyclyl-$C_{1-4}$-alkyl is optionally substituted with one or more substituents independently selected from fluorine, hydroxyl and $C_{1-4}$-alkoxy, and (vi) said $C_{6-10}$-aryl or the $C_{6-10}$-aryl part of said $C_{6-10}$-aryl-$C_{1-4}$-alkyl is optionally substituted with one more substituents independently selected from halogen, hydroxy, cyano, nitro, $C_{1-4}$-alkyl, $C_{1-4}$-alkoxy, fluoro-$C_{1-4}$-alkyl, fluoro-$C_{1-4}$-alkoxy, $C_{1-4}$-alkoxy-$C_{1-4}$-alkyl and fluoro-$C_{1-4}$-alkoxy-$C_{1-4}$-alkyl;

$R^{8A}$, $R^{8B}$ and $R^9$ are each independently selected from hydrogen, $C_{3-5}$-cycloalkyl, $C_{1-6}$-alkyl, and $C_{6-10}$-aryl-$C_{1-4}$-alkyl wherein any alkyl residue or cycloalkyl or $C_{6-10}$-aryl ring system is optionally substituted with one or more substituents independently selected from halogen, hydroxyl and $C_{1-4}$-alkoxy, or $R^{8A}$ and $R^{8B}$, together with the nitrogen atom to which they are bound, form a 4- to 7-membered saturated heterocyclic ring which is optionally fused to a $C_{6-10}$-aryl or heteroaryl ring system, the 4- to 7-membered saturated heterocyclic ring or the $C_{6-10}$-aryl or heteroaryl ring systems being optionally substituted with one or more substituents independently selected from halogen, hydroxyl, $C_{1-4}$-alkyl, fluoro-$C_{1-4}$-alkyl and $C_{1-4}$-alkoxy; and $R^{10A}$ and $R^{10B}$ are each independently selected from hydrogen and $C_{1-6}$-alkyl, wherein said $C_{1-6}$-alkyl is optionally substituted with one or more substituents independently selected from fluorine, hydroxyl and $C_{1-4}$-alkoxy, or $R^{10A}$ and $R^{10B}$, together with the nitrogen atom to which they are bound, form a 4- to 7-membered saturated heterocyclic ring or a heteroaryl ring, optionally substituted with one or more substituents independently selected from fluorine, hydroxyl, $C_{1-4}$-alkyl, fluoro-$C_{1-4}$-alkyl and $C_{1-4}$-alkoxy; provided that when Y is a piperazine of formula (H) wherein n=1, then $R^2$ is not piperidine wherein p=1, and o=2; and when Y is a piperazine of formula (H) wherein n=1 then $R^2$ is not an alkyl amino of formula (S).

Compounds of formula (I) above may be prepared in the form of salts, especially pharmaceutically acceptable salts, N-oxides, hydrates, solvates and polymorphic forms thereof. Any claim to a compound herein, or reference herein to "compounds of the invention", "compounds with which the invention is concerned", "compounds of formula (I)" and the like, includes salts, N-oxides, hydrates, solvates and polymorphs of such compounds;

Although the above definition potentially includes molecules of high molecular weight, it is preferable, in line with general principles of medicinal chemistry practice, that the compounds with which this invention is concerned should have molecular weights of no more than 600.

The compounds of the invention are antagonists of the CXCR4 receptor. Therefore, in another broad aspect the invention provides the use of a compound of the invention in the treatment of, or in the preparation of a composition for treatment of, diseases or conditions responsive to the reduction of CXCR4 mediated activity.

Examples of diseases or conditions which are responsive to the reduction of CXCR4 mediated activity include cancer including cancers of the haematopoietic system such as multiple myeloma and non-Hodgkin's lymphoma, non-small cell lung, breast and neuroblastoma, cancer metastasis, HIV/AIDS, neuropathy, HIV related neuropathy, pain, inflammation, brain inflammation, neurodegeneration, cognative degeneration, diabetic retinopathy, age related macular degeneration, retinal neo-vascularisation, and viral infections.

The compounds with which the invention is concerned may be used for the reduction of CXCR4 mediated activity, ex vivo or in vivo.

In one aspect of the invention, the compounds of the invention may be used in the preparation of a composition for the treatment of cancer including cancers of the haematopoietic system such as multiple myeloma and non-Hodgkin's lymphoma, non-small cell lung, breast and neuroblastoma, cancer metastasis, HIV/AIDS, neuropathy, HIV related neuropathy, pain, inflammation, brain inflammation, neurodegeneration, cognative degeneration, diabetic retinopathy, age related macular degeneration, retinal neo-vascularisation, and viral infections.

In another aspect, the invention provides a method for the treatment of the foregoing disease types, which comprises administering to a subject suffering such disease an effective amount of a compound of the invention.

In another aspect, the compounds of the invention may be used for stem cell apheresis including haematopoietic stem cell mobilisation and non-haematopoietic stem and progenitor cell mobilization. Apheresis in its broadest meaning is a procedure in which blood is drawn and separated into its components, for example by dialysis; some components are retained and the rest are used for further medical procedures such as being returned to the donor or another subject by transfusion. Thus, apheresis may be applied, for example, to harvest stem cells from plasma for subsequent use in stem cell transplantation. A further example of a therapeutic application of stem cell apheresis is in reducing leukopenia which would otherwise be a consequence of chemotherapy or radiotherapy. Stem cells are damaged during chemo- or radiotherapy, and stem cell apheresis may be used to harvest stem cells from the body prior to such treatment, and then returned undamaged to the body once the radio- or chemotherapy is finished.

In another aspect, the apheresis procedure may be implemented prior to treatment of a subject by chemotherapy or radiotherapy, in order to reduce chemotherapy- or radiotherapy-induced leukopenia.

In another aspect, the compounds of the invention may be administered as an adjunct to chemotherapy or radiotherapy to sensitize tumours to such chemotherapy or radiotherapy.

In another aspect, the compounds of the invention may be used for inhibition of neo-vascularisation, angiogenesis, or vasculogenesis.

In another aspect of the invention, there is provided a pharmaceutical composition comprising a compound of the invention together with one or more pharmaceutically acceptable carriers and/or excipients.

In another aspect, there is provided a pharmaceutical composition comprising a compound of the invention together with one or more anti-angiogenic agents. In one embodiment the anti-angiogenic agent is an inhibitor of the VEGF receptor. In another embodiment the anti-angiogenic agent is an inhibitor of the PDGF receptor. In another embodiment the anti-angiogenic agent is selected from cediranib, sunitinib, sorafenib, pazopanib, tivozanib vatalanib, vandertanib, brivanib, dovitinib, motesanib, telatinib and axitinib.

The compounds of the invention may be administered in a variety of dosage forms. Thus, they can be administered orally, for example as tablets, capsules, troches, lozenges, aqueous or oily suspensions, dispersible powders or granules. The compounds can be administered in a sublingual formulation, for example a buccal formulation. The compounds of the invention may also be administered parenterally, whether subcutaneously, intravenously, intramuscularly, intrasternally, transdermally, by inhalation, intranasally, or by infusion techniques. The compounds may also be administered as suppositories. Thus, the compounds of the invention are administered orally, or by inhalation, or intranasally, but preferably the compounds of the invention are administered orally and more preferably, the compounds of the invention are administered as a tablet or capsule. In the latter connection, administration of the compounds in a hard gelatine capsule form, or in one of the many sustained release formulations known in the art will often be preferred.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol. Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Since the compounds of the invention are preferably administered orally, the present invention further provides a pharmaceutical composition containing a compound of the invention or a pharmaceutically acceptable salt thereof, as defined above, and a pharmaceutically acceptable carrier in the form of a capsule or tablet.

Solutions for injection or infusion may contain as carrier, for example, sterile water or preferably they may be in the form of sterile, aqueous, isotonic saline solutions.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the art. However, it is expected that a typical dose will be in the range from about 0.001 to 50 mg per kg of body weight.

Terminology

The following definitions shall apply throughout the specification and the appended claims, unless otherwise stated or indicated.

Where elements present in the compounds of the invention exist as different isotopes, for example carbon ($C^{13}$ and $C^{14}$) nitrogen ($N^{14}$ and $N^{15}$) and hydrogen ($H^1$ and $H^2$ ie deuterium), such compounds form part of the invention irrespective of the isotopic form of the element present in the compound. In particular, where a compound of the invention has a hydrogen atom in any position, that hydrogen may be replaced by deuterium. It is known in the art that deuterium substitution can increase the metabolic stability of biologically active molecules.

The term "halogen" denotes a fluoro, chloro, bromo or iodo substituent. In a presently preferred embodiment halogen is fluoro or chloro.

The term "$C_{a-b}$-alkyl" wherein a and b are integers denotes a straight or branched alkyl group having from a to b carbon atoms. For example "$C_{1-4}$-alkyl" includes methyl, ethyl, n-propyl, isopropyl, n-butyl, iso-butyl, sec-butyl and tert-butyl and "$C_{1-6}$-alkyl" includes the foregoing and straight- and branched-chain pentyl and hexyl.

The term "fluoro-$C_{a-b}$-alkyl" wherein a and b are integers denotes a straight or branched $C_{a-b}$-alkyl group substituted by one or more fluorine atoms. For example fluoro-$C_{1-4}$-alkyl includes fluoromethyl, trifluoromethyl, 2-fluoroethyl and 2,2,2-trifluoroethyl.

The term "$C_{a-b}$-alkoxy" wherein a and b are integers refers to a straight or branched $C_{a-b}$-alkyl group which is attached to the remainder of the molecule through an oxygen atom. For example $C_{1-4}$-alkoxy includes methoxy, ethoxy, n-propoxy, iso-propoxy, n-butoxy, iso-butoxy, sec-butoxy and tert-butoxy.

The term "fluoro-$C_{a-b}$-alkoxy" wherein a and b are integers denotes a fluoro-$C_{a-b}$-alkyl group which is attached to the remainder of the molecule through an oxygen atom. For example "fluoro-$C_{1-4}$-alkoxy" groups include trifluoromethoxy and 2,2,2-trifluoroethoxy.

The term "$C_{a-b}$-alkoxy-$C_{c-d}$-alkyl" wherein a, b, c and d are integers denotes a straight or branched alkoxy group having from a to b carbon atoms connected to a straight or branched alkyl group having from c to d carbon atoms. For example "$C_{1-4}$-alkoxy-$C_{1-4}$-alkyl" includes methoxymethyl, methoxyethyl, ethoxyethyl, iso-propoxyethyl, n-butoxyethyl and tert-butoxyethyl. In an alternative example "$C_{1-2}$-alkoxy-$C_{1-4}$-alkyl" includes methoxymethyl, methoxyethyl, and ethoxyethyl.

The term fluoro-$C_{a-b}$-alkoxy-$C_{c-d}$-alkyl wherein a, b, c and d are integers denotes a $C_{a-b}$-alkoxy-$C_{c-d}$-alkyl group substituted by one or more fluorine atoms. For example "fluoro-$C_{1-4}$-alkoxy-$C_{1-4}$-alkyl" includes trifluoromethoxymethyl and trifluoromethoxyethyl.

The term "$C_{a-b}$-cycloalkyl" wherein a and b are integers denotes a saturated monocyclic hydrocarbon ring having from a to b carbon atoms. For examples "$C_{3-5}$-cycloalkyl" includes cyclopropyl, cyclobutyl and cyclopentyl. The term "$C_{3-5}$-cycloalkyl" also includes a cyclopropyl, cyclobutyl or cyclopentyl ring system which is fused to a $C_{6-10}$-aryl group such as phenyl.

The term "$C_{a-b}$-cycloalkyl-$C_{c-d}$-alkyl" wherein a, b, c and d are integers denotes a saturated monocyclic hydrocarbon ring having from a to b carbon atoms connected to a straight or branched alkyl group having from c to d carbon atoms. For example "$C_{3-5}$-cycloalkyl-$C_{1-4}$-alkyl" includes cyclopropylmethyl and cyclobutylmethyl.

Unless otherwise particularised, the term "heterocyclyl" or "heterocyclic ring" denotes a saturated, monocyclic ring having from 4 to 7 ring atoms with at least one heteroatom such as O, N, or S, and the remaining ring atoms are carbon. Examples of heterocyclic rings include piperidinyl, tetrahydropyranyl, tetrahydrofuranyl, oxetanyl, azetidinyl, pyrrolidinyl, morpholinyl, thiomorpholinyl, dioxanyl, piperazinyl and homopiperazinyl. When present, the sulfur atom may be in an oxidized form (i.e., S=O or O=S=O). Exemplary heterocyclic groups containing sulfur in oxidized form are 1,1-dioxido-thiomorpholinyl and 1,1-dioxido-isothiazolidinyl. The term "heterocyclyl" or "heterocyclic ring" also includes a ring system in which the "heterocyclyl" or "heterocyclic ring" is fused to a $C_{6-10}$-aryl ring system, such as phenyl.

Unless otherwise particularised the term "heterocyclyl-$C_{a-b}$-alkyl" wherein a and b are integers denotes a heterocyclic ring as defined above that is directly attached to a straight or branched $C_{a-b}$-alkyl group via a carbon or nitrogen atom of said ring. For example "heterocyclyl-$C_{1-4}$-alkyl" groups include piperidin-1-ylmethyl, piperidin-4-ylmethyl and morpholin-4-ylmethyl.

Unless otherwise particularised the term "heteroaryl" denotes a monocyclic or fused bicyclic heteroaromatic ring system comprising 5 to 10 ring atoms in which one or more of the ring atoms are other than carbon, such as nitrogen, sulphur or oxygen. Only one ring need to be aromatic and said heteroaryl moiety can be linked to the remainder of the molecule via a carbon or nitrogen atom in any ring. Examples of heteroaryl groups include furyl, pyrrolyl, thienyl, oxazolyl, isoxazolyl, imidazolyl, thiazolyl, isothiazolyl, pyridinyl, pyrimidinyl, tetrazolyl, quinazolinyl, indolyl, indolinyl, isoindolyl, isoindolinyl, pyrazolyl, pyridazinyl, pyrazinyl, quinolinyl, quinoxalinyl, oxadiazolyl, thiadiazolyl, benzofuranyl, 2,3-dihydrobenzofuranyl, 1,3-benzodioxolyl, 1,4-benzodioxinyl, benzothiazolyl, benzimidazolyl, azabenzimidazole, benzotriazolyl and chromanyl.

Unless otherwise particularised the term "$C_{a-b}$-aryl" wherein a and b are integers denotes a monocyclic or fused bicyclic hydrocarbon ring system comprising a to b ring atoms and wherein at least one ring is an aromatic ring. For example "$C_{6-10}$-aryl" groups include phenyl, indenyl, 2,3-dihydroindenyl (indanyl), 1-naphthyl, 2-naphthyl or 1,2,3,4-tetrahydronaphthyl.

Unless otherwise particularised the term "$C_{a-b}$-aryl-$C_{c-d}$-alkyl" wherein a, b, c and d are integers refers to a $C_{a-b}$-aryl group that is directly linked to a straight or branched $C_{c-d}$-alkyl group. For example "$C_{6-10}$-aryl-$C_{1-4}$-alkyl" groups include phenylmethyl (i.e., benzyl) and phenylethyl.

Unless otherwise particularised the term "heteroaryl-$C_{a-b}$-alkyl" wherein a and b are integers denotes a heteroaryl ring as defined above that is directly linked to a straight or branched $C_{a-b}$-alkyl group via a carbon or nitrogen atom of said ring. For examples "heteroaryl-$C_{1-4}$-alkyl" groups include 2-(pyridin-2-yl)-ethyl and 1,2,4-oxadiazol-5-ylmethyl.

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

As used herein the term "salt" includes base addition, acid addition and ammonium salts. As briefly mentioned above compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds (I) which have a basic nitrogen can also form quaternary ammonium salts with a pharmaceutically acceptable counter-ion such as chloride, bromide, acetate, formate, p-toluenesulfonate, succinate, hemi-succinate, naphthalene-bis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002).

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts, hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in an amorphous form and/or several polymorphic forms and may be obtained in different crystal habits. Any reference herein, including the claims herein, to "compounds with which the invention is concerned" or "compounds of the invention" or "the present compounds", and the like, includes reference to the compounds irrespective of amorphous or polymorphic form.

Some compounds of the invention, having a nitrogen atom in an aromatic ring, may form N-oxides, and the invention includes compounds of the invention in their N-oxide form.

In the compounds of the invention, in any compatible combination, and bearing in mind that the compounds preferably have a molecular weight of less than 600:

The group $R^1$

As defined above, $R^1$ is selected from hydrogen, $C_{1-4}$-alky such as methyl, ethyl, n- or iso-propyl, n-, sec- or tert-butyl, cyano, —$COR^3$, —$CONR^3R^4$ and heteroaryl such as furyl, pyrrolyl, thienyl, oxazolyl, isoxazolyl, imidazolyl, thiazolyl, isothiazolyl, pyridinyl, pyrimidinyl, tetrazolyl, quinazolinyl, indolyl, indolinyl, isoindolyl, isoindolinyl, pyrazolyl, pyridazinyl, pyrazinyl, quinolinyl, quinoxalinyl, oxadiazolyl, thiadiazolyl, benzofuranyl, 2,3-dihydrobenzofuranyl, 1,3-benzodioxolyl, 1,4-benzodioxinyl, benzothiazolyl, benzimidazolyl, benzotriazolyl and chromanyl, wherein (a) said heteroaryl is optionally substituted with one more substituents independently selected from halogen such as fluoro, chloro, bromo, hydroxy, cyano, nitro, $C_{1-6}$-alkyl such as methyl, ethyl, n- or iso-propyl, n-butyl, isobutyl, sec-butyl and t-butyl, and straight or branched pentyl or hexyl, $C_{3-5}$-cycloalkyl such as cyclopropyl, cyclobutyl and cyclopentyl, $C_{1-4}$-alkoxy such as methoxy, ethoxy, n-propoxy, isopropoxy, n-butoxy, iso-butoxy, sec-butoxy and tert-butoxy, fluoro-$C_{1-6}$-alkyl such as mono-, di- or tri-fluoromethyl, 2-fluoroethyl and 2,2,2-trifluoroethyl, fluoro-$C_{1-4}$-alkoxy such as trifluoromethoxy and 2,2,2-trifluoroethoxy, $C_{1-4}$-alkoxy-$C_{1-4}$-alkyl such as methoxymethyl, methoxyethyl, ethoxyethyl, isopropoxyethyl, n-butoxyethyl and tert-butoxyethyl, fluoro-$C_{1-4}$-alkoxy-$C_{1-4}$-alkyl such as trifluoromethoxymethyl and trifluoromethoxyethyl, $C_{6-10}$-aryl such as phenyl, indenyl, 2,3-dihydroindenyl (indanyl), 1-naphthyl, 2-naphthyl or 1,2,3,4-tetrahydronaphthyl, heteroaryl such as such as furyl, pyrrolyl, thienyl, oxazolyl, isoxazolyl, imidazolyl, thiazolyl, isothiazolyl, pyridinyl, pyrimidinyl, tetrazolyl, quinazolinyl, indolyl, indolinyl, isoindolyl, isoindolinyl, pyrazolyl, pyridazinyl, pyrazinyl, quinolinyl, quinoxalinyl, oxadiazolyl, thiadiazolyl, benzofuranyl, 2,3-dihydrobenzofuranyl, 1,3-benzodioxolyl, 1,4-benzodioxinyl, benzothiazolyl, benzimidazolyl, benzotriazolyl and chromanyl, —NR$^{5A}$R$^{5B}$, —C$_{1-4}$-alkyl-NR$^{5A}$R$^{5B}$, —NR$^4$C(O)O—C$_{1-4}$-alkyl, —NR$^4$C(O)—C$_{1-4}$-alkyl, —NR$^4$C(O)O-fluoro-C$_{1-4}$-alkyl, —NR$^4$C(O)-fluoro-C$_{1-4}$-alkyl, —NR$^4$C(O)NR$^{5A}$R$^{5B}$, —C(O)NR$^{5A}$R$^{5B}$, —C(O)R$^4$, —C(O)OR$^4$, —NR$^4$S(O)$_2$—C$_{1-4}$-alkyl and —NR$^4$S(O)$_2$-fluoro-C$_{1-4}$-alkyl, and (b) said $C_{1-4}$-alkyl is optionally substituted with one or more substituents independently selected from fluorine, hydroxyl and $C_{1-4}$-alkoxy such as methoxy, ethoxy, n-propoxy, iso-propoxy, n-butoxy, iso-butoxy, sec-butoxy and tert-butoxy;

The Group X

As defined above, X is selected from radicals of formulae (A), (B), (C), (D), (E), or (F) inclusive, any of which being optionally substituted with one more substituents independently selected from halogen such as fluoro, chloro, bromo, cyano, nitro, $C_{1-4}$-alkyl such as methyl, ethyl, n- or iso-propyl, n-, sec- or tert-butyl, $C_{1-4}$-alkoxy such as methoxy, ethoxy, n-propoxy, iso-propoxy, n-butoxy, iso-butoxy, sec-butoxy and tert-butoxy, fluoro-$C_{1-4}$-alkyl such as fluoromethyl, trifluoromethyl, 2-fluoroethyl and 2,2,2-trifluoroethyl, and fluoro-$C_{1-4}$-alkoxy such as trifluoromethoxy and 2,2,2-trifluoroethoxy, The Group Y As defined above, Y is selected from radicals of formulae (H) such as piperazine and homopiperazine, (J) such as amino-piperidine and amino-homopiperidine, (K) such as amino-piperidine and amino-homopiperidine, (L) such as 1,2-diaminoethane and 1,3-diamino propane, and (M) such as oxy-piperidine, any of which is optionally substituted with one more substituents independently selected from, fluorine, hydroxyl, $C_{1-4}$-alkyl such as methyl, ethyl, n- or iso-propyl, n-, sec- or tert-butyl a divalent $C_{1-4}$-alkylene radical which forms a bridge between ring carbons of said homopiperazine or piperazine, examples include —CH$_2$—, —CH$_2$CH$_2$— and —CH$_2$CH$_2$CH$_2$—, $C_{1-4}$-alkoxy such as methoxy, ethoxy, n-propoxy, iso-propoxy, n-butoxy, iso-butoxy, sec-butoxy and tert-butoxy, fluoro-$C_{1-4}$-alkyl such as fluoromethyl, trifluoromethyl, 2-fluoroethyl and 2,2,2-trifluoroethyl, a divalent fluoro-$C_{1-4}$-alkylene radical which forms a bridge between ring carbons of said homopiperazine or piperazine, examples include —CH$_2$—, —CH$_2$CH$_2$— and —CH$_2$CH$_2$CH$_2$— wherein one or more hydrogens are replaced by fluorine, and fluoro-$C_{1-4}$-alkoxy such as trifluoromethoxy and 2,2,2-trifluoroethoxy.

The Group R$^2$

As defined above, R$^2$ is selected from radicals of formulae (N), (O), (P), (Q), (R), and (S) inclusive, any of which is optionally substituted with one more substituents independently selected from fluorine, hydroxyl, $C_{1-4}$-alkyl such as methyl, ethyl, n- or iso-propyl, n-, sec- or tert-butyl, $C_{1-4}$-alkoxy such as methoxy, ethoxy, n-propoxy, iso-propoxy, n-butoxy, iso-butoxy, sec-butoxy and tert-butoxy, fluoro-$C_{1-4}$-alkyl such as fluoromethyl, trifluoromethyl, 2-fluoroethyl and 2,2,2-trifluoroethyl and fluoro-$C_{1-4}$-alkoxy such as trifluoromethoxy and 2,2,2-trifluoroethoxy, The Group R$^3$ As defined above, R$^3$ is selected from hydrogen, $C_{1-6}$-alkyl such as methyl, ethyl, n- or iso-propyl, n-butyl, isobutyl, sec-butyl and tert-butyl, straight or branched pentyl and hexyl, $C_{3-5}$-cycloalkyl such as cyclopropyl, cyclobutyl and cyclopentyl, $C_{3-5}$-cycloalkyl-$C_{1-4}$-alkyl such as cyclopropylmethyl and cyclobutylmethyl, heterocyclyl such as piperidinyl, tetrahydropyranyl, tetrahydrofuranyl, oxetanyl, azetidinyl, pyrrolidinyl, morpholinyl, imidazolidinyl, thiomorpholinyl, dioxanyl, piperazinyl, homopiperazinyl1,1-dioxido-thiomorpholinyl and 1,1-dioxido-isothiazolidinyl, heterocyclyl-$C_{1-4}$-alkyl such as piperidin-1-ylmethyl, piperidin-4-ylmethyl and morpholin-4-ylmethyl, $C_{6-10}$-aryl such as phenyl, indenyl, 2,3-dihydroindenyl (indanyl), 1-naphthyl, 2-naphthyl or 1,2,3,4-tetrahydronaphthyl, $C_{6-10}$-aryl-$C_{1-4}$-alkyl such as phenylmethyl (i.e., benzyl) and phenylethyl, heteroaryl such as furyl, pyrrolyl, thienyl, oxazolyl, isoxazolyl, imidazolyl, thiazolyl, isothiazolyl, pyridinyl, pyrimidinyl, tetrazolyl, quinazolinyl, indolyl, indolinyl, isoindolyl, isoindolinyl, pyrazolyl, pyridazinyl, pyrazinyl, quinolinyl, quinoxalinyl, oxadiazolyl, thiadiazolyl, benzofuranyl, 2,3-dihydrobenzofuranyl, 1,3-benzodioxolyl, 1,4-benzodioxinyl, benzothiazolyl, benzimidazolyl, benzotriazolyl and chromanyl, and heteroaryl-$C_{1-4}$-alkyl such as 2-(pyridin-2-yl)-ethyl and 1,2,4-oxadiazol-5-ylmethyl, wherein (i) said $C_{1-6}$-alkyl, $C_{3-5}$-cycloalkyl, heterocyclyl or the heterocyclyl part of said heterocyclyl-$C_{1-4}$-alkyl, or the $C_{1-6}$-alkyl part of said heterocyclyl-$C_{1-4}$-alkyl, $C_{6-10}$-aryl-$C_{1-4}$-alkyl or heteroaryl-$C_{1-4}$-alkyl, is optionally substituted with one or more substituents independently selected from fluorine, hydroxy, $C_{1-4}$-alkoxy such as methoxy, ethoxy, n-propoxy, isopropoxy, n-butoxy, isobutoxy, sec-butoxy and tert-butoxy, and —NR$^{5A}$R$^{5B}$, and (ii) said $C_{6-10}$-aryl or heteroaryl, or the $C_{6-10}$-aryl part of said $C_{6-10}$-aryl-$C_{1-4}$-alkyl or the heteroaryl part of said heteroaryl-$C_{1-4}$-alkyl, is optionally substituted with one more substituents independently selected from halogen such as fluoro, chloro or bromo, hydroxy, cyano, nitro, $C_{1-4}$-alkyl- such as methyl, ethyl, n- or iso-propyl, n-, sec- or tert-butyl, $C_{1-4}$-alkoxy such as methoxy, ethoxy, n-propoxy, iso-propoxy, n-butoxy, iso-butoxy, sec-butoxy and tert-butoxy, fluoro-$C_{1-4}$-alkyl such as fluoromethyl, trifluoromethyl, 2-fluoroethyl and 2,2,2-trifluoroethyl, fluoro-$C_{1-4}$-alkoxy such as trifluoromethoxy and 2,2,2-trifluoroethoxy, $C_{1-4}$-alkoxy-$C_{1-4}$-alkyl such as methoxymethyl, methoxyethyl, ethoxyethyl, iso-propoxyethyl, n-butoxyethyl and t-butoxyethyl, fluoro-$C_{1-4}$-alkoxy-$C_{1-4}$-alkyl such as trifluoromethoxymethyl and trifluoromethoxyethyl, —$NR^{5A}R^{5B}$, —$C_{1-4}$-alkyl-$NR^{5A}R^{5B}$, —$NR^4C(O)O$—$C_{1-4}$alkyl, —$NR^4C(O)$—$C_{1-4}$alkyl, —$NR^4C(O)O$-fluoro-$C_{1-4}$ alkyl, —$NR^4C(O)$-fluoro-$C_{1-4}$alkyl, —$NR^4C(O)NR^{5A}R^{5B}$, —$C(O)NR^{5A}R^{5B}$, —$C(O)R^4$, —$C(O)OR^4$, —$NR^4S(O)_2$—$C_{1-4}$ alkyl and —$NR^4S(O)_2$-fluoro-$C_{1-4}$ alkyl;

The Groups $R^4$, $R^{5A}$ and $R^{5B}$

As defined above, $R^4$, $R^{5A}$ and $R^{5B}$ are each independently selected from hydrogen, $C_{1-4}$-alkyl such as methyl, ethyl, n- or iso-propyl, n-, sec- or tert-butyl, and fluoro-$C_{1-4}$-alkyl such as fluoromethyl, trifluoromethyl, 2-fluoroethyl and 2,2,2-trifluoroethyl, or $R^3$ and $R^4$, together with the nitrogen atom to which they are bound, form a 4- to 7-membered saturated heterocyclic ring such as pyrrolidine, piperidine, homopiperidine, piperazine, homopiperazine and morpholine, or a heteroaryl ring such as pyrrole, imidazole, indole, isoindole, indazole, or purine, said ring being optionally substituted with one or more substituents independently selected from fluorine, hydroxyl, $C_{1-4}$-alkyl such as methyl, ethyl, n- or iso-propyl, n-, sec- or tert-butyl, fluoro-$C_{1-4}$-alkyl such as fluoromethyl, trifluoromethyl, 2-fluoroethyl and 2,2,2-trifluoroethyl, and $C_{1-4}$-alkoxy such as methoxy, ethoxy, n-propoxy, isopropoxy, n-butoxy, iso-butoxy, sec-butoxy and tert-butoxy Group $R^6$ As defined above, $R^6$ is selected from $C_{1-6}$-alkyl such as methyl, ethyl, n- or iso-propyl, n-butyl, isobutyl, sec-butyl and tert-butyl, and straight or branched pentyl and hexyl, $C_{3-5}$-cycloalkyl such as cyclopropyl, cyclobutyl and cyclopentyl, $C_{3-5}$-cycloalkyl-$C_{1-4}$-alkyl such as cyclopropylmethyl and cyclobutylmethyl, heterocyclyl such as piperidinyl, tetrahydropyranyl, tetrahydrofuranyl, oxetanyl, azetidinyl, pyrrolidinyl, morpholinyl, imidazolidinyl, thiomorpholinyl, dioxanyl, piperazinyl, homopiperazinyl1,1-dioxido-thiomorpholinyl and 1,1-dioxido-isothiazolidinyl, heterocyclyl-$C_{1-4}$-alkyl such as piperidin-1-ylmethyl, piperidin-4-ylmethyl and morpholin-4-ylmethyl, $C_{6-10}$-aryl such as phenyl, indenyl, 2,3-dihydroindenyl (indanyl), 1-naphthyl, 2-naphthyl or 1,2,3,4-tetrahydronaphthyl, heteroaryl, and $C_{6-10}$-aryl-$C_{1-4}$-alkyl such as phenylmethyl (i.e., benzyl) and phenylethyl, wherein (iii) said $C_{1-6}$-alkyl, $C_{3-5}$-cycloalkyl, heterocyclyl, or the $C_{1-6}$-alkyl part of said heterocyclyl-$C_{1-4}$-alkyl or $C_{6-10}$-aryl-$C_{1-4}$-alkyl, or the heterocyclyl part of said heterocyclyl-$C_{1-4}$-alkyl is optionally substituted with one or more substituents independently selected from fluorine, hydroxyl and $C_{1-4}$-alkoxy such as methoxy, ethoxy, n-propoxy, iso-propoxy, n-butoxy, iso-butoxy, sec-butoxy and tert-butoxy, and (iv) said $C_{6-10}$-aryl or the $C_{6-10}$-aryl part of said $C_{6-10}$-aryl-$C_{1-4}$-alkyl is optionally substituted with one more substituents independently selected from halogen including fluoro or chloro, hydroxy, cyano, nitro, $C_{1-4}$-alkyl such as methyl, ethyl, n- or iso-propyl, n-, sec- or tert-butyl, $C_{1-4}$-alkoxy such as methoxy, ethoxy, n-propoxy, iso-propoxy, n-butoxy, iso-butoxy, sec-butoxy and tert-butoxy, fluoro-$C_{1-4}$-alkyl such as fluoromethyl, trifluoromethyl, 2-fluoroethyl and 2,2,2-trifluoroethyl, fluoro-$C_{1-4}$-alkoxy such as trifluoromethoxy and 2,2,2-trifluoroethoxy, $C_{1-4}$-alkoxy-$C_{1-4}$-alkyl such as methoxymethyl, methoxyethyl, ethoxyethyl, isopropoxyethyl, n-butoxyethyl and t-butoxyethyl, and fluoro-$C_{1-4}$-alkoxy-$C_{1-4}$-alkyl such as trifluoromethoxymethyl and trifluoromethoxyethyl;

The Groups $R^{8A}$, $R^{8B}$ and $R^9$

As defined above, $R^{8A}$, $R^{8B}$ and $R^9$ are each independently selected from hydrogen, $C_{3-5}$-cycloalkyl such as cyclopropyl or cyclobutyl or cyclopentyl, $C_{6-10}$aryl-$C_{1-4}$alkyl such as phenyl methyl (benxyl) and $C_{1-6}$-alkyl such as methyl, ethyl, n- or iso-propyl, n-butyl, isobutyl, sec-butyl and t-butyl, and straight or branched pentyl and hexyl, wherein any alkyl residue is optionally substituted with one or more substituents independently selected from fluorine, hydroxyl and $C_{1-4}$-alkoxy such as methoxy, ethoxy, n-propoxy, isopropoxy, n-butoxy, isobutoxy, sec-butoxy and tert-butoxy, or $R^{8A}$ and $R^{8B}$, together with the nitrogen atom to which they are bound, form a 4- to 7-membered saturated heterocyclic ring such as pyrrolidine, piperidine homopiperidine, piperazine, homopiperazine and morpholine, optionally substituted with one or more substituents independently selected from halogen such as fluoro or chloro, hydroxyl, $C_{1-4}$-alkyl such as methyl, ethyl, n- or iso-propyl, n-, sec- or tert-butyl, fluoro-$C_{1-4}$-alkyl and $C_{1-4}$-alkoxy such as methoxy, ethoxy, n-propoxy, isopropoxy, n-butoxy, isobutoxy, sec-butoxy and tert-butoxy or the 4-7 membered saturated heterocyclic ring is optionally fused to a $C_{6-10}$aryl or heteroaryl ring system, the 4-7 membered saturated heterocyclic ring or the $C_{6-10}$aryl being optionally substituted with one or more substituents independently selected from halogen such as fluoro or chloro, hydroxyl, $C_{1-4}$-alkyl such as methyl, ethyl, n- or iso-propyl, n-, sec- or tert-butyl, fluoro-$C_{1-4}$-alkyl and $C_{1-4}$-alkoxy such as methoxy, ethoxy, n-propoxy, isopropoxy, n-butoxy, isobutoxy, sec-butoxy and tert-butoxy;

The Groups $R^{10A}$ and $R^{10B}$

As defined above, $R^{10A}$ and $R^{10B}$ are each independently selected from hydrogen and $C_{1-6}$-alkyl such as methyl, ethyl, n- or iso-propyl, n-butyl, isobutyl, sec-butyl and t-butyl, straight or branched pentyl and hexyl, wherein said $C_{1-6}$-alkyl is optionally substituted with one or more substituents independently selected from fluorine, hydroxyl and $C_{1-4}$-alkoxy such as methoxy, ethoxy, n-propoxy, isopropoxy, n-butoxy, isobutoxy, sec-butoxy and tert-butoxy, or $R^{10A}$ and $R^{10B}$, together with the nitrogen atom to which they are bound, form a 4- to 7-membered saturated heterocyclic ring such as pyrrolidine, piperidine homopiperidine, piperazine, homopiperazine and morpholine or a heteroaryl ring such as pyrrole, imidazole, indole, isoindole, indazole, and purine, optionally substituted with one or more substituents independently selected from fluorine, hydroxyl, $C_{1-4}$-alkyl such as methyl, ethyl, n- or iso-propyl, n-, sec- or tert-butyl, fluoro-$C_{1-4}$-alkyl such as fluoromethyl, trifluoromethyl, 2-fluoroethyl and 2,2,2-trifluoroethyl and $C_{1-4}$-alkoxy such as methoxy, ethoxy, n-propoxy, isopropoxy, n-butoxy, isobutoxy, sec-butoxy and tert-butoxy.

In a presently preferred embodiment of the invention $R^1$ is CONR$^3$R$^4$ or heteroaryl such as benzoxazolyl, indolyl, azaindolyl, imidazolyl, benzimidazolyl, oxazolyl, oxadiazolyl or tetrazolyl, any of which may be optionally substituted with one or more substituents independently selected from, for example, halogen such as fluoro, chloro, cyano, $C_{1-6}$-alkyl such as methyl, ethyl, propyl, iso-propyl, tert-butyl, n-butyl, $C_{3-5}$-cycloalkyl such as cyclopropyl, cyclopentyl, $C_{1-4}$-alkoxy such as methoxy, fluoro-$C_{1-6}$-alkyl such as trifluoromethyl, fluoro-$C_{1-4}$-alkoxy, and heteroaryl such as pyridyl.

In an alternative presently preferred embodiment of the invention $R^1$ is CONR$^3$R$^4$ wherein $R^4$ is hydrogen or methyl and $R^3$ is selected from tetrahydropyranyl, isopropylmethyl, tetrahydropyranylmethyl, imidazolylethyl, methoxyethyl, N-methylimidazolylmethyl, tetrahydrofuranylmethyl, 1-fluorothyl, oxazolylmethyl, pyridylmethyl, 2,2-difluoromethyl, tetrahydrofuranyl, methyl, ethyl, n- or iso-propyl, n-sec- or tert-butyl, cyclopropyl, hydroxyethyl, cyanoethyl, phenyl, pyridyl, chlorophenyl, methoxyphenyl, methylphenyl, hydroxyphenyl, thiazoloylmethyl, indolyl, methoxypropyl, tetrahydroisoquinolinyl, furylmethylpyridylethyl, thiazolyl, cyclopropylmethyl. In a preferred embodiment any one of the R³ substituents are optionally substituted with one or more optional substituents such as halogen or $C_{1-4}$ alkyl.

In a presently preferred embodiment of the invention X is a 2,6-pyridyl radical of formula (A).

In an alternative presently preferred embodiment of the invention Y is a homopiperazinyl radical of formula (H) when n is 2, or a piperazine radical of formula (H) when n is 1, either of which being optionally substituted with one more substituents independently selected from fluorine, hydroxyl, $C_{1-4}$-alkyl such as methyl, a divalent $C_{1-4}$-alkylene radical which forms a bridge between ring carbons of said homopiperazine or piperazine such as —CH₂CH₂— or —CH₂CH₂CH₂—, $C_{1-4}$-alkoxy such as methoxy, fluoro-$C_{1-4}$-alkyl such as di- and trifluoromethyl, or a divalent fluoro-$C_{1-4}$-alkylene radical which forms a bridge between ring carbons of said homopiperazine or piperazine, and fluoro-$C_{1-4}$-alkoxy such as mono-, di-, and tri-fluoromethoxy.

In a yet further presently preferred embodiment of the invention Y is a homopiperazinyl radical of formula (H) when n is 2, or a piperazine radical of formula (H) when n is 1, either of which being optionally substituted with one more substituents independently selected from fluorine, hydroxyl, $C_{1-4}$-alkyl such as methyl, a divalent $C_{1-4}$-alkylene radical which forms a bridge between ring carbons of said homopiperazine or piperazine such as -ethylene- or -propylene-, $C_{1-4}$-alkoxy such as methoxy, fluoro-$C_{1-4}$-alkyl such as di- and trifluoromethyl, or a divalent fluoro-$C_{1-4}$-alkylene radical which forms a bridge between ring carbons of said homopiperazine or piperazine, and fluoro-$C_{1-4}$-alkoxy such as mono-, di-, and tri-fluoromethoxy, and R² is selected from a 4-piperidine radical of formula (N) wherein o is 2 and p is 1, a 1,4-cyclohexyl radical of formula (R) or a —CH₂-morpholin-3-yl radical of formula (Q) wherein w is O, and wherein said 4-piperidine, and said 1,4-cyclohexyl and said —CH₂-morpholin-3-yl radicals are optionally substituted with one more substituents independently selected from fluorine, hydroxyl, $C_{1-4}$-alkyl such as methyl, ethyl, $C_{1-4}$-alkoxy such as methoxy, fluoro-$C_{1-4}$-alkyl such as mono-, di-, and tri-fluoromethyl, and fluoro-$C_{1-4}$-alkoxy such as mono, di-, and tri-fluoromethoxy.

In an alternative presently preferred embodiment of the invention Y is a piperazine radical of formula (H) wherein n is 1, optionally substituted as defined above, and R² is a 4-azepine radical of formula (N) wherein 0 is 2 and p is 2, said 4-azepine radical being optionally substituted with one more substituents independently selected from fluorine, hydroxyl, $C_{1-4}$-alkyl such as methyl, $C_{1-4}$-alkoxy such as methoxy, fluoro-$C_{1-4}$-alkyl such as trifluoromethyl, and fluoro-$C_{1-4}$-alkoxy.

In a preferred embodiment R³ is pyridyl optionally substituted with one or more substituents selected from halogen such as fluoro or chloro, $C_{1-4}$-alkyl such as methyl or ethyl or isopropyl, $C_{1-4}$-alkoxy such as methoxy, of fluoro-$C_{1-4}$-alkyl.

In an alternative embodiment R³ is 4-pyridyl optionally substituted with one or more methyl groups.

Utilities

The compounds of the invention are useful in the treatment of cancers. Examples of such cancers include cancers of the haematopoietic system such as multiple myeloma and non-Hodgkin's lymphoma. Examples of other drugs which may be used in combination with the compounds of the invention for the treatment of cancers, including for example cancers of the haematopoietic system, include agents that inhibit growth factors such as GCSF and VEGF (e.g. avastin and aflibercept).

The compounds of the invention are also useful in the treatment of injuries including damage to the heart, liver, kidney, brain, and bone. Examples of other drugs which may be used in combination with the compounds of the invention for the treatment of such injuries include agents that inhibit growth factors such as GCSF and VEGF.

The compounds of the invention are useful in the treatment of viral infections, for example HIV/AIDS. Examples of other drugs which may be used in combination with the compounds of the invention for the treatment of viral infections include, for example, CCR5 antagonists including maraviroc and SCH532702, and antiretrovirals including reverse transcriptase inhibitors (e.g. zidovudine, abacavir, didanosine, zalcitabine, stavudine, lamivudine, emtricitabine, tenofovir, adefovir, nevirapine efavirenz, etravirine, delavirdineetc), and HIV protease inhibitors (e.g. saquinavir, ritonavir, indinavir, nelfinavir, amprenavir), and integrase inhibitors (e.g. raltegravir), and antivirals such as acyclovir and plecoranil.

The compounds of the invention are useful in the treatment of neuropathy. An example of neuropathy is HIV related peripheral neuropathy, which affects approximately 50% of HIV patients. Examples of other drugs which may be used in combination with the compounds of the invention for the treatment of neuropathy, including HIV related peripheral neuropathy, include opiates such as fentanyl, anti-epileptics such as gabapentin and pregabalin, and tricyclics such as amitryptiline.

The compounds of the invention are useful in the treatment of retinal neo-vascularisation, which is a major cause of blindness in patients with diabetes and age related macular degeneration. Examples of other drugs which may be used in combination with the compounds of the invention for the treatment of retinal neo-vascularisation include VEGF inhibitors such as avastin and lucentis.

The compounds of the invention are useful in the treatment of several types of cancers, including non-small cell lung, breast and neuroblastoma. Examples of other drugs which may be used in combination with the compounds of the invention for the treatment of cancer include other anti-cancer drugs including anti-angiogenic agents such as avastin and inhibitors of VEGF and PDGF receptors such as lucentis and sutent.

Synthesis

The compounds of formula (I) above may be prepared by, or in analogy with, conventional methods. The preparation of intermediates and compounds according to the examples of the present invention may in particular be illuminated by, but not limited to, the following Schemes. Definitions of variables in the structures in the schemes herein are commensurate with those of the corresponding positions in the formulae delineated herein.

Scheme 1. Preparation of compounds of formula (I) wherein X is 2,6-pyridyl radical of formula (A).

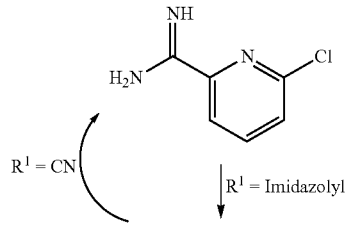

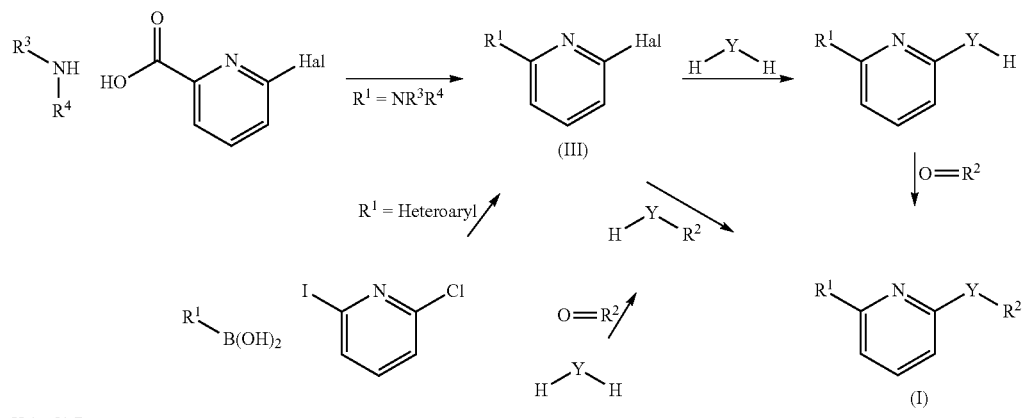

Hal = Cl, Br wherein R¹, R², R³, R⁴, X and Y are as defined in formula (I).

Compounds of general formula (I) wherein X is a 2,6-pyridyl radical can easily be prepared from intermediate compounds of general formula (III) (as illustrated in Scheme 1 above) by displacement of the halogen with H—Y—R² or alternatively by displacement of the halogen with H—Y—H (or a suitably protected version thereof) and subsequent addition of the R² group, for example by reductive alkylation with a carbonyl compound of formula O=R². The group H—Y—R² can be prepared for example by reductive alkylation of H—Y—H (or a suitably protected version thereof) with a carbonyl compound of formula O=R². Intermediate compounds of general formula (III) can be readily prepared for example by Suzuki reaction of a boronic acid R¹B(OH)₂ with 2-chloro-6-iodopyridine, by condensation of an amine R³R⁴NH₂ with 6-chloropyridine-2-carboxylic acid or by condensation of an α-halo ketone with 6-chloropyridine-2-carboximidamide. All of these alternatives are exemplified in the experimental section below.

Scheme 2. Alternative preparation of compounds of formula (I) wherein X is 2,6-pyridyl radical of formula (A).

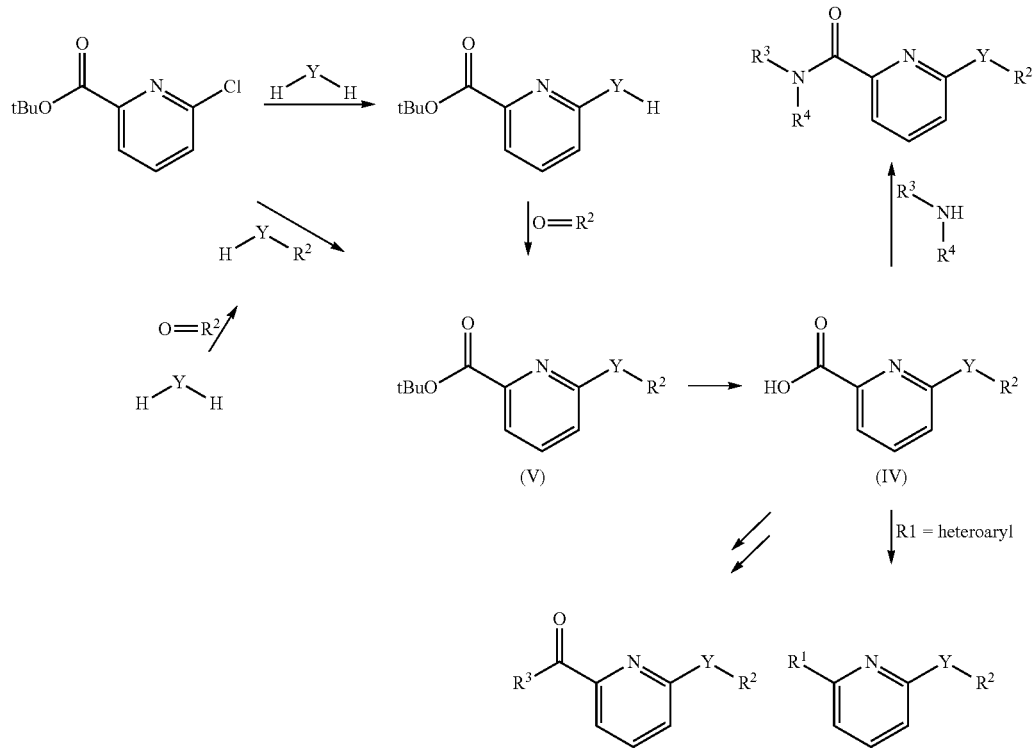

wherein R', R², R³, R⁴, X and Y are as defined in formula (I).

Compounds of general formula (I) wherein X is a 2,6-pyridyl radical can alternatively be readily prepared from intermediate compounds of general formula (IV) (as illustrated in Scheme 2 above) for example by condensation with an amine $R^3R^4NH_2$, by conversion of the carboxylic acid group into a ketone group $R^3CO$, or by conversion of the carboxylic group into a heteroaryl group by standard procedures. Intermediate compounds of general formula (IV) can be easily prepared from intermediate compounds of general formula (V) by deprotection of the tert-butyl ester. Intermediate compounds of general formula (V) can in turn be readily prepared from tert-butyl 6-chloropyridine-2-carboxylate by displacement of the halogen with $H$—$Y$—$R^2$ or alternatively by displacement of the halogen with $H$—$Y$—$H$ (or a suitably protected version thereof) and subsequent addition of the $R^2$ group, for example by reductive alkylation with a carbonyl compound of formula $O=R^2$. The group $H$—$Y$—$R^2$ can be prepared for example by reductive alkylation of $H$—$Y$—$H$ (or a suitably protected version thereof) with a carbonyl compound of formula $O=R^2$. All of these alternatives are exemplified in the experimental section below.

The groups $R^1$ and $R^2$ in Schemes 1 and 2 can also be converted by standard synthetic methods into alternative groups $R^1$ and $R^2$. The routes described in Schemes 1 and 2 refer to X being a 2,6-pyridyl radical of formula (A). Analogous methods can be used to prepare compounds of formula (I) where X is alternatively a radical of formulae (B)-(G) inclusive.

Appropriate reaction conditions for the individual reaction steps are known to a person skilled in the art. Particular reaction conditions for examples of the invention are also described in the experimental section. The necessary starting materials for preparing the compounds of formula (I) are either commercially available, or may be prepared by methods known in the art.

The processes described below in the experimental section may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of formula (I) may possess one or more chiral carbon atoms, and they may therefore be obtained in the form of optical isomers, e.g., as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents. Examples of protecting groups are t-butoxycarbonyl (Boc) and benzyl. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The following abbreviations have been used:

| | |
|---|---|
| aq | aqueous |
| BINAP | 2,2'-Bis(diphenylphosphino)-1,1'-binaphthyl |
| Boc | tert-Butyloxycarbonyl |
| DAST | Diethylaminosulfur trifluoride |
| DCE | 1,2-Dichloroethane |
| DCM | Dichloromethane |
| DIPEA | N,N-Diisopropylethylamine |
| DMA | Dimethylacetamide |
| DME | 1,2-Dimethoxyethane |
| DMF | N,N-Dimethylformamide |
| EDC•HCl | 1-Ethyl-3-(3-dimethylaminopropyl)carbodiimide hydrochloride |
| ES$^+$ | Electrospray |
| ESI$^+$ | Electrospray ionization |
| Et$_3$N | Triethylamine |
| Et$_2$O | Diethyl ether |
| EtOAc | Ethyl acetate |
| EtOH | Ethanol |
| HBTU | 2-(1H-Benzotriazole-1-yl)-1,1,3,3-tetramethyluronium hexafluorophosphate |
| HOBt | N-Hydroxybenzotriazole |
| HONB | endo-N-Hydroxybicyclo[2.2.1]hept-5-ene-2,3-dicarboximide |
| HPLC | High Performance Liquid Chromatography |
| HPLC-MS | High Performance Liquid Chromatography-Mass Spectrometry |
| HRMS | High Resolution Mass Spectrometry |
| IBX | 2-Iodoxybenzoic acid |
| Int | Intermediate |
| IPA | Isopropanol |
| LCMS | Liquid Chromatography Mass Spectrometry |
| M | Molar |
| MeCN | Acetonitrile |
| MeOH | Methanol |
| [MH]$^+$ | Protonated molecular ion |
| MSD-TOF | Mass Selective Detector-Time of Flight |
| NEM | N-Ethylmorpholine |
| NMP | N-methylpyrrolidone |
| PPh$_3$ | Triphenylphosphine |
| Proc | Procedure |
| sat | saturated |
| SM | Starting material |
| TFA | Trifluoroacetic acid |
| THF | Tetrahydrofuran |
| TLC | Thin Layer Chromatography |

The recitation of a listing of chemical groups in any definition of a variable herein includes definitions of that variable as any single group or combination of listed groups. The recitation of an embodiment herein includes that embodiment as any single embodiment or in combination with any other embodiments or portions thereof.

The invention will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All references and publications cited herein are hereby incorporated by reference in their entirety.

EXAMPLES AND INTERMEDIATE COMPOUNDS

Experimental Methods

All reagents were commercial grade and were used as received without further purification, unless otherwise specified. Reagent grade solvents were used in all cases. High-resolution mass spectra (HRMS) were obtained on an Agilent MSD-TOF connected to an Agilent 1100 HPLC system. During the analyses the calibration was checked by two masses and automatically corrected when needed. Spectra were acquired in positive electrospray mode. The acquired mass range was m/z 100-1100. Profile detection of the mass peaks was used. Analytical HPLC was performed on an Agilent 1100 system using a Phenomenex Synergi, RP-Hydro, 150× 4.6 mm, 4 μm column with a flow rate of 1.5 mL per min at 30° C. and a gradient of 5-100% acetonitrile (+0.085% TFA) in water (+0.1% TFA) over 7 min, (200-300 nm), unless otherwise stated. Flash chromatography was performed on either a CombiFlash Companion system equipped with RediSep or GraceResolv silica columns or a Flash Master Personal system equipped with Strata SI-1 silica gigatubes or in a glass column under gravity (ICN silica, 18-32 μm, 60 Å). Reverse Phase HPLC was performed on a Gilson system (Gilson 322 pump with Gilson 321 equilibration pump and Gilson 215 autosampler) equipped with Phenomenex Synergi Hydro RP 150×10 mm, ACE-5AQ, 100×21.20 mm or YMC ODS-A 100/150×20 mm columns. Reverse phase column chromatography was performed on a Gilson system (Gilson 321 pump and Gilson FC204 fraction collector) equipped with Merck LiChroprep® RP-18 (40-63 um) silica columns. Microwave irradiations were carried out using a Biotage or CEM microwave. Hydrogenations were performed using a Thales H-cube or H-cube midi. The compounds were automatically named using ACD 6.0. All compounds were dried in a vacuum oven overnight. Yields have been rounded to the nearest %. Where yields are not included, the intermediates were used crude. Reactions were monitored by TLC, LCMS or HPLC. Reactions were performed at room temperature unless otherwise stated.

Intermediate 1

2-(Dibenzylamino)cyclopentan-1-ol

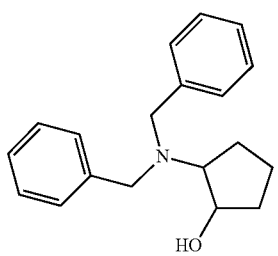 [SMILES: OC1CCCC1N(Cc1ccccc1)Cc1ccccc1]

2-Aminocyclopentanol hydrochloride (500 mg, 3.63 mmol) and benzaldehyde (810 mg, 7.63 mmol) were dissolved in DCM (20 mL), NaBH(OAc)$_3$ (2.31 g, 10.9 mmol) was added and the reaction mixture was stirred for 24 h. The reaction mixture was diluted with DCM (50 mL), washed with sat aq Na$_2$CO$_3$, (40 mL), brine (30 mL) and dried (MgSO$_4$). The reaction mixture was stirred with isocyanate resin for 18 h, filtered and concentrated in vacuo to give the crude title compound (436 mg, 43%) as a colourless oil. LCMS (ES$^+$): 282.1 [MH]$^+$.

Intermediate 2

N,N-Dibenzyl-2-fluorocyclopentan-1-amine

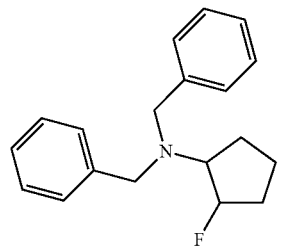 [SMILES: FC1CCCC1N(Cc1ccccc1)Cc1ccccc1]

Intermediate 1 (400 mg, 1.42 mmol) was dissolved in DCM (20 mL) and DAST (344 mg, 2.13 mmol) was added. The reaction mixture was stirred for 4 h, diluted with DCM (30 mL), washed with sat aq NaHCO$_3$ (40 mL), dried (MgSO$_4$) and concentrated in vacuo to give the crude title compound (330 mg, 82%) as a light brown gum. LCMS (ES$^+$): 284.1 [MH]$^+$.

Intermediate 3

2-Fluorocyclopentan-1-amine

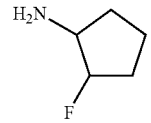

Intermediate 2 (330 mg, 116 mmol) was dissolved in MeOH (15 mL) and hydrogenated using an H-Cube (80 bar, 60° C., 1 mL/min) over 10% Pd/C. The resulting MeOH solution was used without purification. LCMS (ES$^+$): 104.0 [MH]$^+$.

Intermediate 4

1-Fluoropropan-2-amine

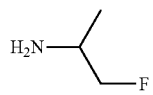

Fluoroacetone (500 mg, 6.57 mmol), benzylamine (704 mg, 6.57 mmol) and NaBH(OAc)$_3$ (4.18 g, 19.7 mmol) were dissolved in DCM (20 mL) and stirred for 18 h. The reaction mixture was diluted with DCM (80 mL), washed with sat aq Na$_2$CO$_3$ (75 mL), brine (75 mL), dried (MgSO$_4$) and concentrated in vacuo. The residue was dissolved in MeOH (10 mL), 10% Pd/C (100 mg) was added and the reaction mixture was stirred for 4 d under an atmosphere of H$_2$. The reaction mixture was filtered through celite and the resulting MeOH solution was used without purification. LCMS (ES$^+$): 77.8 [MH]$^+$.

Intermediate 5

4,4,4-Trifluorobutan-2-amine

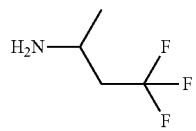

Intermediate 5 was prepared similarly to Intermediate 4 using 4,4,4-trifluoro-2-butanone instead of fluoroacetone. LCMS (ES$^+$): 128.1 [MH]$^+$.

Intermediate 6

1,1-Difluoropropan-2-amine

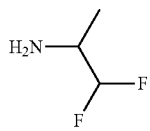

Intermediate 6 was prepared similarly to Intermediate 4 using 1,1-difluoroacetone instead of fluoroacetone. LCMS (ES$^+$): 96.0 [MH]$^+$.

Intermediate 7

1-(2-Fluoro-1-fluoromethyl-ethyl)-piperidin-4-one

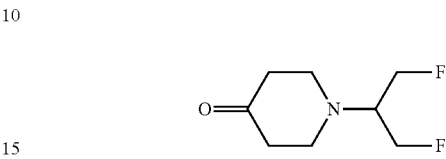

1,4-Pentadien-3-ol (200 mg, 2.38 mmol) and IBX (999 mg, 3.57 mmol) were dissolved in DCE (15 mL) and heated at 70° C. for 3 h. The reaction mixture was filtered, diluted with MeOH (10 mL) and 2-fluoro-1-fluoromethyl-ethylamine (226 mg, 2.38 mmol) was added. The reaction mixture was stirred at 70° C. for 3 h. Isocyanate resin was added and the reaction mixture stirred at room temperature for 6 h, filtered and concentrated in vacuo to give the crude title compound (160 mg, 38%) as an orange gum. LCMS (ES$^+$): 178.1 [MH]$^+$.

Intermediates 8-20

Intermediates 8-20 were prepared similarly to Intermediate 7; see Table 1 below.

TABLE 1

Preparation of piperidin-4-one intermediates

| Int | Structure | SM | Yield | LCMS (ES$^+$) | Intermediate Name |
|---|---|---|---|---|---|
| 8 | 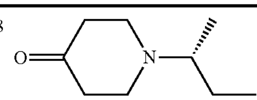 | * | 44% | 156.2 [MH]$^+$ | 1-[(2R)-Butan-2-yl]piperidin-4-one |
| 9 | 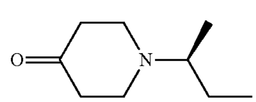 | * | 46% | 156.2 [MH]$^+$ | 1-[(2S)-Butan-2-yl]piperidin-4-one |
| 10 | 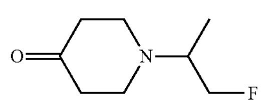 | Int 4 | 37% | 160.1 [MH]$^+$ | 1-(1-Fluoropropan-2-yl)piperidin-4-one |
| 11 | 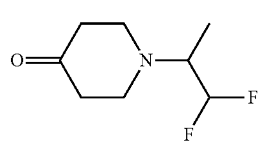 | Int 6 | 38% | 178.1 [MH]$^+$ | 1-(1,1-Difluoropropan-2-yl)piperidin-4-one |
| 12 | 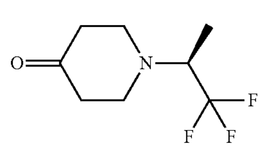 | * | 33% | 196.2 [MH]$^+$ | 1-[(2S)-1,1,1-Trifluoropropan-2-yl]piperidin-4-one |

TABLE 1-continued

Preparation of piperidin-4-one intermediates

| Int | Structure | SM | Yield | LCMS (ES+) | Intermediate Name |
|---|---|---|---|---|---|
| 13 | 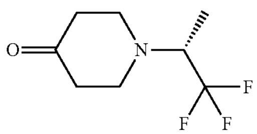 | * | 33% | 196.2 [MH]+ | 1-[(2R)-1,1,1-Trifluoropropan-2-yl]piperidin-4-one |
| 14 | 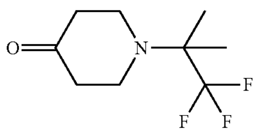 | * | 29% | 210.1 [MH]+ | 1-(1,1,1-Trifluoro-2-methylpropan-2-yl)piperidin-4-one |
| 15 | 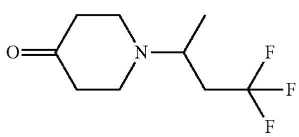 | Int 5 | 29% | 210.1 [MH]+ | 1-(4,4,4-Trifluorobutan-2-yl)piperidin-4-one |
| 16 | 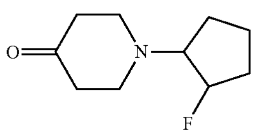 [SMILES: O=C1CCN(C2CCCC2F)CC1] | Int 3 | 20% | 186.1 [MH]+ | 1-(2-Fluorocyclopentyl)piperidin-4-one |
| 17 | 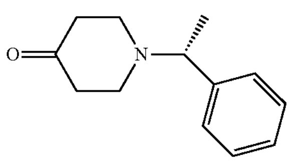 | * | 45% | 204.1 [MH]+ | 1-[(1R)-1-Phenylethyl]piperidin-4-one |
| 18 | 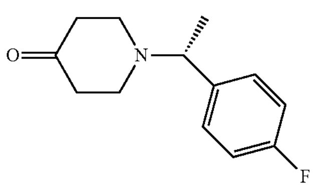 [SMILES: C[C@H](c1ccc(F)cc1)N1CCC(=O)CC1] | * | 39% | 222.1 [MH]+ | 1-[(1R)-1-(4-Fluorophenyl)ethyl]piperidin-4-one |
| 19 | 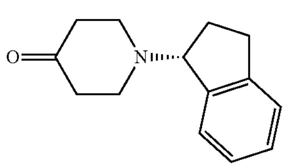 [SMILES: O=C1CCN([C@@H]2CCc3ccccc32)CC1] | * | 43% | — | 1-[(1R)-2,3-Dihydro-1H-inden-1-yl]piperidin-4-one |
| 20 | 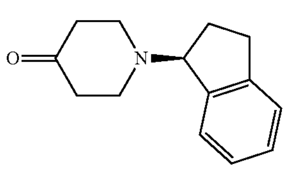 [SMILES: O=C1CCN([C@H]2CCc3ccccc32)CC1] | * | 45% | 216.1 [MH]+ | 1-[(1S)-2,3-Dihydro-1H-inden-1-yl]piperidin-4-one |

* Commercially available

Intermediate 21

1-(2-Methoxyethyl)piperidin-4-one

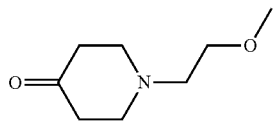

4-Piperidone hydrochloride monohydrate (1.00 g, 6.50 mmol), 2-bromoethyl methyl ether (1.00 g, 7.20 mmol) and $K_2CO_3$ (1.80 g, 13.0 mmol) were dissolved in MeCN (20 mL) and the reaction mixture was stirred at 75° C. for 6 h. The reaction mixture was filtered and the solvents removed in vacuo. The residue was dissolved in DCM (30 mL), stirred with isocyanate resin for 2 h, dried ($MgSO_4$) and concentrated in vacuo to give the crude title compound (180 mg, 18%) as a colourless gum.

Intermediates 22-25

Intermediates 22-25 were prepared similarly to Intermediate 21; see Table 2 below.

TABLE 2

Preparation of piperidin-4-one intermediates

| Int | Structure | Yield | LCMS (ES+) | Intermediate Name |
|---|---|---|---|---|
| 22 | 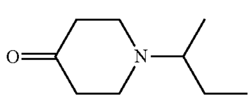 | 20% | 156.2 [MH]+ | 1-(Butan-2-yl)piperidin-4-one |
| 23 | 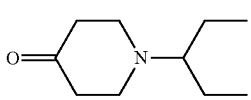 | 11% | 170.2 [MH]+ | 1-(Pentan-3-yl)piperidin-4-one |
| 24 | 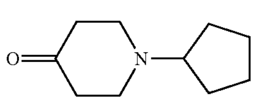 [SMILES: O=C1CCN(C2CCCC2)CC1] | 11% | 168.2 [MH]+ | 1-Cyclopentyl-piperidin-4-one |
| 25 | 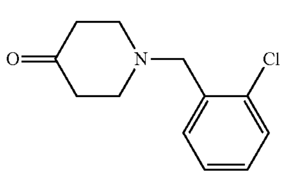 [SMILES: O=C1CCN(Cc2ccccc2Cl)CC1] | 91% | 224.0 [MH]+ | 1-[(2-Chlorophenyl)methyl]piperidin-4-one |

Intermediate 26

1-Bromopentan-2-one

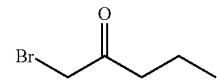

2-Pentanone (10.6 mL, 100 mmol) was dissolved in MeOH (60 mL) and cooled to −5° C. Bromine (5.13 mL, 100 mmol) was added and the reaction mixture was stirred for 4 h keeping the temperature below 10° C. Water (30 mL) was added and the reaction mixture was stirred overnight at room temperature. The reaction mixture was poured into water (100 mL) and extracted with DCM (2×200 mL). The combined organic fractions were washed with sat aq $NaHCO_3$ (200 mL), water (200 mL), dried ($CaCl_2$) and concentrated in vacuo. The residue was purified by Kugelrohr distillation to give the title compound as a pale yellow oil (8.22 g, 50%).

Intermediates 27-32

Intermediates 27-32 were prepared similarly to Intermediate 26; see Table 3 below.

TABLE 3

Preparation of alpha-bromoketones

| Int | Structure | Yield | Intermediate Name |
|---|---|---|---|
| 27 | 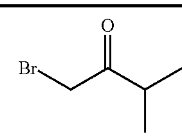 | 61% | 1-Bromo-3-methylbutan-2-one |
| 28 | 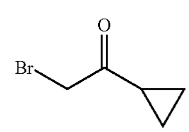 | 97% | 2-Bromo-1-cyclopropylethan-1-one |
| 29 | 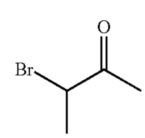 | 32% | 3-Bromobutan-2-one |
| 30 | 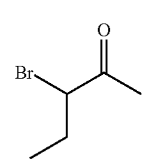 | 32% | 3-Bromopentan-2-one |
| 31 | 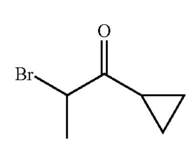 | 50% | 2-Bromo-1-cyclopropylpropan-1-one |

TABLE 3-continued

Preparation of alpha-bromoketones

| Int | Structure | Yield | Intermediate Name |
|---|---|---|---|
| 32 | 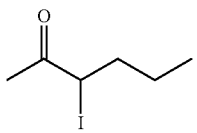 | 63% | 2-Bromo-1-cyclopropylbutan-1-one |

Intermediate 33

3-Iodohexan-2-one

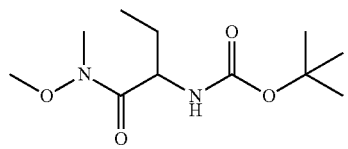 [SMILES: CCC(NC(=O)OC(C)(C)C)C(=O)N(C)OC]

2-Hexanone (4.94 mL, 39.9 mmol) and iodine (20.2 g, 79.9 mmol) were dissolved in DME (100 mL) and stirred for 24 h. The reaction mixture was diluted with EtOAc (200 mL) and washed with 1M aq potassium thiosulfate (200 mL), 1M aq Na$_2$CO$_3$ (200 mL) and water (100 mL). The organic fraction was dried (MgSO$_4$) and concentrated in vacuo. The residue was purified by Kugelrohr distillation (120° C., 1 mBar) to give the title compound as a dark brown oil (2.46 g, 27%).

Intermediate 34 tert-Butyl N-{1-[methoxy(methyl)carbamoyl]propyl}carbamate

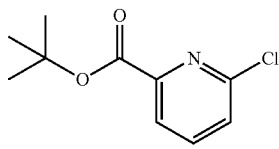

2-tert-Butoxycarbonylamino-butyric acid (500 mg, 2.46 mmol), HBTU (1.03 g, 2.71 mmol) and DIPEA (1.22 mL, 7.38 mmol) were dissolved in DMF (10 mL) and stirred for 30 min. N,O-dimethylhydroxylamine hydrochloride (360 mg, 3.69 mmol) was added and the reaction mixture was stirred for 1 h. The solvents were removed in vacuo and the residue was purified by column chromatography to give the title compound (380 mg, 63%) as a cream oil. LCMS (ES$^+$): 269.2 [MNa]$^+$.

Intermediate 35

4-Aminohexan-3-one 2,2,2-trifluoroacetic acid

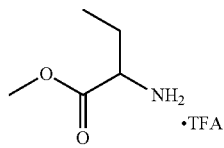

Intermediate 34 (4.97 g, 20.2 mmol) was dissolved in THF (100 mL) and ethylmagnesium bromide (20.0 mL, 3.2 M in 2-methyltetrahydrofuran, 64.0 mmol) was added. The reaction mixture was stirred for 4 h, quenched with sat aq NH$_4$Cl (20 mL) and extracted with EtOAc (2×200 mL). The combined organic fractions were washed with 1 M aq HCl (200 mL), 1 M aq Na$_2$CO$_3$ (200 mL), dried (MgSO$_4$) and concentrated in vacuo. The residue was dissolved in DCM (100 mL), TFA (25 mL) was added and the reaction mixture was stirred for 3 h and concentrated in vacuo to give the crude title compound (4.98 g) as a red gum. LCMS (ES$^+$): 116.2 [MH]$^+$.

Intermediate 36 tert-Butyl 6-chloropyridine-2-carboxylate

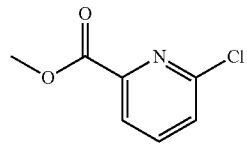

6-Chloropyridine-2-carboxylic acid (5.00 g, 31.7 mmol) was dissolved in DCM (150 mL) and oxalyl chloride (5.45 mL, 63.5 mmol) and DMF (1 mL) were added. The reaction mixture was stirred for 3 h, concentrated in vacuo and azeotroped with DCM. The residue was dissolved in THF (150 mL) and potassium tert-butoxide (3.39 mg, 47.6 mmol) was added. The reaction mixture was stirred for 18 h, quenched with water (250 mL) and extracted with DCM (3×150 mL). The combined organic fractions were washed with sat aq NaHCO$_3$ (150 mL), dried (MgSO$_4$) and concentrated in vacuo. The residue was purified by column chromatography to give the title compound (3.11 g, 46%) as a white solid. LCMS (ES$^+$): 236.1 [MNa]$^+$.

Intermediate 37

Methyl 6-chloropyridine-2-carboxylate

6-Chloropyridine-2-carboxylic acid (15.0 g, 0.11 mol) was dissolved in DCM (300 mL) and DMF (1.5 mL) and oxalyl chloride (27.4 g, 0.22 mol) was added dropwise over 10 min. The reaction mixture was stirred for 1 h, MeOH (50 mL) was added dropwise over 5 min and the reaction mixture was stirred for 1.5 h. The solvents were removed in vacuo and the residue azeotroped with DCM (2×150 mL) to give the crude title compound (16.5 g, 100%) as a green solid. LCMS (ES+): 154.5 [MH]+.

Intermediate 38

6-chloro-N-(cyclopropylmethyl)pyridine-2-carboxamide

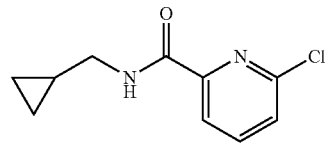 [SMILES: O=C(NCC1CC1)c1cccc(Cl)n1]

6-Chloropyridine-2-carboxylic acid (5.00 g, 31.7 mmol) was dissolved in DCM (100 mL) and DMF (0.5 mL) and oxalyl chloride (6.54 mL, 76.2 mmol) were added dropwise. The reaction mixture was stirred for 2 h, concentrated in vacuo and azeotroped with DCM. The residue was dissolved in DCM (100 mL), DIPEA (22.6 mL, 127 mmol) and aminomethylcyclopropane (5.51 mL, 63.5 mmol) were added dropwise and the reaction mixture was stirred for 4 h. The reaction mixture was washed with sat aq NaHCO$_3$ solution (250 mL), dried (MgSO$_4$) and concentrated in vacuo to give the crude title compound (6.50 g, 97%) as a light brown gum. LCMS (ES+): 211.2 [MH]+.

Intermediates 39-44

Intermediates 39-44 were prepared similarly to Intermediate 38; see Table 4 below.

TABLE 4

Preparation of 6-chloro-pyridine-2-carboxamide intermediates

| Int | R³\N\R⁴ | Crude yield | LCMS (ES+) | Intermediate Name |
|---|---|---|---|---|
| 39 | (pyridin-4-yl-NH) | 37% | 234.2 [MH]+ | 6-Chloro-N-(pyridin-4-yl)pyridine-2-carboxamide |
| 40 | (2-methylpyridin-4-yl-NH) | 100% | 248.0 [MH]+ | 6-Chloro-N-(2-methylpyridin-4-yl)pyridine-2-carboxamide |
| 41 | (3-methylpyridin-4-yl-NH) | 96% | 248.2 [MH]+ | 6-Chloro-N-(3-methylpyridin-4-yl)pyridine-2-carboxamide |
| 42 | (2,6-dimethylpyridin-4-yl-NH) | 46% | 262.1 [MH]+ | 6-Chloro-N-(2,6-dimethylpyridin-4-yl)pyridine-2-carboxamide |
| 43 | (pyridin-3-ylmethyl-NH) | 94% | 248.3 [MH]+ | 6-Chloro-N-(pyridin-3-ylmethyl)pyridine-2-carboxamide |
| 44 | (1,3-thiazol-2-ylmethyl-NH) | 71% | 254.2 [MH]+ | 6-Chloro-N-(1,3-thiazol-2-ylmethyl)pyridine-2-carboxamide |

Intermediate 45

6-Chloropyridine-2-carboxamide

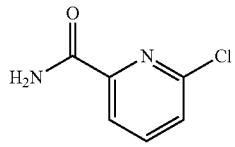

6-Chloropyridine-2-carboxylic acid (1.20 g, 7.62 mmol) and ammonium chloride (0.81 g, 15.2 mmol) were dissolved in DMF (20 mL) and DIPEA (5.31 mL, 30.5 mmol), HONB (2.05 g, 11.4 mmol) and HBTU (4.33 g, 11.4 mmol) were added. The reaction mixture was stirred for 1 h and the solvents were removed in vacuo. The residue was partitioned between DCM (50 mL) and 1 M aq HCl (50 mL) and the aq fraction was extracted with DCM (2×25 mL). The combined organic fractions were washed with sat aq $NaHCO_3$ (50 mL), brine (50 mL), dried ($MgSO_4$) and concentrated in vacuo. The residue was recrystallised from MeOH/water to give the title compound (1.12 g, 94%) as a white solid. LCMS ($ES^+$): 157.4 $[MH]^+$.

Intermediate 46

6-Chloro-N-(4-oxohexan-3-yl)pyridine-2-carboxamide

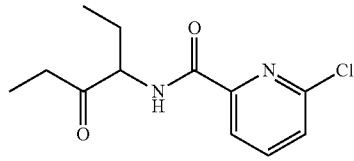 [SMILES: CCC(=O)C(CC)NC(=O)c1cccc(Cl)n1]

Intermediate 46 was prepared similarly to Intermediate 45, using Intermediate 35 instead of ammonium chloride, to give the crude title compound (33%) as an orange oil. LCMS ($ES^+$): 255.1 $[MH]^+$.

Intermediate 47

N-Butyl-6-chloropyridine-2-carboxamide

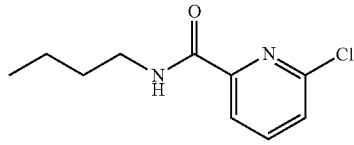

6-Chloro-pyridine-2-carboxylic acid (500 mg, 3.17 mmol), EDC.HCl (1.34 g, 6.98 mmol) and HOBN (1.42 g, 7.93 mmol) were dissolved in DCM (30 mL) and NEM (914 mg, 7.93 mmol) and n-butylamine (376 µL, 3.81 mmol) were added. The reaction mixture was stirred for 16 h, washed with sat aq $NaHCO_3$ (2×20 mL), 1 M aq HCl (2×20 mL), brine (20 mL), dried ($MgSO_4$) and concentrated in vacuo. The residue was purified by column chromatography to give the title compound (321 mg, 48%) as a colourless liquid. LCMS ($ES^+$): 213.5 $[MH]^+$.

Intermediate 48

6-Chloro-N-ethylpyridine-2-carboxamide

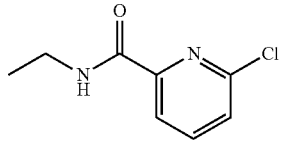

Intermediate 48 was prepared similarly to Intermediate 47, using ethylamine instead of n-butylamine to give the crude title compound (45%) as a colourless liquid. LCMS ($ES^+$): 185.5 $[MH]^+$.

Intermediate 49

6-Chloro-N-[3-(1H-imidazol-1-yl)propyl]pyridine-2-carboxamide

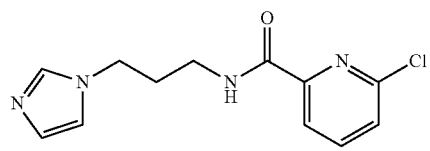 [SMILES: O=C(NCCCn1ccnc1)c1cccc(Cl)n1]

6-Chloro-pyridine-2-carboxylic acid (1.00 g, 6.35 mmol) was dissolved in DCM (20 mL) and HOBt (1.03 g, 7.62 mmol), EDC.HCl (1.46 g, 7.62 mmol) and 1-(3-aminopropyl)imidazole (0.95 g, 7.62 mmol) were added. The reaction mixture was stirred for 18 h, diluted with DCM (130 mL) washed with sat aq $Na_2CO_3$ (100 mL), brine (30 mL), water (30 mL), dried ($MgSO_4$) and concentrated in vacuo. The residue was triturated with water to give the crude title compound (1.05 g, 63%) as an off-white solid. LCMS ($ES^+$): 266 $[MH]^+$.

Intermediate 50

2-(6-Chloropyridin-2-yl)-1-methyl-1H-indole

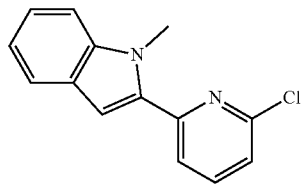 [SMILES: Cn1c(-c2cccc(Cl)n2)cc2ccccc21]

2-Chloro-6-iodopyridine (400 mg, 1.67 mmol), N-methylindole-2-boronic acid (292 mg, 1.67 mmol), tetrakis(triphenylphosphine)palladium (0) (154 mg, 0.13 mmol) and $Na_2CO_3$ (442 mg, 4.18 mmol) were dissolved in water (10 mL) and dioxane (10 mL) and heated using a microwave (110° C., absorption high) for 1 h. The solvents were removed in vacuo and the residue was partitioned between DCM (50 mL) and water (30 mL). The aq fraction was extracted with DCM (30 mL) and the combined organic fractions were dried ($MgSO_4$) and concentrated in vacuo to give the crude title compound (406 mg) as a brown gum. LCMS ($ES^+$): 243.2 $[MH]^+$.

Intermediates 51-60

Intermediates 51-60 were prepared similarly to Intermediate 50; see Table 5 below.

TABLE 5

Suzuki reactions with 2-Chloro-6-iodopyridine

| Int | R¹ | Crude yield | LCMS (ES⁺) | Intermediate Name |
|---|---|---|---|---|
| 51 | (1H-pyrrolo[3,2-b]pyridin-2-yl, NBoc) | 62% | 330.3 [MH]⁺ | tert-Butyl 2-(6-chloropyridin-2-yl)-1H-pyrrolo[3,2-b]pyridine-1-carboxylate |
| 52 | (1H-pyrrolo[3,2-c]pyridin-2-yl, NBoc) | 100% | 330.3 [MH]⁺ | tert-Butyl 2-(6-chloropyridin-2-yl)-1H-pyrrolo[3,2-c]pyridine-1-carboxylate |
| 53 | (1H-pyrrolo[2,3-c]pyridin-2-yl, NBoc) | 60% | 330.3 [MH]⁺ | tert-Butyl 2-(6-chloropyridin-2-yl)-1H-pyrrolo[2,3-c]pyridine-1-carboxylate |
| 54 | (1H-pyrrolo[2,3-b]pyridin-2-yl, NBoc) | 90% | 330.3 [MH]⁺ | tert-Butyl 2-(6-chloropyridin-2-yl)-1H-pyrrolo[2,3-b]pyridine-1-carboxylate |
| 55 | (1H-indol-2-yl, NBoc) | 67% | 329.0 [MH]⁺ | tert-Butyl 2-(6-chloropyridin-2-yl)-1H-indole-1-carboxylate |
| 56 | (1-(benzenesulfonyl)-1H-pyrrolo[2,3-b]pyridin-3-yl) | 39%* | 370.2 [MH]⁺ | 2-[1-(Benzenesulfonyl)-1H-pyrrolo[2,3-b]pyridin-3-yl]-6-chloropyridine |
| 57 | (1H-indol-3-yl, Boc N) | 78% | 329.0 [MH]⁺ | tert-Butyl 3-(6-chloropyridin-2-yl)-1H-indole-1-carboxylate |
| 58 | (6-cyano-1H-indol-2-yl, NC, NBoc) | 100% | 355.2 [MH]⁺ | tert-Butyl 2-(6-chloropyridin-2-yl)-6-cyano-1H-indole-1-carboxylate |

TABLE 5-continued

Suzuki reactions with 2-Chloro-6-iodopyridine

| Int | R¹ | Crude yield | LCMS (ES⁺) | Intermediate Name |
|---|---|---|---|---|
| 59 | —O— (indole-NBoc, 6-linked) | 100% | 359.1 [MH]⁺ | tert-Butyl 2-(6-chloropyridin-2-yl)-6-methoxy-1H-indole-1-carboxylate |
| 60 | —O— (indole-NBoc, 5-linked) | 100% | 359.4 [MH]⁺ | tert-Butyl 2-(6-chloropyridin-2-yl)-5-methoxy-1H-indole-1-carboxylate |

*Used the corresponding pinacol boronic ester derivative instead of the boronic acid

Intermediate 61

6-Chloropyridine-2-carboximidamide

2-Chloro-6-cyanopyridine (11.2 g, 80.8 mmol) was dissolved in EtOH (200 mL), HCl gas was passed through the solution for 5 min and the reaction mixture was stirred for 18 h. The solvent was removed in vacuo and the residue was dissolved in a 7 M solution of ammonia in MeOH (100 mL) and stirred for 3 d. The solvent was removed in vacuo and the residue triturated with EtOAc (3×50 mL) to give the crude title compound as a pale pink solid (12.3 g, 98%). LCMS (ES⁺): 156.2 [MH]⁺.

Intermediate 62

2-Chloro-6-(5-methyl-1H-imidazol-2-yl)pyridine

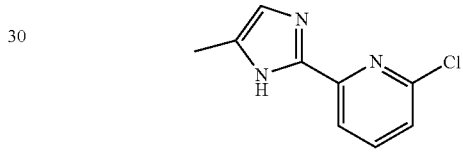

Intermediate 61 (500 mg, 3.21 mmol), bromoacetone (296 μL, 3.53 mmol) and K₂CO₃ (444 mg, 3.21 mmol) were dissolved in EtOH (10 mL) and heated at reflux for 2 h. Further bromoacetone (148 μL, 1.77 mmol) was added and the reaction mixture was heated at reflux for 4 h. The solvents were removed in vacuo and the residue was dissolved in 1 M aq Na₂CO₃ (50 mL) and extracted with EtOAc (3×50 mL). The combined organic fractions were dried (MgSO₄) and concentrated in vacuo. The residue was purified by column chromatography to give the title compound (420 mg, 68%) as an orange gum. LCMS (ES⁺): 194.1 [MH]⁺.

Intermediates 63-74

Intermediates 63-74 were prepared similarly to Intermediate 62 using the appropriate alpha-bromoketone intermediate; see Table 6 below.

TABLE 6

Preparation of imidazoles from Intermediate 61

| Int | R¹ | SM | Crude yield | LCMS (ES⁺) | Intermediate Name |
|---|---|---|---|---|---|
| 63 | ethyl-imidazole | * | 32% | — | 2-Chloro-6-(5-ethyl-1H-imidazol-2-yl)pyridine |

TABLE 6-continued

Preparation of imidazoles from Intermediate 61

| Int | R¹ | SM | Crude yield | LCMS (ES⁺) | Intermediate Name |
|---|---|---|---|---|---|
| 64 | 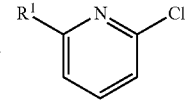 | Int 26 | 77% | 222.2 [MH]⁺ | 2-Chloro-6-(5-propyl-1H-imidazol-2-yl)pyridine |
| 65 | 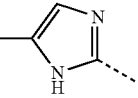 | Int 27 | 73% | 222.1 [MH]⁺ | 2-Chloro-6-[5-(propan-2-yl)-1H-imidazol-2-yl]pyridine |
| 66 | 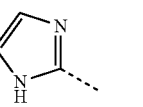 | Int 28 | 88% | 220.2 [MH]⁺ | 2-Chloro-6-(5-cyclopropyl-1H-imidazol-2-yl)pyridine |
| 67 | 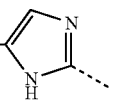 | * | 27% | 248.1 [MH]⁺ | 2-Chloro-6-[5-(trifluoromethyl)-1H-imidazol-2-yl]pyridine |
| 68 | 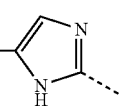 | * | 54% | 236.2 [MH]⁺ | 2-(5-Tert-butyl-1H-imidazol-2-yl)-6-chloropyridine |
| 69 | 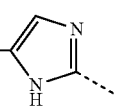 | * | 25% | 256.2 [MH]⁺ | 2-Chloro-6-(5-phenyl-1H-imidazol-2-yl)pyridine |
| 70 | 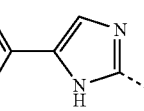 | Int 29 | 50% | 208.1 [MH]⁺ | 2-Chloro-6-(4,5-dimethyl-1H-imidazol-2-yl)pyridine |
| 71 | 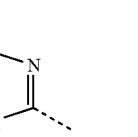 | Int 30 | 42% | 222.2 [MH]⁺ | 2-Chloro-6-(5-ethyl-4-methyl-1H-imidazol-2-yl)pyridine |
| 72 | 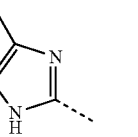 | Int 31 | 13% | 234.1 [MH]⁺ | 2-Chloro-6-(5-cyclopropyl-4-methyl-1H-imidazol-2-yl)pyridine |
| 73 | 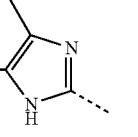 | Int 32 | 15% | 248.1 [MH]⁺ | 2-Chloro-6-(5-cyclopropyl-4-ethyl-1H-imidazol-2-yl)pyridine |

TABLE 6-continued

Preparation of imidazoles from Intermediate 61

| Int | R¹ | SM | Crude yield | LCMS (ES⁺) | Intermediate Name |
|---|---|---|---|---|---|
| 74 | (4-methyl-5-propyl-imidazolyl) | Int 33 | 45% | 236.1 [MH]⁺ | 2-Chloro-6-(4-methyl-5-propyl-1H-imidazol-2-yl)pyridine |

* Commercially available

Intermediate 75

2-Chloro-6-(4,5-diethyl-1H-imidazol-2-yl)pyridine

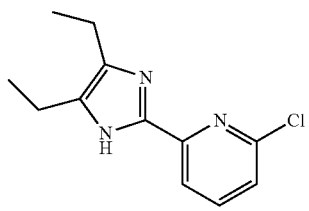 [SMILES: CCc1nc(-c2cccc(Cl)n2)[nH]c1CC]

Intermediate 46 (1.81 g, 7.11 mmol) and ammonium acetate (274 mg, 3.55 mmol) were dissolved in 7 M ammonia in methanol (15 mL) and heated using a microwave at 100° C. for 30 min and at 120° C. for 30 min. Further ammonium acetate (1.00 g, 13.0 mmol) was added and the reaction mixture was heated using a microwave at 120° C. for 2 h, poured into water (100 mL) and extracted with DCM (3×100 mL). The combined organic fractions were dried (MgSO₄) and concentrated in vacuo. The residue was purified by column chromatography to give the title compound (1.54 g, 92%) as a yellow oil. LCMS (ES⁺): 236.1 [MH]⁺.

Intermediate 76

2-Chloro-6-(4-ethyl-1-methyl-1H-imidazol-2-yl)pyridine

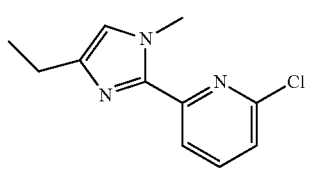

Intermediate 63 (203 mg, 0.98 mmol) and NaH (47.0 mg, 60% dispersion in mineral oil, 1.17 mmol) were dissolved in THF (10 mL), iodomethane (67.0 µL, 1.08 mmol) was added and the reaction mixture was stirred for 2 h, poured into water (25 mL) and extracted with EtOAc (3×25 mL). The combined organic fractions were dried (MgSO₄) and concentrated in vacuo to give the crude title compound as a pale yellow oil (212 mg, 98%). LCMS (ES⁺): 222.2 [MH]⁺.

Intermediate 77

2-Chloro-6-{1H-imidazo[4,5-c]pyridin-2-yl}pyridine

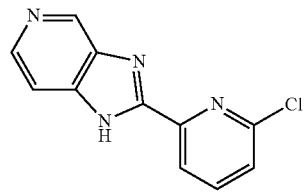 [SMILES: Clc1cccc(-c2nc3cnccc3[nH]2)n1]

6-Chloropyridine-2-carboxylic acid (2.00 g, 12.7 mmol), 3,4-diaminopyridine (1.52 g, 14.0 mmol) and DIPEA (2.43 mL, 14.0 mmol) were dissolved in DMF (20 mL) and HBTU (5.29 g, 14.0 mmol) was added. The reaction mixture was stirred for 48 h and concentrated in vacuo. The residue was dissolved in EtOAc (100 mL), washed with 1 M aq Na₂CO₃ (2×100 mL), water (100 mL), dried (MgSO₄) and concentrated in vacuo. The residue was purified by column chromatography, dissolved in AcOH and heated at 120° C. for 50 min. The solvent was removed in vacuo and the residue was suspended in 1 M aq Na₂CO₃ (50 mL) and extracted with EtOAc (5×50 mL). The combined organic fractions were dried (MgSO₄) and concentrated in vacuo. The residue was purified by column chromatography and recrystallisation from MeOH to give the title compound (534 mg, 37%) as a white solid.

Intermediate 78 tert-Butyl 6-(1,4-diazepan-1-yl)pyridine-2-carboxylate

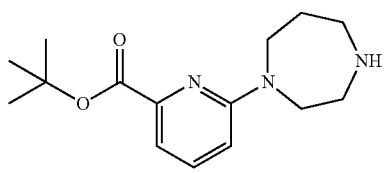 [SMILES: CC(C)(C)OC(=O)c1cccc(N2CCCNCC2)n1]

Intermediate 36 (3.00 g, 14.0 mmol) was dissolved in DMA (60 mL) and homopiperazine (7.03 g, 70.2 mmol) was added. The reaction mixture was heated using a microwave (180° C., absorption high) for 35 min and the solvents were removed in vacuo. The residue was dissolved in DCM (150 mL) and washed with sat aq $Na_2CO_3$ (100 mL), brine (100 mL), dried ($MgSO_4$) and the solvents were removed in vacuo to give the crude title compound (3.37 g, 87%) as a yellow liquid. LCMS ($ES^+$): 278.1 $[MH]^+$.

Intermediates 79-118

Intermediates 79-118 were prepared similarly to Intermediate 78, by reacting 6-chloro-2-substituted pyridines with homopiperazine; see Table 7 below.

TABLE 7

Preparation of 6-(1,4-diazepany-1-yl)-2-substituted pyridine intermediates

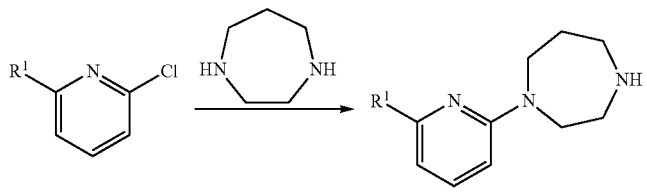

| Int | $R^1$ | SM | Crude yield | LCMS ($ES^+$) | Intermediate Name |
|---|---|---|---|---|---|
| 79 | H₂N-C(=O)- | Int 45 | — | 221.2 $[MH]^+$ | 6-(1,4-Diazepan-1-yl)pyridine-2-carboxamide |
| 80 | Et-NH-C(=O)- | Int 48 | 66% | 249.6 $[MH]^+$ | 6-(1,4-Diazepan-1-yl)-N-ethylpyridine-2-carboxamide |
| 81 | cyclopropylmethyl-NH-C(=O)- | Int 38 | 87% | 275.4 $[MH]^+$ | N-(Cyclopropylmethyl)-6-(1,4-diazepan-1-yl)pyridine-2-carboxamide |
| 82 | n-Bu-NH-C(=O)- | Int 47 | 63% | 277.7 $[MH]^+$ | N-Butyl-6-(1,4-diazepan-1-yl)pyridine-2-carboxamide |
| 83 | pyridin-4-yl-NH-C(=O)- | Int 39 | 90% | 298.2 $[MH]^+$ | 6-(1,4-Diazepan-1-yl)-N-(pyridin-4-yl)pyridine-2-carboxamide |
| 84 | (2-methylpyridin-4-yl)-NH-C(=O)- | Int 40 | 78% | 312.2 $[MH]^+$ | 6-(1,4-Diazepan-1-yl)-N-(2-methylpyridin-4-yl)pyridine-2-carboxamide |
| 85 | (3-methylpyridin-4-yl)-NH-C(=O)- | Int 41 | — | 312.2 $[MH]^+$ | 6-(1,4-Diazepan-1-yl)-N-(3-methylpyridin-4-yl)pyridine-2-carboxamide |

TABLE 7-continued

Preparation of 6-(1,4-diazepany-1-yl)-2-substituted pyridine intermediates

| Int | R¹ | SM | Crude yield | LCMS (ES⁺) | Intermediate Name |
|---|---|---|---|---|---|
| 86 | 2,6-dimethylpyridin-4-yl carboxamide group | Int 42 | 70% | 326.3 [MH]⁺ | 6-(1,4-Diazepan-1-yl)-N-(2,6-dimethylpyridin-4-yl)pyridine-2-carboxamide |
| 87 | pyridin-3-ylmethyl carboxamide | Int 43 | 80% | 312.4 [MH]⁺ | 6-(1,4-Diazepan-1-yl)-N-(pyridin-3-ylmethyl)pyridine-2-carboxamide |
| 88 | 1,3-thiazol-2-ylmethyl carboxamide | Int 44 | — | 318.3 [MH]⁺ | 6-(1,4-Diazepan-1-yl)-N-(1,3-thiazol-2-ylmethyl)pyridine-2-carboxamide |
| 89 | 3-(1H-imidazol-1-yl)propyl carboxamide | Int 49 | 76% | — | 6-(1,4-Diazepan-1-yl)-N-[3-(1H-imidazol-1-yl)propyl]pyridine-2-carboxamide |
| 90 | 1-methyl-1H-indol-2-yl | Int 50 | — | 307.2 [MH]⁺ | 2-[6-(1,4-Diazepan-1-yl)pyridin-2-yl]-1-methyl-1H-indole |
| 91 | 1H-pyrrolo[3,2-b]pyridin-2-yl | Int 51* | — | 294.4 [MH]⁺ | 1-(6-{1H-Pyrrolo[3,2-b]pyridin-2-yl}pyridin-2-yl)-1,4-diazepane |
| 92 | 1H-pyrrolo[3,2-c]pyridin-2-yl | Int 52* | 90% | 294.4 [MH]⁺ | 1-(6-{1H-Pyrrolo[3,2-c]pyridin-2-yl}pyridin-2-yl)-1,4-diazepane |
| 93 | 1H-pyrrolo[2,3-c]pyridin-2-yl | Int 53* | — | 294.4 [MH]⁺ | 1-(6-{1H-Pyrrolo[2,3-c]pyridin-2-yl}pyridin-2-yl)-1,4-diazepane |
| 94 | 1H-pyrrolo[2,3-b]pyridin-2-yl | Int 54* | — | 294.4 [MH]⁺ | 1-(6-{1H-Pyrrolo[2,3-b]pyridin-2-yl}pyridin-2-yl)-1,4-diazepane |

TABLE 7-continued

Preparation of 6-(1,4-diazepany-1-yl)-2-substituted pyridine intermediates

| Int | R¹ | SM | Crude yield | LCMS (ES+) | Intermediate Name |
|---|---|---|---|---|---|
| 95 | 2-indolyl (NH) | Int 55* | — | 293.1 [MH]+ | 2-[6-(1,4-Diazepan-1-yl)pyridin-2-yl]-1H-indole |
| 96 | 1H-pyrrolo[2,3-b]pyridin-3-yl | Int 56* | — | 294.4 [MH]+ | 1-(6-{1H-Pyrrolo[2,3-b]pyridin-3-yl}pyridin-2-yl)-1,4-diazepane |
| 97 | 3-indolyl | Int 57* | 90% | 293.1 [MH]+ | 3-[6-(1,4-Diazepan-1-yl)pyridin-2-yl]-1H-indole |
| 98 | 6-cyano-2-indolyl | Int 58* | — | 318.2 [MH]+ | 2-[6-(1,4-Diazepan-1-yl)pyridin-2-yl]-1H-indole-6-carbonitrile |
| 99 | 6-methoxy-2-indolyl | Int 59* | — | 323.2 [MH]+ | 2-[6-(1,4-Diazepan-1-yl)pyridin-2-yl]-6-methoxy-1H-indole |
| 100 | 5-methoxy-2-indolyl | Int 60* | — | 323.4 [MH]+ | 2-[6-(1,4-Diazepan-1-yl)pyridin-2-yl]-5-methoxy-1H-indole |
| 101 | 5-methyl-1H-imidazol-2-yl | Int 62 | — | 258.3 [MH]+ | 1-[6-(5-Methyl-1H-imidazol-2-yl)pyridin-2-yl]-1,4-diazepane |
| 102 | 1H-imidazo[4,5-c]pyridin-2-yl | Int 77 | 74% | 295.2 [MH]+ | 1-(6-{1H-Imidazo[4,5-c]pyridin-2-yl}pyridin-2-yl)-1,4-diazepane |
| 103 | 5-ethyl-1H-imidazol-2-yl | Int 63 | 26% | 272 [MH]+ | 1-[6-(5-Ethyl-1H-imidazol-2-yl)pyridin-2-yl]-1,4-diazepane |

TABLE 7-continued

Preparation of 6-(1,4-diazepany-1-yl)-2-substituted pyridine intermediates

| Int | R¹ | SM | Crude yield | LCMS (ES⁺) | Intermediate Name |
|---|---|---|---|---|---|
| 104 | 5-propyl-1H-imidazol-2-yl | Int 64 | — | 286.3 [MH]⁺ | 1-[6-(5-Propyl-1H-imidazol-2-yl)pyridin-2-yl]-1,4-diazepane |
| 105 | 5-(propan-2-yl)-1H-imidazol-2-yl | Int 65 | — | 286.3 [MH]⁺ | 1-{6-[5-(Propan-2-yl)-1H-imidazol-2-yl]pyridin-2-yl}-1,4-diazepane |
| 106 | 5-cyclopropyl-1H-imidazol-2-yl | Int 66 | — | 284.2 [MH]⁺ | 1-[6-(5-Cyclopropyl-1H-imidazol-2-yl)pyridin-2-yl]-1,4-diazepane |
| 107 | 5-(trifluoromethyl)-1H-imidazol-2-yl | Int 67 | 61% | 312.3 [MH]⁺ | 1-{6-[5-(Trifluoromethyl)-1H-imidazol-2-yl]pyridin-2-yl}-1,4-diazepane |
| 108 | 5-tert-butyl-1H-imidazol-2-yl | Int 68 | — | 300.3 [MH]⁺ | 1-[6-(5-tert-Butyl-1H-imidazol-2-yl)pyridin-2-yl]-1,4-diazepane |
| 109 | 5-phenyl-1H-imidazol-2-yl | Int 69 | — | 320.3 [MH]⁺ | 1-[6-(5-Phenyl-1H-imidazol-2-yl)pyridin-2-yl]-1,4-diazepane |
| 110 | 4,5-dimethyl-1H-imidazol-2-yl | Int 70 | — | 272.2 [MH]⁺ | 1-[6-(4,5-Dimethyl-1H-imidazol-2-yl)pyridin-2-yl]-1,4-diazepane |
| 111 | 5-ethyl-4-methyl-1H-imidazol-2-yl | Int 71 | — | 286.3 [MH]⁺ | 1-[6-(5-Ethyl-4-methyl-1H-imidazol-2-yl)pyridin-2-yl]-1,4-diazepane |
| 112 | 4,5-diethyl-1H-imidazol-2-yl | Int 75 | — | 300.3 [MH]⁺ | 1-[6-(4,5-Dimethyl-1H-imidazol-2-yl)pyridin-2-yl]-1,4-diazepane |
| 113 | 5-cyclopropyl-4-methyl-1H-imidazol-2-yl | Int 72 | 83% | 298.2 [MH]⁺ | 1-[6-(5-Cyclopropyl-4-methyl-1H-imidazol-2-yl)pyridin-2-yl]-1,4-diazepane |

TABLE 7-continued

Preparation of 6-(1,4-diazepany-1-yl)-2-substituted pyridine intermediates

| Int | R¹ | SM | Crude yield | LCMS (ES⁺) | Intermediate Name |
|---|---|---|---|---|---|
| 114 | (5-cyclopropyl-4-ethyl-1H-imidazol-2-yl) | Int 73 | 73% | 312.3 [MH]⁺ | 1-[6-(5-Cyclopropyl-4-ethyl-1H-imidazol-2-yl)pyridin-2-yl]-1,4-diazepane |
| 115 | (4-methyl-5-propyl-1H-imidazol-2-yl) | Int 74 | — | 300.2 [MH]⁺ | 1-[6-(4-Methyl-5-propyl-1H-imidazol-2-yl)pyridin-2-yl]-1,4-diazepane |
| 116 | N≡C— | # | 58% | 203.1 [MH]⁺ | 6-(1,4-Diazepan-1-yl)pyridine-2-carbonitrile |
| 117 | (4-ethyl-1-methyl-1H-imidazol-2-yl) | Int 76 | — | 286.2 [MH]⁺ | 1-[6-(4-Ethyl-1-methyl-1H-imidazol-2-yl)pyridin-2-yl]-1,4-diazepane |
| 118 | methoxycarbonyl | Int 37 | 46% | 236.6 [MH]⁺ | Methyl 6-(1,4-diazepan-1-yl)pyridine-2-carboxylate |

\* The Boc/benzenesulfonyl protecting group is removed during the course of this reaction
\# Commercially available

Intermediate 119

N-(Cyclopropylmethyl)-6-[4-(piperidin-4-yl)-1,4-diazepan-1-yl]pyridine-2-carboxamide

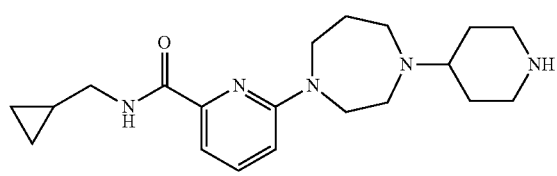 [SMILES: O=C(NCC1CC1)c1cccc(N2CCCN(C3CCNCC3)CC2)n1]

Intermediate 81 (1.50 g, 5.50 mmol) and 4-oxo-piperidine-1-carboxylic acid tert butylester (1.09 g, 5.50 mmol) were dissolved in DCM (30 mL) and NaBH(OAc)₃ (5.79 g, 27.3 mmol) was added. The reaction mixture was stirred for 4 d, diluted with DCM (150 mL), washed with sat aq Na₂CO₃ (2×75 mL), brine (75 mL) and dried (MgSO₄). The reaction mixture was stirred with isocyanate resin for 2 h and the solvents were removed in vacuo. The residue was dissolved in DCM (40 mL), TFA (4 mL) was added and the reaction mixture was stirred for 18 h. The solvents were removed in vacuo and the residue was desalted (K₂CO₃ in DCM) and purified by column chromatography to give the title compound (600 mg, 31%) as a colourless gum. LCMS (ES⁺): 357.8 [MH]⁺.

Intermediates 120-124

Intermediates 120-124 were prepared similarly to Intermediate 119, by reacting 6-(1,4-diazepany-1-yl)-2-substituted pyridines with 4-oxo-piperidine-1-carboxylic acid tert butylester and removing the Boc protecting group; see Table 8 below.

TABLE 8

Preparation of 6-[4-(piperidin-4-yl)-1,4-diazepan-1-yl]-2-substituted pyridine intermediates

| Int | R¹ | SM | Yield | LCMS (ES⁺) | Intermediate Name |
|---|---|---|---|---|---|
| 120 | (carboxamide H₂N-C(O)-) | Int 79 | 33% | 304.2 [MH]⁺ | 6-[4-(Piperidin-4-yl)-1,4-diazepan-1-yl]pyridine-2-carboxamide |
| 121 | (N-ethyl carboxamide) | Int 80 | — | — | N-Ethyl-6-[4-(piperidin-4-yl)-1,4-diazepan-1-yl]pyridine-2-carboxamide |
| 122 | (N-butyl carboxamide) | Int 82 | — | — | N-Butyl-6-[4-(piperidin-4-yl)-1,4-diazepan-1-yl]pyridine-2-carboxamide |
| 123 | (N-[3-(imidazol-1-yl)propyl] carboxamide) | Int 89 | 38% | — | N-[3-(1H-Imidazol-1-yl)propyl]-6-[4-(piperidin-4-yl)-1,4-diazepan-1-yl]pyridine-2-carboxamide |
| 124 | (methyl ester) | Int 118 | 33% | 319.7 [MH]⁺ | Methyl 6-[4-(piperidin-4-yl)-1,4-diazepan-1-yl]pyridine-2-carboxylate |

Intermediate 125

6-[4-(3-Fluoropiperidin-4-yl)-1,4-diazepan-1-yl]-N-(pyridin-4-yl)pyridine-2-carboxamide

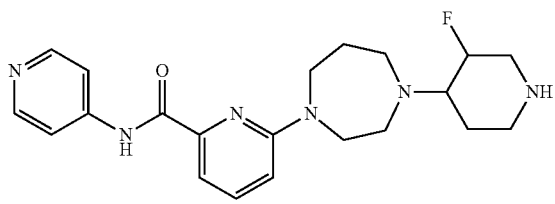 [SMILES: O=C(Nc1ccncc1)c1cccc(N2CCCN(C3CCNCC3F)CC2)n1]

Intermediate 125 was prepared similarly to Intermediate 119, using Intermediate 83 instead of Intermediate 81 and tert-butyl 3-fluoro-4-oxopiperidine-1-carboxylate instead of 4-oxo-piperidine-1-carboxylic acid tert butylester, to give the title compound (9%) as a colourless gum. LCMS (ES⁺): 399.4 [MH]⁺.

Intermediate 126

1-[6-(5-Cyclopropyl-1H-imidazol-2-yl)pyridin-2-yl]-4-(3-fluoropiperidin-4-yl)-1,4-diazepane

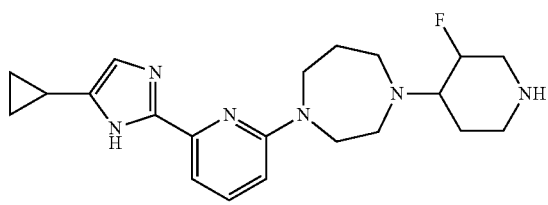 [SMILES: FC1CNCCC1N1CCCN(c2cccc(-c3ncc(C4CC4)[nH]3)n2)CC1]

Intermediate 126 was prepared similarly to Intermediate 119, using Intermediate 106 instead of Intermediate 81 and tert-butyl 3-fluoro-4-oxopiperidine-1-carboxylate instead of 4-oxo-piperidine-1-carboxylic acid tert butylester, to give the title compound (1%) as a pale yellow solid.

Intermediate 127

6-[4-(2-Methylpiperidin-4-yl)-1,4-diazepan-1-yl]-N-(pyridin-3-ylmethyl)pyridine-2-carboxamide Intermediate 127 was prepared similarly to Intermediate 119, using Intermediate 87 instead of Intermediate 81 and tert-butyl 2-methyl-4-oxopiperidine-1-carboxylate instead of 4-oxo-piperidine-1-carboxylic acid tert butylester, to give the title compound (49%) as a colourless gum.

Intermediate 128

6-{4-[(3R,4R)-3-Hydroxypiperidin-4-yl]-1,4-diazepan-1-yl}-N-(pyridin-3-ylmethyl)pyridine-2-carboxamide

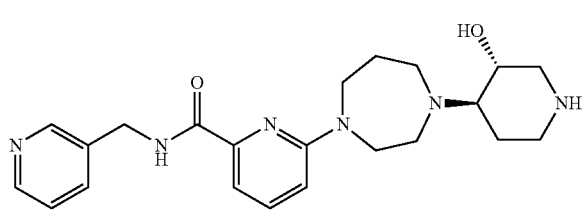 [SMILES: O=C(NCc1cccnc1)c1cccc(N2CCCN([C@@H]3CCNC[C@H]3O)CC2)n1]

Intermediate 87 (2.00 g, 7.29 mmol) was dissolved in EtOH (30 mL) and tert-butyl 7-oxa-3-azabicyclo[4.1.0]heptane-3-carboxylate (4.36 g, 21.9 mmol) and Et$_3$N (2.03 mL, 14.6 mmol) were added. The reaction mixture was heated at reflux for 20 h, diluted with DCM (200 mL), washed with sat aq Na$_2$CO$_3$ (100 mL), dried (MgSO$_4$) and concentrated in vacuo. The residue was purified by column chromatography and reverse phase HPLC. The residue was dissolved in DCM (2 mL), TFA (0.5 mL) was added and the reaction mixture was stirred for 5 h. The solvents were removed in vacuo and the residue was dissolved in DCM (50 mL), washed with sat aq Na$_2$CO$_3$ (25 mL), dried (MgSO$_4$) and concentrated in vacuo to give the crude title compound.

Intermediate 129 tert-Butyl 6-{4-[1-(propan-2-yl)piperidin-4-yl]-1,4-diazepan-1-yl}pyridine-2-carboxylate

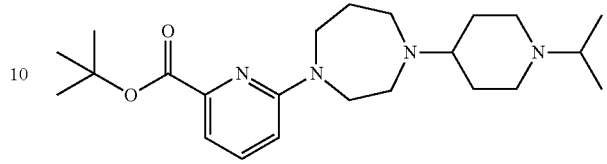

Intermediate 78 (3.37 g, 12.2 mmol) was dissolved in DCM (125 mL) and 1-(propan-2-yl)piperidin-4-one (3.61 mL, 24.3 mmol) and NaBH(OAc)$_3$ (12.9 g, 60.8 mmol) were added. The reaction mixture was stirred for 18 h, diluted with DCM (250 mL) and quenched with sat aq Na$_2$CO$_3$ (150 mL). The aq fraction was extracted with DCM (2×100 mL) and the combined organic fractions were dried (MgSO$_4$) and concentrated in vacuo. The residue was purified by column chromatography to give the title compound (3.29 g, 67%) as a yellow liquid. LCMS (ES$^+$): 403.5 [MH]$^+$.

Intermediates 130-133

Intermediates 130-133 were prepared similarly to Intermediate 129, by reductive alkylation of 6-(1,4-diazepany-1-yl)-2-substituted pyridines; see Table 9 below.

TABLE 9

Reductive alkylation of 6-(1,4-diazepany-1-yl)-2-substituted pyridines

| Int | R$^1$ | R$^6$ | SMs/Yield | LCMS (ES$^+$) | Intermediate Name |
|---|---|---|---|---|---|
| 130 | tert-butyloxycarbonyl | 2-chlorobenzyl | Int 25, Int 78, 67% | 403.5 [MH]$^+$ | tert-Butyl 6-(4-{1-[(2-chlorophenyl)methyl]piperidin-4-yl}-1,4-diazepan-1-yl)pyridine-2-carboxylate |
| 131 | N≡ | isopropyl | Int 116, 45% | 328.2 [MH]$^+$ | 6-{4-[1-(Propan-2-yl)piperidin-4-yl]-1,4-diazepan-1-yl}pyridine-2-carbonitrile |
| 132 | N≡ | (2R)-butan-2-yl | Int 8, Int 116, 1% | 342.2 [MH]$^+$ | 6-(4-{1-[(2R)-Butan-2-yl]piperidin-4-yl}-1,4-diazepan-1-yl)pyridine-2-carbonitrile |
| 133 | methoxycarbonyl | 2-chlorobenzyl | Int 25, Int 124, 26% | 443.7 [MH]$^+$ | Methyl 6-(4-{1-[(2-chlorophenyl)methyl]piperidin-4-yl}-1,4-diazepan-1-yl)pyridine-2-carboxylate |

Intermediate 134

6-[4-(4-tert-Butylcyclohexyl)-1,4-diazepan-1-yl]pyridine-2-carboxylic acid

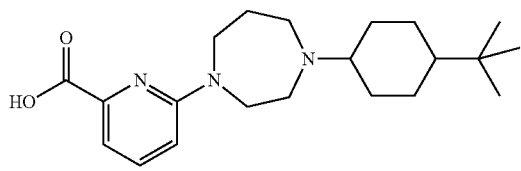 [SMILES: CC(C)(C)C1CCC(N2CCCN(c3cccc(C(=O)O)n3)CC2)CC1]

Intermediate 78 (1.00 g, 3.61 mmol) and 4-tert-butylcyclohexanone (560 mg, 3.61 mmol) were dissolved in DCM (50 mL) and NaBH(OAc)₃ (3.06 g, 14.4 mmol) was added. The reaction mixture was stirred for 3 d, diluted with DCM (150 mL), washed with sat aq Na₂CO₃ (100 mL), brine (75 mL), dried (MgSO₄) and concentrated in vacuo. The residue was dissolved in DCM (75 mL) and TFA (6 mL) and stirred for 8 d. The solvents were removed in vacuo and the residue was purified by reverse phase column chromatography to give the title compound (536 mg, 41%) as a white solid. LCMS (ES⁺): 360.5 [MH]⁺.

Intermediate 135

6-{4-[1-(propan-2-yl)piperidin-4-yl]-1,4-diazepan-1-yl}pyridine-2-carboxylic acid

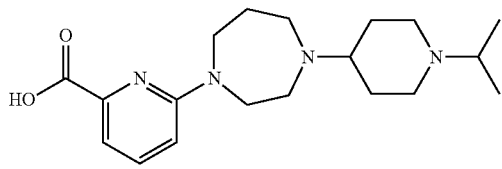 [SMILES: CC(C)N1CCC(N2CCCN(c3cccc(C(=O)O)n3)CC2)CC1]

Intermediate 129 (3.29 g, 8.17 mmol) was dissolved in DCM (80 mL), TFA (40 mL) was added and the reaction mixture was stirred for 18 h. The solvents were removed in vacuo and the residue was neutralised with 1M aq Na₂CO₃. The aq solution was washed with DCM, concentrated in vacuo and purified by reverse phase column chromatography to give the title compound (2.19 g, 77%) as a white solid. LCMS (ES⁺): 347.5 [MH]⁺.

Intermediate 136

6-(4-{1-[(2-Chlorophenyl)methyl]piperidin-4-yl}-1,4-diazepan-1-yl)pyridine-2-carboxylic acid

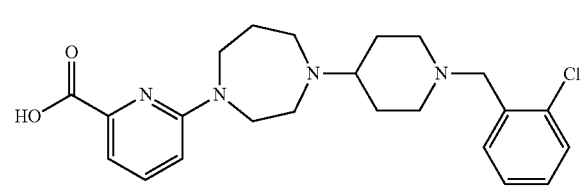 [SMILES: O=C(O)c1cccc(N2CCCN(C3CCN(Cc4ccccc4Cl)CC3)CC2)n1]

Intermediate 136 was prepared similarly to Intermediate 135, using Intermediate 130 instead of Intermediate 129 to give the title compound (77%) as a white solid. LCMS (ES⁺): 347.5 [MH]⁺.

Intermediate 137

N-Hydroxy-6-{4-[1-(propan-2-yl)piperidin-4-yl]-1,4-diazepan-1-yl}pyridine-2-carboximidamide

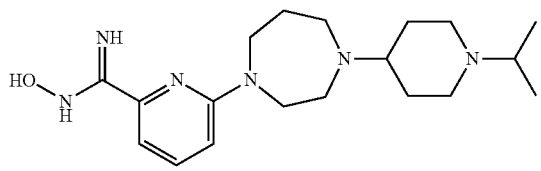 [SMILES: CC(C)N1CCC(N2CCCN(c3cccc(C(=N)NO)n3)CC2)CC1]

Intermediate 131 (830 mg, 2.53 mmol) was dissolved in EtOH (20 mL) and hydroxylamine hydrochloride (880 mg, 12.7 mmol) and NaHCO₃ (1.06 g, 12.7 mmol) were added. The reaction mixture was heated under reflux at 80° C. for 2 h. The reaction mixture was concentrated and the precipitate removed by filtration. The mother liquor was concentrated in vacuo to give the crude title compound (910 mg, 99%) as a light yellow gum. LCMS (ES⁺): 361.1 [MH]⁺.

Intermediate 138

1-[6-(5-Methyl-1,2,4-oxadiazol-3-yl)pyridin-2-yl]-4-[1-(propan-2-yl)piperidin-4-yl]-1,4-diazepane

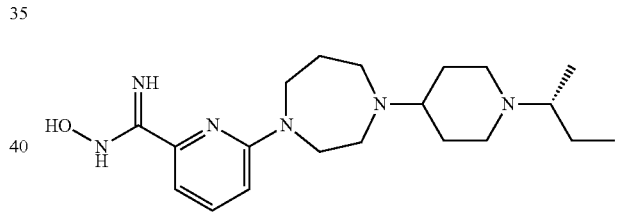

Intermediate 138 was prepared similarly to Intermediate 137, using Intermediate 132 instead of Intermediate 131, to give the crude title compound (65%) as a yellow gum. LCMS (ES⁺): 375.3 [MH]⁺.

Intermediate 139

1-[1-(Propan-2-yl)piperidin-4-yl]-4-[6-(2H-1,2,3,4-tetrazol-5-yl)pyridin-2-yl]-1,4-diazepane

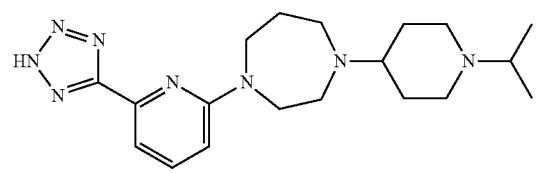 [SMILES: CC(C)N1CCC(N2CCCN(c3cccc(-c4nn[nH]n4)n3)CC2)CC1]

Intermediate 131 (982 mg, 3.00 mmol), NaN₃ (215 mg, 3.30 mmol) and NH₄Cl (250 mg, 4.50 mmol) were dissolved in DMF (5 mL) and heated at 120° C. for 4 h. Further NH₄Cl (125 mg, 2.25 mmol) was added and the reaction mixture was heated at 120° C. for 5.5 h. The solvent was removed in vacuo, NaN₃ (100 mg, 1.53 mmol) was added and the reaction mixture was heated at 120° C. for 7 h. The residue was purified by column chromatography to give the title compound (168 mg, 15%) as a dark red solid.

Intermediate 140 tert-Butyl N-{[methoxy(methyl)carbamoyl]methyl}carbamate

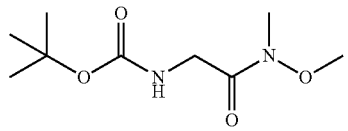

2-{[(tert-Butoxy)carbonyl]amino}acetic acid (5.00 g, 28.5 mmol) was dissolved in DCM (50 mL), CDI (5.09 g, 31.4 mmol) was added and the reaction mixture was stirred for 1 h. N,O-dimethylhydroxylamine hydrochloride (3.06 g, 31.4 mmol) was added and the reaction mixture was stirred for 16 h. EtOAc (150 mL) was added and the reaction mixture was washed with 1 M aq HCl (50 mL), sat aq NaHCO₃ (2×50 mL), dried (Na₂SO₄) and concentrated in vacuo to give the crude title compound (5.13 g, 82%) as a white solid.

Intermediate 141 tert-Butyl N-(2-oxohexyl)carbamate

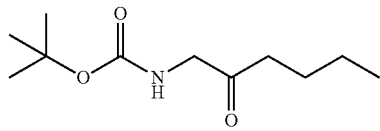

Intermediate 140 (1.09 g, 5.00 mmol) was dissolved in THF (10 mL) at −10° C., n-butylmagnesium chloride (7.50 mL, 2.0 M in THF, 15.0 mmol) was added and the reaction mixture was warmed to room temperature overnight. Sat aq NH₄Cl (60 mL) was added and the reaction mixture was extracted with EtOAc (3×20 mL), dried (MgSO₄) and concentrated in vacuo to give the crude title compound (1.00 g, 93%) as a colourless oil.

Intermediate 142

1-Aminohexan-2-one hydrochloride

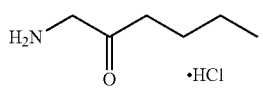

Intermediate 141 (995 mg, 4.62 mmol) was dissolved in HCl (10 mL, 4.0 M in dioxane) and the reaction mixture was stirred for 4 h. The solvents were removed in vacuo to give the crude title compound (653 mg, 94%) as an off-white solid.

Intermediate 143

N-(2-Oxohexyl)-6-{4-[1-(propan-2-yl)piperidin-4-yl]-1,4-diazepan-1-yl}pyridine-2-carboxamide

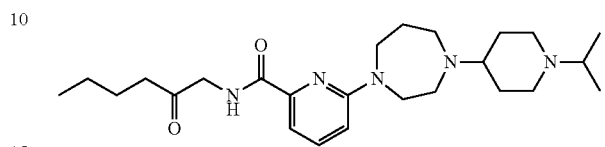

Intermediate 142 (252 mg, 1.66 mmol), Intermediate 135 (1.33 g, 1.66 mmol) and HBTU (760 mg, 1.99 mmol) were dissolved in DCM (7.5 mL) and DMF (2.5 mL), DIPEA (1.72 g, 13.3 mmol) was added and the reaction mixture was stirred overnight. DCM (10 mL) was added and the reaction mixture was washed with water (3×5 mL), dried (MgSO₄) and concentrated in vacuo. The residue was purified by column chromatography to give the title compound (457 mg, 62%) as an off-white solid.

Intermediate 144

Methyl 6-{4-[1-(propan-2-yl)piperidin-4-yl]-1,4-diazepan-1-yl}pyridine-2-carboxylate

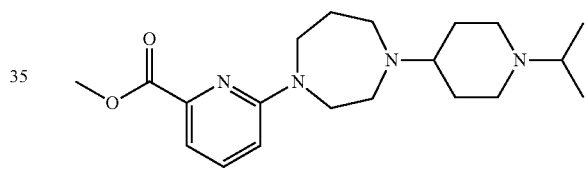

Intermediate 129 (105 mg, 0.26 mmol) was dissolved in HCl (2 mL, 4.0 M in dioxane) and DCM (2 mL) and the reaction mixture was stirred overnight. MeOH (4 mL) was added, the reaction mixture was heated at 110° C. for 7.5 h and the solvents were removed in vacuo. The residue was partitioned between EtOAc and sat aq NaHCO₃, and the organic fraction was dried (MgSO₄) and concentrated in vacuo to give the crude title compound (59.0 mg, 63%) as an orange oil.

Intermediate 145

6-{4-[1-(Propan-2-yl)piperidin-4-yl]-1,4-diazepan-1-yl}pyridine-2-carbohydrazide

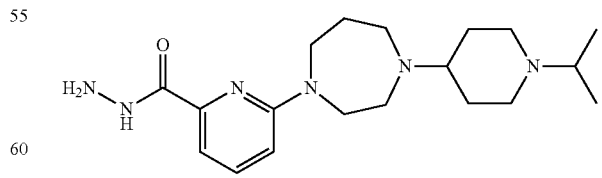

Intermediate 144 (300 mg, 0.83 mmol) and hydrazine hydrate (280 mg, 5.60 mmol) were dissolved in MeOH (5 ml) and stirred overnight. The solvents were removed in vacuo, the residue was dissolved in MeOH and the solvents were removed in vacuo to give the crude title compound (265 mg, 89%) as a pale yellow glass.

Intermediate 146

N'-[(6-{4-[1-(Propan-2-yl)piperidin-4-yl]-1,4-diazepan-1-yl]pyridin-2-yl)carbonyl}cyclopropanecarbohydrazide

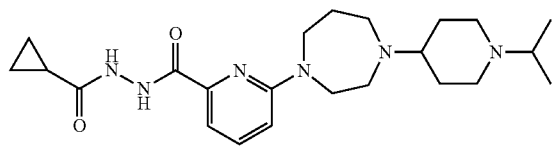 [SMILES: CC(C)N1CCC(N2CCCN(c3cccc(C(=O)NNC(=O)C4CC4)n3)CC2)CC1]

Intermediate 145 (60.0 mg, 0.16 mmol) and Et₃N (81.0 mg, 0.80 mmol) were dissolved in DCM, cooled to 0° C. and a solution of cyclopropanecarbonyl chloride (16.7 mg, 0.16 mmol) in DCM was added. The reaction mixture was warmed to room temperature overnight. DCM was added and the reaction mixture was washed twice with sat aq Na₂CO₃, dried (MgSO₄) and concentrated in vacuo to give the crude title compound (58.0 mg, 85%) as an off-white solid. LCMS (ES⁺): 429 [MH]⁺.

Intermediate 147

1-(6-{4-[1-(Propan-2-yl)piperidin-4-yl]-1,4-diazepan-1-yl}pyridin-2-yl)propan-1-one

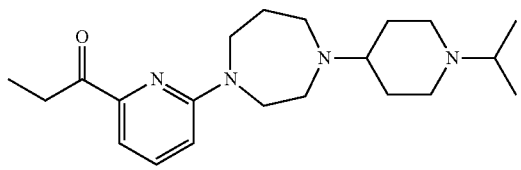 [SMILES: CCC(=O)c1cccc(N2CCCN(C3CCN(C(C)C)CC3)CC2)n1]

Intermediate 131 (320 mg, 0.98 mmol) was dissolved in THF (10 mL) and cooled to 0° C. Ethylmagnesium chloride (1.50 mL, 2.0 M in THF, 3.00 mmol) was added dropwise and the reaction mixture was heated at reflux for 4 h. The reaction mixture was quenched with sat aq NH₄Cl (20 mL) and sat aq Na₂CO₃ (20 mL) and extracted with EtOAc (20 mL×2). The combined organic fractions were dried (MgSO₄) and concentrated in vacuo to give the crude title compound (300 mg, 85%) as an orange gum.

Intermediate 148

(2E)-3-(Dimethylamino)-2-methyl-1-(6-{4-[1-(propan-2-yl)piperidin-4-yl]-1,4-diazepan-1-yl}pyridin-2-yl)prop-2-en-1-one

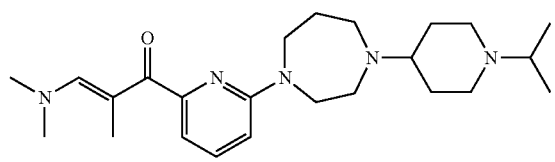 [SMILES: C/C(=C\N(C)C)C(=O)c1cccc(N2CCCN(C3CCN(C(C)C)CC3)CC2)n1]

Intermediate 147 (300 mg, 0.84 mmol) was dissolved in DMF/DMA (3 mL) and heated at reflux overnight. The sol vents were removed in vacuo and the residue was purified by reverse phase HPLC to give the title compound (45.0 mg, 20%) as an orange gum. LCMS (ES⁺): 414.4 [MH]⁺.

Intermediate 149 tert-Butyl 5-methyl-1,4-diazepane-1-carboxylate

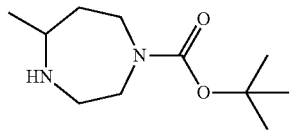

5-Methyl-[1,4]diazepane (600 mg, 5.25 mmol) was dissolved in DMF (7.5 mL) and cooled to 0° C. A solution of di-tert-butyl-dicarbonate (1.03 g, 4.70 mmol) and triethylamine (3.60 mL, 26.0 mmol) in DCM (1 mL) was added dropwise over 3 h. The solvents were removed in vacuo and the residue dissolved in DCM (20 mL) and washed with sat aq Na₂CO₃ (5 mL). The aq fraction was extracted with DCM (3×50 mL) and the combined organic fractions were dried (MgSO₄) and concentrated in vacuo. The residue was purified by column chromatography, dissolved in DCM (20 mL) and washed with 2 M aq NaOH (10 mL). The aq fraction was extracted with DCM (3×50 mL) and the combined organic fractions were dried (MgSO₄) and concentrated in vacuo to give the title compound (194 mg, 17%) as a yellow oil. LCMS (ES⁺): 215.3 [MH]⁺.

Intermediate 150

N-(Cyclopropylmethyl)-6-(7-methyl-1,4-diazepan-1-yl)pyridine-2-carboxamide

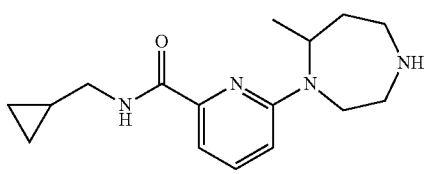 [SMILES: CC1CCNCCN1c1cccc(C(=O)NCC2CC2)n1]

Intermediate 38 (60.5 mg, 0.29 mmol), Intermediate 149 (123 mg, 0.57 mmol) and DIPEA (200 µL, 1.15 mmol) was dissolved in NMP (750 µL) and heated using a microwave (185° C., absorption high) for 80 min. The solvents were removed in vacuo and the residue was dissolved in DCM (10 mL) and washed with sat aq Na₂CO₃ (1 mL). The aq fraction was extracted with DCM (3×20 mL) and the combined organic fractions were dried (MgSO₄) and concentrated in vacuo. The residue was purified by column chromatography to give the crude title compound (50.0 mg) as a brown oil. LCMS (ES⁺): 289.4 [MH]⁺.

Intermediate 151

1-Benzyl-5,5-dihydrogenio-1,4-diazepane

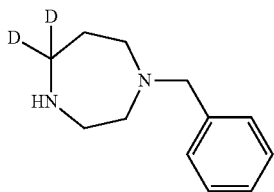 [SMILES: [2H]C1([2H])CCN(Cc2ccccc2)CCN1]

1-Benzyl-1,4-diazepan-5-one (2.00 g, 9.79 mmol) was dissolved in THF (40 mL), LiAlD$_4$ (9.80 mL, 2.0 M in THF, 19.6 mmol) was added dropwise over 5 min and the reaction mixture was stirred for 24 h. The reaction mixture was quenched with sat aq NaHCO$_3$, filtered and concentrated in vacuo to give the crude title compound (1.80 g, 96%) as a pale yellow gum.

Intermediate 152

6-(4-Benzyl-7,7-dihydrogenio-1,4-diazepan-1-yl)-N-(pyridin-4-yl)pyridine-2-carboxamide

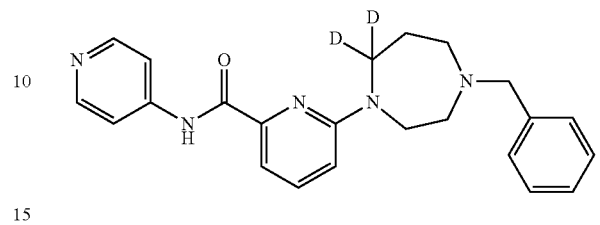

Intermediate 39 (800 mg, 3.42 mmol) and Intermediate 151 (988 mg, 5.14 mmol) were dissolved in NMP (2 mL) and the reaction mixture was heated using a microwave (200° C., absorption high) for 3 h. The residue was purified by reverse phase HPLC to give the title compound (320 mg, 24%) as a pale yellow gum. LCMS (ES$^+$): 390.4 [MH]$^+$.

Intermediates 153-156

Intermediates 153-156 were prepared similarly to Intermediate 152, by reacting 6-chloro-2-substituted pyridines with substituted homopiperazines; see Table 10 below.

TABLE 10

Preparation of piperidin-4-one intermediates

| Int | Structure | SMs/Yield | LCMS (ES$^+$) | Intermediate Name |
|---|---|---|---|---|
| 153 | 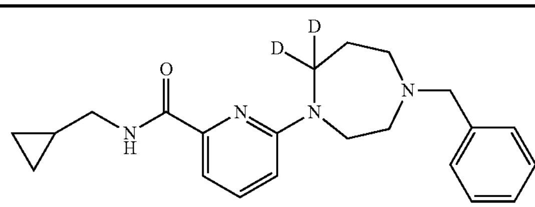 | Int 38<br>Int 151<br>48% | 277.4 [MH]$^+$ | 6-(4-Benzyl-7,7-dihydrogenio-1,4-diazepan-1-yl)-N-(cyclopropylmethyl)pyridine-2-carboxamide |
| 154 | 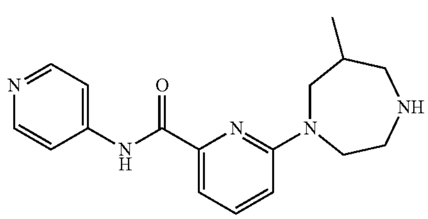 [SMILES: CC1CNCCN(c2cccc(C(=O)Nc3ccncc3)n2)C1] | Int 39<br>53% | 312.4 [MH]$^+$ | 6-(6-Methyl-1,4-diazepan-1-yl)-N-(pyridin-4-yl)pyridine-2-carboxamide |
| 155 | 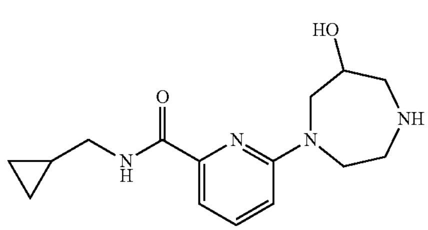 [SMILES: O=C(NCC1CC1)c1cccc(N2CCNCC(O)C2)n1] | Int 38<br>47% | 291.1 [MH]$^+$ | N-(Cyclopropylmethyl)-6-(6-hydroxy-1,4-diazepan-1-yl)pyridine-2-carboxamide |

TABLE 10-continued

Preparation of piperidin-4-one intermediates

| Int | Structure | SMs/Yield | LCMS (ES+) | Intermediate Name |
|---|---|---|---|---|
| 156 | 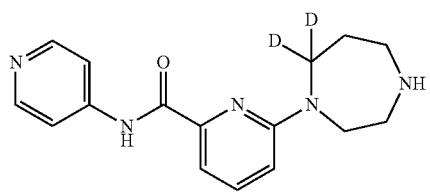 [SMILES: [2H]C1([2H])CCNCCN1c1cccc(C(=O)Nc2ccncc2)n1] | Int 38<br>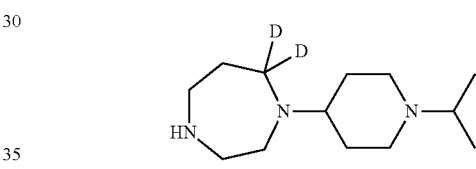<br>93% | 289.4 [MH]+ | N-(Cyclopropylmethyl)-6-(5-methyl-1,4-diazepan-1-yl)pyridine-2-carboxamide |

Intermediate 157

6-(7,7-Dihydrogenio-1,4-diazepan-1-yl)-N-(pyridin-4-yl)pyridine-2-carboxamide

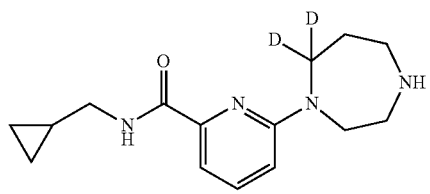 [SMILES: [2H]C1([2H])CCNCCN1c1cccc(C(=O)NCC2CC2)n1]

Intermediate 152 (315 mg, 0.81 mmol) was dissolved in MeOH (60 mL) and hydrogenated using an H-Cube (80 bar, 60° C., 1 mL/min) over 10% Pd/C. The solvents were removed in vacuo to give the crude title compound (186 mg, 77%) as a white solid. LCMS (ES+): 300.5 [MH]+.

Intermediate 158

N-(Cyclopropylmethyl)-6-(7,7-dihydrogenio-1,4-diazepan-1-yl)pyridine-2-carboxamide Intermediate 158 was prepared similarly to Intermediate 157, using Intermediate 153 instead of Intermediate 152, to give the title compound (48%) as a light yellow gum. LCMS (ES+): 277.4 [MH]+.

Intermediate 159

7,7-Dihydrogenio-1-[1-(propan-2-yl)piperidin-4-yl]-1,4-diazepane

Intermediate 151 (150 mg, 0.78 mmol), 1-(propan-2-yl)piperidin-4-one (110 mg, 0.78 mmol) and NaBH(OAc)$_3$ (496 mg, 2.34 mmol) were dissolved in DCM (15 mL) and stirred for 4 d. The reaction mixture was diluted with DCM (25 mL), washed with sat aq Na$_2$CO$_3$ (40 mL), brine (40 mL), dried (MgSO$_4$) and stirred with isocyanate resin for 3 h. The reaction mixture was filtered and the solvents removed in vacuo. The residue was dissolved in MeOH (25 mL) and hydrogenated using an H-Cube (80 bar, 60° C., 1 mL/min) over 10% Pd/C. The solvents were removed in vacuo to give the crude title compound (135 mg, 76%) as a colourless gum. LCMS (ES+): 228.5 [MH]+.

Intermediate 160

1-Benzyl-3-methyl-1,4-diazepan-5-one

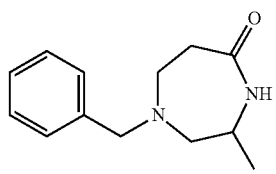 [SMILES: CC1CN(Cc2ccccc2)CCC(=O)N1]

1-Benzyl-3-methyl-piperidin-4-one (5.00 g, 24.6 mmol) was dissolved in CHCl$_3$ (50 mL), the reaction mixture was cooled to 0° C. and conc H$_2$SO$_4$ (12 mL) was added dropwise. NaN$_3$ (3.20 g, 49.2 mmol) was added portionwise over 10 min and the reaction mixture was stirred at room temperature for 18 h and at 50° C. for 2 h. Iced water (120 mL) was added and the reaction mixture was neutralized with NaOH, extracted with DCM (2×50 mL), dried (MgSO$_4$) and concentrated in vacuo to give the crude title compound (4.86 g, 91%) as an off-white solid. LCMS (ES$^+$): 219.3 [MH]$^+$.

Intermediate 161

1-Benzyl-3-methyl-1,4-diazepane

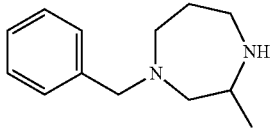

Intermediate 160 (4.86 g, 22.3 mmol) was dissolved in Et$_2$O (100 mL) and LiAlH$_4$ (11.7 mL, 4.0 M in Et$_2$O, 46.8 mmol) was added dropwise over 10 min. The reaction mixture was stirred for 4 h, quenched with water, filtered, dried (MgSO$_4$) and concentrated in vacuo to give the crude title compound (4.15 g, 91%) as a colourless gum. LCMS (ES$^+$): 205.3 [MH]$^+$.

Intermediate 162

1-Benzyl-5,5-dihydrogenio-3-methyl-1,4-diazepane

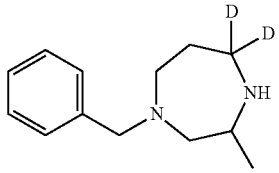 [SMILES: [2H]C1([2H])CCN(Cc2ccccc2)CC(C)N1]

Intermediate 162 was prepared similarly to Intermediate 161, using LiAlD$_4$ instead of LiAlH$_4$, to give the crude title compound (84%) as a light yellow gum. LCMS (ES$^+$): 207.3 [MH]$^+$.

Intermediates 163-172

Intermediates 163-172 were prepared similarly to Intermediate 159, by reductive alkylation of substituted benzyl homopiperazines with the appropriate ketone and subsequent debenzylation; see Table 11 below.

TABLE 11

Preparation of piperidin-4-yl-homopiperazine intermediates

| Int | Structure | SMs/Yield | LCMS (ES$^+$) | Intermediate Name |
|---|---|---|---|---|
| 163 | 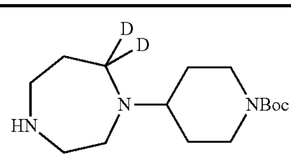 | Int 151 99% | 286.5 [MH]$^+$ | tert-Butyl 4-(7,7-dihydrogenio-1,4-diazapan-1-yl)piperidine-1-carboxylate |
| 164 | 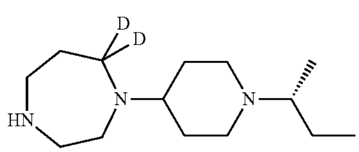 [SMILES: [2H]C1([2H])CCNCCN1C1CCN([C@H](C)CC)CC1] | Int 151 Int 8 47% | 242.3 [MH]$^+$ | 1-{1-[(2R)-Butan-2-yl]piperidin-4-yl}-7,7-dihydrogenio-1,4-diazepane |
| 165 | 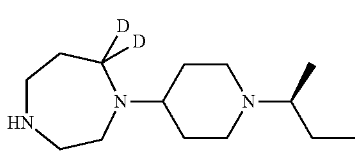 [SMILES: [2H]C1([2H])CCNCCN1C1CCN([C@@H](C)CC)CC1] | Int 151 Int 9 75% | 242.3 [MH]$^+$ | 1-{1-[(2S)-Butan-2-yl]piperidin-4-yl}-7,7-dihydrogenio-1,4-diazepane |
| 166 | 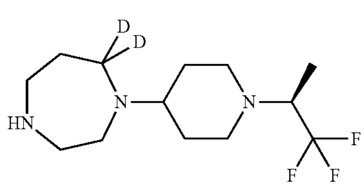 [SMILES: [2H]C1([2H])CCNCCN1C1CCN([C@@H](C)C(F)(F)F)CC1] | Int 151 Int 12 46% | 282.3 [MH]$^+$ | 7,7-Dihydrogenio-1-{1-[(2S)-1,1,1-trifluoropropan-2-yl]piperidin-4-yl}-1,4-diazepane |

TABLE 11-continued

Preparation of piperidin-4-yl-homopiperazine intermediates

| Int | Structure | SMs/Yield | LCMS (ES+) | Intermediate Name |
|---|---|---|---|---|
| 167 | 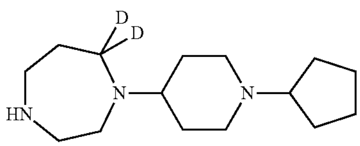 [SMILES: [2H]C1([2H])CCNCCN1C1CCN(C2CCCC2)CC1] | Int 151<br>Int 24<br>30% | 254.3 [MH]+ | 1-(1-Cyclopentylpiperidin-4-yl)-7,7-dihydrogenio-1,4-diazepane |
| 168 | 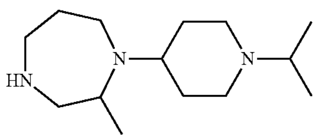 [SMILES: CC(C)N1CCC(N2CCCNCC2C)CC1] | Int 161<br>69% | 240.4 [MH]+ | 2-Methyl-1-[1-(propan-2-yl)piperidin-4-yl]-1,4-diazepane |
| 169 | 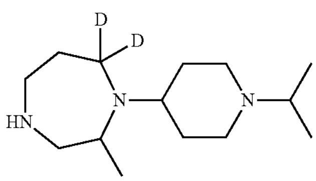 [SMILES: [2H]C1([2H])CCNCC(C)N1C1CCN(C(C)C)CC1] | Int 162<br>62% | 242.5 [MH]+ | 7,7-Dihydrogenio-2-methyl-1-[1-(propan-2-yl)piperidin-4-yl]-1,4-diazepane |
| 170 | 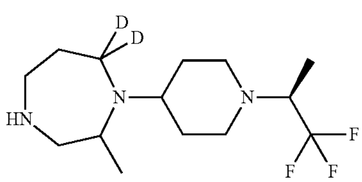 [SMILES: [2H]C1([2H])CCNCC(C)N1C1CCN([C@@H](C)C(F)(F)F)CC1] | Int 162<br>Int 12<br>54% | 296.5 [MH]+ | 7,7-Dihydrogenio-2-methyl-1-{1-[(2S)-1,1,1-trifluoropropan-2-yl]piperidin-4-yl}-1,4-diazepane |
| 171 | 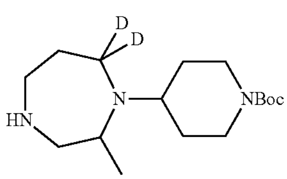 [SMILES: [2H]C1([2H])CCNCC(C)N1C1CCN(C(=O)OC(C)(C)C)CC1] | Int 162<br>45% | 300.3 [MH]+ | tert-Butyl 4-(7,7-dihydrogenio-2-methyl-1,4-diazepan-1-yl)piperidine-1-carboxylate |
| 172 | 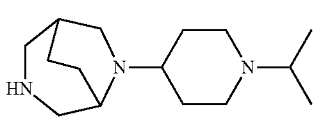 [SMILES: CC(C)N1CCC(N2CC3CCC2CNC3)CC1] | 65% | 252.2 [MH]+ | 6-[1-(Propan-2-yl)piperidin-4-yl]-3,6-diazabicyclo[3.2.2]nonane |

* Commercially available

Intermediate 173

6-Bromo-N-(pyridin-4-yl)pyridine-2-carboxamide

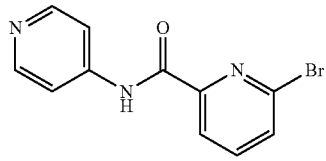 [SMILES: O=C(Nc1ccncc1)c1cccc(Br)n1]

2-Bromopyridine-6-carboxylic acid (5.00 g, 24.8 mmol) was dissolved in DCM (100 mL) and DMF (1 mL), and oxalyl chloride (7.54 g, 59.4 mmol) was added dropwise over 5 min. The reaction mixture was stirred for 2 h and the solvents were removed in vacuo. The reaction mixture was azeotroped twice with DCM and dissolved in DCM (100 mL). DIPEA (12.8 g, 99.0 mmol) and 4-aminopyridine (4.66 g, 49.5 mmol) were added dropwise and the reaction mixture was stirred for 2 h, washed with sat aq NaHCO$_3$ (50 mL), dried (MgSO$_4$) and concentrated in vacuo. The residue was recrystallised from MeOH to give the title compound (5.00 g, 73%) as an off white solid. LCMS (ES$^+$): 278.2 [MH]$^+$.

Intermediate 174

6-Bromo-N-(cyclopropylmethyl)pyridine-2-carboxamide

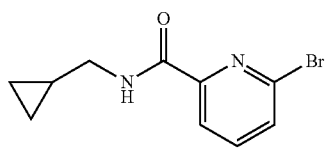 [SMILES: O=C(NCC1CC1)c1cccc(Br)n1]

Intermediate 174 was prepared similarly to Intermediate 173, using aminomethylcyclopropane instead of 4-aminopyridine, to give the title compound (77%) as a light yellow solid. LCMS (ES$^+$): 255.2 [MH]$^+$.

Intermediate 175

6-[5,5-Dihydrogenio-4-(piperidin-4-yl)-1,4-diazepan-1-yl]-N-(pyridin-4-yl)pyridine-2-carboxamide

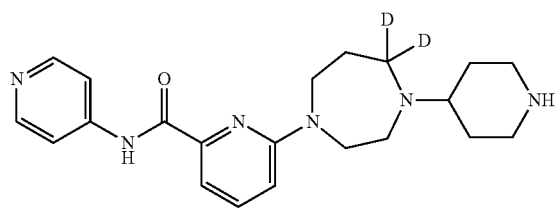 [SMILES: [2H]C1([2H])CCN(c2cccc(C(=O)Nc3ccncc3)n2)CCN1C1CCNCC1]

Intermediate 163 (734 mg, 2.57 mmol), Intermediate 173 (650 mg, 2.34 mmol), caesium carbonate (1.14 g, 3.51 mmol), palladium acetate (37.0 mg, 0.16 mmol) and BINAP (146 mg, 0.23 mmol) were suspended in dioxane (10 ml). The reaction mixture was degassed for 15 min and heated at 95° C. for 18 h. The reaction mixture was concentrated in vacuo, dissolved in DCM, filtered and concentrated in vacuo. The residue was purified by column chromatography. The residue was dissolved in DCM (8 mL), TFA (4 mL) was added and the reaction mixture was stirred for 2 h. The solvents were removed in vacuo and the residue was partitioned between DCM (40 mL) and sat aq Na$_2$CO$_3$ (40 mL). The aq fraction was extracted with DCM (2×40 mL) and the combined organic fractions were dried (MgSO$_4$) and concentrated in vacuo to give the title compound (602 mg, 67%) as a yellow liquid. LCMS (ES$^+$): 383.6 [MH]$^+$.

Intermediate 176

6-[4-(3-Fluoropiperidin-4-yl)-7,7-dihydrogenio-1,4-diazepan-1-yl]-N-(pyridin-4-yl)pyridine-2-carboxamide

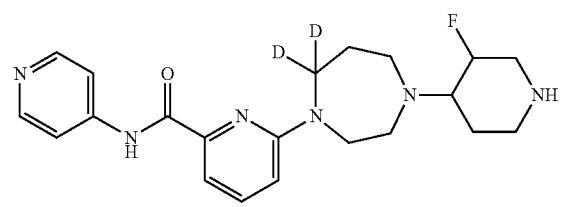 [SMILES: [2H]C1([2H])CCN(C2CCNCC2F)CCN1c1cccc(C(=O)Nc2ccncc2)n1]

Intermediate 157 (75.0 mg, 0.25 mmol) and tert-butyl 3-fluoro-4-oxopiperidine-1-carboxylate (54.4 mg, 0.25 mmol) were dissolved in DCM (10 mL) and NaBH(OAc)$_3$ (266 mg, 1.25 mmol) was added. The reaction mixture was stirred for 20 d, diluted with DCM (50 mL), washed with sat aq Na$_2$CO$_3$ (40 mL), brine (30 mL), dried (MgSO$_4$) and concentrated in vacuo. The residue was purified by reverse phase HPLC and dissolved in MeOH (10 mL) and TFA (1 mL). The reaction mixture was stirred for 18 h and the solvents were removed in vacuo to give the title compound.

Intermediate 177

1-[6-(5-Cyclopropyl-4-methyl-1H-imidazol-2-yl)pyridin-2-yl]-4-(3-fluoropiperidin-4-yl)-1,4-diazepane

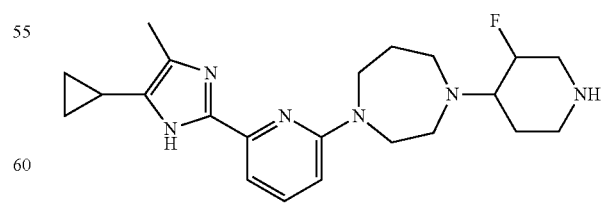

Intermediate 177 was prepared similarly to Intermediate 176, using Intermediate 113 instead of Intermediate 157, to give the crude title compound (100%) as a yellow liquid. LCMS (ES$^+$): 399.2 [MH]$^+$.

Intermediate 178 tert-Butyl 4-(4-benzyl-7,7-dihydrogenio-1,4-diazepan-1-yl)-3-fluoropiperidine-1-carboxylate

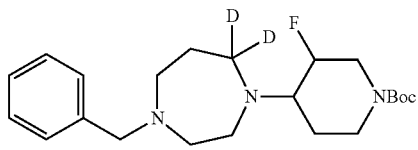 [SMILES: [2H]C1([2H])CCN(Cc2ccccc2)CCN1C1CCN(C(=O)OC(C)(C)C)CC1F]

Intermediate 151 (400 mg, 2.08 mmol), 3-fluoro-4-oxopiperidine-1-carboxylic acid tert-butyl ester (452 mg, 2.08 mmol) and NaBH(OAc)$_3$ (1.32 g, 6.24 mmol) were dissolved in DCM (25 mL) and stirred for 4 d. The reaction mixture was diluted with DCM (25 mL), washed with sat aq Na$_2$CO$_3$ (40 mL), brine (40 mL), dried (MgSO$_4$) and stirred with isocyanate resin for 3 h. The reaction mixture was filtered and concentrated in vacuo to give the crude title compound (480 mg, 59%) as a colourless gum. LCMS (ES$^+$): 394.5 [MH]$^+$.

Intermediate 179 tert-Butyl 4-(4-benzyl-1,4-diazepan-1-yl)-3-fluoropiperidine-1-carboxylate

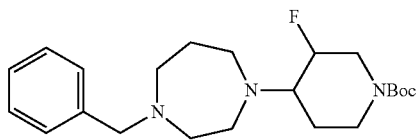 [SMILES: CC(C)(C)OC(=O)N1CCC(N2CCCN(Cc3ccccc3)CC2)C(F)C1]

Intermediate 179 was prepared similarly to Intermediate 178, using 1-benzyl-1,4-diazepane instead of Intermediate 151, to give the crude title compound (42%) as a colourless gum. LCMS (ES$^+$): 392.5 [MH]$^+$.

Intermediate 180

1-Benzyl-4-[3-fluoro-1-(propan-2-yl)piperidin-4-yl]-5,5-dihydrogenio-1,4-diazepane

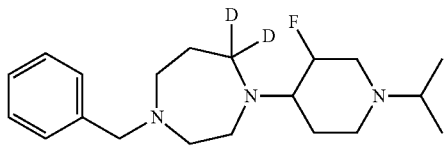 [SMILES: [2H]C1([2H])CCN(Cc2ccccc2)CCN1C1CCN(C(C)C)CC1F]

Intermediate 178 (480 mg, 1.22 mmol) was dissolved in MeOH (20 mL) and TFA (2 mL) and stirred for 18 h. The solvents were removed in vacuo, the residue was dissolved in DCM (20 mL) and acetone (142 mg, 2.44 mmol) and NaBH(OAc)$_3$ (1.29 g, 6.10 mmol) were added. The reaction mixture was stirred for 18 h, diluted with DCM (20 mL), washed with sat aq Na$_2$CO$_3$ (25 mL), dried (MgSO$_4$) and stirred with isocyanate resin for 18 h. The reaction mixture was filtered and concentrated in vacuo to give the crude title compound (300 mg, 73%) as a colourless gum. LCMS (ES$^+$): 336.5 [MH]$^+$.

Intermediate 181

1-benzyl-4-[3-fluoro-1-(propan-2-yl)piperidin-4-yl]-1,4-diazepane

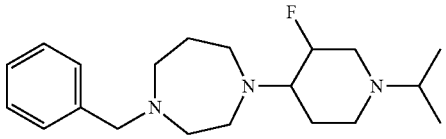 [SMILES: CC(C)N1CCC(N2CCCN(Cc3ccccc3)CC2)C(F)C1]

Intermediate 181 was prepared similarly to Intermediate 180, using Intermediate 179 instead of Intermediate 178, to give the title compound (71%) as a white solid. LCMS (ES$^+$): 334.5 [MH]$^+$.

Intermediate 182

1-[3-Fluoro-1-(propan-2-yl)piperidin-4-yl]-7,7-dihydrogenio-1,4-diazepane

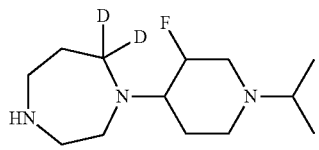

Intermediate 180 was dissolved in MeOH (30 mL) and hydrogenated using an H-Cube (80 bar, 60° C., 1 mL/min) over 10% Pd/C. The solvents were removed in vacuo to give the crude title compound (155 mg, 71%) as a colourless gum. LCMS (ES$^+$): 246.4 [MH]$^+$.

Intermediate 183

1-[3-Fluoro-1-(propan-2-yl)piperidin-4-yl]-1,4-diazepane

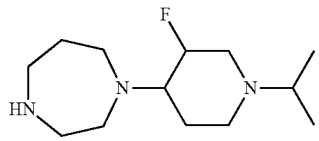

Intermediate 183 was prepared similarly to Intermediate 182, using Intermediate 181 instead of Intermediate 180, to give the crude title compound (73%) as a colourless gum. LCMS (ES$^+$): 244.4 [MH]$^+$.

Intermediate 184

N-Methoxy-N-methyl-6-{4-[1-(propan-2-yl)piperidin-4-yl]-1,4-diazepan-1-yl}pyridine-2-carboxamide

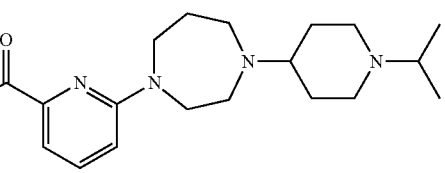

Intermediate 135 (500 mg, 1.44 mmol), N,O-dimethylhydroxylamine hydrochloride (422 mg, 4.33 mmol), DIPEA (1.76 mL, 10.1 mmol) and HBTU (547 mg, 1.44 mmol) were dissolved in DMF (8 mL) and stirred for 20 h. The solvents were removed in vacuo and the residue was diluted with DCM (50 mL), washed with sat aq Na$_2$CO$_3$ (30 mL), dried (MgSO$_4$) and concentrated in vacuo. The residue was purified by column chromatography to give the title compound (380 mg, 68%) as a white solid. LCMS (ES$^+$): 390.5 [MH]$^+$.

Intermediate 185

6-[5,5-Dihydrogenio-3-methyl-4-(piperidin-4-yl)-1,4-diazepan-1-yl]-N-(pyridin-4-yl)pyridine-2-carboxamide

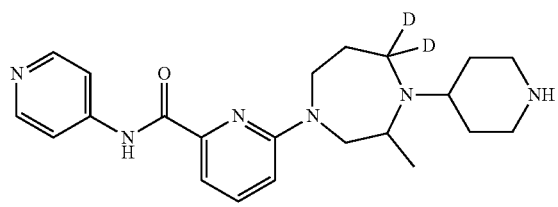 [SMILES: [2H]C1([2H])CCN(c2cccc(C(=O)Nc3ccncc3)n2)CC(C)N1C1CCNCC1]

Intermediate 185 was prepared similarly to Intermediate 175, using Intermediate 171 instead of Intermediate 163, to give the title compound (21%) as a yellow liquid. LCMS (ES$^+$): 397.2 [MH]$^+$.

Intermediate 186 tert-Butyl 4-{3-benzyl-3,6-diazabicyclo[3.2.2]nonan-6-yl}-3-fluoropiperidine-1-carboxylate

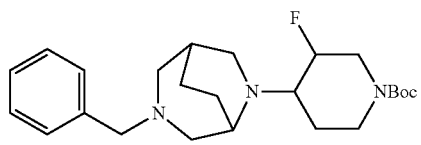 [SMILES: CC(C)(C)OC(=O)N1CCC(N2CC3CCC2CN(Cc2ccccc2)C3)C(F)C1]

Intermediate 186 was prepared similarly to Intermediate 178, using 3-benzyl-3,6-diazabicyclo[3.2.2]nonane instead of Intermediate 151, to give the title compound (93%) as a pale yellow gum. LCMS (ES$^+$): 418.4 [MH]$^+$.

Intermediate 187

3-Benzyl-6-[3-fluoro-1-(propan-2-yl)piperidin-4-yl]-3,6-diazabicyclo[3.2.2]nonane

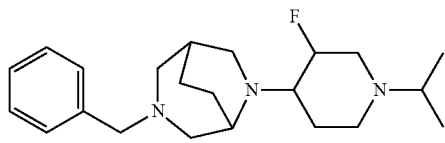 [SMILES: CC(C)N1CCC(N2CC3CCC2CN(Cc2ccccc2)C3)C(F)C1]

Intermediate 187 was prepared similarly to Intermediate 180, using Intermediate 186 instead of Intermediate 178, to give the title compound (90%) as a pale yellow gum. LCMS (ES$^+$): 360.4 [MH]$^+$.

Intermediate 188

6-[3-Fluoro-1-(propan-2-yl)piperidin-4-yl]-3,6-diazabicyclo[3.2.2]nonane

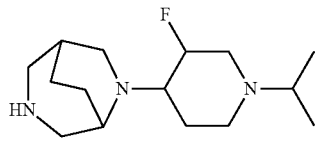 [SMILES: CC(C)N1CCC(N2CC3CCC2CNC3)C(F)C1]

Intermediate 188 was prepared similarly to Intermediate 182, using Intermediate 187 instead of Intermediate 180, to give the title compound (44%) as a pale yellow gum. LCMS (ES$^+$): 270.4 [MH]$^+$.

Intermediate 189 tert-Butyl 4-{3-benzyl-3,6-diazabicyclo[3.2.2]nonan-6-yl}piperidine-1-carboxylate

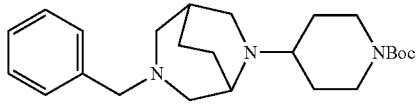 [SMILES: CC(C)(C)OC(=O)N1CCC(N2CC3CCC2CN(Cc2ccccc2)C3)CC1]

Intermediate 189 was prepared similarly to Intermediate 186, using tert-butyl 4-oxopiperidine-1-carboxylate instead of 3-fluoro-4-oxo-piperidine-1-carboxylic acid tert-butyl ester, to give the crude title compound as a yellow liquid. LCMS (ES$^+$): 400.3 [MH]$^+$.

Intermediate 190 tert-Butyl 4-{3,6-diazabicyclo[3.2.2]nonan-6-yl}piperidine-1-carboxylate

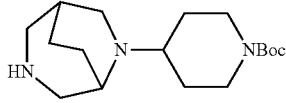 [SMILES: CC(C)(C)OC(=O)N1CCC(N2CC3CCC2CNC3)CC1]

Intermediate 189 (1.29 g, 3.24 mmol) was dissolved in MeOH (100 mL) and hydrogenated using an H-cube (80 bar, 60° C., 1 mL/min) over 10% Pd/C. The solvents were removed in vacuo and the residue was purified by column chromatography to give the title compound (596 mg, 60%) as a yellow gum. LCMS (ES$^+$): 310.3 [MH]$^+$.

Intermediate 191

6-[6-(Piperidin-4-yl)-3,6-diazabicyclo[3.2.2]nonan-3-yl]-N-(pyridin-4-yl)pyridine-2-carboxamide

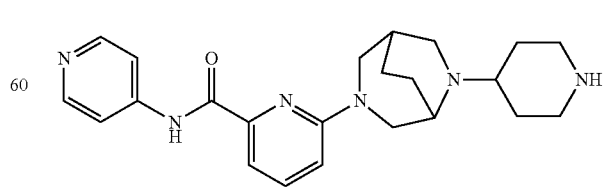

Intermediate 191 was prepared similarly to Intermediate 175, using Intermediate 190 instead of Intermediate 163, to give the crude title compound (42%) as a yellow liquid. LCMS (ES+): 407.2 [MH]+.

Intermediate 192

N-(Cyclopropylmethyl)-6-{3,10-diazabicyclo[4.3.1]decan-3-yl}pyridine-2-carboxamide

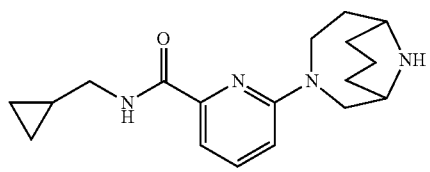 [SMILES: O=C(NCC1CC1)c1cccc(N2CCC3CCCC(C2)N3)n1]

10-Benzyl-3,10-diaza-bicyclo[4.3.1]decane (785 mg, 3.41 mmol), Intermediate 174 (790 mg, 3.10 mmol), cesium carbonate (1.00 g, 3.04 mmol), palladium acetate (45.0 mg, 0.20 mmol) and BINAP (192 mg, 0.31 mmol) were suspended in dioxane (25 mL), degassed and heated at 95° C. for 18 h. The solvents were removed in vacuo, the residue was diluted with DCM, filtered and concentrated in vacuo. The residue was purified by column chromatography, dissolved in EtOH (20 mL) and hydrogenated using a hydrogen balloon at 50° C. over 10% Pd(OH)$_2$/C for 60 h. The reaction mixture was filtered through celite, washing with EtOH and concentrated in vacuo. The residue was purified by column chromatography to give the title compound (89.0 mg, 49%).

Intermediate 193

6-{3,10-Diazabicyclo[4.3.1]decan-3-yl}-N-(pyridin-4-yl)pyridine-2-carboxamide

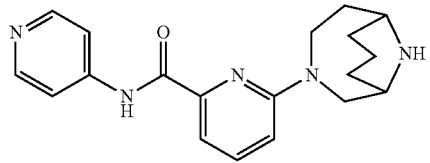 [SMILES: O=C(Nc1ccncc1)c1cccc(N2CCC3CCCC(C2)N3)n1]

Intermediate 193 was prepared similarly to Intermediate 192, using Intermediate 39 instead of Intermediate 174, to give the crude title compound (28%) as a yellow gum. LCMS (ES+): 338.5 [MH]+.

Intermediate 194

6-Chloro-N-(cyclopropylmethyl)-3-methylpyridine-2-carboxamide

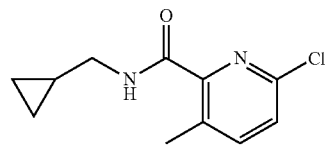

6-Chloro-3-methylpyridine-2-carboxylic acid (595 mg, 3.47 mmol), aminomethylcyclopropane (356 µL, 4.16 mmol), EDC.HCl (1.46 g, 7.63 mmol), HOBN (1.54 g, 8.67 mmol) and NEM (1.10 mL, 8.67 mmol) were dissolved in DCM (30 mL) and stirred for 16 h. The reaction mixture was washed with sat aq NaHCO$_3$ (30 mL), 1M aq HCl (30 mL), brine (30 mL), dried (MgSO$_4$) and concentrated in vacuo. The residue was purified by column chromatography to give the title compound (215 mg, 28%) as a yellow solid. LCMS (ES+): 225.5 [MH]+.

Intermediate 195

N-(Cyclopropylmethyl)-6-(1,4-diazepan-1-yl)-3-methylpyridine-2-carboxamide

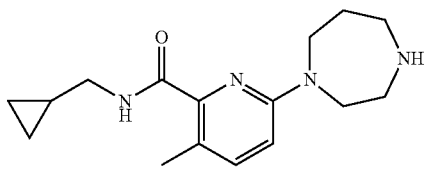 [SMILES: Cc1ccc(N2CCCNCC2)nc1C(=O)NCC1CC1]

Intermediate 195 was prepared similarly to Intermediate 81, using Intermediate 194 instead of Intermediate 38, to give the crude title compound as a yellow liquid. LCMS (ES+): 289.2 [MH]+.

Intermediate 196

1-(1,3-Thiazol-2-yl)-1,4-diazepane

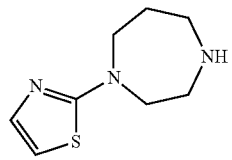 [SMILES: c1csc(N2CCCNCC2)n1]

2-Bromothiazole (1.00 g, 6.10 mmol) and homopiperazine (2.44 g, 24.4 mmol) were dissolved in DMA (1 mL) and heated using a microwave (180° C., absorption high) for 30 min. The reaction mixture was dissolved in DCM (50 mL), washed with sat aq Na$_2$CO$_3$ (50 mL), brine (50 mL), dried (MgSO$_4$) and concentrated in vacuo to give the crude title compound (1.05 g, 94%) as a yellow solid. LCMS (ES+): 184.2 [MH]+.

Intermediate 197

6-[(1-Benzylpiperidin-4-yl)oxy]pyridine-2-carboxylic acid

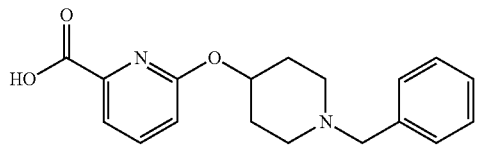 [SMILES: O=C(O)c1cccc(OC2CCN(Cc3ccccc3)CC2)n1]

Tert-butyl 6-chloropyridine-2-carboxylate (1.00 g, 4.68 mmol) and N-benzylpiperidin-4-ol (1.88 g, 9.83 mmol) were dissolved in dioxane (10 mL). NaH (393 mg, 60% dispersion in mineral oil, 9.83 mmol) was added and the reaction mixture was heated using a microwave (80° C., absorption high) for 1 h. The solvents were removed in vacuo and the residue was dissolved in MeOH (100 mL), filtered and concentrated in vacuo. The residue was purified by reverse phase column chromatography to give the title compound (860 mg, 59%) as a white solid. LCMS (ES⁺): 313.1 [MH]⁺.

Intermediate 198

6-[(1-Benzylpiperidin-4-yl)oxy]-N-(pyridin-4-yl)pyridine-2-carboxamide

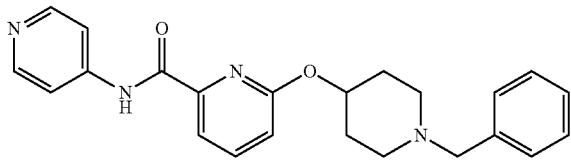 [SMILES: O=C(Nc1ccncc1)c1cccc(OC2CCN(Cc3ccccc3)CC2)n1]

Intermediate 197 (430 mg, 1.38 mmol) was dissolved in DCM (20 mL) and oxalyl chloride (419 mg, 3.30 mmol) was added. The reaction mixture was stirred for 2 h, the solvents were removed in vacuo and the residue was dissolved in DCM (20 mL). DIPEA (711 mg, 5.51 mmol) and 4-aminopyridine (259 mg, 2.75 mmol) were added and the reaction mixture was stirred for 3 h. The reaction mixture was diluted with DCM (50 mL), washed with sat aq Na₂CO₃ (75 mL), dried (MgSO₄) and concentrated in vacuo. The residue was purified by column chromatography to give the title compound (360 mg, 67%) as a white solid. LCMS (ES⁺): 389.2 [MH]⁺.

Intermediate 199

6-(Piperidin-4-yloxy)-N-(pyridin-4-yl)pyridine-2-carboxamide

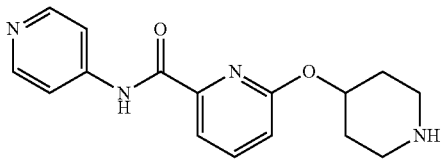 [SMILES: O=C(Nc1ccncc1)c1cccc(OC2CCNCC2)n1]

Intermediate 198 (360 mg, 0.93 mmol) was dissolved in MeOH (30 mL) and the reaction mixture was hydrogenated using an H-Cube (80 bar, 60° C., 1.0 mL/min) over 10% Pd/C. The solvents were removed in vacuo to give the crude title compound (231 mg, 84%) as a white solid. LCMS (ES⁺): 299.2 [MH]⁺.

Intermediate 200

6-{[1-(Azepan-4-yl)piperidin-4-yl]oxy}-N-(pyridin-4-yl)pyridine-2-carboxamide

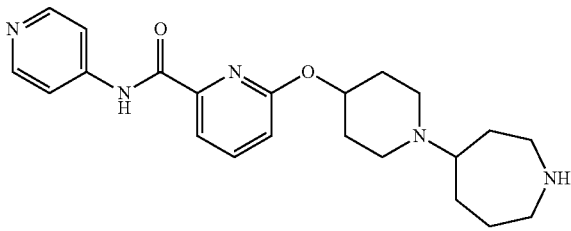 [SMILES: O=C(Nc1ccncc1)c1cccc(OC2CCN(C3CCCNCC3)CC2)n1]

Intermediate 199 (77.0 mg, 0.26 mmol) was dissolved in DCM (6 mL) and N-Boc-hexahydro-1H-azepine-4-one (110 mg, 0.52 mmol) and NaBH(OAc)₃ (273 mg, 1.30 mmol) were added. The reaction mixture was stirred for 4 d, diluted with DCM (10 mL), washed with sat aq Na₂CO₃ (10 mL), dried (MgSO₄) and concentrated in vacuo. The residue was dissolved in DCM (6 mL), TFA (3 mL) was added and the reaction mixture was stirred for 2 h. The reaction mixture was concentrated in vacuo, dissolved in DCM (10 mL), washed with sat aq Na₂CO₃ (10 mL), dried (MgSO₄) and concentrated in vacuo to give the crude title compound (102 mg, 100%) as a yellow liquid. LCMS (ES⁺): 396.2 [MH]⁺.

Intermediate 201 tert-Butyl 3-({6-[(pyridin-4-yl)carbamoyl]pyridin-2-yl}amino)piperidine-1-carboxylate

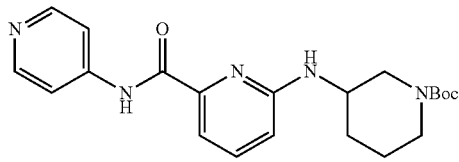 [SMILES: CC(C)(C)OC(=O)N1CCCC(Nc2cccc(C(=O)Nc3ccncc3)n2)C1]

Intermediate 39 (250 mg, 1.07 mmol), 3-amino-piperidine-1-carboxylic acid tert-butyl ester (515 μL, 2.67 mmol) and DIPEA (746 μL, 4.28 mmol) were dissolved in NMP (2 mL) and heated using a microwave (185° C., absorption high) for 200 min. The reaction mixture was dissolved in DCM (20 mL), washed with sat aq NH₄Cl (10 mL×5), dried (MgSO₄) and concentrated in vacuo. The residue was partially purified by column to give the crude title compound as a brown oil. LCMS (ES⁺): 398.2 [MH]⁺.

Intermediate 202 tert-Butyl N-(1-{6-[(cyclopropylmethyl)carbamoyl]pyridin-2-yl}piperidin-4-yl)carbamate

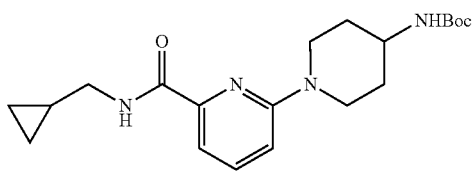 [SMILES: CC(C)(C)OC(=O)NC1CCN(c2cccc(C(=O)NCC3CC3)n2)CC1]

Intermediate 202 was prepared similarly to Intermediate 201, using Intermediate 38 instead of Intermediate 39 and 4-N-(tert-butoxycarbonyl)aminopiperidine instead of 3-amino-piperidine-1-carboxylic acid tert-butyl ester, to give the title compound (584 mg, 99%) as a white solid. LCMS (ES⁺): 375.7 [MH]⁺.

Intermediate 203

6-(4-Aminopiperidin-1-yl)-N-(cyclopropylmethyl)pyridine-2-carboxamide

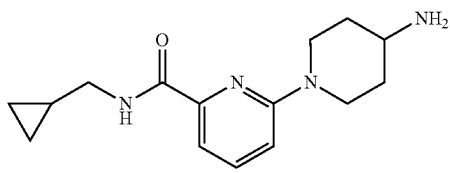 [SMILES: NC1CCN(c2cccc(C(=O)NCC3CC3)n2)CC1]

Intermediate 202 (584 mg, 1.56 mmol) was dissolved in MeOH (2 mL) and HCl (4 mL, 2M in Et$_2$O) was added. The reaction mixture was stirred for 16 h and the solvents were removed in vacuo to give the crude title compound (484 mg) as a light pink gum.

Intermediate 204

(3R)-1-[6-(5-Cyclopropyl-1H-imidazol-2-yl)pyridin-2-yl]pyrrolidin-3-amine

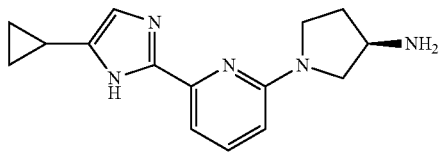 [SMILES: N[C@@H]1CCN(c2cccc(-c3ncc(C4CC4)[nH]3)n2)C1]

Intermediate 66 (2.00 g, 9.10 mmol), (R)-pyrrolidin-3-yl-carbamic acid tert-butyl ester (5.08 g, 27.3 mmol) and DIPEA (6.34 mL, 36.4 mmol) were dissolved in DMA (40 mL) and the reaction mixture was heated using a microwave (180° C., absorption high) for 2 h. The solvents were removed in vacuo and the residue dissolved in DCM (100 mL), washed with sat aq Na$_2$CO$_3$ (50 mL), dried (MgSO$_4$) and concentrated in vacuo. The residue was purified by column chromatography, dissolved in DCM (8 mL) and TFA (4 mL) was added. The reaction mixture was stirred for 4 h, the solvents were removed in vacuo and the residue was de-salted using a MP-TsOH SPE cartridge, eluting with 7 N ammonia in MeOH. The solvents were removed in vacuo to give the crude title compound (2.45 g) as a brown liquid. LCMS (ES$^+$): 270.2 [MH]$^+$.

Intermediate 205 tert-Butyl 4-{[(3R)-1-[6-(5-cyclopropyl-1H-imidazol-2-yl)pyridin-2-yl]pyrrolidin-3-yl]carbamoyl}piperidine-1-carboxylate

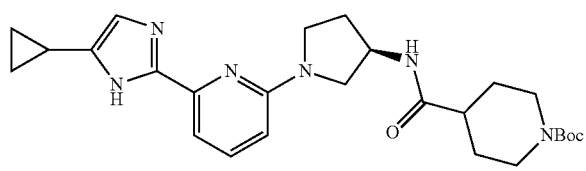 [SMILES: CC(C)(C)OC(=O)N1CCC(C(=O)N[C@@H]2CCN(c3cccc(-c4ncc(C5CC5)[nH]4)n3)C2)CC1]

Intermediate 204 (400 mg, 1.49 mmol) and 1-(tert-butyloxycarbonyl)piperidine-4-carboxylic acid (341 mg, 1.49 mmol) were dissolved in DCM (5 mL) and DIPEA (0.65 mL, 3.71 mmol), EDC (346 mg, 2.23 mmol) and HONB (399 mg, 2.23 mmol) were added. The reaction mixture was stirred for 18 h and partitioned between DCM (50 mL) and sat aq Na$_2$CO$_3$ (30 mL). The aq fraction was extracted with DCM (2×20 mL) and the combined organic fractions were dried (MgSO$_4$) and concentrated in vacuo. The residue was purified by column chromatography to give the title compound (241 mg, 34%) as a yellow liquid. LCMS (ES$^+$): 481.1 [MH]$^+$.

Intermediate 206

N-[(3R)-1-[6-(5-Cyclopropyl-1H-imidazol-2-yl)pyridin-2-yl]pyrrolidin-3-yl]-1-(propan-2-yl)piperidine-4-carboxamide

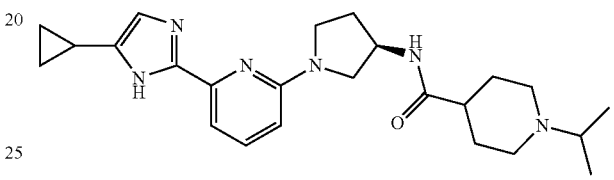

Intermediate 205 (241 mg, 0.50 mmol) was dissolved in DCM (6 mL), TFA (3 mL) was added and the reaction mixture was stirred for 3 h. The solvents were removed in vacuo and the residue was de-salted using a MP-TsOH SPE cartridge, eluting with 7 N ammonia in MeOH. The solvents were removed in vacuo and the residue was dissolved in DCM (10 mL). Acetone (0.33 mL, 4.51 mmol) and NaBH(OAc)$_3$ (1.06 g, 5.01 mmol) were added and the reaction mixture was stirred for 18 h and quenched with sat aq Na$_2$CO$_3$ (50 mL). DCM (50 mL) was added and the aq fraction was extracted with DCM (2×30 mL). The combined organic fractions were dried (MgSO$_4$) and concentrated in vacuo. The residue was purified by column chromatography to give the title compound (75.0 mg, 35%) as a yellow gum. LCMS (ES$^+$): 423.2 [MH]$^+$.

Intermediate 207

(3R)-1-[6-(5-Cyclopropyl-4-methyl-1H-imidazol-2-yl)pyridin-2-yl]pyrrolidin-3-amine

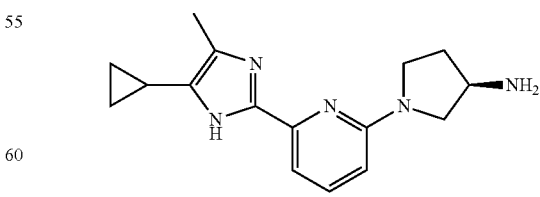

Intermediate 207 was prepared similarly to Intermediate 204, using Intermediate 72 instead of Intermediate 66, to give the crude title compound as a brown liquid. LCMS (ES$^+$): 284.3 [MH]$^+$.

Intermediate 208

(3R)—N-[(3R)-1-[6-(5-Cyclopropyl-4-methyl-1H-imidazol-2-yl)pyridin-2-yl]pyrrolidin-3-yl]pyrrolidine-3-carboxamide

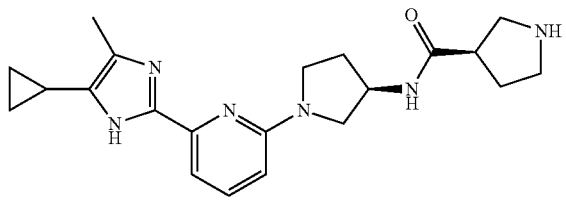 [SMILES: Cc1nc(-c2cccc(N3CC[C@@H](NC(=O)[C@@H]4CCNC4)C3)n2)[nH]c1C1CC1]

(R)-Pyrrolidine-1,3-dicarboxylic acid 1-tert-butyl ester (912 mg, 4.23 mmol), DIPEA (5.16 mL, 29.6 mmol), HBTU (1.61 g, 4.23 mmol) and Intermediate 207 (1.20 g, 4.23 mmol) were dissolved in DMF (10 mL) and stirred for 20 h. The reaction mixture was concentrated in vacuo, diluted with DCM (100 mL) and washed with sat aq Na$_2$CO$_3$ (50 mL). The aq fraction was extracted with DCM (2×100 mL) and the combined organic fractions were dried (MgSO$_4$) and concentrated in vacuo. The residue was purified by column chromatography and dissolved in DCM (6 mL). TFA (3 mL) was added and the reaction mixture was stirred for 3 h. The reaction mixture was concentrated in vacuo and de-salted using an SCX cartridge, eluting with 7 N ammonia in MeOH. The reaction mixture was concentrated in vacuo to give the crude title compound (806 mg) as a brown solid. LCMS (ES$^+$): 381.2 [MH]$^+$.

Intermediate 209

(3S)—N-[(3R)-1-[6-(5-Cyclopropyl-4-methyl-1H-imidazol-2-yl)pyridin-2-yl]pyrrolidin-3-yl]pyrrolidine-3-carboxamide

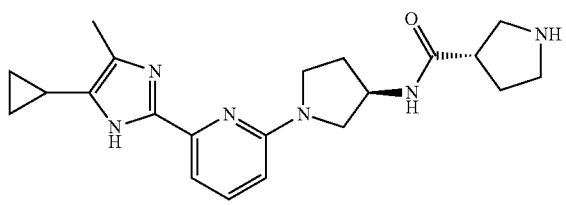 [SMILES: Cc1nc(-c2cccc(N3CC[C@@H](NC(=O)[C@H]4CCNC4)C3)n2)[nH]c1C1CC1]

Intermediate 209 was prepared similarly to Intermediate 208, using (S)-pyrrolidine-1,3-dicarboxylic acid 1-tert-butyl ester instead of (R)-pyrrolidine-1,3-dicarboxylic acid 1-tert-butyl ester, to give the crude title compound as a brown liquid. LCMS (ES$^+$): 381.2 [MH]$^+$.

Intermediate 210

(3R)-1-Cyclopentyl-N-[(3R)-1-[6-(5-cyclopropyl-4-methyl-1H-imidazol-2-yl)pyridin-2-yl]pyrrolidin-3-yl]pyrrolidine-3-carboxamide

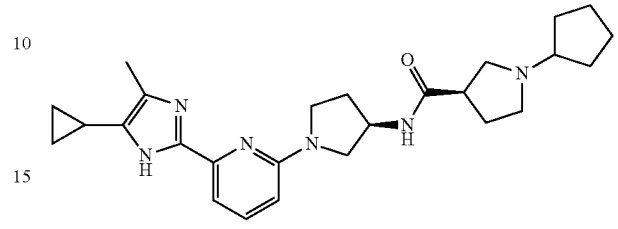

Intermediate 208 (269 mg, 0.71 mmol) was dissolved in DCM (10 mL), cyclopentanone (188 µL, 2.12 mmol) and NaBH(OAc)$_3$ (749 mg, 3.53 mmol) were added and the reaction mixture was stirred for 18 h. The reaction mixture was quenched with sat aq Na$_2$CO$_3$ (30 mL) and diluted with DCM (30 mL). The aq fraction was extracted with DCM (2×20 mL) and the combined organic fractions were dried (MgSO$_4$) and concentrated in vacuo. The residue was purified by column chromatography to give the title compound (52.0 mg, 16%) as a white solid. LCMS (ES$^+$): 449.1 [MH]$^+$.

Intermediate 211

(3S)-1-Cyclopentyl-N-[(3R)-1-[6-(5-cyclopropyl-4-methyl-1H-imidazol-2-yl)pyridin-2-yl]pyrrolidin-3-yl]pyrrolidine-3-carboxamide

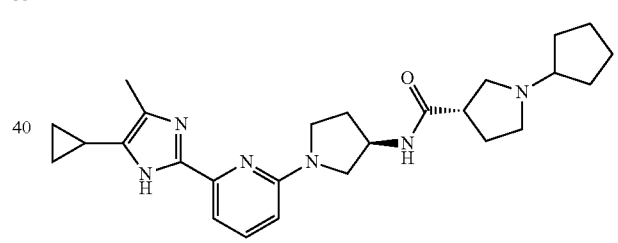

Intermediate 211 was prepared similarly to Intermediate 210, using Intermediate 209 instead of Intermediate 208, to give the title compound (68.0 mg, 24%) as a yellow gum. LCMS (ES$^+$): 449.1 [MH]$^+$.

Intermediate 212

6-[(3R)-3-Aminopyrrolidin-1-yl]-N-(pyridin-4-yl)pyridine-2-carboxamide

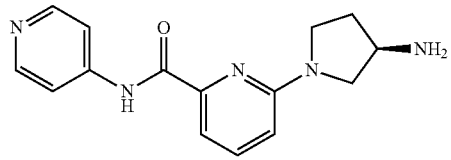 [SMILES: N[C@@H]1CCN(c2cccc(C(=O)Nc3ccncc3)n2)C1]

Intermediate 212 was prepared similarly to Intermediate 204, using Intermediate 39 instead of Intermediate 66, to give the crude title compound as a white solid. LCMS (ES$^+$): 284.2 [MH]$^+$.

Intermediate 213

N-(Pyridin-4-yl)-6-[(3R)-3-{[(3R)-pyrrolidin-3-ylmethyl]amino}pyrrolidin-1-yl]pyridine-2-carboxamide

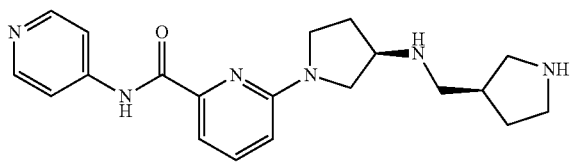 [SMILES: O=C(Nc1ccncc1)c1cccc(N2CC[C@@H](NC[C@@H]3CCNC3)C2)n1]

Intermediate 212 (500 mg, 1.76 mmol) was dissolved in DCM (15 mL). Benzyl (3R)-3-formylpyrrolidine-1-carboxylate (412 mg, 1.76 mmol) and NaBH(OAc)$_3$ (411 mg, 1.94 mmol) were added and the reaction mixture was stirred overnight. The reaction mixture was diluted with DCM (10 mL), quenched with water (5 mL) and the organic fraction was washed with sat aq Na$_2$CO$_3$ (5 mL), dried (MgSO$_4$) and concentrated in vacuo. The residue was purified by column chromatography and dissolved in MeOH (21 mL). The solution was hydrogenated using an H-Cube (80 bar, 60° C., 1 mL/min) over 10% Pd/C. The solvents were removed in vacuo to give the crude title compound (300 mg, 80%). LCMS (ES$^+$): 367.3 [MH]$^+$.

Intermediate 214

N-(Pyridin-4-yl)-6-[(3R)-3-{[(3S)-pyrrolidin-3-ylmethyl]amino}pyrrolidin-1-yl]pyridine-2-carboxamide

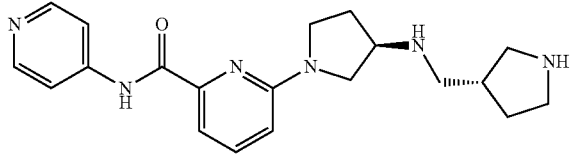 [SMILES: O=C(Nc1ccncc1)c1cccc(N2CC[C@@H](NC[C@H]3CCNC3)C2)n1]

Intermediate 214 was prepared similarly to Intermediate 213, using benzyl (3S)-3-formylpyrrolidine-1-carboxylate instead of benzyl (3R)-3-formylpyrrolidine-1-carboxylate, to give the crude title compound as a yellow gum (93%). LCMS (ES$^+$): 367.3 [MH]$^+$.

Intermediate 215

6-[(3R)-3-[(Piperidin-4-ylmethyl)amino]pyrrolidin-1-yl]-N-(pyridin-4-yl)pyridine-2-carboxamide

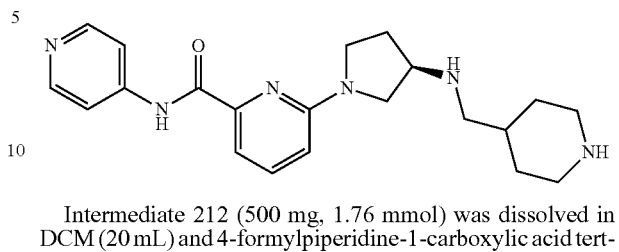

Intermediate 212 (500 mg, 1.76 mmol) was dissolved in DCM (20 mL) and 4-formylpiperidine-1-carboxylic acid tert-butyl ester (376 mg, 1.76 mmol) and NaBH(OAc)$_3$ (748 mg, 3.52 mmol) were added. The reaction mixture was stirred at for 18 h, diluted with DCM (100 mL) and quenched with water (50 mL). The organic fraction was washed with sat aq Na$_2$CO$_3$ (50 mL), dried (MgSO$_4$) and concentrated in vacuo. The residue was purified by column chromatography, dissolved in DCM (40 mL) and TFA (10 mL) was added. The reaction mixture was stirred for 6 h and de-salted using a MP-TsOH SPE cartridge, eluting with 7 N ammonia in MeOH, to give the crude title compound as a yellow gum. LCMS (ES$^+$): 381.2 [MH]$^+$.

Intermediate 216

N-(2-Aminoethyl)-6-(5-cyclopropyl-1H-imidazol-2-yl)pyridin-2-amine

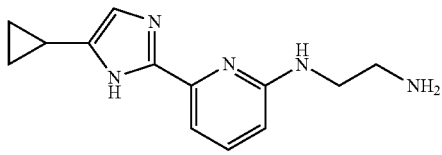 [SMILES: NCCNc1cccc(-c2ncc(C3CC3)[nH]2)n1]

Intermediate 66 (770 mg, 3.51 mmol), ethylene diamine (1.17 mL, 17.5 mmol) and DIPEA (2.44 mL, 14.0 mmol) were dissolved in NMP (13 mL) and the reaction mixture was heated using a microwave (200-220° C., absorption high) for 80 min. Further ethylene diamine (1.17 mL, 17.5 mmol) was added and the reaction mixture was heated using a microwave (220° C., absorption high) for 50 min. The reaction mixture was diluted with DCM (20 mL), washed with sat aq Na$_2$CO$_3$ (20 mL), dried (MgSO$_4$) and concentrated in vacuo. The residue was partially purified by column chromatography to give the crude title compound (1.20 g) as a yellow gum. LCMS (ES$^+$): 244.2 [MH]$^+$.

Intermediates 217-223

Intermediates 217-223 were prepared similarly to Intermediate 216, by SNAr reaction of amines with 6-chloro-2-substituted pyridines; see Table 12 below.

TABLE 12

SNAr reactions of amines with 6-chloro-2-substituted pyridines

| Int | Structure | SMs/Yield | LCMS (ES$^+$) | Intermediate Name |
|---|---|---|---|---|
| 217 | ![structure] | Int 63 94% | 232.2 [MH]$^+$ | N-(2-Aminoethyl)-6-(5-ethyl-1H-imidazol-2-yl)pyridin-2-amine |

TABLE 12-continued

SNAr reactions of amines with 6-chloro-2-substituted pyridines

| Int | Structure | SMs/ Yield | LCMS (ES+) | Intermediate Name |
|---|---|---|---|---|
| 218 | 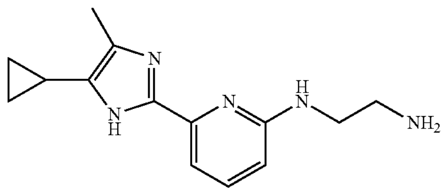 [SMILES: Cc1nc(-c2cccc(NCCN)n2)[nH]c1C1CC1] | Int 72 95% | 258.3 [MH]+ | N-(2-Aminoethyl)-6-(5-cyclopropyl-4-methyl-1H-imidazol-2-yl)pyridin-2-amine |
| 219 | 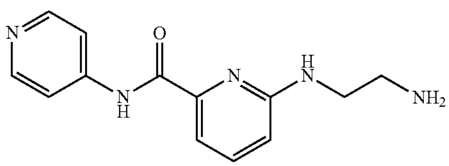 [SMILES: NCCNc1cccc(C(=O)Nc2ccncc2)n1] | Int 39 Used crude | 258.3 [MH]+ | 6-[(2-Aminoethyl)amino]-N-(pyridin-4-yl)pyridine-2-carboxamide |
| 220 | 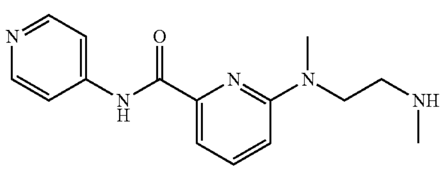 [SMILES: CNCCN(C)c1cccc(C(=O)Nc2ccncc2)n1] | Int 39 Used crude | 286.4 [MH]+ | 6-{Methyl[2-(methylamino)ethyl]amino}-N-(pyridin-4-yl)pyridine-2-carboxamide |
| 221 | 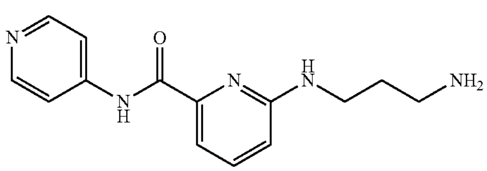 [SMILES: NCCCNc1cccc(C(=O)Nc2ccncc2)n1] | Int 39 Used crude | 272.4 [MH]+ | 6-[(3-Aminopropyl)amino]-N-(pyridin-4-yl)pyridine-2-carboxamide |
| 222 | 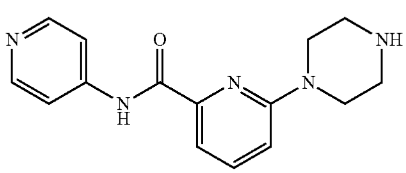 [SMILES: O=C(Nc1ccncc1)c1cccc(N2CCNCC2)n1] | Int 39 78% | 284.4 [MH]+ | 6-(Piperazin-1-yl)-N-(pyridin-4-yl)pyridine-2-carboxamide |
| 223 | 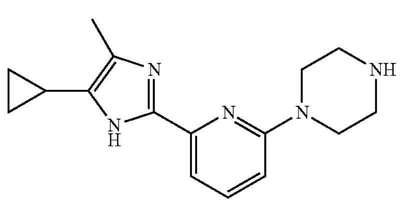 [SMILES: Cc1nc(-c2cccc(N3CCNCC3)n2)[nH]c1C1CC1] | Int 72 64% | 284.2 [MH]+ | 1-[6-(5-Cyclopropyl-4-methyl-1H-imidazol-2-yl)pyridin-2-yl]piperazine |

Intermediate 224 tert-Butyl 3-[(2-{[6-(5-cyclopropyl-1H-imidazol-2-yl)pyridin-2-yl]amino}ethyl)carbamoyl]pyrrolidine-1-carboxylate

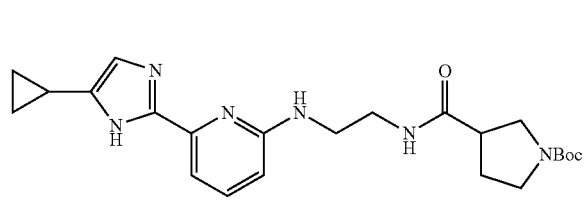 [SMILES: CC(C)(C)OC(=O)N1CCC(C(=O)NCCNc2cccc(-c3ncc(C4CC4)[nH]3)n2)C1]

Pyrrolidine-1,3-dicarboxylic acid 1-tert-butyl ester (221 mg, 1.03 mmol), DIPEA (1.25 mL, 7.19 mmol), HBTU (390 mg, 1.03 mmol) and Intermediate 216 (250 mg, 1.03 mmol) were dissolved in DMF (10 mL) and stirred for 20 h. The solvents were removed in vacuo and the residue was diluted with DCM (20 mL) and washed with sat aq Na$_2$CO$_3$ (10 mL). The aq fraction was extracted with DCM (2×20 mL) and the combined organic fractions were dried (MgSO$_4$) and concentrated in vacuo. The residue was purified by column chromatography to give the title compound (335 mg, 74%) as a yellow gum. LCMS (ES$^+$): 441.1 [MH]$^+$.

Intermediate 225

1-Cyclopentyl-N-(2-{[6-(5-cyclopropyl-1H-imidazol-2-yl)pyridin-2-yl]amino}ethyl)pyrrolidine-3-carboxamide

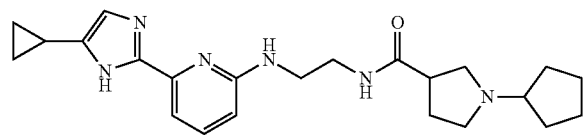 [SMILES: O=C(NCCNc1cccc(-c2ncc(C3CC3)[nH]2)n1)C1CCN(C2CCCC2)C1]

Intermediate 224 (335 mg, 0.76 mmol) was dissolved in DCM (4 mL), TFA (1 mL) was added and the reaction mixture was stirred for 2 h. The solvents were removed in vacuo and the residue was partitioned between DCM (20 mL) and 1M aq NaOH (20 mL). The aq fraction was basified to pH 14 with NaOH and extracted with DCM (3×50 mL). The combined organic fractions were dried (MgSO$_4$) and concentrated in vacuo. Half of the residue was dissolved in DCM (5 mL) and cyclopentanone (60.0 µL, 0.57 mmol) and NaBH(OAc)$_3$ (161 mg, 0.76 mmol) were added. The reaction mixture was stirred overnight, diluted with DCM (10 mL) and quenched with water (5 mL). The organic fraction was washed with sat aq Na$_2$CO$_3$ (5 mL), dried (MgSO$_4$) and concentrated in vacuo to give the crude title compound (150 mg) as a yellow oil. LCMS (ES$^+$): 409.2 [MH]$^+$.

Intermediate 226

(3R)—N-(2-{[6-(5-Cyclopropyl-4-methyl-1H-imidazol-2-yl)pyridin-2-yl]amino}ethyl)pyrrolidine-3-carboxamide

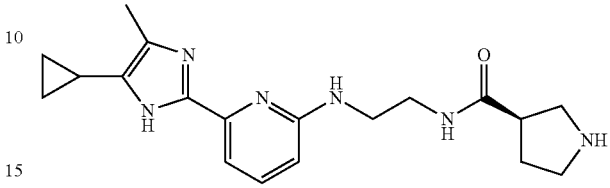

Intermediate 226 was prepared similarly to Intermediate 208, using Intermediate 218 instead of Intermediate 207, to give the crude title compound as a yellow gum. LCMS (ES$^+$): 355.2 [MH]$^+$.

Intermediate 227

(3R)-1-Cyclopentyl-N-(2-{[6-(5-cyclopropyl-4-methyl-1H-imidazol-2-yl)pyridin-2-yl]amino}ethyl)pyrrolidine-3-carboxamide

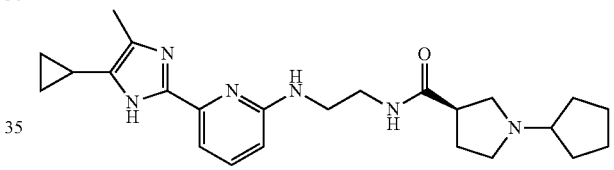

Intermediate 227 was prepared similarly to Intermediate 210, using Intermediate 226 instead of Intermediate 208, to give the crude title compound (91%) as a yellow gum. LCMS (ES$^+$): 423.2 [MH]$^+$.

Intermediate 228 tert-Butyl 3-[(2-{[6-(5-cyclopropyl-1H-imidazol-2-yl)pyridin-2-yl]amino}ethyl)amino]piperidine-1-carboxylate

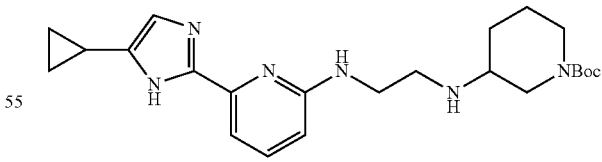

Intermediate 216 (300 mg, 1.23 mmol) was dissolved in DCM (5 mL) and tert-butyl 3-oxopiperidine-1-carboxylate (270 mg, 1.36 mmol) and NaBH(OAc)$_3$ (523 mg, 2.47 mmol) were added. The reaction mixture was stirred overnight, diluted with DCM (10 mL) and quenched with water (5 mL). The organic fraction was washed with sat aq Na$_2$CO$_3$ (5 mL), dried (MgSO$_4$) and concentrated in vacuo. The residue was purified by column chromatography to give the title compound (226 mg, 43%) as a yellow gum. LCMS (ES$^+$): 427.1 [MH]$^+$.

Intermediates 229-233

Intermediates 229-233 were prepared similarly to Intermediate 228, by reductive alkylation of Intermediates 216, 218 and 219; see Table 13 below.

TABLE 13

Reductive alkylation of Intermediates 205, 207 and 208

| Int | Structure | SMs/Yield | LCMS (ES$^+$) | Intermediate Name |
|---|---|---|---|---|
| 229 | 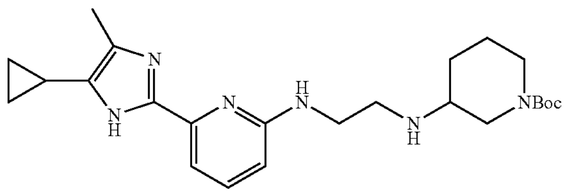 [SMILES: Cc1nc(-c2cccc(NCCNC3CCCN(C(=O)OC(C)(C)C)C3)n2)[nH]c1C1CC1] | Int 218 47% | 441.2 [MH]$^+$ | tert-Butyl 3-[(2-{[6-(5-cyclopropyl-4-methyl-1H-imidazol-2-yl)pyridin-2-yl]amino}ethyl)amino]piperidine-1-carboxylate |
| 230 | 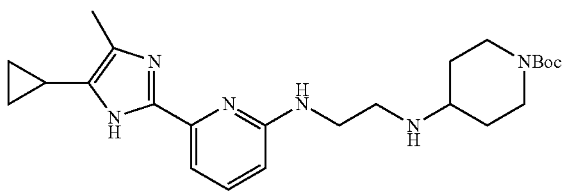 [SMILES: Cc1nc(-c2cccc(NCCNC3CCN(C(=O)OC(C)(C)C)CC3)n2)[nH]c1C1CC1] | Int 218 63% | 441.2 [MH]$^+$ | tert-Butyl 4-[(2-{[6-(5-cyclopropyl-4-methyl-1H-imidazol-2-yl)pyridin-2-yl]amino}ethyl)amino]piperidine-1-carboxylate |
| 231 | 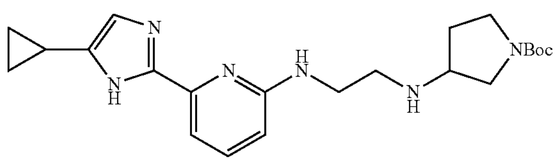 [SMILES: CC(C)(C)OC(=O)N1CCC(NCCNc2cccc(-c3ncc(C4CC4)[nH]3)n2)C1] | Int 216 55% | 413.1 [MH]$^+$ | tert-Butyl 3-[(2-{[6-(5-cyclopropyl-1H-imidazol-2-yl)pyridin-2-yl]amino}ethyl)amino]pyrrolidine-1-carboxylate |
| 232 | 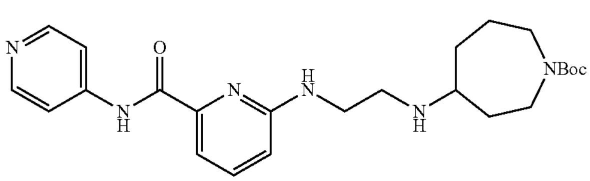 [SMILES: CC(C)(C)OC(=O)N1CCCC(NCCNc2cccc(C(=O)Nc3ccncc3)n2)CC1] | Int 219 Used crude | 455.2 [MH]$^+$ | tert-Butyl 4-{[2-({6-[(pyridin-4-yl)carbamoyl]pyridin-2-yl}amino)ethyl]amino}azepane-1-carboxylate |
| 233 | 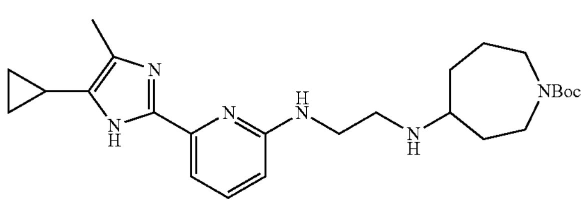 [SMILES: Cc1nc(-c2cccc(NCCNC3CCCN(C(=O)OC(C)(C)C)CC3)n2)[nH]c1C1CC1] | Int 218 64% | 455.2 [MH]$^+$ | tert-Butyl 4-[(2-{[6-(5-cyclopropyl-4-methyl-1H-imidazol-2-yl)pyridin-2-yl]amino}ethyl)amino]azepane-1-carboxylate |

Intermediate 234 tert-Butyl N-{2-[(2-{[6-(5-cyclopropyl-1H-imidazol-2-yl)pyridin-2-yl]amino}ethyl)carbamoyl]ethyl}carbamate

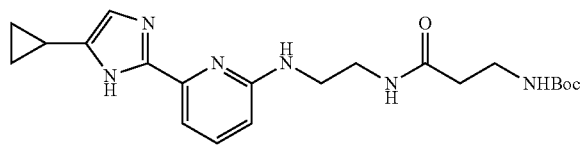 [SMILES: CC(C)(C)OC(=O)NCCC(=O)NCCNc1cccc(-c2ncc(C3CC3)[nH]2)n1]

Intermediate 234 was prepared similarly to Intermediate 224, using 3-tert-butoxycarbonylaminopropionic acid instead of pyrrolidine-1,3-dicarboxylic acid 1-tert-butyl ester, to give the crude title compound (61%) as a yellow gum. LCMS (ES$^+$): 415.1 [MH]$^+$.

Intermediate 235

3-(Cyclopentylamino)-N-(2-{[6-(5-cyclopropyl-1H-imidazol-2-yl)pyridin-2-yl]amino}ethyl)propanamide

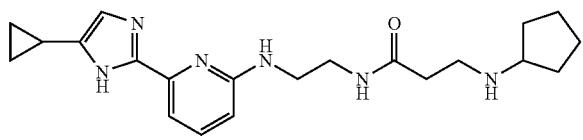 [SMILES: O=C(CCNC1CCCC1)NCCNc1cccc(-c2ncc(C3CC3)[nH]2)n1]

Intermediate 235 was prepared similarly to Intermediate 225, using Intermediate 234 instead of Intermediate 224, to give the crude title compound (77%) as a pale yellow oil. LCMS (ES$^+$): 383.2 [MH]$^+$.

Intermediate 236

1-(Propan-2-yl)azepan-4-one

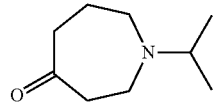

N-Boc-hexahydro-1H-azepine-4-one (3.00 g, 14.1 mmol) was dissolved in DCM (50 mL), TFA (15 mL) was added and the reaction mixture was stirred for 2 h. The solvents were removed in vacuo and the residue partitioned between DCM (500 mL) and sat aq Na$_2$CO$_3$ (500 mL). The aq fraction was extracted with DCM (2×250 mL) and the combined organic fractions were dried (MgSO$_4$) and concentrated in vacuo. The residue was dissolved in DCM (50 mL) and acetone (10 mL) and NaBH(OAc)$_3$ (2.18 g, 141 mmol) were added. The reaction mixture was stirred for 18 h, diluted with DCM (200 mL) and quenched with sat aq Na$_2$CO$_3$ (150 mL). The organic fraction was dried (MgSO$_4$) and concentrated in vacuo to give the crude title compound (2.18 g) as a brown liquid. LCMS (ES$^+$): 156.2 [MH]$^+$.

Intermediate 237 tert-Butyl 4-(4-{6-[(pyridin-4-yl)carbamoyl]pyridin-2-yl}piperazin-1-yl)azepane-1-carboxylate

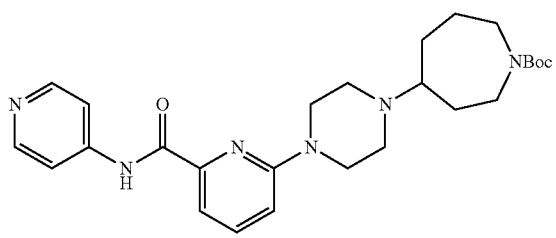 [SMILES: CC(C)(C)OC(=O)N1CCCC(N2CCN(c3cccc(C(=O)Nc4ccncc4)n3)CC2)CC1]

Intermediate 222 (1.88 g, 6.64 mmol) was dissolved in DCM (125 mL) and tert-butyl 4-oxoazepane-1-carboxylate (2.12 g, 9.95 mmol) and NaBH(OAc)$_3$ (7.03 g, 33.2 mmol) were added. The reaction mixture was stirred for 20 h, diluted with DCM (50 mL), washed with sat aq Na$_2$CO$_3$ (75 mL), brine (50 mL), dried (MgSO$_4$) and concentrated in vacuo. The residue was dissolved in DCM (100 mL), shaken with isocyanate resin (4 g) for 1.5 h, filtered and concentrated in vacuo. The residue was purified by reverse phase column chromatography to give the title compound (2.17 g, 68%) as a white solid. LCMS (ES$^+$): 481.5 [MH]$^+$.

Intermediate 238

Tetrakis(2,2,2-trifluoroacetic acid); 6-[4-(azepan-4-yl)piperazin-1-yl]-N-(pyridin-4-yl)pyridine-2-carboxamide

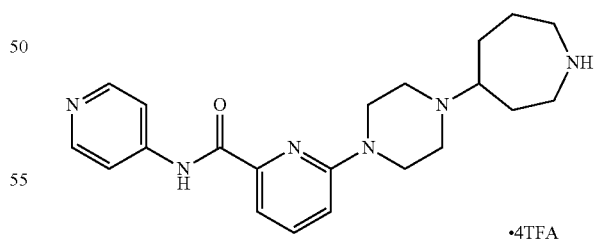

Intermediate 237 (1.88 g, 6.64 mmol) was dissolved in DCM (100 mL), TFA (15 mL) was added and the reaction mixture was stirred for 20 h. The solvents were removed in vacuo and the residue was purified reverse by phase column chromatography to give the title compound (3.94 g, 71%) as a dark red solid. LCMS (ES$^+$): 381.5 [MH]$^+$.

Intermediate 239 tert-Butyl 2-({4-[6-(butylcarbamoyl)pyridin-2-yl]-1,4-diazepan-1-yl}methyl)morpholine-4-carboxylate

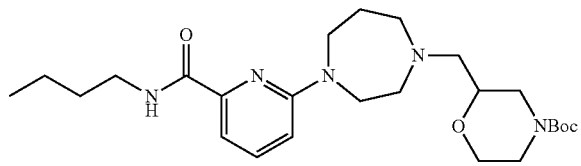 [SMILES: CCCCNC(=O)c1cccc(N2CCCN(CC3CN(C(=O)OC(C)(C)C)CCO3)CC2)n1]

Intermediate 82 (130 mg, 0.47 mmol) was dissolved in DCM (6 mL) and 2-formyl-morpholine-4-carboxylic acid tert-butyl ester (111 mg, 0.52 mmol) and NaBH(OAc)$_3$ (498 mg, 2.40 mmol) were added. The reaction mixture was stirred overnight. Further 2-formyl-morpholine-4-carboxylic acid tert-butyl ester (50.6 mg, 0.24 mmol) and NaBH(OAc)$_3$ (50.9 mg, 0.24 mmol) were added and the reaction mixture was stirred overnight. The reaction mixture was diluted with DCM (10 mL), quenched with water (5 mL) and the organic fraction was washed with sat aq Na$_2$CO$_3$ (5 mL), dried (MgSO$_4$) and concentrated in vacuo. The residue was partially purified by column chromatography to give the title compound as a yellow oil (156 mg, 70%). LCMS (ES$^+$): 476.4 [MH]$^+$.

Intermediate 240 tert-Butyl 4-{4-[6-(5-cyclopropyl-4-methyl-1H-imidazol-2-yl)pyridin-2-yl]piperazin-1-yl}azepane-1-carboxylate

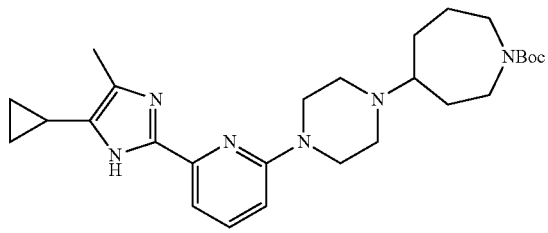 [SMILES: Cc1nc(-c2cccc(N3CCN(C4CCCN(C(=O)OC(C)(C)C)CC4)CC3)n2)[nH]c1C1CC1]

Intermediate 240 was prepared similarly to Intermediate 237, using Intermediate 223 instead of Intermediate 222, to give the crude title compound (56%) as a pale yellow gum. LCMS (ES$^+$): 481.3 [MH]$^+$.

Intermediate 241 tert-Butyl 3-[2-(4-benzyl-1,4-diazepan-1-yl)-2-oxoethyl]morpholine-4-carboxylate

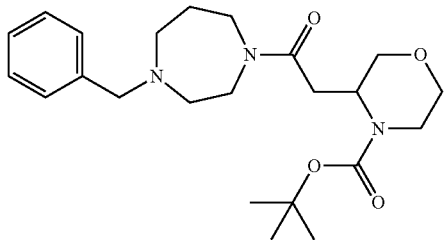 [SMILES: CC(C)(C)OC(=O)N1CCOCC1CC(=O)N1CCCN(Cc2ccccc2)CC1]

4-N-Boc-morpholine-3-acetic acid (500 mg, 2.04 mmol) and benzyl homopiperazine (388 mg, 2.04 mmol) were dissolved in DMF (20 mL) and cooled to 0° C. DIPEA (553 mg, 4.28 mmol) and HBTU (773 mg, 2.04 mmol) were added and the reaction mixture was stirred for 2 h. The solvents were removed in vacuo and the residue was partitioned between DCM (100 mL) and water (50 mL). The organic fraction was washed with 1 M aq Na$_2$CO$_3$ (25 mL), brine (25 mL), dried (MgSO$_4$) and concentrated in vacuo. The residue was purified by reverse phase column chromatography to give the title compound (730 mg, 86%) as a light yellow gum. LCMS (ES$^+$): 418.4 [MH]$^+$.

Intermediate 242

1-(4-Benzyl-1,4-diazepan-1-yl)-2-[4-(propan-2-yl)morpholin-3-yl]ethan-1-one

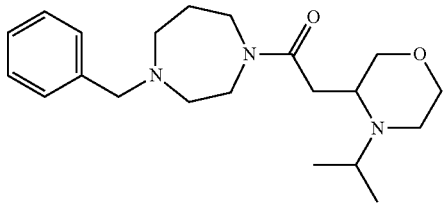 [SMILES: CC(C)N1CCOCC1CC(=O)N1CCCN(Cc2ccccc2)CC1]

Intermediate 241 (730 mg, 1.75 mmol) was dissolved in DCM (20 mL) and TFA (2 mL) was added. The reaction mixture was stirred for 16 h and concentrated in vacuo. The residue was dissolved in DCM (20 mL) and acetone (1 mL) was added. The reaction mixture was stirred for 30 min, NaBH(OAc)$_3$ (1.11 g, 5.25 mmol) was added and the reaction mixture was stirred for 6 d. The reaction mixture was diluted with DCM (50 mL), washed with sat aq Na$_2$CO$_3$ solution (25 mL), brine (25 mL), dried (MgSO$_4$) and concentrated in vacuo to give the title compound (0.62 g, 99%) as a light yellow gum. LCMS (ES$^+$): 360.5 [MH]$^+$.

Intermediate 243

1-{2-[4-(Propan-2-yl)morpholin-3-yl]ethyl}-1,4-diazepane

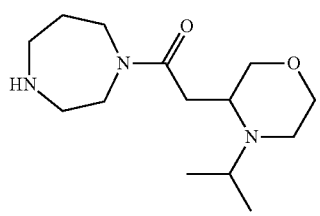 [SMILES: CC(C)N1CCOCC1CC(=O)N1CCCNCC1]

Intermediate 242 (0.62 g, 1.73 mmol) was dissolved in THF (20 mL), LiAlH$_4$ (0.71 mL, 2.4 M THF, 1.70 mmol) was added and the reaction mixture was stirred for 16 h. The reaction mixture was quenched with brine (10 mL) and partitioned between DCM (50 mL) and water (20 mL). The aq fraction was extracted with DCM (2×20 mL) and the combined organic fractions were washed with brine (25 mL), dried (MgSO$_4$) and concentrated in vacuo. The residue was hydrogenated using an H-Cube (80 bar, 60° C., 1 mL/min) over 10% Pd/C to give the title compound (0.42 g, 95%) as a yellow gum. LCMS (ES$^+$): 256.5 [MH]$^+$.

Intermediate 244

3-(1,2,3,4-Tetrahydroisoquinolin-2-yl)propyl methanesulfonate

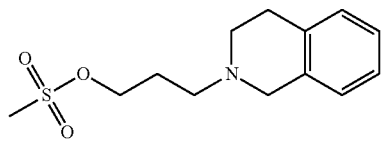 [SMILES: CS(=O)(=O)OCCCN1CCc2ccccc2C1]

3-Bromo-1-propanol (100 mg, 0.72 mmol), K₂CO₃ (249 mg, 1.80 mmol) and 1,2,3,4-tetrahydrisoquinoline (95.8 mg, 0.72 mmol) were dissolved in MeCN (2 mL) and the reaction mixture was heated at 60° C. for 18 h. The reaction mixture was filtered and concentrated in vacuo. The residue was dissolved in DCM (10 mL) and methanesulphonyl chloride (82.4 mg, 0.72 mmol) and Et₃N (87.4 mg, 0.86 mmol) were added. The reaction mixture was stirred for 1 h, diluted with DCM (20 mL), washed with sat aq NaHCO₃ (20 mL), dried (MgSO₄) and concentrated in vacuo to give the crude title compound (72.2 mg) as a colourless gum. LCMS (ES⁺): 270.3 [MH]⁺.

Intermediate 245

3-(3,3-Difluoropyrrolidin-1-yl)propyl methanesulfonate

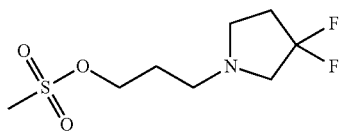

Intermediate 245 was prepared similarly to Intermediate 244, using 3,3-difluoropyrrolidine hydrochloride instead of 1,2,3,4-tetrahydrisoquinoline, to give the title compound (150 mg, 86%) as a colourless gum. LCMS (ES⁺): 244.2 [MH]⁺.

Intermediate 246

6-[4-(3-Chloro-2-hydroxypropyl)-1,4-diazepan-1-yl]-N-(pyridin-3-ylmethyl)pyridine-2-carboxamide

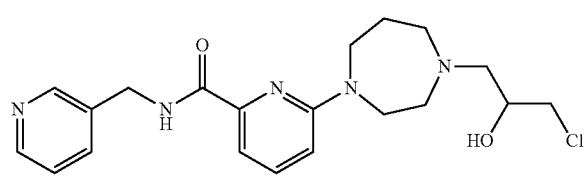 [SMILES: O=C(NCc1cccnc1)c1cccc(N2CCCN(CC(O)CCl)CC2)n1]

Intermediate 87 (500 mg, 1.61 mmol) and NaHCO₃ (141 mg, 1.69 mmol) were suspended in EtOH (20 mL), epichlorohydrin (156 mg, 1.69 mmol) was added and the reaction mixture was stirred for 2 d. Further epichlorohydrin (78.0 mg, 0.85 mmol) was added and the reaction mixture was stirred for 3 d. The reaction mixture was concentrated in vacuo and purified by column chromatography to give the title compound (206 mg, 32%) as a white solid. LCMS (ES⁺): 404 [MH]⁺.

Intermediate 247 tert-Butyl 3-[(4-benzyl-1,4-diazepan-1-yl)carbonyl]-4-methylpiperazine-1-carboxylate

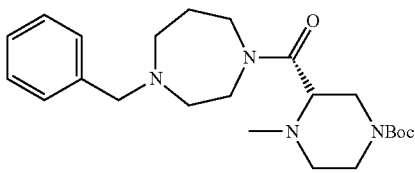

(S)-4-Boc-2-piperazinecarboxylic acid (530 mg, 2.17 mmol) was dissolved in MeOH (25 mL) and formaldehyde (1.76 mL, 37 wt % in water, 21.7 mmol) was added. The reaction mixture was stirred for 30 min, NaBH(OAc)₃ (0.92 g, 4.34 mmol) was added and the reaction mixture was stirred for 2 h. The solvents were removed in vacuo and the residue was purified by reverse phase column chromatography. The residue and benzyl homopiperazine (0.41 g, 2.17 mmol) were dissolved in DMF (20 mL) and cooled to 0° C. DIPEA (0.59 g, 4.56 mmol) and HBTU (0.82 g, 2.17 mmol) were added and the reaction mixture was stirred for 3 h. The solvents were removed in vacuo and the residue was partitioned between DCM (100 mL) and water (50 mL). The organic fraction was washed with 1M aq Na₂CO₃ (25 mL), brine (25 mL), dried (MgSO₄) and concentrated in vacuo. The residue was purified by reverse phase column chromatography to give the title compound (0.64 g, 71%) as a light yellow gum. LCMS (ES⁺): 417.4 [MH]⁺.

Intermediate 248

1-Benzyl-4-{[1-methyl-4-(propan-2-yl)piperazin-2-yl]carbonyl}-1,4-diazepane

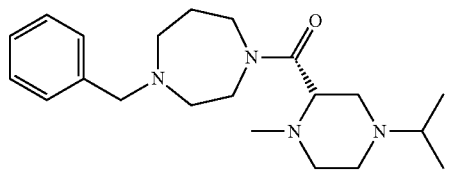

Intermediate 247 (0.64 g, 1.54 mmol) was dissolved in DCM (20 mL), TFA (2 mL) was added and the reaction mixture was stirred for 16 h. The solvents were removed in vacuo and the residue was dissolved in DCM (20 mL) and acetone (1 mL) was added. The reaction mixture was stirred for 30 min and NaBH(OAc)₃ (0.98 g, 4.63 mmol) was added. The reaction mixture was stirred for 1.5 h, diluted with DCM (50 mL), washed with sat aq Na₂CO₃ (25 mL), brine (25 mL), dried (MgSO₄) and concentrated in vacuo to give the title compound (0.46 g, 82%) as a light yellow gum. LCMS (ES⁺): 359.5 [MH]⁺.

Intermediate 249

1-{[1-Methyl-4-(propan-2-yl)piperazin-2-yl]methyl}-1,4-diazepane

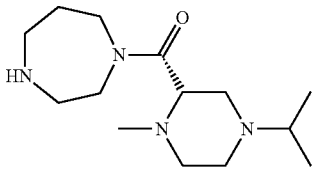

Intermediate 248 (0.46 g, 1.27 mmol) was dissolved in THF (20 mL) and LiAlH₄ (0.54 mL, 2.4 M in THF, 1.27 mmol) was added. The reaction mixture was stirred for 16 h, quenched with brine (10 mL) and partitioned between DCM (50 mL) and water (20 mL). The aq fraction was extracted with DCM (2×20 mL) and the combined organic fractions were washed with brine (25 mL), dried (MgSO₄) and concentrated in vacuo. The residue was hydrogenated using an H-Cube (80 bar, 60° C., 1 mL/min) over 10% Pd/C to give the title compound (0.29 g, 89%) as a yellow gum. LCMS (ES⁺): 255.5 [MH]⁺.

Intermediate 250 tert-Butyl (2S)-2-(hydroxymethyl)morpholine-4-carboxylate

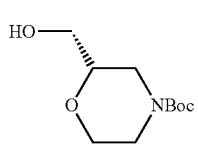

(S)—N-Boc-2-morpholine carboxylic acid (2.00 g, 8.65 mmol) was dissolved in THF (30 mL) and borane (25.9 mL, 1.0 M in THF, 25.9 mmol) was added dropwise. The reaction mixture was heated at reflux for 2.5 h and quenched with water (10 mL). The reaction mixture was concentrated in vacuo and the residue dissolved in DCM (30 mL), washed with sat aq Na₂CO₃ (2×20 mL), dried (MgSO₄) and concentrated in vacuo to give the crude title compound (1.74 g, 92%) as a pale yellow oil. LCMS (ES⁺): 240.3 [MNa]⁺.

Intermediate 251 tert-Butyl (2S)-2-(hydroxymethyl)morpholine-4-carboxylate

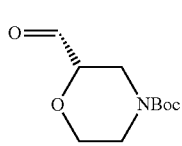

Intermediate 250 (500 mg, 2.30 mmol) and IBX (1.29 g, 4.60 mmol) were dissolved in DCE (20 mL) and heated at 70° C. for 18 h. The reaction mixture was filtered, washed with sat aq Na₂CO₃ (10 mL), dried (MgSO₄) and concentrated in vacuo to give the crude title compound (684 mg) as a pale yellow oil.

Intermediate 252 tert-Butyl (2R)-2-[(4-{6-[(pyridin-4-yl)carbamoyl]pyridin-2-yl]-1,4-diazepan-1-yl)methyl}morpholine-4-carboxylate

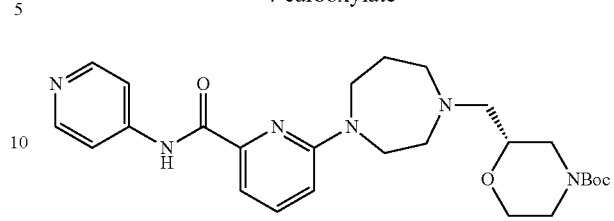

Intermediate 83 (150 mg, 0.50 mmol) was dissolved in DCM (6 mL) and Intermediate 251 (119 mg, 0.55 mmol) and NaBH(OAc)₃ (535 mg, 2.52 mmol) were added. The reaction mixture was stirred overnight. Further Intermediate 251 (52.7 mg, 0.25 mmol) and NaBH(OAc)₃ (51.9 mg, 0.25 mmol) were added and the reaction mixture was stirred for 2 h. The reaction mixture was diluted with DCM (10 mL) and quenched with water (5 mL). The organic fraction was washed with sat aq Na₂CO₃ (5 mL), dried (MgSO₄) and concentrated in vacuo. The residue was purified by column chromatography to give the title compound as a yellow oil (211 mg, 84% yield).

Intermediate 253

N-(Cyclopropylmethyl)-6-{4-[3-(1,3-dioxo-2,3-dihydro-1H-isoindol-2-yl)propyl]-1,4-diazepan-1-yl}pyridine-2-carboxamide

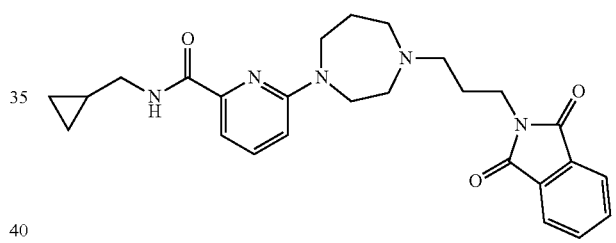

Intermediate 81 (150 mg, 0.55 mmol), N-(3-bromopropyl)-phthalimide (147 mg, 0.55 mmol) and K₂CO₃ (113 mg, 0.82 mmol) were dissolved in MeCN (2 mL) and the reaction mixture was stirred at 60° C. for 12 h. The reaction mixture was filtered, washed with DCM, stirred with isocyanate resin for 2 h, filtered and concentrated in vacuo to give the title compound (240 mg, 95%) as a pale yellow gum. LCMS (ES⁺): 462.8 [MH]⁺.

Intermediate 254

1-(Pyridin-2-yl)-1,4-diazepane

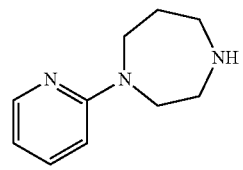 [SMILES: c1ccc(N2CCCNCC2)nc1]

2-Chloropyridine (3.00 g, 26.4 mmol), DIPEA (9.20 mL, 52.8 mmol) and homopiperazine (7.90 g, 79.3 mmol) were dissolved in DMA (10 mL) and heated using a microwave (180-200° C., absorption high) for 40 min. The reaction mixture was diluted with DCM (150 mL), washed with sat aq Na₂CO₃ (100 mL), brine (100 mL), dried (MgSO₄) and concentrated in vacuo to give the title compound (3.41 g, 72%) as a brown liquid. LCMS (ES⁺): 178.6 [MH]⁺.

Intermediates 255-257

Intermediates 255-257 were prepared similarly to Intermediate 254, by SNAr reaction of 2-chloropyridines with homopiperazine; see Table 14 below.

TABLE 14

SNAr reactions of 2-chloropyridines

| Int | Structure | Yield | LCMS (ES+) | Intermediate Name |
|---|---|---|---|---|
| 255 | 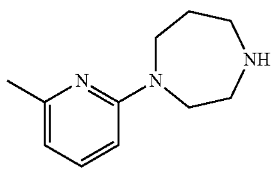 | — | 192.5 [MH]+ | 1-(6-Methyl-pyridin-2-yl)-1,4-diazepane |
| 256 | 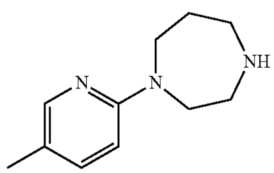 | — | 192.5 [MH]+ | 1-(5-Methyl-pyridin-2-yl)-1,4-diazepane |
| 257 | 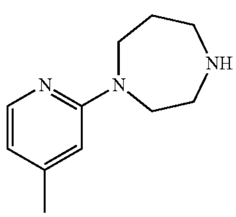 | — | 192.5 [MH]+ | 1-(4-Methyl-pyridin-2-yl)-1,4-diazepane |

Intermediate 258

1-(Piperidin-4-yl)-4-(pyridin-2-yl)-1,4-diazepane

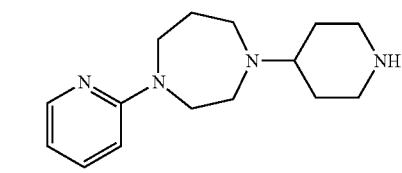 [SMILES: c1ccc(N2CCCN(C3CCNCC3)CC2)nc1]

Intermediate 254 (400 mg, 2.26 mmol) was dissolved in DCM (5 mL) and Boc-Piperidone (540 mg, 2.71 mmol) and NaBH(OAc)$_3$ (2.39 g, 11.3 mmol) were added. The reaction mixture was stirred for 18 h, diluted with DCM (20 mL) and quenched with water (15 mL). The organic fraction was washed with sat aq Na$_2$CO$_3$ (10 mL), dried (MgSO$_4$) and concentrated in vacuo. The residue was dissolved in DCM (2 mL), TFA (1 mL) was added and the reaction mixture was stirred for 3 h. The solvents were removed in vacuo and the residue dissolved in DCM (10 mL), washed with sat aq Na$_2$CO$_3$ (5 mL), dried (MgSO$_4$) and concentrated in vacuo to give the crude title compound (361 mg, 61%) as a yellow solid. LCMS (ES+): 261.7 [MH]+.

Intermediates 259-261

Intermediates 259-261 were prepared similarly to Intermediate 258, by reductive alkylation and deprotection of Intermediates 255-257; see Table 15 below.

TABLE 15:

Preparation of 4-(piperidin-4-yl)-1,4-diazepan-1-yl]pyridine intermediates

| Int | Structure | Int/Yield | LCMS (ES+) | Intermediate Name |
|---|---|---|---|---|
| 259 | 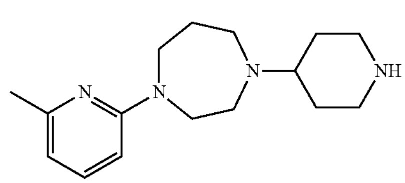 [SMILES: Cc1cccc(N2CCCN(C3CCNCC3)CC2)n1] | Int 255 77% | 275.7 [MH]+ | 1-(6-Methylpyridin-2-yl)-4-(piperidin-4-yl)-1,4-diazepane |

TABLE 15:-continued

Preparation of 4-(piperidin-4-yl)-1,4-diazepan-1-yl]pyridine intermediates

| Int | Structure | Int/Yield | LCMS (ES+) | Intermediate Name |
|---|---|---|---|---|
| 260 | 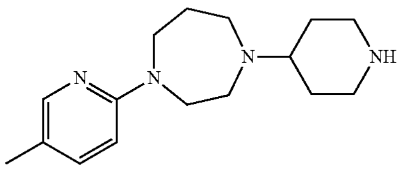 [SMILES: Cc1ccc(N2CCCN(C3CCNCC3)CC2)nc1] | Int 256 41% | 275.7 [MH]+ | 1-(5-Methylpyridin-2-yl)-4-(piperidin-4-yl)-1,4-diazepane |
| 261 | 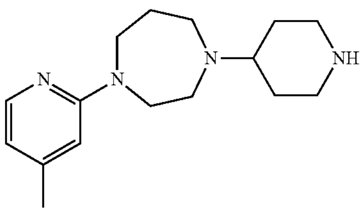 [SMILES: Cc1ccnc(N2CCCN(C3CCNCC3)CC2)c1] | Int 257 43% | 275.8 [MH]+ | 1-(4-Methylpyridin-2-yl)-4-(piperidin-4-yl)-1,4-diazepane |

Intermediate 262 tert-Butyl 4-{1-[(2-chlorophenyl)methyl]piperidin-4-yl}-1,4-diazepane-1-carboxylate

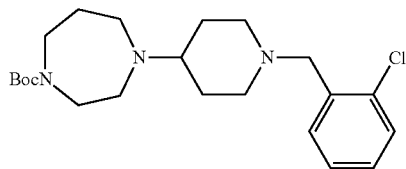 [SMILES: CC(C)(C)OC(=O)N1CCCN(C2CCN(Cc3ccccc3Cl)CC2)CC1]

Intermediate 25 (10.0 g, 44.7 mmol) and Boc-homopiperazine (9.85 g 49.2 mmol) were dissolved in DCM (250 mL) and NaBH(OAc)$_3$ (47.4 g, 224 mmol) was added portionwise. The reaction mixture was stirred for 18 h and quenched with water (200 mL). The organic fraction was washed with 1M aq Na$_2$CO$_3$ (200 mL), brine (100 mL), dried (MgSO$_4$) and concentrated in vacuo. The residue was purified by column chromatography to give the title compound (11.0 g, 60%) as a colourless liquid. LCMS (ES+): 408.7 [MH]+.

Intermediate 263

1-{1-[(2-Chlorophenyl)methyl]piperidin-4-yl}-1,4-diazepane

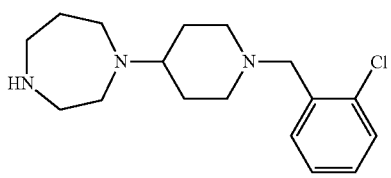 [SMILES: Clc1ccccc1CN1CCC(N2CCCNCC2)CC1]

Intermediate 262 (11.0 g, 27.0 mmol) was dissolved in DCM (100 mL), TFA (10.0 mL, 135 mmol) was added and the reaction mixture was stirred for 16 h. The solvents were removed in vacuo and the residue was partitioned between DCM (200 mL) and water (200 mL). The aq fraction was basified to pH 14 with NaOH, extracted with DCM (3×100 mL) and the combined organic fractions were dried (MgSO$_4$) and concentrated in vacuo to give the title compound (7.42 g, 89%) as a pale yellow liquid. LCMS (ES+): 308.7 [MH]+.

Intermediate 264

2-Bromo-N-(cyclopropylmethyl)-1,3-thiazole-4-carboxamide

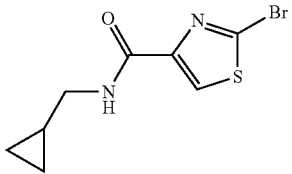 [SMILES: O=C(NCC1CC1)c1csc(Br)n1]

2-Bromothiazole-4-carboxylic acid (500 mg, 2.40 mmol), aminomethylcyclopropane (247 µL, 2.88 mmol), EDC.HCl (1.01 g, 5.29 mmol), HOBN (1.08 g, 6.01 mmol) and NEM (765 µL, 6.01 mmol) were dissolved in DCM (30 mL) and the reaction mixture was stirred for 16 h. The organic fraction was washed with sat aq NaHCO$_3$ (30 mL), 1 M aq HCl (30 mL), dried (MgSO$_4$) and concentrated in vacuo. The residue was purified by column chromatography to give the title compound (404 mg, 64%) as a white solid. LCMS (ES+): 261.4 [MH]+.

Intermediate 265

2-Chloro-N-[3-(1H-imidazol-1-yl)propyl]-6-methylpyrimidine-4-carboxamide

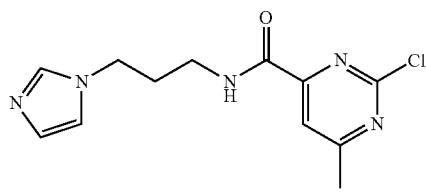 [SMILES: Cc1cc(C(=O)NCCCn2ccnc2)nc(Cl)n1]

Intermediate 265 was prepared similarly to Intermediate 264, using 2-chloro-4-methylpyrimidine-5-carboxylic acid instead of 2-bromothiazole-4-carboxylic acid and 1-(3-aminopropyl)imidazole instead of aminomethylcyclopropane, to give the crude title compound. LCMS (ES$^+$): 280.5 [MH]$^+$.

Intermediate 266

6-Chloro-N-(cyclopropylmethyl)-4-methylpyridine-2-carboxamide

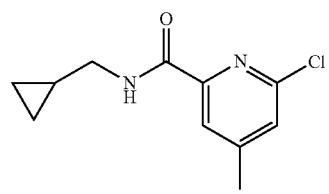

6-Chloro-4-methylpyridine-2-carboxylic acid (422 mg, 2.46 mmol) was dissolved in DCM (10 mL) and oxalyl chloride (422 μL, 4.92 mmol) and DMF (100 μL) were added. The reaction mixture was stirred for 3 h, the solvents were removed in vacuo and the residue was azeotroped with DCM. The residue was dissolved in DCM (10 mL), DIPEA (1.63 mL, 9.84 mmol) and aminomethylcyclopropane (427 μL, 4.92 mmol) were added and the reaction mixture was stirred for 1 h. The reaction mixture was diluted with DCM (40 mL), washed with sat aq NaHCO$_3$ (50 mL), 1 M aq HCl (50 mL), dried (MgSO$_4$) and concentrated in vacuo. The residue was purified by column chromatography to give the title compound (494 mg, 69%) as a yellow liquid. LCMS (ES$^+$): 225.5 [MH]$^+$.

Intermediate 267

2-Chloro-N-(cyclopropylmethyl)pyridine-4-carboxamide

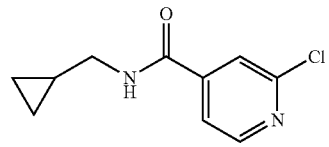 [SMILES: O=C(NCC1CC1)c1ccnc(Cl)c1]

Intermediate 267 was prepared similarly to Intermediate 264, using 2-chloroisonicotinic acid instead of 2-bromothiazole-4-carboxylic acid, to give the title compound (58%) as a pale yellow solid. LCMS (ES$^+$): 211.5 [MH]$^+$.

Intermediate 268

N-(Cyclopropylmethyl)-2-(1,4-diazepan-1-yl)pyridine-4-carboxamide

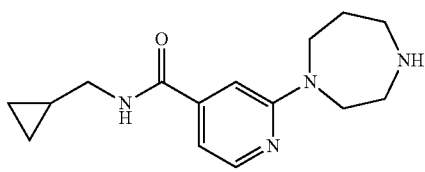 [SMILES: O=C(NCC1CC1)c1ccnc(N2CCCNCC2)c1]

Intermediate 268 was prepared similarly to Intermediate 81, using Intermediate 267 instead of Intermediate 38, to give the crude title compound as a yellow liquid. LCMS (ES$^+$): 275.7 [MH]$^+$.

Intermediate 269

N-(Cyclopropylmethyl)-2-[4-(piperidin-4-yl)-1,4-diazepan-1-yl]pyridine-4-carboxamide

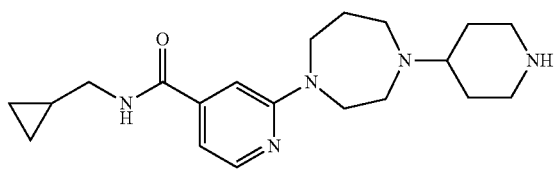 [SMILES: O=C(NCC1CC1)c1ccnc(N2CCCN(C3CCNCC3)CC2)c1]

Intermediate 269 was prepared similarly to Intermediate 119, using Intermediate 268 instead of Intermediate 81, to give the title compound (37%) as a yellow liquid. LCMS (ES$^+$): 358.7 [MH]$^+$.

Intermediate 270

6-Chloro-N-(cyclopropylmethyl)-5-methoxypyridine-2-carboxamide

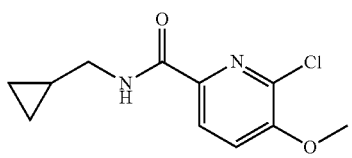 [SMILES: COc1ccc(C(=O)NCC2CC2)nc1Cl]

Intermediate 270 was prepared similarly to Intermediate 264, using 6-chloro-5-methoxypyridine-2-carboxylic acid instead of 2-bromothiazole-4-carboxylic acid, to give the title compound (75%) as a colourless liquid. LCMS (ES$^+$): 241.5 [MH]$^+$.

Intermediate 271

N-(Cyclopropylmethyl)-6-(1,4-diazepan-1-yl)-5-methoxypyridine-2-carboxamide

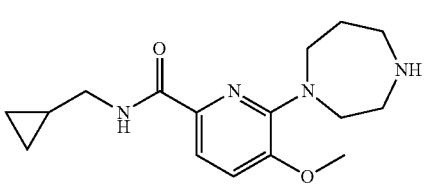 [SMILES: COc1ccc(C(=O)NCC2CC2)nc1N1CCCNCC1]

Intermediate 271 was prepared similarly to Intermediate 81, using Intermediate 270 instead of Intermediate 38, to give the crude title compound as a yellow liquid. LCMS (ES$^+$): 305.7 [MH]$^+$.

Intermediate 272

N-(Cyclopropylmethyl)-5-methoxy-6-[4-(piperidin-4-yl)-1,4-diazepan-1-yl]pyridine-2-carboxamide

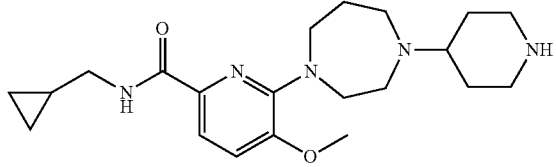 [SMILES: COc1ccc(C(=O)NCC2CC2)nc1N1CCCN(C2CCNCC2)CC1]

Intermediate 272 was prepared similarly to Intermediate 119, using Intermediate 271 instead of Intermediate 81, to give the title compound (24%) as a yellow liquid. LCMS (ES$^+$): 388.7 [MH]$^+$.

Intermediate 273

6-[4-(piperidin-4-yl)-7,7-dihydrogenio-1,4-diazepan-1-yl]-N-(pyridin-4-yl)pyridine-2-carboxamide

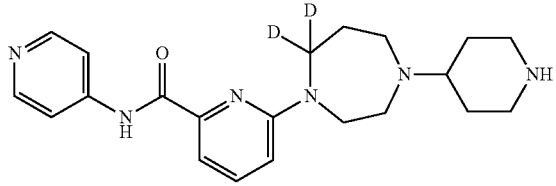 [SMILES: [2H]C1([2H])CCN(C2CCNCC2)CCN1c1cccc(C(=O)Nc2ccncc2)n1]

Intermediate 273 was prepared similarly to Intermediate 176, using tert-butyl 4-oxopiperidine-1-carboxylate instead of tert-butyl 3-fluoro-4-oxopiperidine-1-carboxylate, to give the crude title compound (100%) as a yellow liquid. LCMS (ES$^+$): 383.5 [MH]$^+$.

Intermediate 274 tert-Butyl N-(1-{6-[(pyridin-4-yl)carbamoyl]pyridin-2-yl}piperidin-4-yl)carbamate

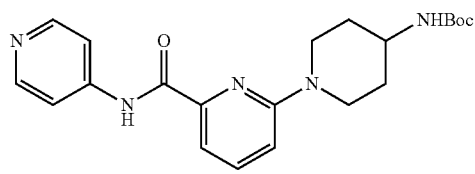 [SMILES: CC(C)(C)OC(=O)NC1CCN(c2cccc(C(=O)Nc3ccncc3)n2)CC1]

Intermediate 274 was prepared similarly to Intermediate 201, using 4-N-(tert-butoxycarbonyl)aminopiperidine instead of 3-amino-piperidine-1-carboxylic acid tert-butyl ester, to give the crude title compound as a white solid. LCMS (ES$^+$): 398.4 [MH]$^+$.

Example 1

General Procedure A

N-(Oxan-4-ylmethyl)-6-{4-[1-(propan-2-yl)piperidin-4-yl]-1,4-diazepan-1-yl}pyridine-2-carboxamide

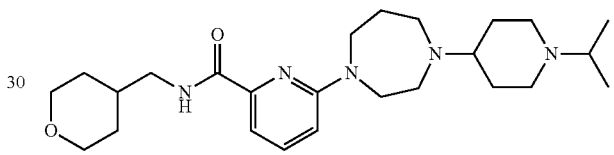

Intermediate 135 (75.0 mg, 0.22 mmol), EDC.HCl (91.3 mg, 0.48 mmol), HONB (97.0 mg, 0.54 mmol) and NEM (275 µL, 2.16 mmol) were dissolved in DCM (1 mL). 4-Aminomethyltetrahydropyran (125 mg, 1.08 mmol) was added and the reaction mixture was stirred for 18 h. The reaction mixture was diluted with DCM (20 mL) and the organic fraction was washed with sat aq Na$_2$CO$_3$ (20 mL), dried (MgSO$_4$) and concentrated in vacuo. The residue was purified by column chromatography and reverse phase HPLC to give the title compound (31.4 mg, 33%) as a colourless gum. HRMS (ESI$^+$) calculated for C$_{25}$H$_{41}$N$_5$O$_2$: 443.326026. found 443.326896. HPLC: Rf 3.70 min, 100% purity.

Example 2

General Procedure B

N-(Oxan-4-yl)-6-{4-[1-(propan-2-yl)piperidin-4-yl]-1,4-diazepan-1-yl}pyridine-2-carboxamide

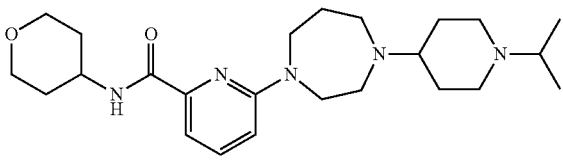 [SMILES: CC(C)N1CCC(N2CCCN(c3cccc(C(=O)NC4CCOCC4)n3)CC2)CC1]

Intermediate 135 (650 mg, 1.88 mmol), 4-aminotetrahydropyran (210 mg, 2.07 mmol), DIPEA (970 mg, 7.52 mmol) and HBTU (710 mg, 1.88 mmol) were dissolved in DMF (10 mL) and the reaction mixture was stirred for 20 h. The solvents were removed in vacuo and the residue was diluted with DCM (100 mL), washed with sat aq Na$_2$CO$_3$ (10 mL), dried (MgSO$_4$) and the solvents were removed in vacuo. The residue was purified by reverse phase HPLC and de-salted (K$_2$CO$_3$ in DCM) to give the title compound (300 mg, 38%) as a colourless gum. HRMS (ESI+) calculated for C24H39N5O2: 429.310376. found 429.311726. HPLC: Rf 3.61 min, 100% purity.

Example 3

N-[3-(1H-Imidazol-1-yl)propyl]-6-{4-[1-(propan-2-yl)piperidin-4-yl]-1,4-diazepan-1-yl}pyridine-2-carboxamide

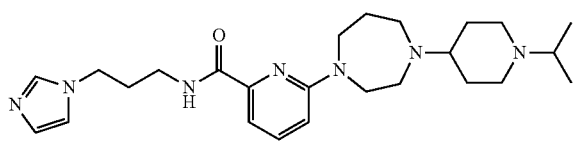 [SMILES: CC(C)N1CCC(N2CCCN(c3cccc(C(=O)NCCCn4ccnc4)n3)CC2)CC1]

Intermediate 135.3TFA (217 mg, 0.32 mmol) was dissolved in DCM (3 mL), oxalyl chloride (232 μL, 2.70 mmol) and DMF (100 μL) were added and the reaction mixture was stirred for 5 h. The solvents were removed in vacuo and the residue was dissolved in DCM (3 mL). DIPEA (446 μL, 2.70 mmol) and 1-(3-aminopropyl)imidazole (129 μL, 1.08 mmol) were added and the reaction mixture was stirred for 2.5 d. DCM (30 mL) was added and the reaction mixture was washed with sat aq Na$_2$CO$_3$ (25 mL), dried (MgSO$_4$) and concentrated in vacuo. The residue was purified by reverse phase HPLC and column chromatography to give the title compound (7.16 mg, 6%) as a yellow gum. HRMS (ESI+) calculated for C25H39N7O: 453.321609. found 453.320079. HPLC: Rf 3.92 min, 100% purity.

Examples 4-58

Examples 4-58 were prepared similarly to Examples 1-2, by reacting Intermediates 135 and 136 with the appropriate amine; see Table 16 below.

TABLE 16

Preparation of amides from Intermediates 135 and 136

| Ex | Structure | Name | Int/Proc/Yield | HRMS (ESI+), HPLC |
|---|---|---|---|---|
| 4 | 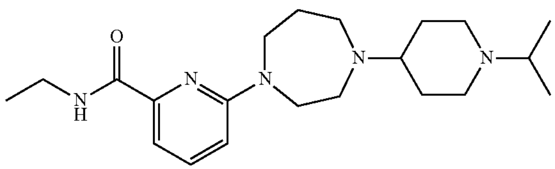 [SMILES: CCNC(=O)c1cccc(N2CCCN(C3CCN(C(C)C)CC3)CC2)n1] | N-Ethyl-6-{4-[1-(propan-2-yl)piperidin-4-yl]-1,4-diazepan-1-yl}pyridine-2-carboxamide | Int 135 B 28% | HRMS (ESI+) calculated for C21H35N5O: 373.284161, found 373.285491. HPLC: Rf 3.53 min, 98.8% purity. |
| 5 | 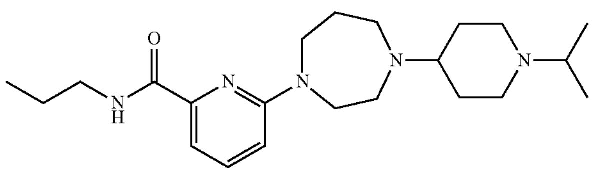 [SMILES: CCCNC(=O)c1cccc(N2CCCN(C3CCN(C(C)C)CC3)CC2)n1] | 6-{4-[1-(Propan-2-yl)piperidin-4-yl]-1,4-diazepan-1-yl}-N-propylpyridine-2-carboxamide | Int 135 B 19% | HRMS (ESI+) calculated for C22H37N5O: 387.299811, found 387.300111. HPLC: Rf 3.77 min, 99.4% purity. |
| 6 | 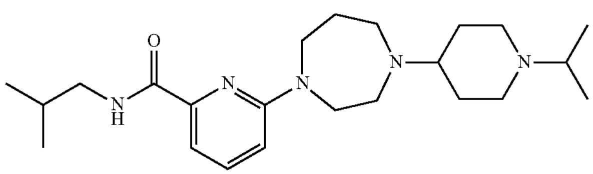 [SMILES: CC(C)CNC(=O)c1cccc(N2CCCN(C3CCN(C(C)C)CC3)CC2)n1] | N-(2-Methylpropyl)-6-{4-[1-(propan-2-yl)piperidin-4-yl]-1,4-diazepan-1-yl}pyridine-2-carboxamide | Int 135 A 23% | HRMS (ESI+) calculated for C23H39N5O: 401.315461, found 401.316091. HPLC: Rf 4.03 min, 100% purity. |
| 7 | 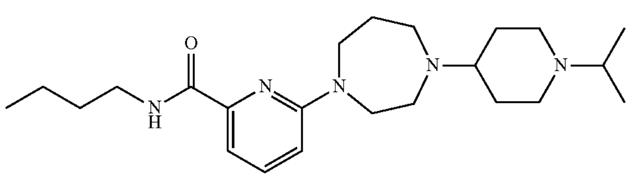 | N-Butyl-6-{4-[1-(propan-2-yl)piperidin-4-yl]-1,4-diazepan-1-yl}pyridine-2-carboxamide | Int 135 B 46% | HRMS (ESI+) calculated for C23H39N5O: 401.315461, found 401.316951. HPLC: Rf 4.05 min, 98.7% purity. |

TABLE 16-continued

Preparation of amides from Intermediates 135 and 136

| Ex | Structure | Name | Int/Proc/Yield | HRMS (ESI+), HPLC |
|---|---|---|---|---|
| 8 | 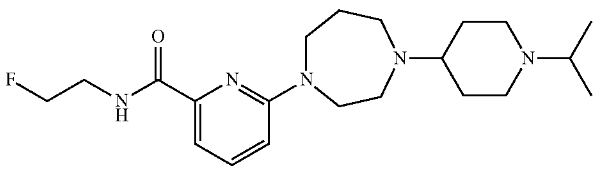 [SMILES: CC(C)N1CCC(N2CCCN(c3cccc(C(=O)NCCF)n3)CC2)CC1] | N-(2-Fluoroethyl)-6-{4-[1-(propan-2-yl)piperidin-4-yl]-1,4-diazepan-1-yl}pyridine-2-carboxamide | Int 135 A 28% | HRMS (ESI+) calculated for C21H34FN5O: 391.274739, found 391.276459. HPLC: Rf 3.51 min, 100% purity. |
| 9 | 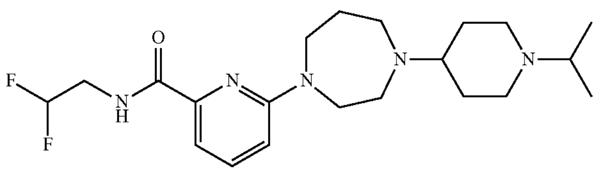 [SMILES: CC(C)N1CCC(N2CCCN(c3cccc(C(=O)NCC(F)F)n3)CC2)CC1] | N-(2,2-Difluoroethyl)-6-{4-[1-(propan-2-yl)piperidin-4-yl]-1,4-diazepan-1-yl}pyridine-2-carboxamide | Int 135 B 45% | HRMS (ESI+) calculated for C21H33F2N5O: 409.265317, found 409.267177. HPLC: Rf 3.72 min, 100% purity. |
| 10 | 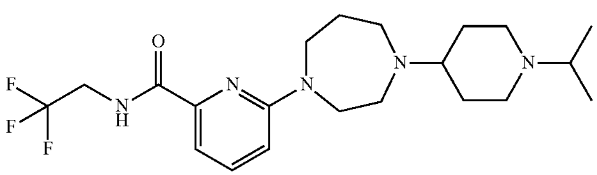 [SMILES: CC(C)N1CCC(N2CCCN(c3cccc(C(=O)NCC(F)(F)F)n3)CC2)CC1] | 6-{4-[1-(Propan-2-yl)piperidin-4-yl]-1,4-diazepan-1-yl}-N-(2,2,2-trifluoroethyl)pyridine-2-carboxamide | Int 135 A 42% | HRMS (ESI+) calculated for C21H32F3N5O: 427.255895, found 427.256005. HPLC: Rf 4.07 min, 100% purity. |
| 11 | 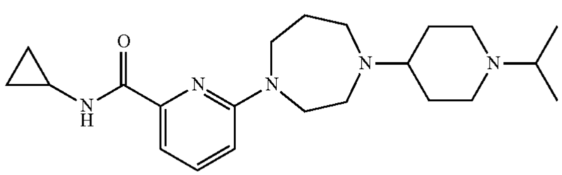 [SMILES: CC(C)N1CCC(N2CCCN(c3cccc(C(=O)NC4CC4)n3)CC2)CC1] | N-Cyclopropyl-6-{4-[1-(propan-2-yl)piperidin-4-yl]-1,4-diazepan-1-yl}pyridine-2-carboxamide | Int 135 B 34% | HRMS (ESI+) calculated for C22H35N5O: 385.284161, found 385.285131. HPLC: Rf 3.58 min, 99.2% purity. |

TABLE 16-continued

Preparation of amides from Intermediates 135 and 136

| Ex | Structure | Name | Int/Proc/Yield | HRMS (ESI+), HPLC |
|---|---|---|---|---|
| 12 | 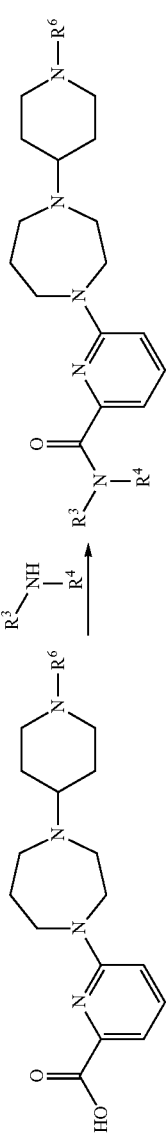 | N-(2-Hydroxyethyl)-6-{4-[1-(propan-2-yl)piperidin-4-yl]-1,4-diazepan-1-yl}pyridine-2-carboxamide | Int 135 B 26% | HRMS (ESI+) calculated for C21H35N5O2: 389.279075, found 389.280655. HPLC: Rf 3.22 min, 100% purity. |
| 13 | 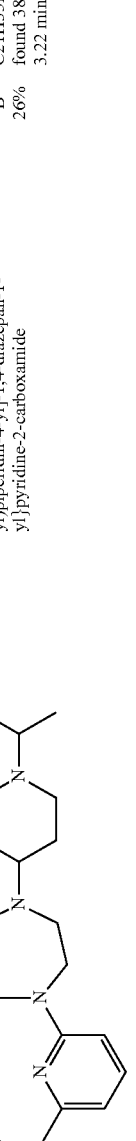 | N-(2-Cyanoethyl)-6-{4-[1-(propan-2-yl)piperidin-4-yl]-1,4-diazepan-1-yl}pyridine-2-carboxamide | Int 135 B 18% | HRMS (ESI+) calculated for C22H34N6O: 398.279941, found 398.28101. HPLC: Rf 3.50 min, 100% purity. |
| 14 | 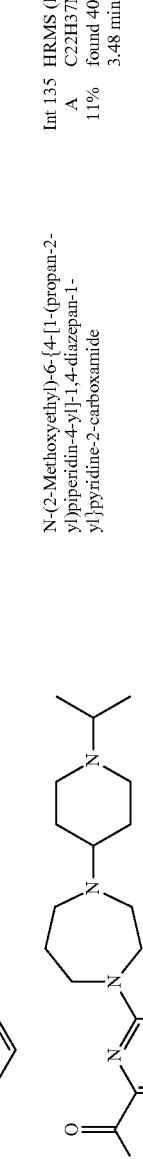 | N-(2-Methoxyethyl)-6-{4-[1-(propan-2-yl)piperidin-4-yl]-1,4-diazepan-1-yl}pyridine-2-carboxamide | Int 135 A 11% | HRMS (ESI+) calculated for C22H37N5O2: 403.294725, found 403.295825. HPLC: Rf 3.48 min, 100% purity. |
| 15 | 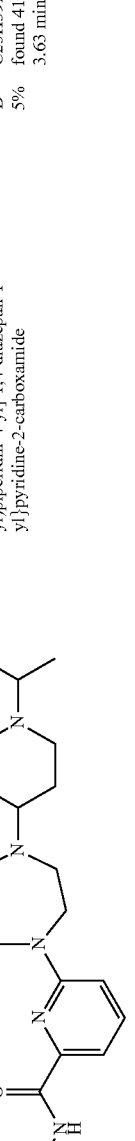 | N-(3-Methoxypropyl)-6-{4-[1-(propan-2-yl)piperidin-4-yl]-1,4-diazepan-1-yl}pyridine-2-carboxamide | Int 135 B 5% | HRMS (ESI+) calculated for C23H39N5O2: 417.310376, found 417.310116. HPLC: Rf 3.63 min, 100% purity. |

TABLE 16-continued

Preparation of amides from Intermediates 135 and 136

| Ex | Structure | Name | Int/ Proc/ Yield | HRMS (ESI+), HPLC |
|---|---|---|---|---|
| 16 | 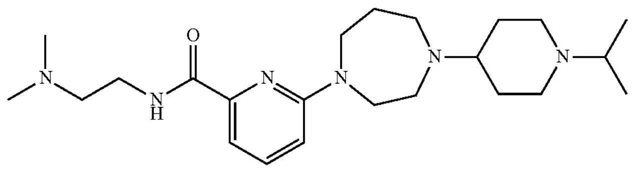 | N-[2-(Dimethylamino)ethyl]-6-{4-[1-(Propan-2-yl)piperidin-4-yl]-1,4-diazepan-1-yl}pyridine-2-carboxamide | Int 135 B 8% | HRMS (ESI+) calculated for C23H40N6O: 416.32636, found 416.32511. HPLC: Rf 3.06 min, 99.2% purity. |
| 17 | 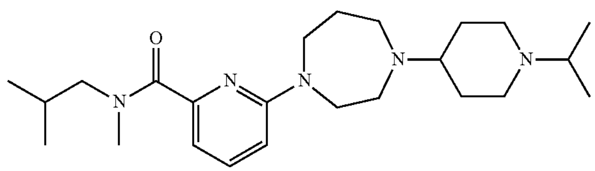 [SMILES: CC(C)CN(C)C(=O)c1cccc(N2CCCN(C3CCN(C(C)C)CC3)CC2)n1] | N-Methyl-N-(2-methyl-propyl)-6-{4-[1-(propan-2-yl)piperidin-4-yl]-1,4-diazepan-1-yl}pyridine-2-carboxamide | Int 135 B 10% | HRMS (ESI+) calculated for C24H41N5O: 415.33111, found 415.330691. HPLC: Rf 4.06 min, 100% purity. |
| 18 | 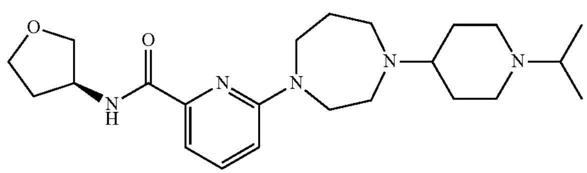 [SMILES: CC(C)N1CCC(N2CCCN(c3cccc(C(=O)N[C@H]4CCOC4)n3)CC2)CC1] | N-[(3S)-Oxolan-3-yl]-6-{4-[1-(propan-2-yl)piperidin-4-yl]-1,4-diazepan-1-yl}pyridine-2-carboxamide | Int 135 B 26% | HRMS (ESI+) calculated for C23H37N5O2: 415.294725, found 415.296125. HPLC: Rf 3.51 min, 100% purity. |
| 19 | 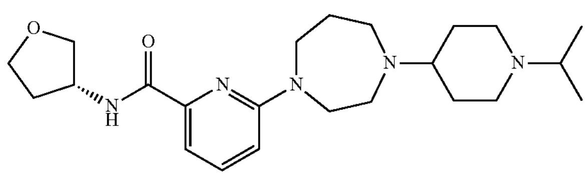 [SMILES: CC(C)N1CCC(N2CCCN(c3cccc(C(=O)N[C@@H]4CCOC4)n3)CC2)CC1] | N-[(3R)-Oxolan-3-yl]-6-{4-[1-(propan-2-yl)piperidin-4-yl]-1,4-diazepan-1-yl}pyridine-2-carboxamide | Int 135 B 22% | HRMS (ESI+) calculated for C23H37N5O2: 415.294725, found 415.295925. HPLC: Rf 3.50 min, 100% purity. |

TABLE 16-continued

Preparation of amides from Intermediates 135 and 136

| Ex | Structure | Name | Int/Proc/Yield | HRMS (ESI+), HPLC |
|---|---|---|---|---|
| 20 | 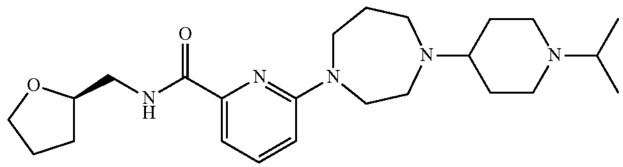 [SMILES: CC(C)N1CCC(N2CCCN(c3cccc(C(=O)NC[C@H]4CCCO4)n3)CC2)CC1] | N-[(2R)-Oxolan-2-ylmethyl]-6-{4-[1-(propan-2-yl)piperidin-4-yl]-1,4-diazepan-1-yl}pyridine-2-carboxamide | Int 135 A 32% | HRMS (ESI+) calculated for C24H39N5O2: 429.310376, found 429.311996. HPLC: Rf 3.69 min, 100% purity. |
| 21 | 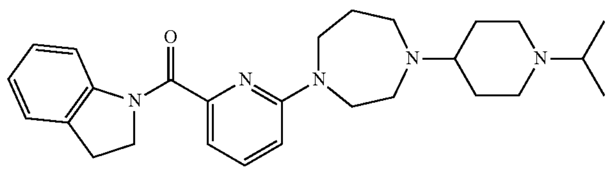 [SMILES: CC(C)N1CCC(N2CCCN(c3cccc(C(=O)N4CCc5ccccc54)n3)CC2)CC1] | 1-[(6-{4-[1-(Propan-2-yl)piperidin-4-yl]-1,4-diazepan-1-yl}pyridin-2-yl)carbonyl]-2,3-dihydro-1H-indole | Int 135 B 18% | HRMS (ESI+) calculated for C27H37N5O: 447.299811, found 447.301341. HPLC: Rf 4.35 min, 99.2% purity. |
| 22 | 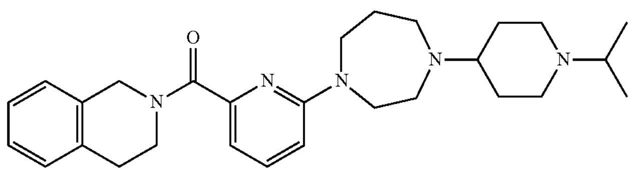 [SMILES: CC(C)N1CCC(N2CCCN(c3cccc(C(=O)N4CCc5ccccc5C4)n3)CC2)CC1] | 2-[(6-{4-[1-(Propan-2-yl)piperidin-4-yl]-1,4-diazepan-1-yl}pyridin-2-yl)carbonyl]-1,2,3,4-tetrahydroisoquinoline | Int 135 B 13% | HRMS (ESI+) calculated for C28H39N5O: 461.315461, found 461.317701. HPLC: Rf 4.39 min, 100% purity. |
| 23 | 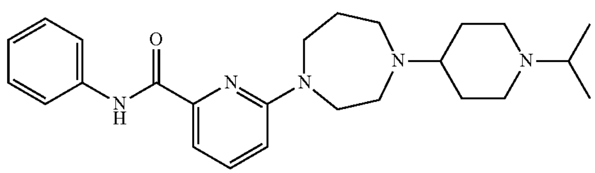 [SMILES: CC(C)N1CCC(N2CCCN(c3cccc(C(=O)Nc4ccccc4)n3)CC2)CC1] | N-Phenyl-6-{4-[1-(propan-2-yl)piperidin-4-yl]-1,4-diazepan-1-yl}pyridine-2-carboxamide | Int 135 B 34% | HRMS (ESI+) calculated for C25H35N5O: 421.284161, found 421.285491. HPLC: Rf 4.38 min, 100% purity. |

TABLE 16-continued

Preparation of amides from Intermediates 135 and 136

| Ex | Structure | Name | Int/Proc/Yield | HRMS (ESI+), HPLC |
|---|---|---|---|---|
| 24 | 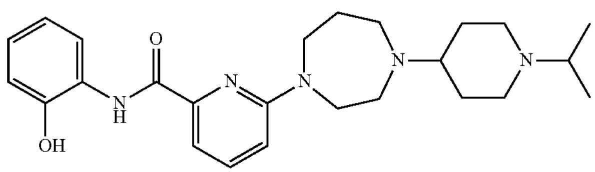 [SMILES: CC(C)N1CCC(N2CCCN(c3cccc(C(=O)Nc4ccccc4O)n3)CC2)CC1] | N-(2-Hydroxyphenyl)-6-{4-[1-(propan-2-yl)piperidin-4-yl]-1,4-diazepan-1-yl}pyridine-2-carboxamide | Int 135 B 3% | HRMS (ESI+) calculated for C25H35N5O2: 437.279075, found 437.280385. HPLC: Rf 4.27 min, 98.9% purity. |
| 25 | 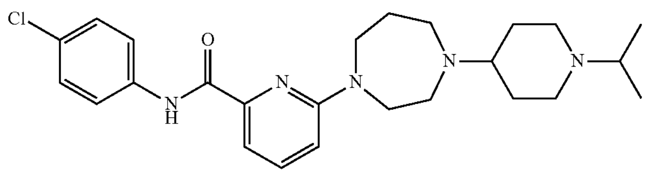 [SMILES: CC(C)N1CCC(N2CCCN(c3cccc(C(=O)Nc4ccc(Cl)cc4)n3)CC2)CC1] | N-(4-Chlorophenyl)-6-{4-[1-(propan-2-yl)piperidin-4-yl]-1,4-diazepan-1-yl}pyridine-2-carboxamide | Int 135 B 22% | HRMS (ESI+) calculated for C25H34ClN5O: 455.245188, found 455.245978. HPLC: Rf 4.81 min, 100% purity. |
| 26 | 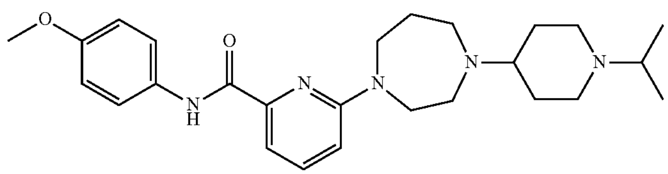 [SMILES: COc1ccc(NC(=O)c2cccc(N3CCCN(C4CCN(C(C)C)CC4)CC3)n2)cc1] | N-(4-Methoxyphenyl)-6-{4-[1-(propan-2-yl)piperidin-4-yl]-1,4-diazepan-1-yl}pyridine-2-carboxamide | Int 135 B 3% | HRMS (ESI+) calculated for C26H37N5O2: 451.294725, found 451.296235. HPLC: Rf 4.32 min, 99.7% purity. |
| 27 | 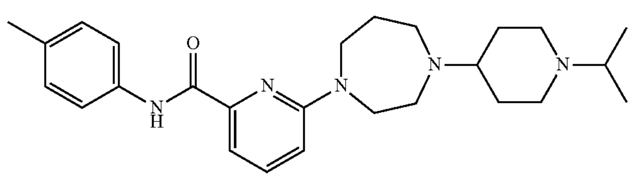 [SMILES: Cc1ccc(NC(=O)c2cccc(N3CCCN(C4CCN(C(C)C)CC4)CC3)n2)cc1] | N-(4-Methylphenyl)-6-{4-[1-(propan-2-yl)piperidin-4-yl]-1,4-diazepan-1-yl}pyridine-2-carboxamide | Int 135 B 4% | HRMS (ESI+) calculated for C26H37N5O: 435.299811, found 435.301201. HPLC: Rf 4.58 min, 99.7% purity. |

TABLE 16-continued

Preparation of amides from Intermediates 135 and 136

| Ex | Structure | Name | Int/Proc/Yield | HRMS (ESI+), HPLC |
|---|---|---|---|---|
| 28 | 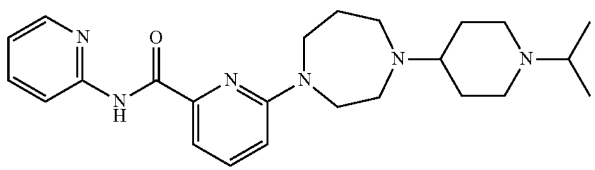 [SMILES: CC(C)N1CCC(N2CCCN(c3cccc(C(=O)Nc4ccccn4)n3)CC2)CC1] | 6-{4-[1-(Propan-2-yl)piperidin-4-yl]-1,4-diazepan-1-yl}-N-(pyridin-2-yl)pyridine-2-carboxamide | Int 135 B 11% | HRMS (ESI+) calculated for C24H34N6O: 422.27941, found 422.28007. HPLC: Rf 3.89 min, 100% purity. |
| 29 | 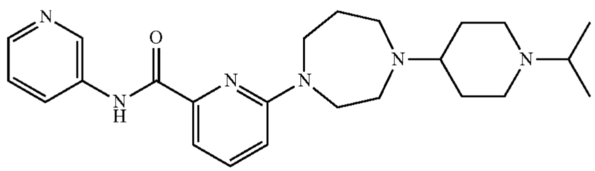 | 6-{4-[1-(Propan-2-yl)piperidin-4-yl]-1,4-diazepan-1-yl}-N-(pyridin-3-yl)pyridine-2-carboxamide | Int 135 B 11% | HRMS (ESI+) calculated for C24H34N6O: 422.27941, found 422.28131. HPLC: Rf 3.31 min, 99.7% purity. |
| 30 | 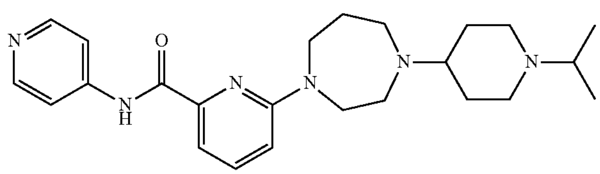 [SMILES: CC(C)N1CCC(N2CCCN(c3cccc(C(=O)Nc4ccncc4)n3)CC2)CC1] | 6-{4-[1-(Propan-2-yl)piperidin-4-yl]-1,4-diazepan-1-yl}-N-(pyridin-4-yl)pyridine-2-carboxamide | Int 135 B 2% | HRMS (ESI+) calculated for C24H34N6O: 422.27941, found 422.27983. HPLC: Rf 3.18 min, 100% purity. |
| 31 | 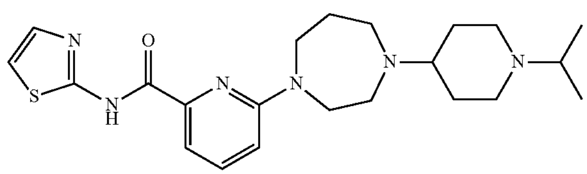 [SMILES: CC(C)N1CCC(N2CCCN(c3cccc(C(=O)Nc4nccs4)n3)CC2)CC1] | 6-{4-[1-(Propan-2-yl)piperidin-4-yl]-1,4-diazepan-1-yl}-N-(1,3-thiazol-2-yl)pyridine-2-carboxamide | Int 135 B 13% | HRMS (ESI+) calculated for C22H32N6OS: 428.23583, found 428.23724. HPLC: Rf 4.15 min, 99.3% purity. |

TABLE 16-continued

Preparation of amides from Intermediates 135 and 136

| Ex | Structure | Name | Int/Proc/Yield | HRMS (ESI+), HPLC |
|---|---|---|---|---|
| 32 | 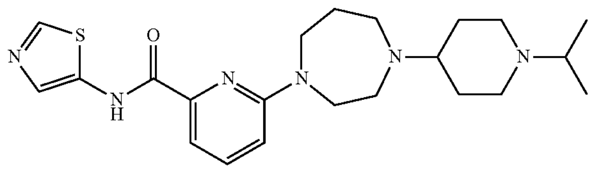 [SMILES: CC(C)N1CCC(N2CCCN(c3cccc(C(=O)Nc4cncs4)n3)CC2)CC1] | 6-{4-[1-(Propan-2-yl)piperidin-4-yl]-1,4-diazepan-1-yl}-N-(1,3-thiazol-5-yl)pyridine-2-carboxamide | Int 135 B 79% | HRMS (ESI+) calculated for C22H32N6OS: 429.24311, found 429.24149. HPLC: Rf 3.89 min, 100% purity. |
| 33 | 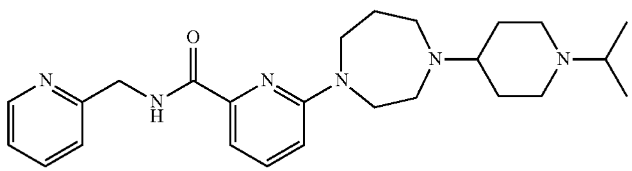 [SMILES: CC(C)N1CCC(N2CCCN(c3cccc(C(=O)NCc4ccccn4)n3)CC2)CC1] | 6-{4-[1-(Propan-2-yl)piperidin-4-yl]-1,4-diazepan-1-yl}-N-(pyridin-2-ylmethyl)pyridine-2-carboxamide | Int 135 B 14% | HRMS (ESI+) calculated for C25H36N6O: 436.29506, found 436.29685. HPLC: Rf 3.18 min, 99.6% purity. |
| 34 | 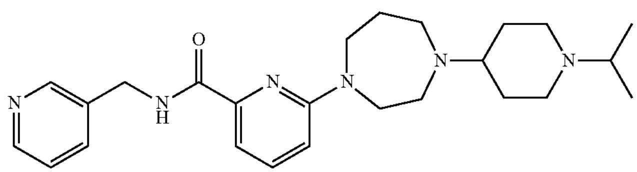 | 6-{4-[1-(Propan-2-yl)piperidin-4-yl]-1,4-diazepan-1-yl}-N-(pyridin-3-ylmethyl)pyridine-2-carboxamide | Int 135 B 36% | HRMS (ESI+) calculated for C25H36N6O: 436.29506, found 436.29575. HPLC: Rf 3.16 min, 99.7% purity. |
| 35 | 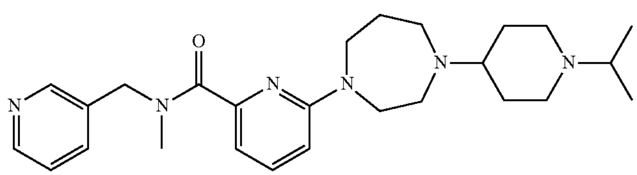 [SMILES: CC(C)N1CCC(N2CCCN(c3cccc(C(=O)N(C)Cc4cccnc4)n3)CC2)CC1] | N-Methyl-6-{4-[1-(propan-2-yl)piperidin-4-yl]-1,4-diazepan-1-yl}-N-(pyridin-3-ylmethyl)pyridine-2-carboxamide | Int 135 B 24% | HRMS (ESI+) calculated for C26H38N6O: 450.31071, found 450.31217. HPLC: Rf 3.07 min, 98.7% purity. |

TABLE 16-continued

Preparation of amides from Intermediates 135 and 136

| Ex | Structure | Name | Int/Proc/Yield | HRMS (ESI+), HPLC |
|---|---|---|---|---|
| 36 | 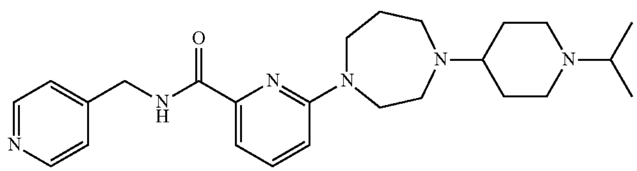 [SMILES: CC(C)N1CCC(N2CCCN(c3cccc(C(=O)NCc4ccncc4)n3)CC2)CC1] | 6-{4-[1-(Propan-2-yl)piperidin-4-yl]-1,4-diazepan-1-yl}-N-(pyridin-4-ylmethyl)pyridine-2-carboxamide | Int 135 B 6% | HRMS (ESI+) calculated for C25H36N6O: 436.29506, found 436.29701. HPLC: Rf 3.14 min, 100% purity. |
| 37 | 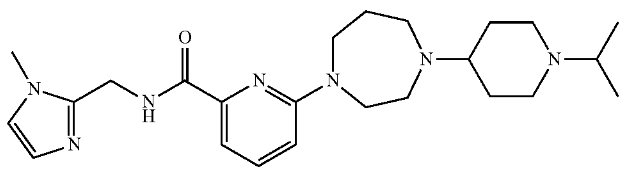 [SMILES: CC(C)N1CCC(N2CCCN(c3cccc(C(=O)NCc4nccn4C)n3)CC2)CC1] | N-[(1-Methyl-1H-imidazol-2-yl)methyl]-6-{4-[1-(propan-2-yl)piperidin-4-yl]-1,4-diazepan-1-yl}pyridine-2-carboxamide | Int 135 A 29% | HRMS (ESI+) calculated for C24H37N7O: 439.305959, found 439.306099. HPLC: Rf 3.16 min, 100% purity. |
| 38 | 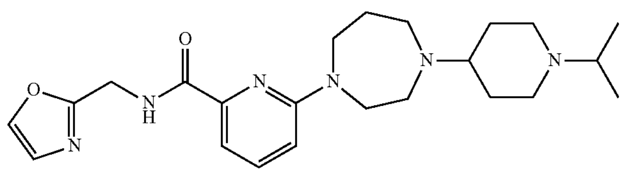 [SMILES: CC(C)N1CCC(N2CCCN(c3cccc(C(=O)NCc4ncco4)n3)CC2)CC1] | N-(1,3-Oxazol-2-ylmethyl)-6-{4-[1-(propan-2-yl)piperidin-4-yl]-1,4-diazepan-1-yl}pyridine-2-carboxamide | Int 135 A 26% | HRMS (ESI+) calculated for C23H34N6O2: 426.274324, found 426.275144. HPLC: Rf 3.55 min, 100% purity. |
| 39 | 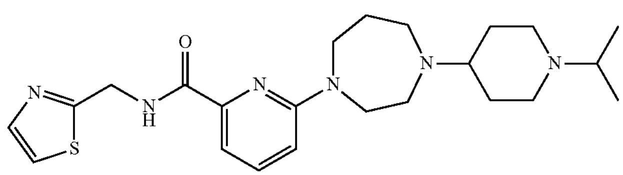 [SMILES: CC(C)N1CCC(N2CCCN(c3cccc(C(=O)NCc4nccs4)n3)CC2)CC1] | 6-{4-[1-(Propan-2-yl)piperidin-4-yl]-1,4-diazepan-1-yl}-N-(1,3-thiazol-2-ylmethyl)pyridine-2-carboxamide | Int 135 B 34% | HRMS (ESI+) calculated for C23H34N6OS: 442.25148, found 442.2535. HPLC: Rf 3.70 min, 100% purity. |

TABLE 16-continued

Preparation of amides from Intermediates 135 and 136

| Ex | Structure | Name | Int/ Proc/ Yield | HRMS (ESI+), HPLC |
|---|---|---|---|---|
| 40 | 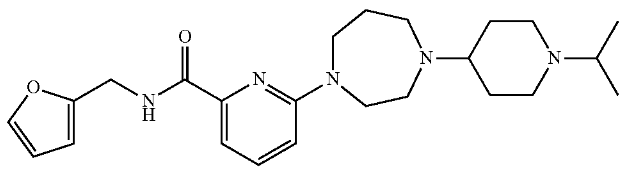 [SMILES: CC(C)N1CCC(N2CCCN(c3cccc(C(=O)NCc4ccco4)n3)CC2)CC1] | N-(Furan-2-ylmethyl)-6-{4-[1-(propan-2-yl)piperidin-4-yl]-1,4-diazepan-1-yl}pyridine-2-carboxamide | Int 135 B 7% | HRMS (ESI+) calculated for C24H35N5O2: 425.279075, found 425.280715. HPLC: Rf 3.92 min, 100% purity. |
| 41 | 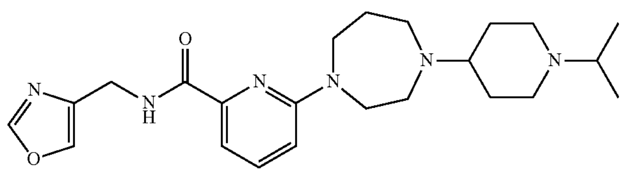 [SMILES: CC(C)N1CCC(N2CCCN(c3cccc(C(=O)NCc4cocn4)n3)CC2)CC1] | N-(1,3-Oxazol-4-ylmethyl)-6-{4-[1-(propan-2-yl)piperidin-4-yl]-1,4-diazepan-1-yl}pyridine-2-carboxamide | Int 135 B 26% | HRMS (ESI+) calculated for C23H34N6O2: 426.274324, found 426.272804. HPLC: Rf 3.51 min, 100% purity. |
| 42 | 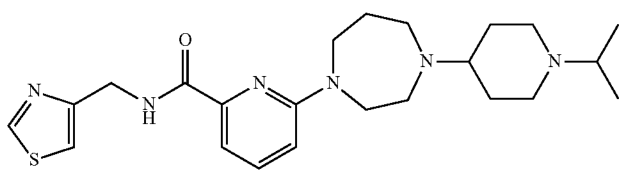 | 6-{4-[1-(Propan-2-yl)piperidin-4-yl]-1,4-diazepan-1-yl}-N-(1,3-thiazol-4-ylmethyl)pyridine-2-carboxamide | Int 135 B 12% | HRMS (ESI+) calculated for C23H34N6OS: 442.25148, found 442.25304. HPLC: Rf 3.61 min, 100% purity. |
| 43 | 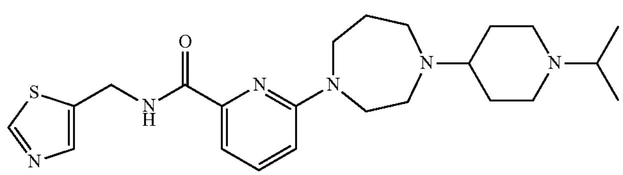 | 6-{4-[1-(Propan-2-yl)piperidin-4-yl]-1,4-diazepan-1-yl}-N-(1,3-thiazol-5-ylmethyl)pyridine-2-carboxamide | Int 135 B 10% | HRMS (ESI+) calculated for C23H34N6OS: 442.25148, found 442.25317. HPLC: Rf 3.24 min, 98.2% purity. |

TABLE 16-continued

Preparation of amides from Intermediates 135 and 136

| Ex | Structure | Name | Int/Proc/Yield | HRMS (ESI+), HPLC |
|---|---|---|---|---|
| 44 | 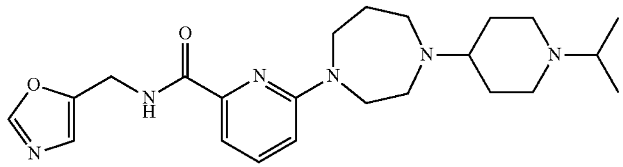 [SMILES: CC(C)N1CCC(N2CCCN(c3cccc(C(=O)NCc4cnco4)n3)CC2)CC1] | N-(1,3-Oxazol-5-ylmethyl)-6-{4-[1-(propan-2-yl)piperidin-4-yl]-1,4-diazepan-1-yl}pyridine-2-carboxamide | Int 135 B 12% | HRMS (ESI+) calculated for C23H34N6O2: 426.274324. found 426.275794. HPLC: Rf 3.19 min, 99.4% purity. |
| 45 | 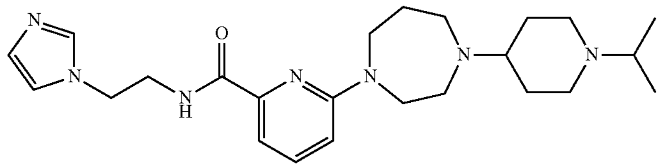 [SMILES: CC(C)N1CCC(N2CCCN(c3cccc(C(=O)NCCn4ccnc4)n3)CC2)CC1] | N-[2-(1H-Imidazol-1-yl)ethyl]-6-{4-[1-(propan-2-yl)piperidin-4-yl]-1,4-diazepan-1-yl}pyridine-2-carboxamide | Int 135 A 24% | HRMS (ESI+) calculated for C24H37N7O: 439.305959, found 439.306109. HPLC: Rf 3.14 min, 100% purity. |
| 46 | 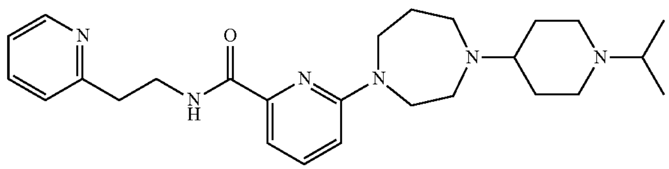 [SMILES: CC(C)N1CCC(N2CCCN(c3cccc(C(=O)NCCc4ccccn4)n3)CC2)CC1] | 6-{4-[1-(Propan-2-yl)piperidin-4-yl]-1,4-diazepan-1-yl}-N-[2-(pyridin-2-yl)ethyl]pyridine-2-carboxamide | Int 135 B 12% | HRMS (ESI+) calculated for C26H38N6O: 450.31071, found 450.3113. HPLC: Rf 3.19 min, 100% purity. |
| 47 | 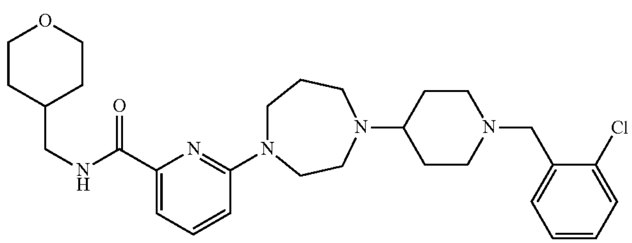 [SMILES: O=C(NCC1CCOCC1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(oxan-4-ylmethyl)pyridine-2-carboxamide | Int 136 A 47% | HRMS (ESI+) calculated for C29H40ClN5O2: 525.287053, found 525.284223. HPLC: Rf 3.96 min, 100% purity. |

TABLE 16-continued

Preparation of amides from Intermediates 135 and 136

| Ex | Structure | Name | Int/Proc/Yield | HRMS (ESI+), HPLC |
|---|---|---|---|---|
| 48 | 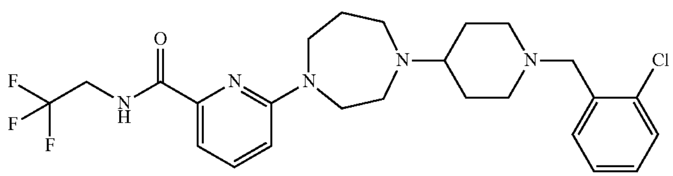 [SMILES: O=C(NCC(F)(F)F)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(2,2,2-trifluoroethyl)pyridine-2-carboxamide | Int 136 A 50% | HRMS (ESI+) calculated for C25H31ClF3N5O: 509.216923, found 509.218693. HPLC: Rf 4.40 min, 99.6% purity. |
| 49 | 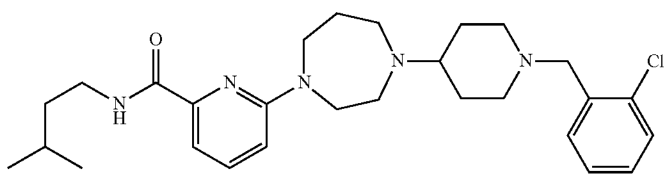 [SMILES: CC(C)CCNC(=O)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(3-methylbutyl)pyridine-2-carboxamide | Int 136 A 56% | HRMS (ESI+) calculated for C28H40ClN5O: 497.292139, found 497.290299. HPLC: Rf 4.66 min, 99.3% purity. |
| 50 | 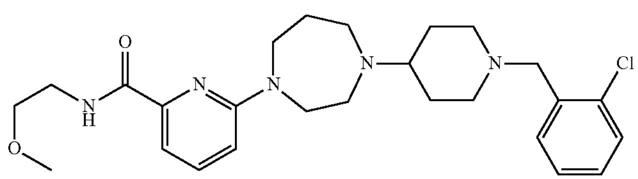 [SMILES: COCCNC(=O)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(2-methoxy-ethyl)pyridine-2-carboxamide | Int 136 A 56% | HRMS (ESI+) calculated for C26H36ClN5O2: 485.255753, found 485.253443. HPLC: Rf 3.94 min, 100% purity. |
| 51 | 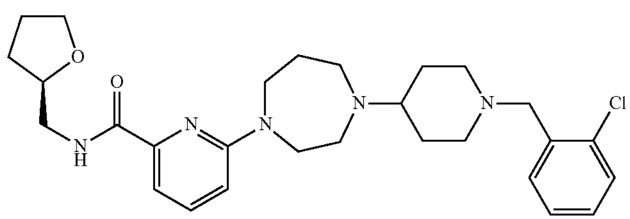 [SMILES: O=C(NC[C@H]1CCCO1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-[(2R)-oxolan-2-ylmethyl]pyridine-2-carboxamide | Int 136 A 48% | HRMS (ESI+) calculated for C28H38ClN5O2: 511.271403, found 511.270223. HPLC: Rf 3.87 min, 99.5% purity. |

TABLE 16-continued

Preparation of amides from Intermediates 135 and 136

| Ex | Structure | Name | Int/Proc/Yield | HRMS (ESI+), HPLC |
|---|---|---|---|---|
| 52 | 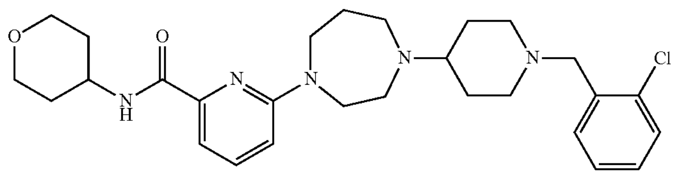 [SMILES: O=C(NC1CCOCC1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(oxan-4-yl)pyridine-2-carboxamide | Int 136 A 43% | HRMS (ESI+) calculated for C28H38ClN5O2: 512.27868, found 512.2796. HPLC: Rf 3.82 min, 100% purity. |
| 53 | 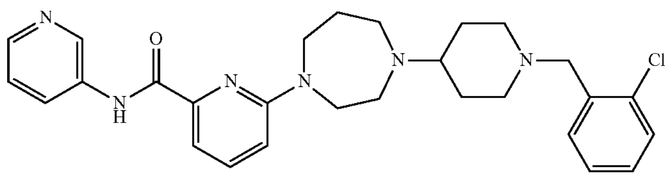 [SMILES: O=C(Nc1cccnc1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(pyridine-3-yl)pyridine-2-carboxamide | Int 136 A 53% | HRMS (ESI+) calculated for C28H33ClN6O: 505.24771, found 505.2475. HPLC: Rf 3.61 min, 99.3% purity. |
| 54 | 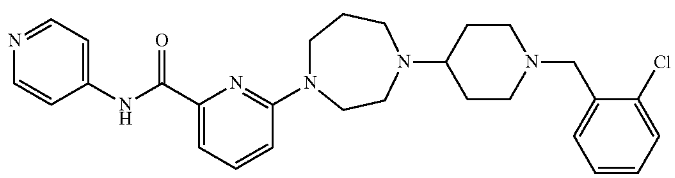 [SMILES: O=C(Nc1ccncc1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(pyridine-4-yl)pyridine-2-carboxamide | Int 136 A 8% | HRMS (ESI+) calculated for C28H33ClN6O: 504.240437, found 504.241067. HPLC: Rf 3.67 min, 100% purity. |
| 55 | 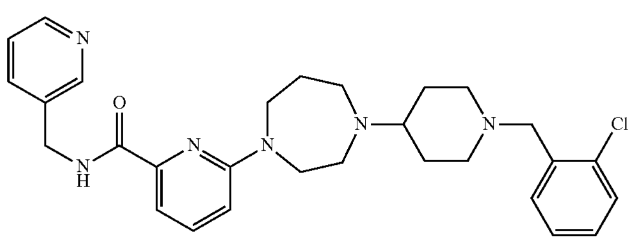 [SMILES: O=C(NCc1cccnc1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(pyridine-3-ylmethyl)pyridine-2-carboxamide | Int 136 A 38% | HRMS (ESI+) calculated for C29H35ClN6O: 518.256087, found 518.254667. HPLC: Rf 3.49 min, 99.5% purity. |

TABLE 16-continued

Preparation of amides from Intermediates 135 and 136

| Ex | Structure | Name | Int/Proc/Yield | HRMS (ESI+), HPLC |
|---|---|---|---|---|
| 56 | 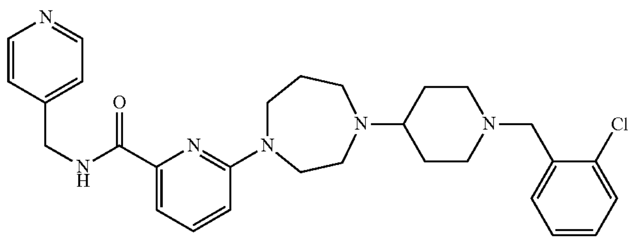 [SMILES: O=C(NCc1ccncc1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(pyridine-4-ylmethyl)pyridine-2-carboxamide | Int 136 A 39% | HRMS (ESI+) calculated for C29H35ClN6O2: 519.26336, found 519.26306. HPLC: Rf 3.39 min, 99.4% purity. |
| 57 | 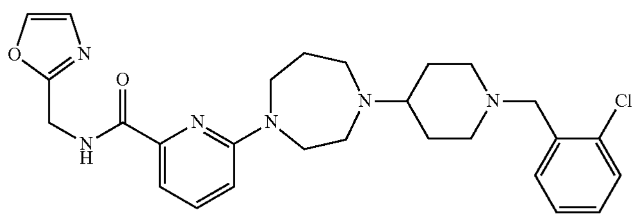 [SMILES: O=C(NCc1ncco1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-((1,3-oxazol-2-ylmethyl)pyridine-2-carboxamide | Int 136 A 29% | HRMS (ESI+) calculated for C27H33ClN6O2: 508.235352, found 508.23531. HPLC: Rf 3.85 min, 99.2% purity. |
| 58 | 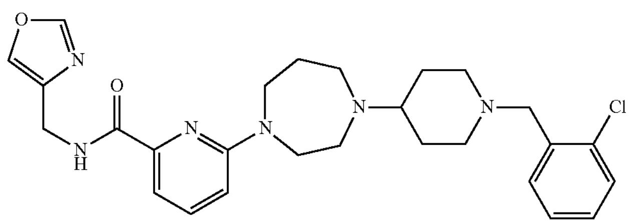 [SMILES: O=C(NCc1cocn1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-((1,3-oxazol-4-ylmethyl)pyridine-2-carboxamide | Int 136 A 48% | HRMS (ESI+) calculated for C27H33ClN6O2: 508.235352, found 508.235412. HPLC: Rf 3.91 min, 99.0% purity. |

Example 59

N-(Cyclopropylmethyl)-6-{4-[1-(1,3-difluoropropan-2-yl)piperidin-4-yl]-1,4-diazepan-1-yl}pyridine-2-carboxamide

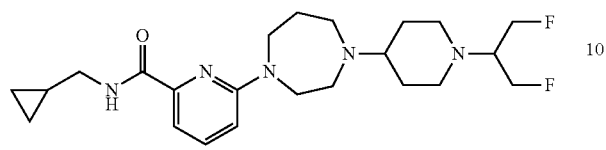

Intermediate 81 (100 mg, 0.36 mmol) and Intermediate 7 (64.6 mg, 0.36 mmol) were dissolved in DCM (10 mL) and NaBH(OAc)$_3$ (386 mg, 1.82 mmol) was added. The reaction mixture was stirred for 4 d, diluted with DCM (50 mL), washed with sat aq Na$_2$CO$_3$ (40 mL), brine (30 mL), dried (MgSO$_4$) and concentrated in vacuo. The residue was purified by reverse phase HPLC to give the title compound (2.80 mg, 2%) as a colourless gum. HRMS (ESI+) calculated for C23H35F2N5O: 435.280967. found 435.280897. HPLC: Rf 3.86 min, 100% purity.

Examples 60-124

Examples 60-124 were prepared similarly to Examples 59, by reacting Intermediates 81-88, 90-115 and 117 with the appropriate piperidin-4-one derivative; see Table 17 below.

TABLE 17

Reductive alkylations of Intermediates 81-88, 90-115 and 117

| Ex | Structure | Name | Ints | Yield | HRMS (ESI+), HPLC |
|---|---|---|---|---|---|
| 60 | 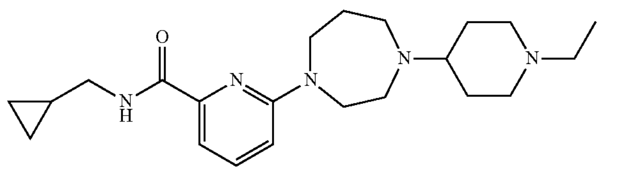 [SMILES: CCN1CCC(N2CCCN(c3cccc(C(=O)NCC4CC4)n3)CC2)CC1] | N-(Cyclopropylmethyl)-6-[4-(1-ethylpiperidin-4-yl)-1,4-diazepan-1-yl]pyridine-2-carboxamide | 81, * | 31% | HRMS (ESI+) calculated for C22H35N5O: 385.284161, found 385.284971. HPLC: Rf 3.87 min, 99.5% purity. |
| 61 | 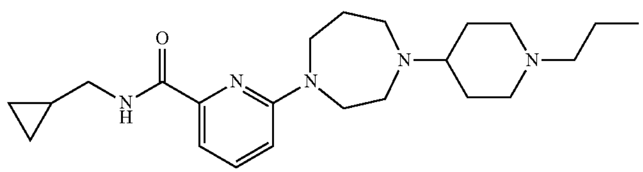 [SMILES: CCCN1CCC(N2CCCN(c3cccc(C(=O)NCC4CC4)n3)CC2)CC1] | N-(Cyclopropylmethyl)-6-[4-(1-propylpiperidin-4-yl)-1,4-diazepan-1-yl]pyridine-2-carboxamide | 81, * | 30% | HRMS (ESI+) calculated for C23H37N5O: 399.299811, found 399.299541. HPLC: Rf 3.93 min, 100% purity. |
| 62 | 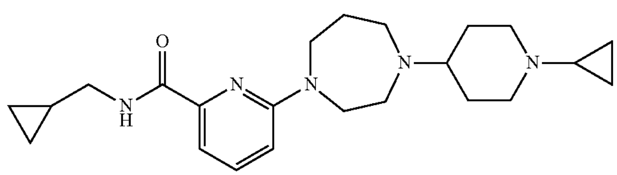 [SMILES: O=C(NCC1CC1)c1cccc(N2CCCN(C3CCN(C4CC4)CC3)CC2)n1] | N-(Cyclopropylmethyl)-6-[4-(1-cyclopropylpiperidin-4-yl)-1,4-diazepan-1-yl]pyridine-2-carboxamide | 81, * | 40% | HRMS (ESI+) calculated for C23H35N5O: 397.284161, found 397.284451. HPLC: Rf 3.89 min, 99.8% purity. |
| 63 | 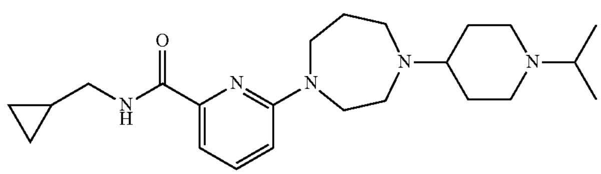 [SMILES: CC(C)N1CCC(N2CCCN(c3cccc(C(=O)NCC4CC4)n3)CC2)CC1] | N-(Cyclopropylmethyl)-6-{4-[1-(Propan-2-yl)piperidin-4-yl]-1,4-diazepan-1-yl}pyridine-2-carboxamide | 81, * | 36% | HRMS (ESI+) calculated for C23H37N5O: 399.299811, found 399.300391. HPLC: Rf 3.90 min, 99.4% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 64 | 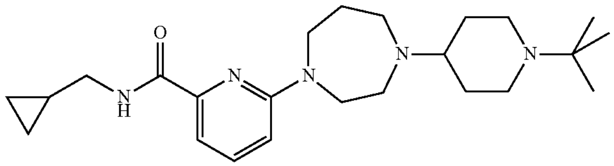 [SMILES: CC(C)(C)N1CCC(N2CCCN(c3cccc(C(=O)NCC4CC4)n3)CC2)CC1] | 6-[4-(1-tert-Butylpiperidin-4-yl)-1,4-diazepan-1-yl]-N-(cyclopropylmethyl)pyridine-2-carboxamide | 81, * | 14% | HRMS (ESI+) calculated for C24H39N5O: 413.315461, found 413.315521. HPLC: Rf 3.90 min, 96.1% purity. |
| 65 | 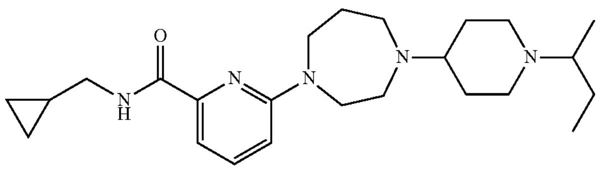 [SMILES: CCC(C)N1CCC(N2CCCN(c3cccc(C(=O)NCC4CC4)n3)CC2)CC1] | 6-{4-[1-(Butan-2-yl)piperidin-4-yl]-1,4-diazepan-1-yl}-N-(cyclopropylmethyl)pyridine-2-carboxamide | 81, 22 | 25% | HRMS (ESI+) calculated for C24H39N5O: 413.315461, found 413.315641. HPLC: Rf 4.05 min, 99.7% purity. |
| 66 | 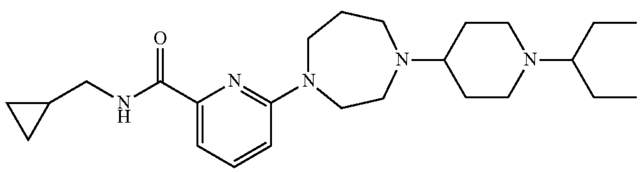 [SMILES: CCC(CC)N1CCC(N2CCCN(c3cccc(C(=O)NCC4CC4)n3)CC2)CC1] | N-(Cyclopropylmethyl)-6-{4-[1-(Pentan-3-yl)piperidin-4-yl]-1,4-diazepan-1-yl}pyridine-2-carboxamide | 81, 23 | 36% | HRMS (ESI+) calculated for C25H41N5O: 427.331111, found 427.331491. HPLC: Rf 4.13 min, 100% purity. |
| 67 | 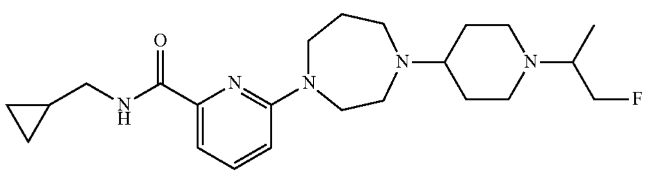 [SMILES: CC(CF)N1CCC(N2CCCN(c3cccc(C(=O)NCC4CC4)n3)CC2)CC1] | N-(Cyclopropylmethyl)-6-{4-[1-(1-fluoropropan-2-yl)piperidin-4-yl]-1,4-diazepan-1-yl}pyridine-2-carboxamide | 81, 10 | 9% | HRMS (ESI+) calculated for C23H36FN5O: 417.290389, found 417.291219. HPLC: Rf 3.59 min, 100% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 68 | 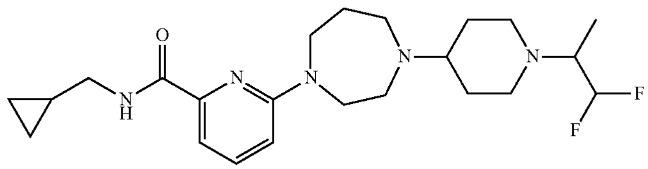 [SMILES: CC(C(F)F)N1CCC(N2CCCN(c3cccc(C(=O)NCC4CC4)n3)CC2)CC1] | N-(Cyclopropylmethyl)-6-{4-[1-(1,1-difluoropropan-2-yl)piperidin-4-yl]-1,4-diazepan-1-yl}pyridine-2-carboxamide | 81, 11 | 21% | HRMS (ESI+) calculated for C23H35F2N5O: 435.280967, found 435.282337. HPLC: Rf 3.99 min, 100% purity. |
| 69 | 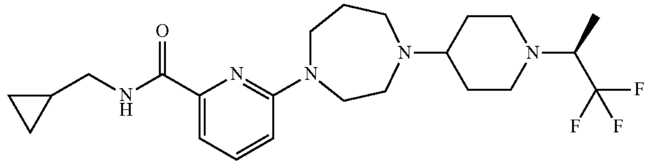 [SMILES: C[C@H](N1CCC(N2CCCN(c3cccc(C(=O)NCC4CC4)n3)CC2)CC1)C(F)(F)F] | N-(Cyclopropylmethyl)-6-(4-{1-[(2S)-1,1,1-trifluoropropan-2-yl]piperidin-4-yl}-1,4-diazepan-1-yl)pyridine-2-carboxamide | 81, 12 | 5% | HRMS (ESI+) calculated for C23H34F3N5O: 453.271545, found 453.273405. HPLC: Rf 5.16 min, 99.2% purity. |
| 70 | 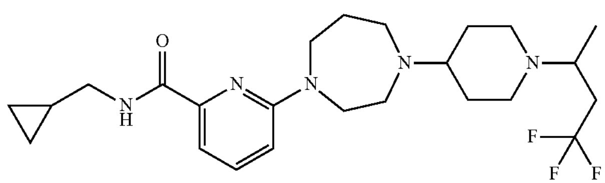 [SMILES: CC(CC(F)(F)F)N1CCC(N2CCCN(c3cccc(C(=O)NCC4CC4)n3)CC2)CC1] | N-(Cyclopropylmethyl)-6-{4-[1-(4,4,4-trifluorobutan-2-yl)piperidin-4-yl]-1,4-diazepan-1-yl}pyridine-2-carboxamide | 81, 15 | 9% | HRMS (ESI+) calculated for C24H36F3N5O: 467.287195, found 467.288465. HPLC: Rf 4.13 min, 100% purity. |
| 71 | 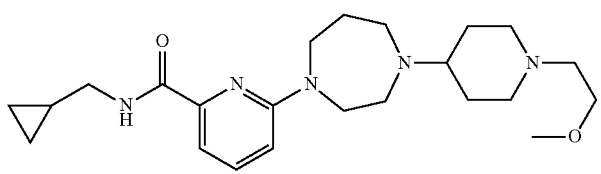 | N-(Cyclopropylmethyl)-6-{4-[1-(2-methoxyethyl)piperidin-4-yl]-1,4-diazepan-1-yl}pyridine-2-carboxamide | 81, 21 | 17% | HRMS (ESI+) calculated for C23H37N5O2: 415.294725, found 415.296525. HPLC: Rf 3.85 min, 100% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 72 | (cyclopentyl-piperidine-diazepane-pyridine-carboxamide-cyclopropylmethyl) | 6-[4-(1-Cyclopentylpiperidin-4-yl)-1,4-diazepan-1-yl]-N-(cyclopropyl-methyl)pyridine-2-carboxamide | 81, 24 | 6% | HRMS (ESI+) calculated for C25H39N5O: 425.315461, found 425.315921. HPLC: Rf 4.07 min, 100% purity. |
| 73 | (2-fluorocyclopentyl-piperidine-diazepane-pyridine-carboxamide-cyclopropylmethyl) | N-(Cyclopropylmethyl)-6-{4-[1-(2-fluorocyclopentyl)piperidin-4-yl]-1,4-diazepan-1-yl}pyridine-2-carboxamide | 81, 16 | 4% | HRMS (ESI+) calculated for C25H38FN5O: 443.306039, found 443.304639. HPLC: Rf 3.87 min, 100% purity (gradient 20-100%). |
| 74 | ((1R)-1-phenylethyl-piperidine-diazepane-pyridine-carboxamide-cyclopropylmethyl) | N-(Cyclopropylmethyl)-6-(4-{1-[(1R)-1-phenylethyl]piperidin-4-yl}-1,4-diazepan-1-yl)pyridine-2-carboxamide | 81, 17 | 5% | HRMS (ESI+) calculated for C28H39N5O: 461.315461, found 461.316741. HPLC: Rf 4.03 min, 100% purity (gradient 20-100%). |
| 75 | ((1R)-1-(4-fluorophenyl)ethyl-piperidine-diazepane-pyridine-carboxamide-cyclopropylmethyl) | N-(Cyclopropylmethyl)-6-(4-{1-[(1R)-1-(4-fluorophenyl)ethyl]piperidin-4-yl}-1,4-diazepan-1-yl)pyridine-2-carboxamide | 81, 18 | 7% | HRMS (ESI+) calculated for C28H38FN5O: 479.306039, found 479.306619. HPLC: Rf 3.96 min, 100% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 76 | 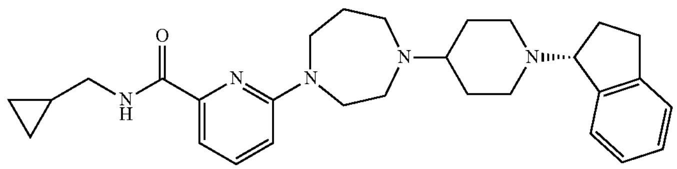 [SMILES: O=C(NCC1CC1)c1cccc(N2CCCN(C3CCN([C@@H]4CCc5ccccc54)CC3)CC2)n1] | N-(Cyclopropylmethyl)-6-(4-{1-[(1R)-2,3-dihydro-1H-inden-1-yl]piperidin-4-yl}-1,4-diazepan-1-yl)pyridine-2-carboxamide | 81, 19 | 10% | HRMS (ESI+) calculated for C29H39N5O: 473.315461, found 473.316401. HPLC: Rf 4.29 min, 99.6% purity. |
| 77 | 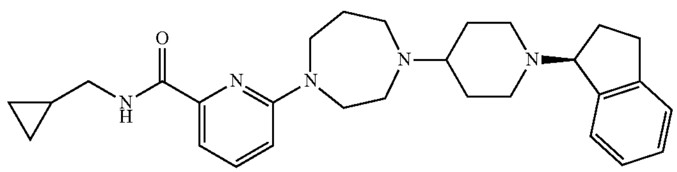 [SMILES: O=C(NCC1CC1)c1cccc(N2CCCN(C3CCN([C@H]4CCc5ccccc54)CC3)CC2)n1] | N-(Cyclopropylmethyl)-6-(4-{1-[(1S)-2,3-dihydro-1H-inden-1-yl]piperidin-4-yl}-1,4-diazepan-1-yl)pyridine-2-carboxamide | 81, 20 | 5% | HRMS (ESI+) calculated for C29H39N5O: 473.315461, found 473.314341. HPLC: Rf 4.12 min, 100% purity. |
| 78 | 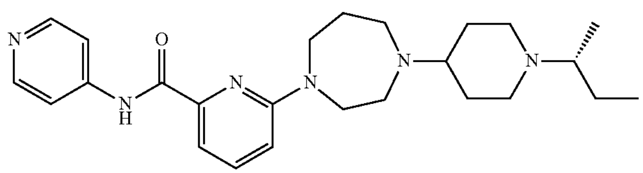 [SMILES: CC[C@@H](C)N1CCC(N2CCCN(c3cccc(C(=O)Nc4ccncc4)n3)CC2)CC1] | 6-(4-{1-[(2R)-Butan-2-yl]piperidin-4-yl}-1,4-diazepan-1-yl)-N-(pyridin-4-yl)pyridine-2-carboxamide | 83, 8 | 20% | HRMS (ESI+) calculated for C25H36N6O: 436.29506, found 436.29509. HPLC: Rf 3.56 min, 100% purity. |
| 79 | 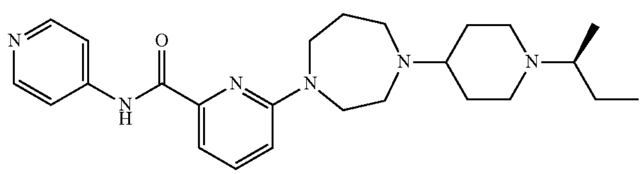 [SMILES: CC[C@H](C)N1CCC(N2CCCN(c3cccc(C(=O)Nc4ccncc4)n3)CC2)CC1] | 6-(4-{1-[(2S)-Butan-2-yl]piperidin-4-yl}-1,4-diazepan-1-yl)-N-(pyridin-4-yl)pyridine-2-carboxamide | 83, 9 | 15% | HRMS (ESI+) calculated for C25H36N6O: 436.29506, found 436.29628. HPLC: Rf 3.57 min, 100% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 80 | 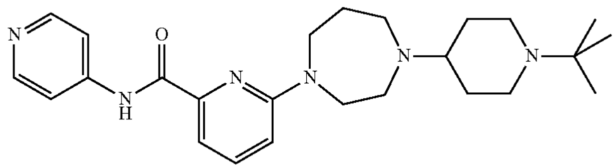 [SMILES: CC(C)(C)N1CCC(N2CCCN(c3cccc(C(=O)Nc4ccncc4)n3)CC2)CC1] | 6-[4-(1-tert-Butylpiperidin-4-yl)-1,4-diazepan-1-yl]-N-(pyridine-4-yl)pyridine-2-carboxamide | 83, * | 17% | HRMS (ESI+) calculated for C25H36N6O: 436.29506, found 436.29503. HPLC: Rf 3.50 min, 100% purity. |
| 81 | 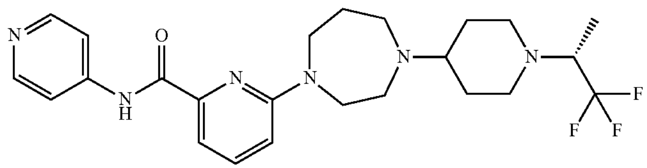 [SMILES: C[C@@H](N1CCC(N2CCCN(c3cccc(C(=O)Nc4ccncc4)n3)CC2)CC1)C(F)(F)F] | N-(Pyridin-4-yl)-6-(4-{1-[(2R)-1,1,1-trifluoropropan-2-yl]piperidin-4-yl}-1,4-diazepan-1-yl)pyridine-2-carboxamide | 83, 13 | 1% | HRMS (ESI+) calculated for C24H31F3N6O: 476.251144, found 476.253024. HPLC: Rf 4.15 min, 98.3% purity. |
| 82 | 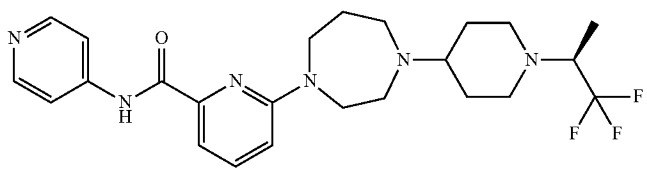 [SMILES: C[C@H](N1CCC(N2CCCN(c3cccc(C(=O)Nc4ccncc4)n3)CC2)CC1)C(F)(F)F] | N-(Pyridin-4-yl)-6-(4-{1-[(2S)-1,1,1-trifluoropropan-2-yl]piperidin-4-yl}-1,4-diazepan-1-yl)pyridine-2-carboxamide | 83, 12 | 11% | HRMS (ESI+) calculated for C24H31F3N6O: 476.251144, found 476.251594. HPLC: Rf 4.36 min, 100% purity. |
| 83 | 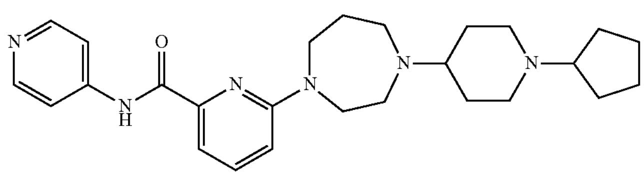 [SMILES: O=C(Nc1ccncc1)c1cccc(N2CCCN(C3CCN(C4CCCC4)CC3)CC2)n1] | 6-[4-(1-Cyclopentylpiperidin-4-yl)-1,4-diazepan-1-yl]-N-(pyridine-4-yl)pyridine-2-carboxamide | 83, 24 | 2% | HRMS (ESI+) calculated for C26H36N6O: 448.29506, found 448.29628. HPLC: Rf 3.61 min, 100% purity. |

TABLE 17-continued

Reductive alkylations of Intermediates 81-88, 90-115 and 117

| Ex | Structure | Name | Ints | Yield | HRMS (ESI+), HPLC |
|----|-----------|------|------|-------|-------------------|
| 84 | 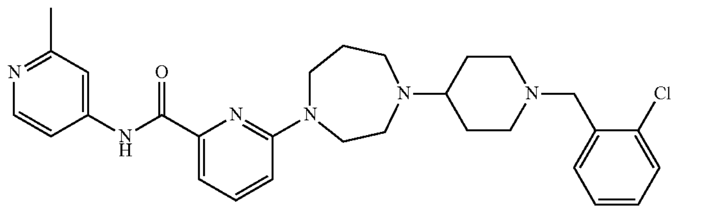 [SMILES: Cc1cc(NC(=O)c2cccc(N3CCCN(C4CCN(Cc5ccccc5Cl)CC4)CC3)n2)ccn1] | 6-(4-{1-[(2-Chlorophenyl)methyl]piperidin-4-yl}-1,4-diazepan-1-yl)-N-(2-methylpyridin-4-yl)pyridine-2-carboxamide | 84, 25 | 13% | HRMS (ESI+) calculated for C29H35ClN6O: 518.256087, found 518.257537. HPLC: Rf 3.74 min, 100% purity. |
| 85 | 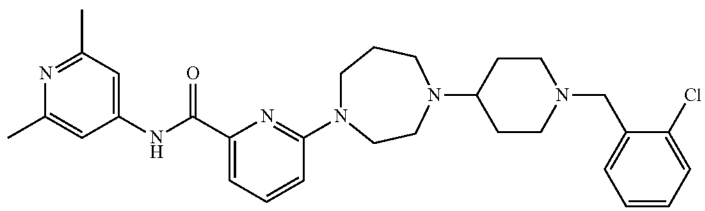 [SMILES: Cc1cc(NC(=O)c2cccc(N3CCCN(C4CCN(Cc5ccccc5Cl)CC4)CC3)n2)cc(C)n1] | 6-(4-{1-[(2-Chlorophenyl)methyl]piperidin-4-yl}-1,4-diazepan-1-yl)-N-(2,6-dimethylpyridin-4-yl)pyridine-2-carboxamide | 86, 25 | 13% | HRMS (ESI+) calculated for C30H37ClN6O: 532.271738, found 532.272528. HPLC: Rf 3.81 min, 100% purity. |
| 86 | 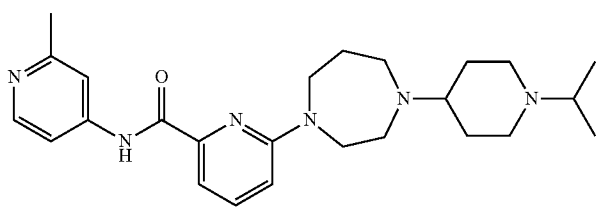 [SMILES: Cc1cc(NC(=O)c2cccc(N3CCCN(C4CCN(C(C)C)CC4)CC3)n2)ccn1] | N-(2-Methylpyridin-4-yl)-6-{4-[1-(Propan-2-yl)piperidin-4-yl]-1,4-diazepan-1-yl}pyridine-2-carboxamide | 84, * | 8% | HRMS (ESI+) calculated for C25H36N6O: 437.30234, found 437.30215. HPLC: Rf 4.44 min, 100% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 87 | 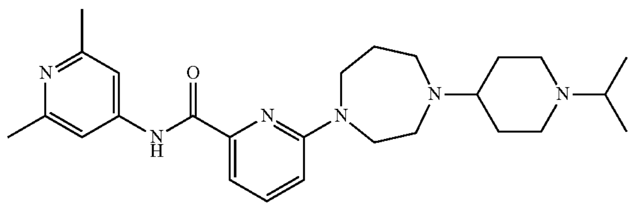 [SMILES: Cc1cc(NC(=O)c2cccc(N3CCCN(C4CCN(C(C)C)CC4)CC3)n2)cc(C)n1] | N-(2,6-Dimethylpyridin-4-yl)-6-{4-[1-(Propan-2-yl)piperidin-4-yl]-1,4-diazepan-1-yl}pyridine-2-carboxamide | 86, * | 30% | HRMS (ESI+) calculated for C26H38N6O: 451.31799, found 451.31717. HPLC: Rf 4.68 min, 99.8% purity. |
| 88 | 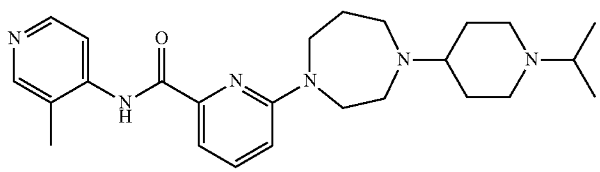 [SMILES: Cc1cnccc1NC(=O)c1cccc(N2CCCN(C3CCN(C(C)C)CC3)CC2)n1] | N-(3-Methylpyridin-4-yl)-6-{4-[1-(Propan-2-yl)piperidin-4-yl]-1,4-diazepan-1-yl}pyridine-2-carboxamide | 85, * | 89% | HRMS (ESI+) calculated for C25H36N6O: 437.30234, found 437.30194. HPLC: Rf 4.37 min, 100% purity. |
| 89 | 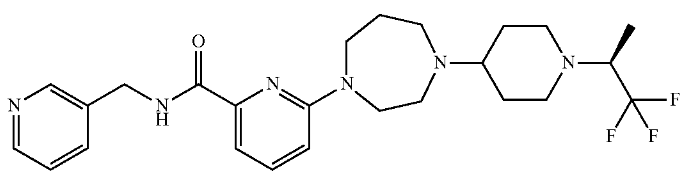 [SMILES: C[C@H](N1CCC(N2CCCN(c3cccc(C(=O)NCc4cccnc4)n3)CC2)CC1)C(F)(F)F] | N-(Pyridin-3-ylmethyl)-6-(4-{1-[(2S)-1,1,1-trifluoropropan-2-yl]piperidin-4-yl}-1,4-diazepan-1-yl)pyridine-2-carboxamide | 87, 12 | 14% | HRMS (ESI+) calculated for C25H33F3N6O: 490.266794, found 490.268534. HPLC: Rf 3.98 min, 97.4% purity. |
| 90 | 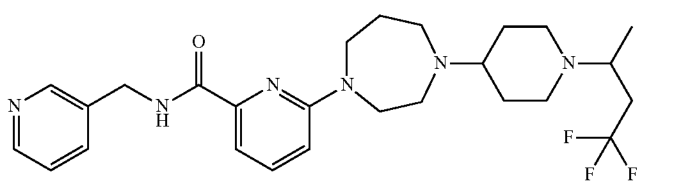 [SMILES: CC(CC(F)(F)F)N1CCC(N2CCCN(c3cccc(C(=O)NCc4cccnc4)n3)CC2)CC1] | N-(Pyridin-3-ylmethyl)-6-{4-[1-(4,4,4-trifluorobutan-2-yl)piperidin-4-yl]-1,4-diazepan-1-yl}pyridine-2-carboxamide | 87, 15 | 23% | HRMS (ESI+) calculated for C26H35F3N6O: 504.282444, found 504.284294. HPLC: Rf 3.39 min, 99.4% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 91 | 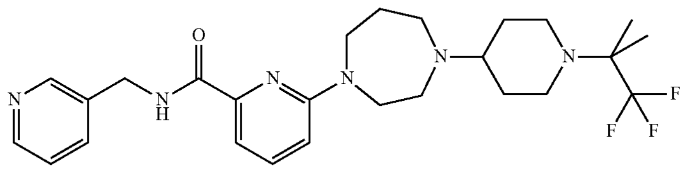 [SMILES: CC(C)(N1CCC(N2CCCN(c3cccc(C(=O)NCc4cccnc4)n3)CC2)CC1)C(F)(F)F] | N-(Pyridin-3-ylmethyl)-6-{4-[1-(1,1,1-trifluoro-2-methylpropan-2-yl)piperidin-4-yl]-1,4-diazepan-1-yl}pyridine-2-carboxamide | 87, 14 | 10% | HRMS (ESI+) calculated for C26H35F3N6O: 504.282444, found 504.283234. HPLC: Rf 3.88 min, 98.7% purity (gradient 20-100%). |
| 92 | 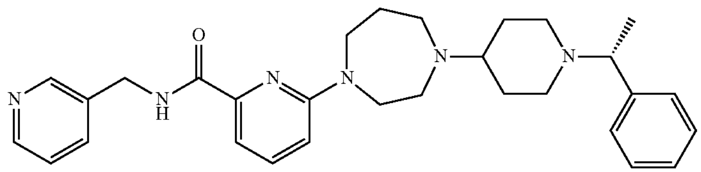 [SMILES: C[C@H](c1ccccc1)N1CCC(N2CCCN(c3cccc(C(=O)NCc4cccnc4)n3)CC2)CC1] | 6-(4-{1-[(1R)-1-Phenylethyl]piperidin-4-yl}-1,4-diazepan-1-yl)-N-(pyridine-3-ylmethyl)pyridine-2-carboxamide | 87, 17 | 5% | HRMS (ESI+) calculated for C30H38N6O: 498.31071, found 498.31218. HPLC: Rf 3.34 min, 99.2% purity (gradient 20-100%). |
| 93 | 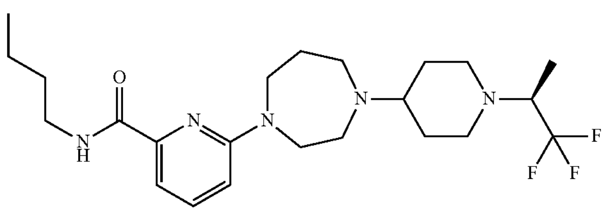 [SMILES: CCCCNC(=O)c1cccc(N2CCCN(C3CCN([C@@H](C)C(F)(F)F)CC3)CC2)n1] | N-Butyl-6-(4-{1-[(2S)-1,1,1-trifluoropropan-2-yl]piperidin-4-yl}-1,4-diazepan-1-yl)pyridine-2-carboxamide | 82, 12 | 46% | HRMS (ESI+) calculated for C23H36F3N5O: 455.287195, found 455.288705. HPLC: Rf 5.45 min, 99.1% purity. |
| 94 | 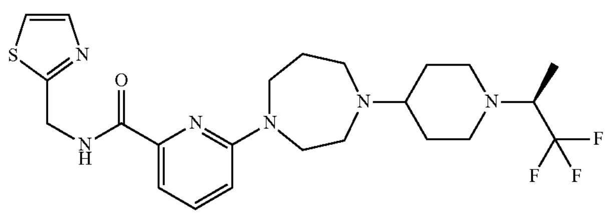 [SMILES: C[C@H](N1CCC(N2CCCN(c3cccc(C(=O)NCc4nccs4)n3)CC2)CC1)C(F)(F)F] | N-(1,3-Thiazol-2-ylmethyl)-6-(4-{1-[(2S)-1,1,1-trifluoropropan-2-yl]piperidin-4-yl}-1,4-diazepan-1-yl)pyridine-2-carboxamide | 88, 12 | 9% | HRMS (ESI+) calculated for C23H31F3N6OS: 496.223215, found 496.225335. HPLC: Rf 4.92 min, 100% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 95 | 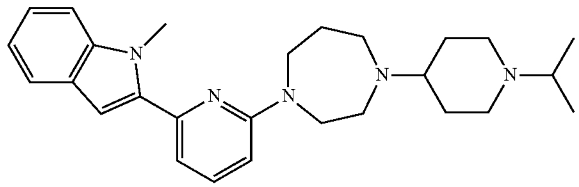 [SMILES: CC(C)N1CCC(N2CCCN(c3cccc(-c4cc5ccccc5n4C)n3)CC2)CC1] | 1-Methyl-2-(6-{4-[1-(propan-2-yl)piperidin-4-yl]-1,4-diazepan-1-yl}pyridin-2-yl)-1H-indole | 90, * | 8% | HRMS (ESI+) calculated for C27H37N5; 432.31217, found 432.31149. HPLC: Rf 5.11 min, 100% purity. |
| 96 | 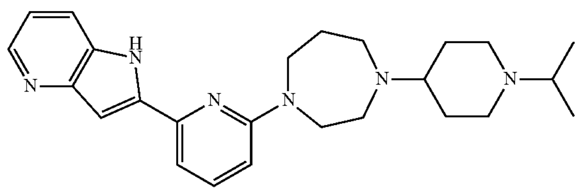 | 1-[(Propan-2-yl)piperidin-4-yl]-4-(6-{1H-pyrrolo[3,2-b]pyridine-2-yl}pyridin-2-yl)-1,4-diazepane | 91, * | 8% | HRMS (ESI+) calculated for C25H34N6; 418.284495, found 418.285865. HPLC: Rf 3.60 min, 100% purity. |
| 97 | 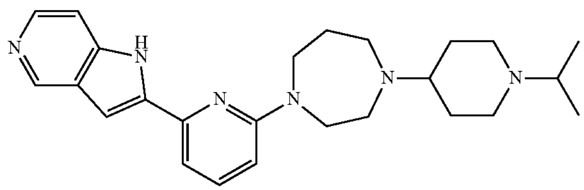 [SMILES: CC(C)N1CCC(N2CCCN(c3cccc(-c4cc5cnccc5[nH]4)n3)CC2)CC1] | 1-[1-(Propan-2-yl)piperidin-4-yl]-4-(6-{1H-pyrrolo[3,2-c]pyridine-2-yl}pyridin-2-yl)-1,4-diazepane | 92, * | 1% | HRMS (ESI+) calculated for C25H34N6; 419.29177, found 419.29028. HPLC: Rf 3.64 min, 99.1% purity. |
| 98 | 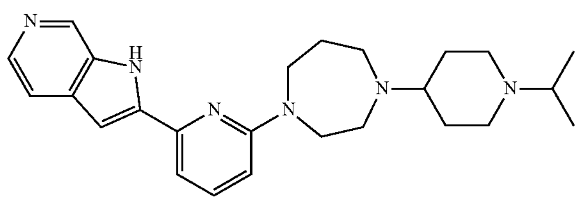 | 1-[1-(Propan-2-yl)piperidin-4-yl]-4-(6-{1H-pyrrolo[2,3-c]pyridine-2-yl}pyridin-2-yl)-1,4-diazepane | 93, * | 1% | HRMS (ESI+) calculated for C25H34N6; 419.29177, found 419.29202. HPLC: Rf 3.79 min, 99.2% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 99 | 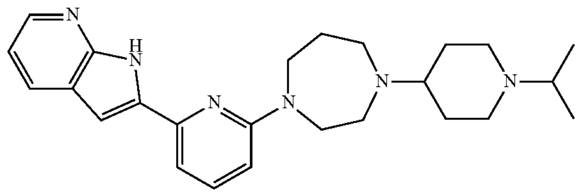 [SMILES: CC(C)N1CCC(N2CCCN(c3cccc(-c4cc5cccnc5[nH]4)n3)CC2)CC1] | 1-[1-(Propan-2-yl)piperidin-4-yl]-4-(6-{1H-pyrrolo[2,3-b]pyridine-2-yl}pyridine-2-yl)-1,4-diazepane | 94, * | 9% | HRMS (ESI+) calculated for C25H34N6: 418.284495, found 418.286015. HPLC: Rf 3.98 min, 98.8% purity. |
| 100 | 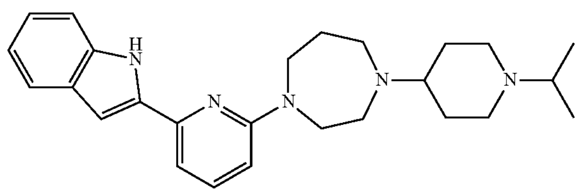 [SMILES: CC(C)N1CCC(N2CCCN(c3cccc(-c4cc5ccccc5[nH]4)n3)CC2)CC1] | 2-(6-{4-[1-(Propan-2-yl)piperidin-4-yl]-1,4-diazepan-1-yl}pyridine-2-yl)-1H-indole | 95, * | 6% | HRMS (ESI+) calculated for C26H35N5: 417.289246, found 417.290196. HPLC: Rf 4.93 min, 100% purity. |
| 101 | 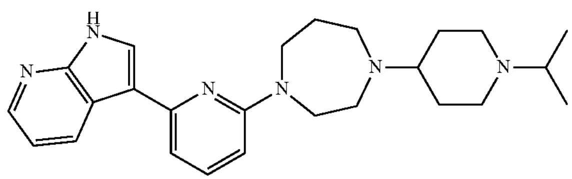 [SMILES: CC(C)N1CCC(N2CCCN(c3cccc(-c4c[nH]c5ncccc45)n3)CC2)CC1] | 1-[1-(Propan-2-yl)piperidin-4-yl]-4-(6-{1H-pyrrolo[2,3-b]pyridine-3-yl}pyridine-2-yl)-1,4-diazepane | 96, * | 14% | HRMS (ESI+) calculated for C25H34N6: 418.284495, found 418.286275. HPLC: Rf 3.57 min, 99.7% purity. |
| 102 | 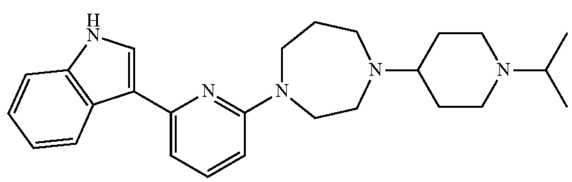 | 3-(6-{4-[1-(Propan-2-yl)piperidin-4-yl]-1,4-diazepan-1-yl}pyridine-2-yl)-1H-indole | 97, * | 2% | HRMS (ESI+) calculated for C26H35N5: 417.289246, found 417.289786. HPLC: Rf 3.67 min, 100% purity. |

TABLE 17-continued

Reductive alkylations of Intermediates 81-88, 90-115 and 117

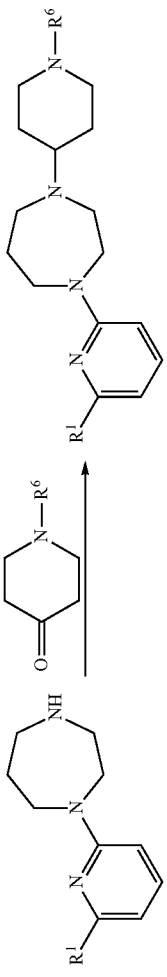

| Ex | Structure | Name | Ints | Yield | HRMS (ESI+), HPLC |
|----|-----------|------|------|-------|-------------------|
| 103 | NC-... | 2-(6-{4-[1-(Propan-2-yl)piperidin-4-yl]-1,4-diazepan-1-yl}pyridine-2-yl)-1H-indole-6-carbonitrile | 98, * | 2% | HRMS (ESI+) calculated for C27H34N6: 443.29177, found 443.29233. HPLC: Rf 5.10 min, 98.4% purity. |
| 104 | MeO-... | 6-Methoxy-2-(6-{4-[1-(propan-2-yl)piperidin-4-yl]-1,4-diazepan-1-yl}pyridine-2-yl)-1H-indole | 99, * | 9% | HRMS (ESI+) calculated for C27H37N5O: 448.30709, found 448.30676. HPLC: Rf 5.04 min, 100% purity. |
| 105 | MeO-... | 5-Methoxy-2-(6-{4-[1-(propan-2-yl)piperidin-4-yl]-1,4-diazepan-1-yl}pyridine-2-yl)-1H-indole | 100, * | 4% | HRMS (ESI+) calculated for C27H37N5O: 447.299811, found 447.299691. HPLC: Rf 4.72 min, 100% purity. |

TABLE 17-continued

Reductive alkylations of Intermediates 81-88, 90-115 and 117

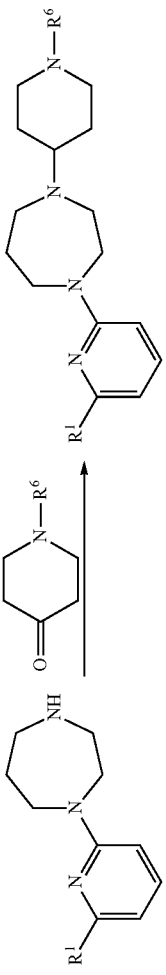

| Ex | Structure | Name | Ints | Yield | HRMS (ESI+), HPLC |
|---|---|---|---|---|---|
| 106 | 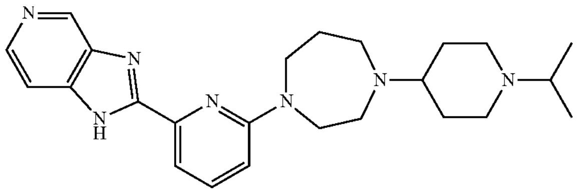 [SMILES: CC(C)N1CCC(N2CCCN(c3cccc(-c4nc5cnccc5[nH]4)n3)CC2)CC1] | 1-(6-{3H-Imidazo[4,5-c]pyridin-2-yl}pyridin-2-yl)-4-[1-(propan-2-yl)piperidin-4-yl]-1,4-diazepane | 102, * | 15% | LCMS (ES+): 420.0 [MH]+. HPLC: Rf 3.37 min, 100% purity. |
| 107 | 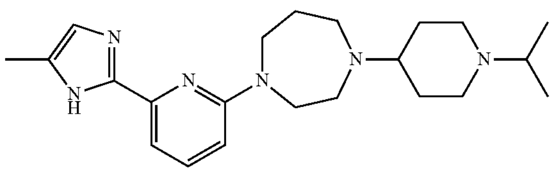 [SMILES: Cc1cnc(-c2cccc(N3CCCN(C4CCN(C(C)C)CC4)CC3)n2)[nH]1] | 1-[6-(4-Methyl-1H-imidazol-2-yl)pyridine-2-yl]-4-[1-(propan-2-yl)piperidin-4-yl]-1,4-diazepane | 101, * | 3% | HRMS (ESI+) calculated for C22H34N6: 383.29177, found 383.29163. HPLC: Rf 3.36 min, 98.7% purity. |
| 108 | 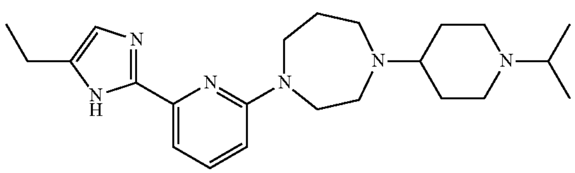 [SMILES: CCc1cnc(-c2cccc(N3CCCN(C4CCN(C(C)C)CC4)CC3)n2)[nH]1] | 1-[6-(4-Ethyl-1H-imidazol-2-yl)pyridine-2-yl]-4-[1-(propan-2-yl)piperidin-4-yl]-1,4-diazepane | 103, * | 31% | HRMS (ESI+) calculated for C23H36N6: 396.300145, found 396.300705. HPLC: Rf 3.41 min, 99.4% purity. |
| 109 | 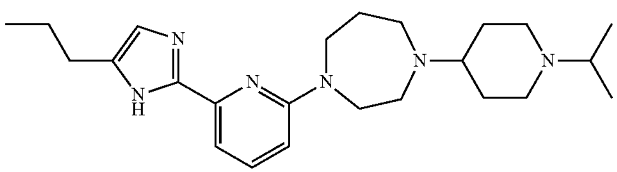 [SMILES: CCCc1cnc(-c2cccc(N3CCCN(C4CCN(C(C)C)CC4)CC3)n2)[nH]1] | 1-[1-(Propan-2-yl)piperidin-4-yl]-4-[6-(4-propyl-1H-imidazol-2-yl)pyridine-2-yl]-1,4-diazepane | 104, * | 10% | HRMS (ESI+) calculated for C24H38N6: 411.32307, found 411.32318. HPLC: Rf 3.76 min, 99.4% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 110 | 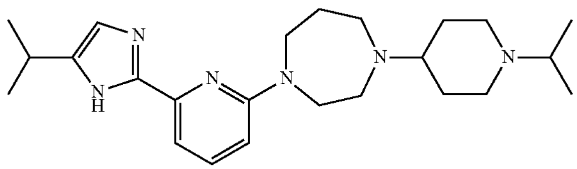 | 1-{6-[4-(Propan-2-yl)-1H-imidazol-2-yl]pyridine-2-yl}-4-[1-(propan-2-yl)piperidin-4-yl]-1,4-diazepane | 105, * | 12% | HRMS (ESI+) calculated for C24H38N6: 411.32307, found 411.32324. HPLC: Rf 3.72 min, 98.9% purity. |
| 111 | 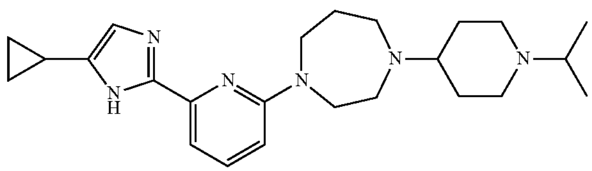 [SMILES: CC(C)N1CCC(N2CCCN(c3cccc(-c4ncc(C5CC5)[nH]4)n3)CC2)CC1] | 1-[6-(4-Cyclopropyl-1H-imidazol-2-yl)pyridine-2-yl]-4-[1-(propan-2-yl)piperidin-4-yl]-1,4-diazepane | 106, * | 17% | HRMS (ESI+) calculated for C24H36N6: 409.30742, found 409.30743. HPLC: Rf 3.61 min, 98.7% purity. |
| 112 | 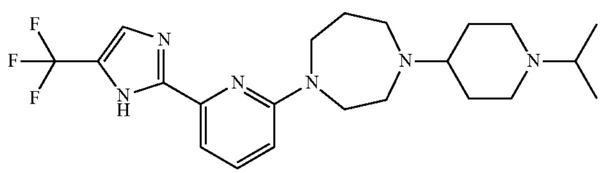 [SMILES: CC(C)N1CCC(N2CCCN(c3cccc(-c4ncc(C(F)(F)F)[nH]4)n3)CC2)CC1] | 1-[1-(Propan-2-yl)piperidin-4-yl]-4-{6-[4-(trifluoromethyl)-1H-imidazol-2-yl]pyridine-2-yl}-1,4-diazepane | 107, * | 4% | HRMS (ESI+) calculated for C22H31F3N6: 436.25623, found 436.25566. HPLC: Rf 4.32 min, 97.2% purity. |
| 113 | 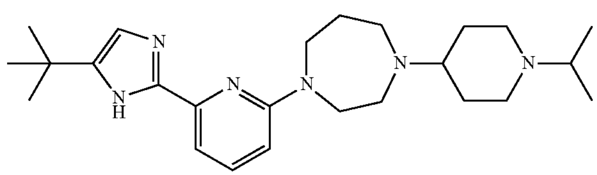 [SMILES: CC(C)N1CCC(N2CCCN(c3cccc(-c4ncc(C(C)(C)C)[nH]4)n3)CC2)CC1] | 1-[6-(4-tert-Butyl-1H-imidazol-2-yl)pyridine-2-yl]-4-[1-(propan-2-yl)piperidin-4-yl]-1,4-diazepane | 108, * | 14% | HRMS (ESI+) calculated for C25H40N6: 424.331445, found 424.330735. HPLC: Rf 5.28 min, 98.0% purity (gradient 5-50%). |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 114 | 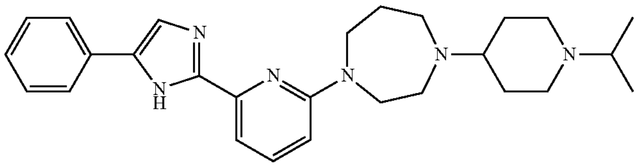 [SMILES: CC(C)N1CCC(N2CCCN(c3cccc(-c4ncc(-c5ccccc5)[nH]4)n3)CC2)CC1] | 1-[6-(4-Phenyl-1H-imidazol-2-yl)pyridine-2-yl]-4-[1-(propan-2-yl)piperidin-4-yl]-1,4-diazepane | 109, * | 28% | HRMS (ESI+) calculated for C27H36N6: 444.300145, found 444.300585. HPLC: Rf 3.97 min, 98.3% purity. |
| 115 | 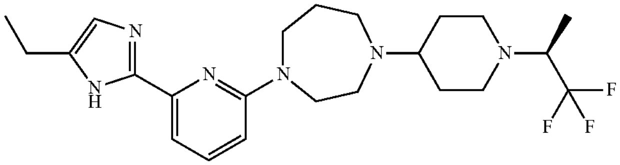 [SMILES: CCc1cnc(-c2cccc(N3CCCN(C4CCN([C@@H](C)C(F)(F)F)CC4)CC3)n2)[nH]1] | 1-[6-(4-Ethyl-1H-imidazol-2-yl)pyridine-2-yl]-4-{1-[(2S)-1,1,1-trifluoropropan-2-yl]piperidin-4-yl}-1,4-diazepane | 103, 12 | 8% | HRMS (ESI+) calculated for C23H33F3N6: 450.27188, found 450.27393. HPLC: Rf 4.42 min, 99.7% purity. |
| 116 | 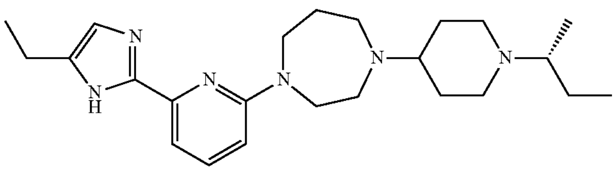 [SMILES: CCc1cnc(-c2cccc(N3CCCN(C4CCN([C@H](C)CC)CC4)CC3)n2)[nH]1] | 1-{1-[(2R)-Butan-2-yl]piperidin-4-yl}-4-[6-(4-ethyl-1H-imidazol-2-yl)pyridine-2-yl]-1,4-diazepane | 103, 8 | 22% | HRMS (ESI+) calculated for C24H38N6: 411.32307, found 411.32349. HPLC: Rf 3.65 min, 100% purity. |
| 117 | 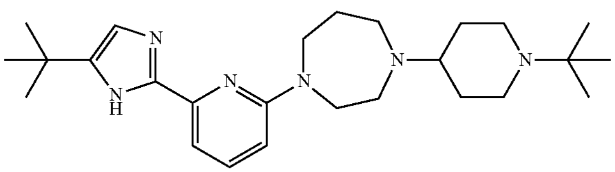 [SMILES: CC(C)(C)c1cnc(-c2cccc(N3CCCN(C4CCN(C(C)(C)C)CC4)CC3)n2)[nH]1] | 1-[6-(4-tert-Butyl-1H-imidazol-2-yl)pyridine-2-yl]-4-(1-tert-butylpiperidin-4-yl)-1,4-diazepane | 108, * | 22% | HRMS (ESI+) calculated for C26H42N6: 438.347095, found 438.348015. HPLC: Rf 3.91 min, 97.1% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 118 | 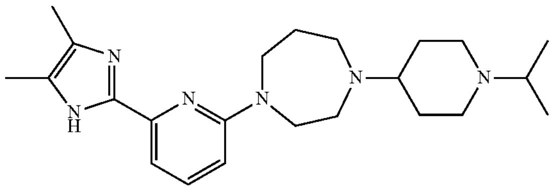 [SMILES: Cc1nc(-c2cccc(N3CCCN(C4CCN(C(C)C)CC4)CC3)n2)[nH]c1C] | 1-[6-(4,5-Dimethyl-1H-imidazol-2-yl)pyridine-2-yl]-4-[1-(propan-4-yl)piperidin-4-yl]-1,4-diazepane | 110, * | 12% | HRMS (ESI+) calculated for C23H36N6; 397.30742, found 397.30603. HPLC: Rf 3.51 min, 100% purity. |
| 119 | 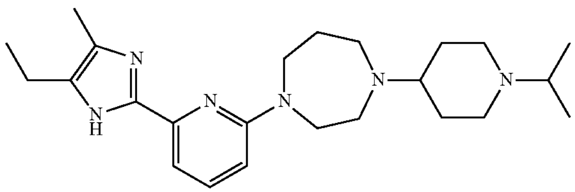 [SMILES: CCc1[nH]c(-c2cccc(N3CCCN(C4CCN(C(C)C)CC4)CC3)n2)nc1C] | 1-[6-(5-Ethyl-4-methyl-1H-imidazol-2-yl)pyridine-2-yl]-4-[1-(propan-2-yl)piperidin-4-yl]-1,4-diazepane | 111, * | 14% | HRMS (ESI+) calculated for C24H38N6; 411.32307, found 411.32303. HPLC: Rf 3.69 min, 96.9% purity. |
| 120 | 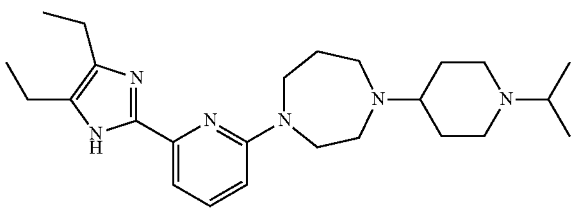 [SMILES: CCc1nc(-c2cccc(N3CCCN(C4CCN(C(C)C)CC4)CC3)n2)[nH]c1CC] | 1-[6-(4,5-Diethyl-1H-imidazol-2-yl)pyridine-2-yl]-4-[1-(propan-2-yl)piperidin-4-yl]-1,4-diazepane | 112, * | 6% | HRMS (ESI+) calculated for C25H40N6; 425.33872, found 425.3381. HPLC: Rf 3.93 min, 96.8% purity. |
| 121 | 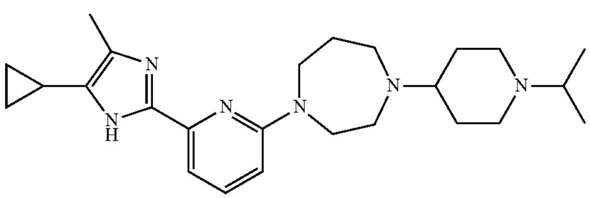 [SMILES: Cc1nc(-c2cccc(N3CCCN(C4CCN(C(C)C)CC4)CC3)n2)[nH]c1C1CC1] | 1-[6-(4-Cyclopropyl-5-methyl-1H-imidazol-2-yl)pyridine-2-yl]-4-[1-(Propan-2-yl)piperidin-4-yl]-1,4-diazepane | 113, * | 8% | HRMS (ESI+) calculated for C25H38N6; 423.32307, found 423.32352. HPLC: Rf 3.79 min, 98.3% purity. |

TABLE 17-continued

Reductive alkylations of Intermediates 81-88, 90-115 and 117

| Ex | Structure | Name | Ints | Yield | HRMS (ESI+), HPLC |
|---|---|---|---|---|---|
| 122 | 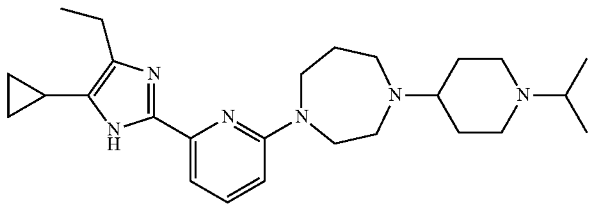 [SMILES: CCc1nc(-c2cccc(N3CCCN(C4CCN(C(C)C)CC4)CC3)n2)[nH]c1C1CC1] | 1-[6-(4-Cyclopropyl-5-ethyl-1H-imidazol-2-yl)pyridine-2-yl]-4-[1-(Propan-2-yl)piperidin-4-yl]-1,4-diazepane | 114, * | 11% | HRMS (ESI+) calculated for C26H40N6: 437.33872, found 437.33795. HPLC: Rf 4.00 min, 99.1% purity. |
| 123 | 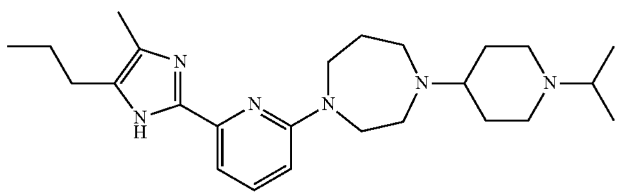 [SMILES: CCCc1[nH]c(-c2cccc(N3CCCN(C4CCN(C(C)C)CC4)CC3)n2)nc1C] | 1-[6-(5-Methyl-4-propyl-1H-imidazol-2-yl)pyridine-2-yl]-4-[1-(propan-2-yl)piperidin-4-yl]-1,4-diazepane | 115, * | 9% | HRMS (ESI+) calculated for C25H40N6: 425.33872, found 425.33743. HPLC: Rf 3.95 min, 100% purity. |
| 124 | 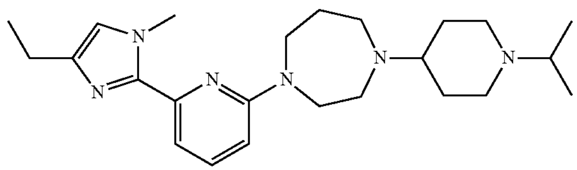 [SMILES: CCc1cn(C)c(-c2cccc(N3CCCN(C4CCN(C(C)C)CC4)CC3)n2)n1] | 1-[6-(4-Ethyl-1-methyl-1H-imidazol-2-yl)pyridine-2-yl]-4-[1-(propan-2-yl)piperidin-4-yl]-1,4-diazepane | 117, * | 35% | HRMS (ESI+) calculated for C24H38N6: 411.32307, found 411.32251. HPLC: Rf 3.47 min, 99.6% purity. |

* Intermediate commercially available

Example 125

N-(Cyclopropylmethyl)-3-methyl-6-{4-[1-(propan-2-yl)piperidin-4-yl]-1,4-diazepan-1-yl}pyridine-2-carboxamide

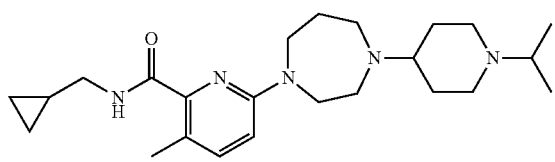

Example 125 was prepared similarly to Example 63, using Intermediate 195 instead of Intermediate 81, to give the title compound (12%) as a yellow gum. HRMS (ESI+) calculated for C24H39N5O: 413.315461. found 413.315661. HPLC: Rf 4.01 min, 98.7% purity.

Example 126

1-[1-(2,3-Dihydro-1H-inden-1-yl)piperidin-4-yl]-4-(1,3-thiazol-2-yl)-1,4-diazepane

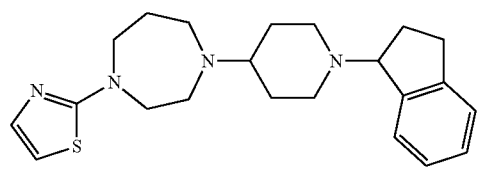 [SMILES: c1ccc2c(c1)CCC2N1CCC(N2CCCN(c3nccs3)CC2)CC1]

Intermediate 196 (150 mg, 0.82 mmol) and racemic Intermediate 19 (176 mg, 0.82 mmol) were dissolved in DCM (15 mL) and NaBH(OAc)₃ (867 mg, 4.09 mmol) was added. The reaction mixture was stirred for 18 h, diluted with DCM (25 mL), washed with sat aq Na₂CO₃ (30 mL), brine (25 mL), dried (MgSO₄) and concentrated in vacuo. The residue was purified by reverse phase HPLC to give the title compound (64.1 mg, 21%) as a white solid. HRMS (ESI+) calculated for C22H30N4S: 382.219118. found 382.220358. HPLC: Rf 3.45 min, 98.9% purity.

Example 127

N-(Cyclopropylmethyl)-6-{4-[1-(1-methoxypropan-2-yl)piperidin-4-yl]-1,4-diazepan-1-yl}pyridine-2-carboxamide

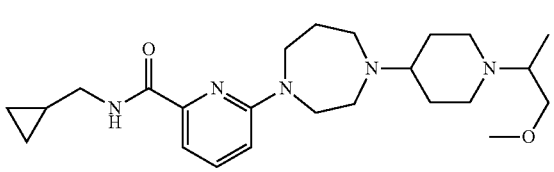 [SMILES: COCC(C)N1CCC(N2CCCN(c3cccc(C(=O)NCC4CC4)n3)CC2)CC1]

Intermediate 119 (90.0 mg, 0.25 mmol) and methoxyacetone (22.2 mg, 0.25 mmol) were dissolved in DCM (7 mL) and NaBH(OAc)₃ (267 mg, 1.25 mmol) was added. The reaction mixture was stirred for 3 d, diluted with DCM (50 mL), washed with sat aq Na₂CO₃ (30 mL), brine (30 mL), dried (MgSO₄) and concentrated in vacuo. The residue was purified by reverse phase HPLC and de-salted (K₂CO₃ in DCM) to give the title compound (13.4 mg, 12%) as a light yellow gum. HRMS (ESI+) calculated for C24H39N5O2: 429.310376. found 429.311516. HPLC: Rf 3.94 min, 99.1% purity.

Examples 128-139

Examples 128-139 were prepared similarly to Example 127, by reacting Intermediates 119-123 with the appropriate aldehyde or ketone; see Table 18 below.

TABLE 18

Reductive alkylations of Intermediates 119-123

| Ex | Structure | Name | SM/Yield | HRMS (ESI⁺), HPLC |
|---|---|---|---|---|
| 128 | 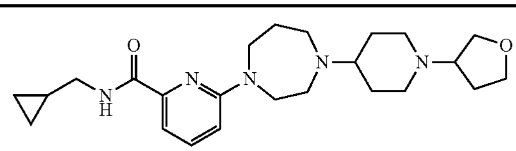 | N-(Cyclopropylmethyl)-6-{4-[1-(oxolan-3-yl)piperidin-4-yl]-1,4-diazepan-1-yl}pyridine-2-carboxamide | Int 119 12% | HRMS (ESI+) calculated for C24H37N5O2: 427.294725, found 427.295685. HPLC: Rf 3.76 min, 99.1% purity. |
| 129 | 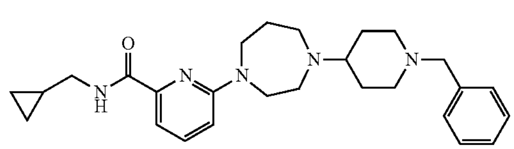 [SMILES: O=C(NCC1CC1)c1cccc(N2CCCN(C3CCN(Cc4ccccc4)CC3)CC2)n1] | 6-[4-(1-Benzylpiperidin-4-yl)-1,4-diazepan-1-yl]-N-(cyclopropylmethyl)pyridine-2-carboxamide | Int 119 23% | HRMS (ESI+) calculated for C27H37N5O: 447.299811, found 447.301461. HPLC: Rf 4.23 min, 97.3% purity. |

TABLE 18-continued

Reductive alkylations of Intermediates 119-123

| Ex | Structure | Name | SM/Yield | HRMS (ESI+), HPLC |
|---|---|---|---|---|
| 130 | 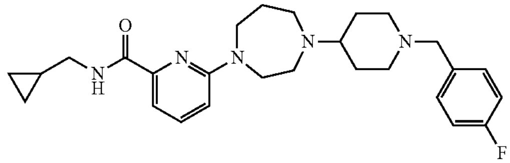 [SMILES: O=C(NCC1CC1)c1cccc(N2CCCN(C3CCN(Cc4ccc(F)cc4)CC3)CC2)n1] | N-(Cyclopropylmethyl)-6-(4-{1-[(4-fluorophenyl)methyl]piperidin-4-yl}-1,4-diazepan-1-yl)pyridine-2-carboxamide | Int 119 25% | HRMS (ESI+) calculated for C27H36FN5O: 465.290389, found 465.291239. HPLC: Rf 4.29 min, 96.9% purity. |
| 131 | 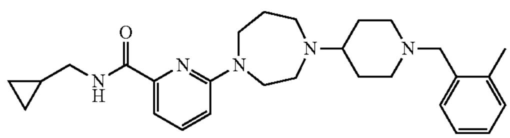 [SMILES: Cc1ccccc1CN1CCC(N2CCCN(c3cccc(C(=O)NCC4CC4)n3)CC2)CC1] | N-(Cyclopropylmethyl)-6-(4-{1-[(2-methylphenyl)methyl]piperidin-4-yl}-1,4-diazepan-1-yl)pyridine-2-carboxamide | Int 119 25% | HRMS (ESI+) calculated for C28H39N5O: 461.315461, found 461.317091. HPLC: Rf 4.32 min, 98.6% purity. |
| 132 | 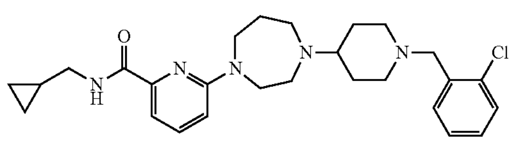 [SMILES: O=C(NCC1CC1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-(cyclopropylmethyl)pyridine-2-carboxamide | Int 119 59% | HRMS (ESI+) calculated for C27H36ClN5O: 481.260839, found 481.262229. HPLC: Rf 5.14 min, 98.4% purity. |
| 133 | 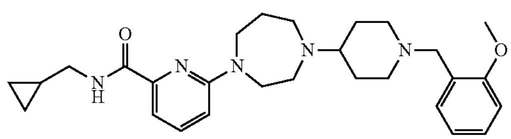 [SMILES: COc1ccccc1CN1CCC(N2CCCN(c3cccc(C(=O)NCC4CC4)n3)CC2)CC1] | N-(Cyclopropylmethyl)-6-(4-{1-[(2-methoxyphenyl)methyl]piperidin-4-yl}-1,4-diazepan-1-yl)pyridine-2-carboxamide | Int 119 45% | HRMS (ESI+) calculated for C28H39N5O2: 477.310376, found 477.311266. HPLC: Rf 4.31 min, 97.8% purity. |
| 134 | 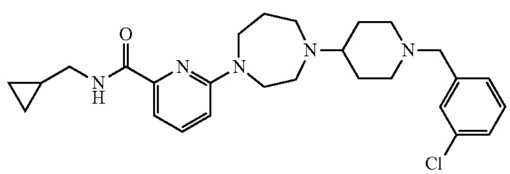 [SMILES: O=C(NCC1CC1)c1cccc(N2CCCN(C3CCN(Cc4cccc(Cl)c4)CC3)CC2)n1] | 6-(4-{1-[(3-Chlorophenyl)methyl]piperidin-4-yl}-1,4-diazepan-1-yl)-N-(cyclopropylmethyl)pyridine-2-carboxamide | Int 119 34% | HRMS (ESI+) calculated for C27H36ClN5O: 481.260839, found 481.262369. HPLC: Rf 4.45 min, 97.6% purity. |
| 135 | 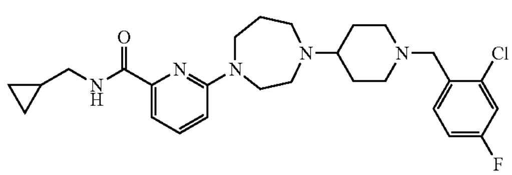 [SMILES: O=C(NCC1CC1)c1cccc(N2CCCN(C3CCN(Cc4ccc(F)cc4Cl)CC3)CC2)n1] | 6-(4-{1-[(2-Chloro-4-fluorophenyl)methyl]piperidin-4-yl}-1,4-diazepan-1-yl)-N-(cyclopropylmethyl)pyridine-2-carboxamide | Int 119 39% | HRMS (ESI+) calculated for C27H35ClFN5O: 499.251417, found 499.253217. HPLC: Rf 4.38 min, 97.2% purity. |
| 136 | 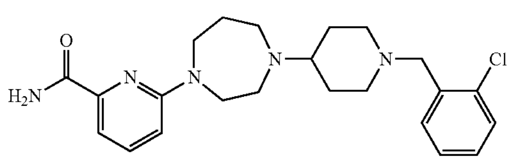 [SMILES: NC(=O)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)pyridine-2-carboxamide | Int 120 20% | HRMS (ESI+) calculated for C23H30ClN5O: 427.213888, found 427.214648. HPLC: Rf 3.72 min, 100% purity. |
| 137 | 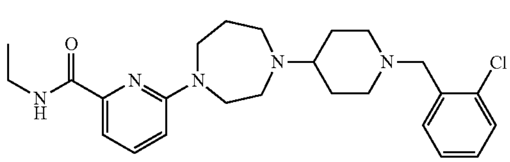 [SMILES: CCNC(=O)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-ethylpyridine-2-carboxamide | Int 121 1% | HRMS (ESI+) calculated for C25H34ClN5O: 455.245188, found 455.247018. HPLC: Rf 3.99 min, 99.1% purity. |

TABLE 18-continued

Reductive alkylations of Intermediates 119-123

| Ex | Structure | Name | SM/Yield | HRMS (ESI+), HPLC |
|---|---|---|---|---|
| 138 | 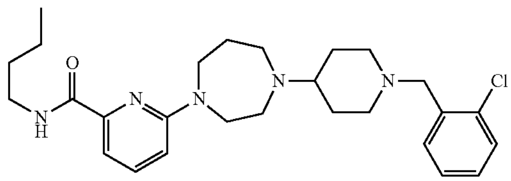 [SMILES: CCCCNC(=O)c1cccc(N2CCCN(C3CCN(Cc4ccccc4Cl)CC3)CC2)n1] | N-Butyl-6-(4-{1-[(2-chlorophenyl)methyl]piperidin-4-yl}-1,4-diazepan-1-yl)pyridine-2-carboxamide | Int 122 7% | HRMS (ESI+) calculated for C27H38ClN5O: 483.276489, found 483.277239. HPLC: Rf 4.44 min, 99.8% purity. |
| 139 | 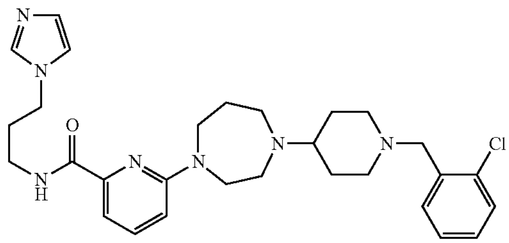 [SMILES: O=C(NCCCn1ccnc1)c1cccc(N2CCCN(C3CCN(Cc4ccccc4Cl)CC3)CC2)n1] | 6-(4-{1-[(2-Chlorophenyl)methyl]piperidin-4-yl}-1,4-diazepan-1-yl)-N-[3-(1H-imidazol-1-yl)propyl]pyridine-2-carboxamide | Int 123 43% | HRMS (ESI+) calculated for C29H38ClN7O: 535.282637, found 535.284117. HPLC: Rf 3.61 min, 97.5% purity. |

Example 140

1-Methyl-2-(6-{4-[1-(propan-2-yl)piperidin-4-yl]-1,4-diazepan-1-yl}pyridin-2-yl)-1H-1,3-benzodiazole

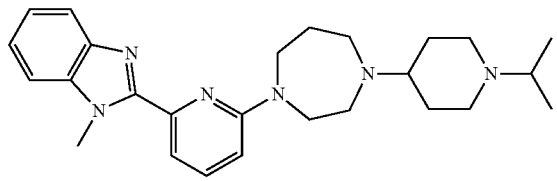 [SMILES: CC(C)N1CCC(N2CCCN(c3cccc(-c4nc5ccccc5n4C)n3)CC2)CC1]

Intermediate 135 (200 mg, 0.58 mmol), EDC.HCl (167 mg, 0.87 mmol), HONB (156 mg, 0.87 mmol), N-methyl-1,2-phenylenediamine (177 mg, 1.45 mmol) and DIPEA (144 mL, 0.87 mmol) were dissolved in DCM (4 mL) and stirred at 45° C. in a sealed tube overnight. The reaction mixture was diluted with DCM (20 mL), washed with sat aq NaHCO3 (25 mL), brine (25 mL) and concentrated in vacuo. The residue was purified by column chromatography, dissolved in acetic acid (2 mL) and heated using a microwave (150° C., absorption high) for 30 min. The solvents were removed in vacuo and the residue dissolved in DCM (25 mL), washed with sat aq NaHCO3 (25 mL), brine (25 mL) and concentrated in vacuo. The product was purified by reverse phase HPLC to give the title compound (44.3 mg, 18%) as a colourless gum. HRMS (ESI+) calculated for C26H36N6; 433.30742. found 433.30667. HPLC: Rf 3.66 min, 100% purity.

Examples 141-152

Examples 141-152 were prepared similarly to Example 140, by reacting Intermediate 135 with the appropriate aniline; see Table 19 below.

TABLE 19

Amide formation and cyclisation with Intermediate 135

| Ex | Structure | Name | Reagent | Yield | HRMS (ESI+), HPLC |
|---|---|---|---|---|---|
| 141 | 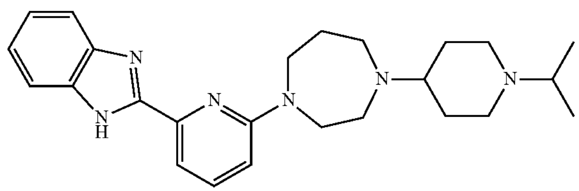 [SMILES: CC(C)N1CCC(N2CCCN(c3cccc(-c4nc5ccccc5[nH]4)n3)CC2)CC1] | 2-(6-{4-[1-(Propan-2-yl)piperidin-4-yl]-1,4-diazepan-1-yl}pyridine-2-yl)-1H-1,3-benzodiazole | benzene-1,2-diamine (NH2, NH2) | 24% | HRMS (ESI+) calculated for C25H34N6: 418.284495, found 418.286455. HPLC: Rf 4.36 min, 99.6% purity. |
| 142 | 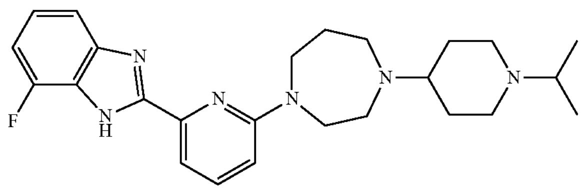 [SMILES: CC(C)N1CCC(N2CCCN(c3cccc(-c4nc5cccc(F)c5[nH]4)n3)CC2)CC1] | 7-Fluoro-2-(6-{4-[1-(propan-2-yl)piperidin-4-yl]-1,4-diazepan-1-yl}pyridine-2-yl)-1H-1,3-benzodiazole | 3-fluorobenzene-1,2-diamine | 2% | HRMS (ESI+) calculated for C25H33FN6: 437.28235, found 437.28098. HPLC: Rf 3.94 min, 100% purity. |
| 143 | 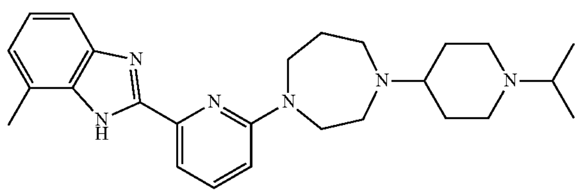 [SMILES: Cc1cccc2nc(-c3cccc(N4CCCN(C5CCN(C(C)C)CC5)CC4)n3)[nH]c12] | 7-Methyl-2-(6-{4-[1-(propan-2-yl)piperidin-4-yl]-1,4-diazepan-1-yl}pyridine-2-yl)-1H-1,3-benzodiazole | 3-methylbenzene-1,2-diamine | 7% | HRMS (ESI+) calculated for C26H36N6: 433.30742, found 433.30569. HPLC: Rf 3.91 min, 100% purity. |
| 144 | 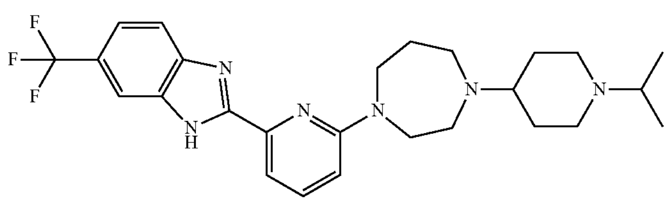 [SMILES: CC(C)N1CCC(N2CCCN(c3cccc(-c4nc5ccc(C(F)(F)F)cc5[nH]4)n3)CC2)CC1] | 2-(6-{4-[1-(Propan-2-yl)piperidin-4-yl]-1,4-diazepan-1-yl}pyridine-2-yl)-6-(trifluoromethyl)-1H-1,3-benzodiazole | 4-(trifluoromethyl)benzene-1,2-diamine | 5% | HRMS (ESI+) calculated for C26H33F3N6: 487.27916, found 487.27872. HPLC: Rf 4.50 min, 98.3% purity. |

TABLE 19-continued

Amide formation and cyclisation with Intermediate 135

| Ex | Structure | Name | Reagent | Yield | HRMS (ESI+), HPLC |
|---|---|---|---|---|---|
| 145 | 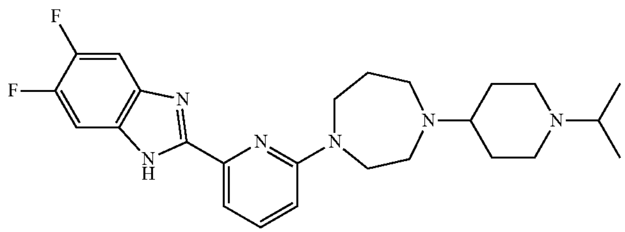 [SMILES: CC(C)N1CCC(N2CCCN(c3cccc(-c4nc5cc(F)c(F)cc5[nH]4)n3)CC2)CC1] | 5,6-Difluoro-2-(6-{4-[1-(propan-2-yl)piperidin-4-yl]-1,4-diazepan-1-yl}pyridine-2-yl)-1H-1,3-benzodiazole | | 6% | HRMS (ESI+) calculated for C25H32F2N6; 455.27293, found 455.27115. HPLC: Rf 4.12 min, 100% purity. |
| 146 | 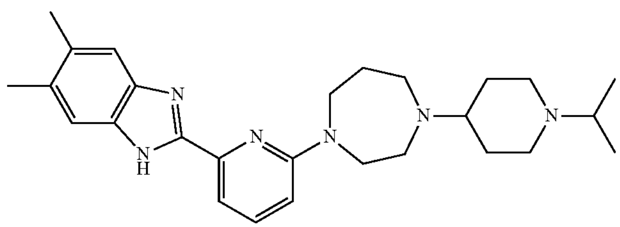 [SMILES: Cc1cc2nc(-c3cccc(N4CCCN(C5CCN(C(C)C)CC5)CC4)n3)[nH]c2cc1C] | 5,6-Dimethyl-2-(6-{4-[1-(propan-2-yl)piperidin-4-yl]-1,4-diazepan-1-yl}pyridine-2-yl)-1H-1,3-benzodiazole | | 2% | HRMS (ESI+) calculated for C27H38N6; 447.32307, found 447.32205. HPLC: Rf 4.17 min, 100% purity. |
| 147 | 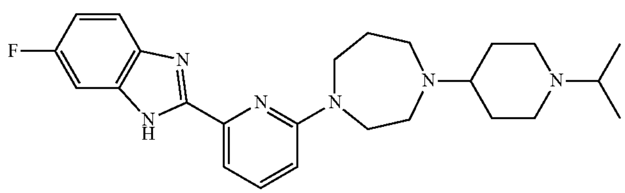 [SMILES: CC(C)N1CCC(N2CCCN(c3cccc(-c4nc5ccc(F)cc5[nH]4)n3)CC2)CC1] | 6-Fluoro-2-(6-{4-[1-(propan-2-yl)piperidin-4-yl]-1,4-diazepan-1-yl}pyridine-2-yl)-1H-1,3-benzodiazole | | 4% | HRMS (ESI+) calculated for C25H33FN6; 437.28235, found 437.28287. HPLC: Rf 3.86 min, 99.2% purity. |

TABLE 19-continued

Amide formation and cyclisation with Intermediate 135

| Ex | Structure | Name | Reagent | Yield | HRMS (ESI+), HPLC |
|---|---|---|---|---|---|
| 148 | 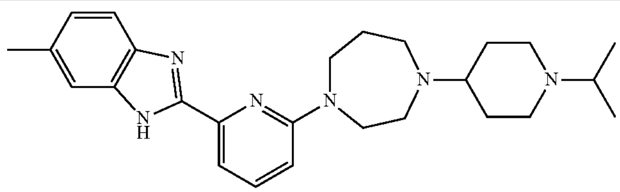 [SMILES: Cc1ccc2nc(-c3cccc(N4CCCN(C5CCN(C(C)C)CC5)CC4)n3)[nH]c2c1] | 6-Methyl-2-(6-{4-[1-(propan-2-yl)piperidin-4-yl]-1,4-diazepan-1-yl}pyridine-2-yl)-1H-1,3-benzodiazole | 2,3-diaminotoluene | 6% | HRMS (ESI+) calculated for C26H36N6; 433.30742, found 433.3064. HPLC: Rf 3.97 min, 99.4% purity. |
| 149 | 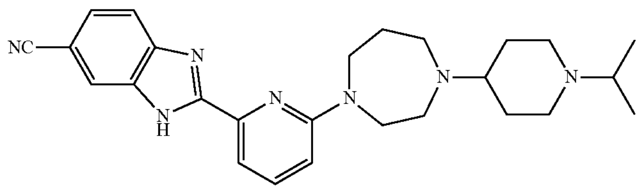 [SMILES: CC(C)N1CCC(N2CCCN(c3cccc(-c4nc5ccc(C#N)cc5[nH]4)n3)CC2)CC1] | 2-(6-{4-[1-(Propan-2-yl)piperidin-4-yl]-1,4-diazepan-1-yl}pyridine-2-yl)-1H-1,3-benzodiazole-6-carbonitrile | 3,4-diaminobenzonitrile | 7% | HRMS (ESI+) calculated for C26H33N7; 444.28702, found 444.2869. HPLC: Rf 4.13 min, 99.1% purity. |
| 150 | 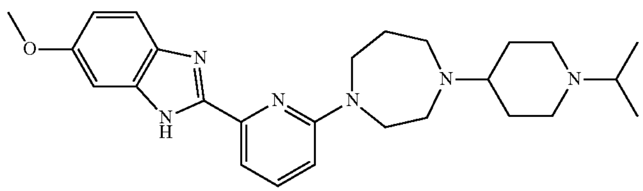 [SMILES: COc1ccc2nc(-c3cccc(N4CCCN(C5CCN(C(C)C)CC5)CC4)n3)[nH]c2c1] | 6-Methoxy-2-(6-{4-[1-(propan-2-yl)piperidin-4-yl]-1,4-diazepan-1-yl}pyridine-2-yl)-1H-1,3-benzodiazole | 4-methoxy-1,2-diaminobenzene | 4% | HRMS (ESI+) calculated for C26H36N6O; 449.30234, found 449.30258. HPLC: Rf 3.91 min, 100% purity. |
| 151 | 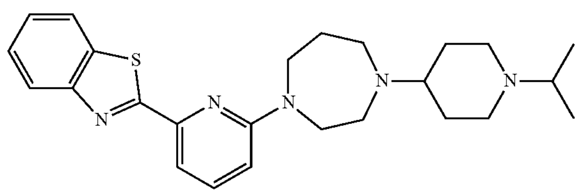 | 2-(6-{4-[1-(Propan-2-yl)piperidin-4-yl]-1,4-diazepan-1-yl}pyridine-2-yl)-1,3-benzothiazole | 2-aminothiophenol | 17% | HRMS (ESI+) calculated for C25H33N5S: 435.245667, found 435.247347. HPLC: Rf 6.21 min, 98.7% purity. |

TABLE 19-continued
Amide formation and cyclisation with Intermediate 135
| Ex | Structure | Name | Reagent | Yield | HRMS (ESI+), HPLC |
|---|---|---|---|---|---|
| 152 | 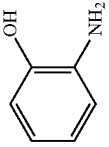 | 2-(6-{4-[1-(Propan-2-yl)piperidin-4-yl]-1,4-diazepan-1-yl}pyridine-2-yl)-1,3-benzoxazole | 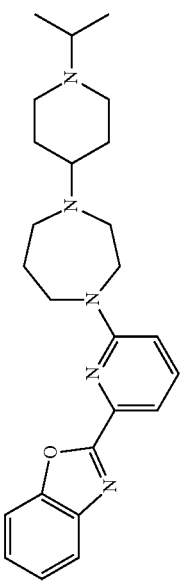 | 20% | HRMS (ESI+) calculated for C25H33N5O: 419.268511, found 419.269101. HPLC: Rf 4.43 min, 100% purity. |

Example 153

1-[6-(5-Methyl-1,2,4-oxadiazol-3-yl)pyridin-2-yl]-4-[1-(propan-2-yl)piperidin-4-yl]-1,4-diazepane

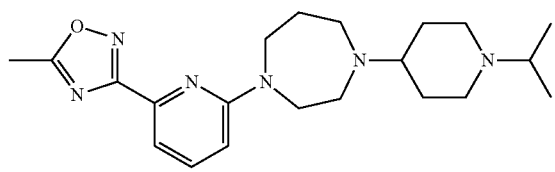 [SMILES: Cc1nc(-c2cccc(N3CCCN(C4CCN(C(C)C)CC4)CC3)n2)no1]

Intermediate 137 (125 mg, 0.35 mmol) and DIPEA (108 mg, 0.83 mmol) were dissolved in DCM (10 mL), acetyl chloride (28.6 mg, 0.36 mmol) was added and the reaction mixture was stirred for 16 h. The reaction mixture was partitioned between DCM (75 mL) and sat aq $Na_2CO_3$ (25 mL) and the organic fraction was separated and washed with brine (25 mL), dried ($MgSO_4$) and concentrated in vacuo. The residue was suspended in MeCN (2 mL) and xylenes (5 mL) and heated to 150° C. for 3 h. The solvents were removed in vacuo and the residue was purified by reverse phase HPLC to give the title compound (10.0 mg, 11%) as a yellow gum. HRMS (ESI+) calculated for C21H32N6O: 384.26376. found 384.26221. HPLC: Rf 3.64 min, 98.5% purity.

Example 154

1-{1-[(2R)-Butan-2-yl]piperidin-4-yl}-4-[6-(5-propyl-1,2,4-oxadiazol-3-yl)pyridin-2-yl]-1,4-diazepane

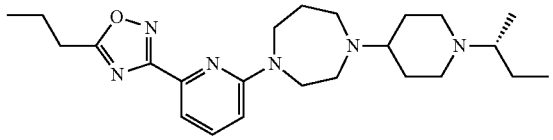 [SMILES: CCCc1nc(-c2cccc(N3CCCN(C4CCN([C@H](C)CC)CC4)CC3)n2)no1]

Example 154 was prepared similarly to Example 153, using Intermediate 138 instead of Intermediate 137 and butanoyl chloride instead of acetyl chloride, to give the title compound (8%) as a yellow gum. HRMS (ESI+) calculated for C24H38N6O; 427.31799. found 427.31772. HPLC: Rf 4.60 min, 100% purity.

Examples 155-167

Examples 155-167 were prepared similarly to Example 153, by reacting Intermediate 137 with the appropriate acyl chloride; see Table 20 below.

TABLE 20

Synthesis of 1,2,4-oxadiazoles from Intermediate 137

| Ex | Structure | Name | Reagent | Yield | HRMS (ESI+), HPLC |
|---|---|---|---|---|---|
| 155 | 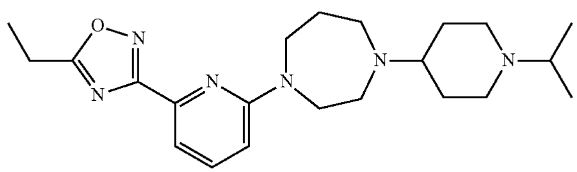 [SMILES: CCc1nc(-c2cccc(N3CCCN(C4CCN(C(C)C)CC4)CC3)n2)no1] | 1-[6-(5-Ethyl-1,2,4-oxadiazol-3-yl)pyridine-2-yl]-4-[1-(propan-2-yl)piperidin-4-yl]-1,4-diazepane trihydrochloride | propionyl chloride | 2% | HRMS (ESI+) calculated for C22H34N6O: 398.27941, found 398.279११. HPLC: Rf 3.98 min, 98.7% purity. |
| 156 | 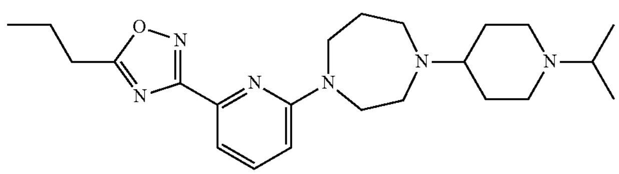 [SMILES: CCCc1nc(-c2cccc(N3CCCN(C4CCN(C(C)C)CC4)CC3)n2)no1] | 1-[1-(Propan-2-yl)piperidin-4-yl]-4-[6-(5-propyl-1,2,4-oxadiazol-3-yl)pyridine-2-yl]-1,4-diazepane | butyryl chloride | 10% | HRMS (ESI+) calculated for C23H36N6O: 412.29506, found 412.2952. HPLC: Rf 4.22 min, 97.8% purity. |
| 157 | 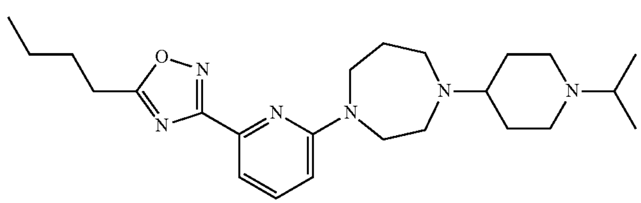 [SMILES: CCCCc1nc(-c2cccc(N3CCCN(C4CCN(C(C)C)CC4)CC3)n2)no1] | 1-[6-(5-Butyl-1,2,4-oxadiazol-3-yl)pyridine-2-yl]-4-[1-(propan-2-yl)piperidin-4-yl]-1,4-diazepane | valeroyl chloride | 8% | HRMS (ESI+) calculated for C24H38N6O: 427.31799, found 427.31738. HPLC: Rf 4.80 min, 100% purity. |
| 158 | 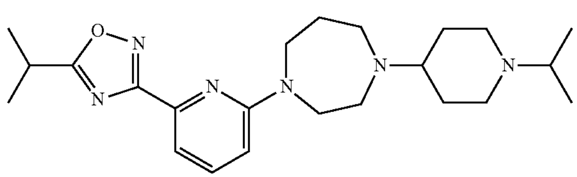 [SMILES: CC(C)c1nc(-c2cccc(N3CCCN(C4CCN(C(C)C)CC4)CC3)n2)no1] | 1-{6-[5-(Propan-2-yl)-1,2,4-oxadiazol-3-yl]pyridine-2-yl}-4-[1-(propan-2-yl)piperidin-4-yl]-1,4-diazepane | isobutyryl chloride | 9% | HRMS (ESI+) calculated for C23H36N6O: 413.30234, found 413.30133. HPLC: Rf 4.44 min, 99.6% purity. |

TABLE 20-continued

Synthesis of 1,2,4-oxadiazoles from Intermediate 137

| Ex | Structure | Name | Reagent | Yield | HRMS (ESI+), HPLC |
|---|---|---|---|---|---|
| 159 | 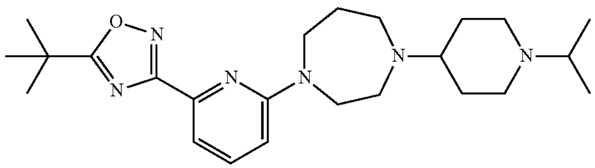 [SMILES: CC(C)N1CCC(N2CCCN(c3cccc(-c4noc(C(C)(C)C)n4)n3)CC2)CC1] | 1-[6-(5-tert-Butyl-1,2,4-oxadiazol-3-yl)pyridine-2-yl]-4-[1-(propan-2-yl)piperidin-4-yl]-1,4-diazepane | | 11% | HRMS (ESI+) calculated for C24H38N6O; 427.31799, found 427.31732. HPLC: Rf 4.69 min, 99.3% purity. |
| 160 | 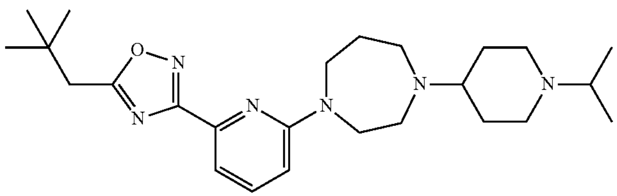 [SMILES: CC(C)N1CCC(N2CCCN(c3cccc(-c4noc(CC(C)(C)C)n4)n3)CC2)CC1] | 1-[6-[5-(2,2-Dimethylpropyl)-1,2,4-oxadiazol-3-yl]pyridine-2-yl]-4-[1-(propan-2-yl)piperidin-4-yl]-1,4-diazepane | | 7% | HRMS (ESI+) calculated for C25H40N6O; 441.33364, found 441.33356. HPLC: Rf 4.93 min, 98.4% purity. |
| 161 | 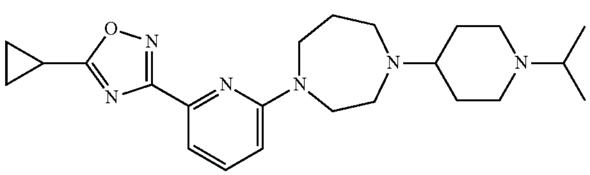 [SMILES: CC(C)N1CCC(N2CCCN(c3cccc(-c4noc(C5CC5)n4)n3)CC2)CC1] | 1-[6-(5-Cyclopropyl-1,2,4-oxadiazol-3-yl)pyridine-2-yl]-4-[1-(propan-2-yl)piperidin-4-yl]-1,4-diazepane | | 10% | HRMS (ESI+) calculated for C23H34N6O; 410.27941, found 410.28114. HPLC: Rf 4.14 min, 100% purity. |
| 162 | 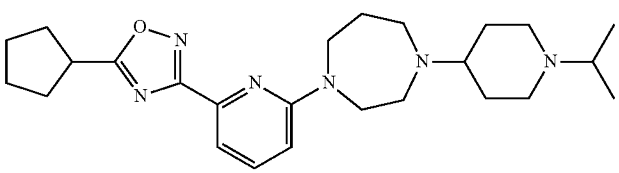 [SMILES: CC(C)N1CCC(N2CCCN(c3cccc(-c4noc(C5CCCC5)n4)n3)CC2)CC1] | 1-[6-(5-Cyclopentyl-1,2,4-oxadiazol-3-yl)pyridine-2-yl]-4-[1-(propan-2-yl)piperidin-4-yl]-1,4-diazepane | | 13% | HRMS (ESI+) calculated for C25H38N6O; 439.31799, found 439.31766. HPLC: Rf 4.84 min, 100% purity. |

TABLE 20-continued

Synthesis of 1,2,4-oxadiazoles from Intermediate 137

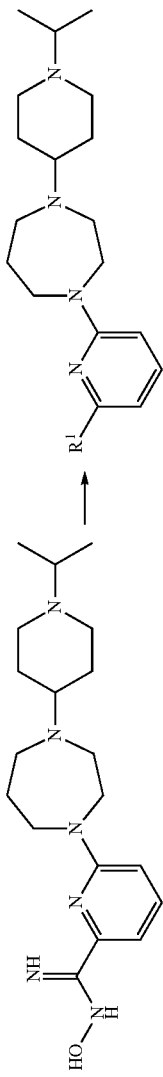

| Ex | Structure | Name | Reagent | Yield | HRMS (ESI+), HPLC |
|---|---|---|---|---|---|
| 163 | 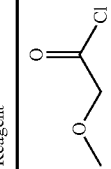 | 1-{6-[5-(Methoxymethyl)-1,2,4-oxadiazol-3-yl]pyridine-2-yl}-4-[1-(propan-2-yl)piperidin-4-yl]-1,4-diazepane | 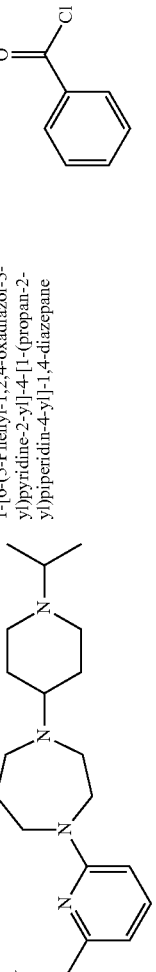 | 9% | HRMS (ESI+) calculated for C22H34N6O2: 414.274324, found 414.275334. HPLC: Rf 3.79 min, 98.7% purity. |
| 164 | 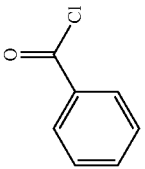 | 1-{6-(5-Phenyl-1,2,4-oxadiazol-3-yl)pyridine-2-yl}-4-[1-(propan-2-yl)piperidin-4-yl]-1,4-diazepane | 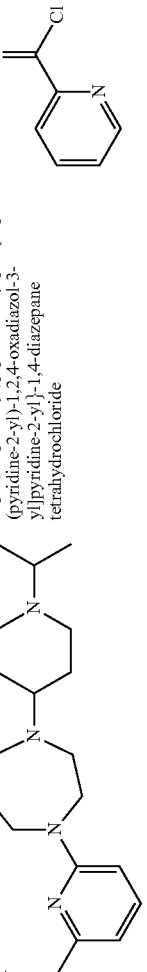 | 2% | HRMS (ESI+) calculated for C26H34N6O: 446.27941, found 446.28124. HPLC: Rf 4.60 min, 97.1% purity. |
| 165 | 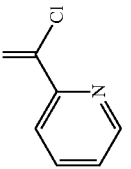 | 1-[1-(Propan-2-yl)piperidin-4-yl]-4-{6-[5-(pyridine-2-yl)-1,2,4-oxadiazol-3-yl]pyridine-2-yl}-1,4-diazepane tetrahydrochloride | 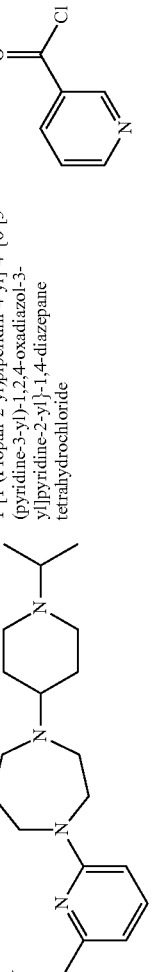 | 5% | HRMS (ESI+) calculated for C25H33N7O: 447.274659, found 447.274189. HPLC: Rf 3.99 min, 98.1% purity. |
| 166 | 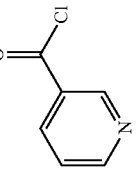 | 1-[1-(Propan-2-yl)piperidin-4-yl]-4-{6-[5-(pyridine-3-yl)-1,2,4-oxadiazol-3-yl]pyridine-2-yl}-1,4-diazepane tetrahydrochloride | | 5% | HRMS (ESI+) calculated for C25H33N7O: 447.274659, found 447.274019. HPLC: Rf 3.90 min, 98.5% purity. |

TABLE 20-continued

Synthesis of 1,2,4-oxadiazoles from Intermediate 137

| Ex | Structure | Name | Reagent | Yield | HRMS (ESI+), HPLC |
|---|---|---|---|---|---|
| 167 | 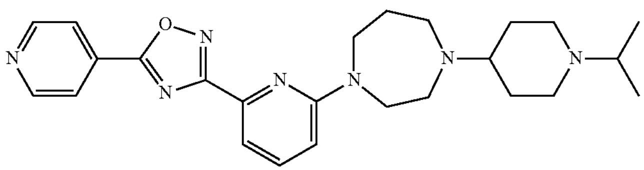 [SMILES: CC(C)N1CCC(N2CCCN(c3cccc(-c4noc(-c5ccncc5)n4)n3)CC2)CC1] | 1-[1-(Propan-2-yl)piperidin-4-yl]-4-{6-[5-(pyridine-4-yl)-1,2,4-oxadiazol-3-yl]pyridine-2-yl]}-1,4-diazepane tetrahydrochloride | | 5% | HRMS (ESI+) calculated for C25H33N7O: 447.274659, found 447.275379, HPLC: Rf 3.70 min, 99.4% purity. |

Example 168

1-[6-(2-Methyl-2H-1,2,3,4-tetrazol-5-yl)pyridin-2-yl]-4-[1-(propan-2-yl)piperidin-4-yl]-1,4-diazepane

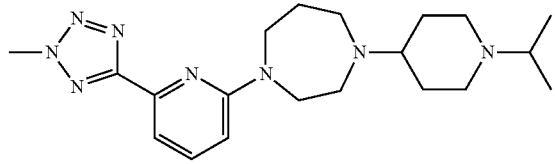 [SMILES: CC(C)N1CCC(N2CCCN(c3cccc(-c4nnn(C)n4)n3)CC2)CC1]

Intermediate 139 (317 mg, 0.86 mmol) was dissolved in DMF (6 mL), NaH (69.0 mg, 60% dispersion in mineral oil, 1.71 mmol) was added and the reaction mixture was stirred for 30 min. The reaction mixture was cooled to 0° C. and a solution of MeI (182 mg, 1.28 mmol) in DMF (1 mL) was added. The reaction mixture was warmed to room temperature overnight and brine (25 mL) was added. The reaction mixture was extracted with EtOAc (3×15 mL) and the combined organic fractions were washed with brine (10 mL), dried (MgSO$_4$) and concentrated in vacuo. The residue was washed with heptane and purified by reverse phase HPLC to give the title compound (14.0 mg, 4%) as yellow solid. HRMS (ESI+) calculated for C20H32N8: 384.274993. found 384.276623. HPLC: Rf 6.20 min, 97.7% purity.

Example 169

1-[6-(3-Cyclopropyl-1,2,4-oxadiazol-5-yl)pyridin-2-yl]-4-[1-(propan-2-yl)piperidin-4-yl]-1,4-diazepane

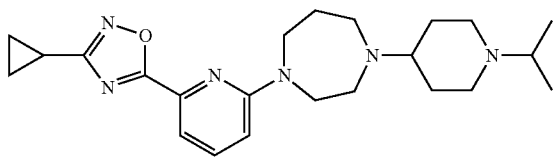 [SMILES: CC(C)N1CCC(N2CCCN(c3cccc(-c4nc(C5CC5)no4)n3)CC2)CC1]

Intermediate 135 (130 mg, 0.36 mmol) was dissolved in DCM (10 mL) and oxalyl chloride (92.0 mg, 0.72 mmol) and DMF (100 µL) were added. The reaction mixture was stirred for 3 h and the solvents were removed in vacuo. The residue and DIPEA (111 mg, 0.86 mmol) were dissolved in DCM (75 mL) and cooled to 0° C. N'-hydroxycyclopropanecarboximidamide (37.0 mg, 0.37 mmol) was added and the reaction mixture was stirred at 0° C. for 1 h and at room temperature for 1 h. The reaction mixture was partitioned between DCM (75 mL) and sat aq Na$_2$CO$_3$ (25 mL) and the organic fraction was washed with brine (25 mL), dried (MgSO$_4$) and concentrated in vacuo. The residue was suspended in xylenes (10 mL) and heated to 150° C. for 1 h. The solvents were removed in vacuo and the residue was purified by reverse phase HPLC to give the title compound (5.20 mg, 4%) as a yellow gum. HRMS (ESI+) calculated for C23H34N6O: 410.27941. found 410.28058. HPLC: Rf 4.18 min, 98.6% purity.

Example 170

1-[6-(3-Phenyl-1,2,4-oxadiazol-5-yl)pyridin-2-yl]-4-[1-(propan-2-yl)piperidin-4-yl]-1,4-diazepane

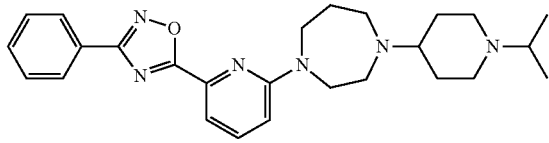 [SMILES: CC(C)N1CCC(N2CCCN(c3cccc(-c4nc(-c5ccccc5)no4)n3)CC2)CC1]

Example 170 was prepared similarly to Example 169, using N'-hydroxybenzenecarboximidamide instead of N'-hydroxycyclopropanecarboximidamide, to give the title compound (6%) as a yellow gum. HRMS (ESI+) calculated for C26H34N6O: 446.27941. found 446.28042. HPLC: Rf 4.73 min, 98.2% purity.

Example 171

1-[6-(5-Butyl-1,3-oxazol-2-yl)pyridin-2-yl]-4-[1-(propan-2-yl)piperidin-4-yl]-1,4-diazepane

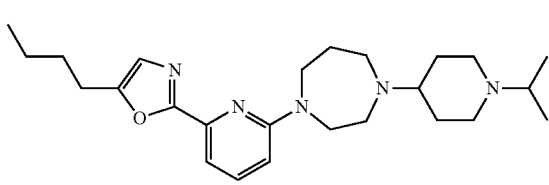 [SMILES: CCCCc1cnc(-c2cccc(N3CCCN(C4CCN(C(C)C)CC4)CC3)n2)o1]

Intermediate 143 (222 mg, 0.50 mmol) was dissolved in MeCN (1.5 mL) and added to a solution of PPh$_3$ (393 mg, 1.50 mmol) and hexachloroethane (355 mg, 1.50 mmol) in MeCN (5 mL). The reaction mixture was stirred for 10 min, Et$_3$N (300 mg, 3.00 mmol) was added and the reaction mixture was heated at 50° C. overnight. A further solution of PPh$_3$ (131 mg, 0.50 mmol) and hexachloroethane (119 mg, 0.50 mmol) in MeCN (1 mL) was added and the reaction mixture was heated at 50° C. overnight. Brine and sat aq NaHCO$_3$ were added and the reaction mixture was extracted with EtOAc (3×10 mL and 2×30 mL), dried (MgSO$_4$) and concentrated in vacuo. The residue was purified by column chromatography and reverse phase HPLC to give the title compound (20.0 mg, 9%) as an orange gum. HRMS (ESI+) calculated for C25H39N5O: 425.315461. found 425.316761. HPLC: Rf 4.74 min, 98.8% purity.

Example 172

1-[6-(5-Cyclopropyl-1,3,4-oxadiazol-2-yl)pyridin-2-yl]-4-[1-(propan-2-yl)piperidin-4-yl]-1,4-diazepane

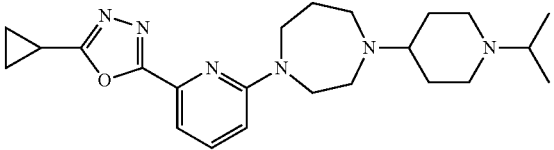 [SMILES: CC(C)N1CCC(N2CCCN(c3cccc(-c4nnc(C5CC5)o4)n3)CC2)CC1]

Intermediate 146 (249 mg, 0.58 mmol) and POCl$_3$ (7 mL) were heated at 100° C. for 3 h. The solvents were removed in vacuo, sat aq Na$_2$CO$_3$ (13 mL) was added and the reaction mixture was extracted with EtOAc (×3), dried (MgSO$_4$) and concentrated in vacuo. The residue was purified by column chromatography and reverse phase HPLC to give the title compound (15.0 mg, 6%) as a light yellow gum. HRMS (ESI+) calculated for C23H34N6O: 410.27941. found 410.28076. HPLC: Rf 3.76 min, 98.1% purity.

Example 173

1-[6-(4-Methyl-1H-pyrazol-3-yl)pyridin-2-yl]-4-[1-(propan-2-yl)piperidin-4-yl]-1,4-diazepane trihydrochloride

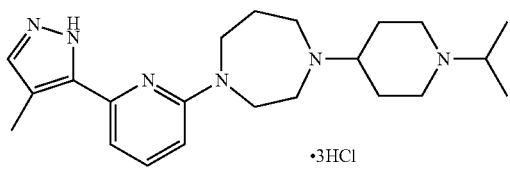 [SMILES: Cc1cn[nH]c1-c1cccc(N2CCCN(C3CCN(C(C)C)CC3)CC2)n1]

·3HCl

Intermediate 148 (45.0 mg, 0.11 mmol), hydrazine hydrate (4 mL) and MeOH (few drops) were heated at reflux for 4 h. The solvents were removed in vacuo and the residue was purified by column chromatography and reverse phase HPLC. The residue was dissolved in DCM (10 mL) and HCl (5 mL, 2.0 M in Et$_2$O) and the solvents were removed in vacuo to give the title compound (3.60 mg, 9%) as a light yellow gum. HRMS (ESI+) calculated for C22H34N6; 382.284495. found 382.285835. HPLC: Rf 3.30 min, 100% purity.

Examples 174-184

Examples 174-184 were prepared similarly to Example 63, by reductive alkylation; see Table 21 below.

TABLE 21

Reductive alkylations of Intermediates 150 and 154-158

| Ex | Structure | Name | Ints | Yield | HRMS (ESI+), HPLC |
|---|---|---|---|---|---|
| 174 | 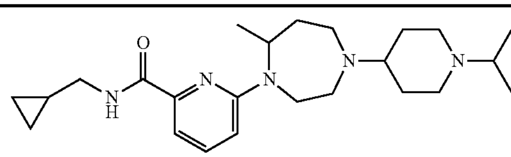 | N-(Cyclopropylmethyl)-6-{7-methyl-4-[1-(propan-2-yl)piperidin-4-yl]-1,4-diazepan-1-yl}pyridine-2-carboxamide | 150* | 8% | HRMS (ESI+) calculated for C24H39N5O: 413.315461, found 413.315301. HPLC: Rf 3.84 min, 97.7% purity. |
| 175 | 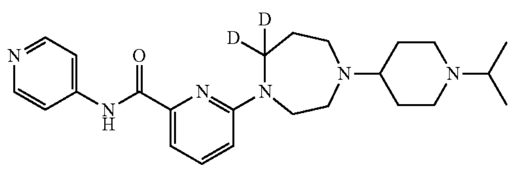 [SMILES: [2H]C1([2H])CCN(C2CCN(C(C)C)CC2)CCN1c1cccc(C(=O)Nc2ccncc2)n1] | 6-{7,7-Dihydrogenio-4-[1-(propan-2-yl)piperidin-4-yl]-1,4-diazepan-1-yl}-N-(pyridine-4-yl)pyridine-2-carboxamide | 157, * | 19% | HRMS (ESI+) calculated for C24H32[2H]2N6O: 424.29506, found 424.29478. HPLC: Rf 3.45 min, 100% purity. |
| 176 | 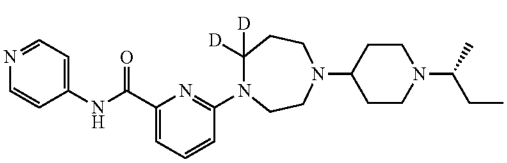 [SMILES: [2H]C1([2H])CCN(C2CCN([C@H](C)CC)CC2)CCN1c1cccc(C(=O)Nc2ccncc2)n1] | 6-(4-{1-[(2R)-Butan-2-yl]piperidin-4-yl}-7,7-dihydrogenio-1,4-diazepan-1-yl)-N-(pyridine-4-yl)pyridine-2-carboxamide | 157, 8 | 11% | HRMS (ESI+) calculated for C25H34[2H]2N6O: 438.31071, found 438.31087. HPLC: Rf 3.56 min, 99.6% purity. |
| 177 | 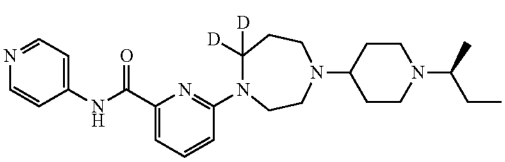 [SMILES: [2H]C1([2H])CCN(C2CCN([C@@H](C)CC)CC2)CCN1c1cccc(C(=O)Nc2ccncc2)n1] | 6-(4-{1-[(2S)-Butan-2-yl]piperidin-4-yl}-7,7-dihydrogenio-1,4-diazepan-1-yl)-N-(pyridine-4-yl)pyridine-2-carboxamide | 157, 9 | 8% | HRMS (ESI+) calculated for C25H34[2H]2N6O: 438.31071, found 438.3108. HPLC: Rf 3.56 min, 99.3% purity. |
| 178 | 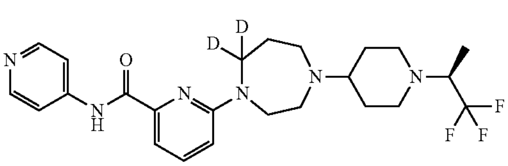 [SMILES: [2H]C1([2H])CCN(C2CCN([C@@H](C)C(F)(F)F)CC2)CCN1c1cccc(C(=O)Nc2ccncc2)n1] | 6-(7,7-Dihydrogenio-4-{1-[(2S)-1,1,1-trifluoropropan-2-yl]piperidin-4-yl}-1,4-diazepan-1-yl)-N-(pyridine-4-yl)pyridine-2-carboxamide | 157, 12 | 10% | HRMS (ESI+) calculated for C24H29[2H]2F3N6O: 478.266794, found 478.264914. HPLC: Rf 4.35 min, 98.6% purity. |
| 179 | 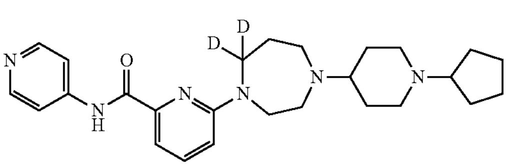 [SMILES: [2H]C1([2H])CCN(C2CCN(C3CCCC3)CC2)CCN1c1cccc(C(=O)Nc2ccncc2)n1] | 6-[4-(1-Cyclopentyl-piperidin-4-yl)-7,7-dihydrogenio-1,4-diazepan-1-yl]-N-(pyridine-4-yl)pyridine-2-carboxamide | 157, 24 | 1% | HRMS (ESI+) calculated for C26H34[2H]2N6O: 450.31071, found 450.30879. HPLC: Rf 3.63 min, 99.3% purity. |

TABLE 21-continued

Reductive alkylations of Intermediates 150 and 154-158

| Ex | Structure | Name | Ints | Yield | HRMS (ESI+), HPLC |
|---|---|---|---|---|---|
| 180 | 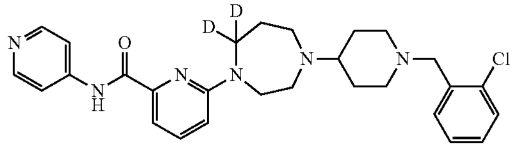 [SMILES: [2H]C1([2H])CCN(C2CCN(Cc3ccccc3Cl)CC2)CCN1c1cccc(C(=O)Nc2ccncc2)n1] | 6-(4-{1-[(2-Chlorophenyl)methyl]piperidin-4-yl}-7,7-dihydrogenio-1,4-diazepan-1-yl)-N-(pyridin-4-yl)pyridine-2-carboxamide | 157, 25 | 39% | HRMS (ESI+) calculated for C28H31[2H]2ClN6O: 506.256087, found 506.256737. HPLC: Rf 3.84 min, 99.6% purity. |
| 181 | 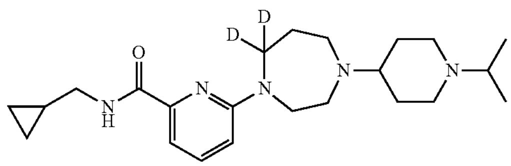 [SMILES: [2H]C1([2H])CCN(C2CCN(C(C)C)CC2)CCN1c1cccc(C(=O)NCC2CC2)n1] | N-(Cyclopropylmethyl)-6-{7,7-dihydrogenio-4-[1-(propan-2-yl)piperidin-4-yl]-1,4-diazepan-1-yl}pyridine-2-carboxamide | 158, * | 9% | LCMS (ES+): 402.4 [MH]+. HPLC: Rf 4.79 min, 99.6% purity. |
| 182 | 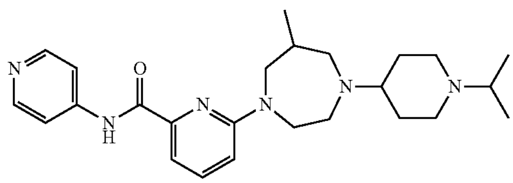 [SMILES: CC1CN(c2cccc(C(=O)Nc3ccncc3)n2)CCN(C2CCN(C(C)C)CC2)C1] | 6-{6-Methyl-4-[1-(propan-2-yl)piperidin-4-yl]-1,4-diazepan-1-yl}-N-(pyridin-4-yl)pyridine-2-carboxamide | 154, * | 46% | HRMS (ESI+) calculated for C25H36N6O: 436.29506, found 436.29564. HPLC: Rf 3.53 min, 99.6% purity. |
| 183 | 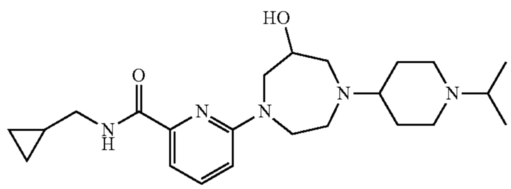 [SMILES: CC(C)N1CCC(N2CCN(c3cccc(C(=O)NCC4CC4)n3)CC(O)C2)CC1] | N-(Cyclopropylmethyl)-6-{6-hydroxy-4-[1-(propan-2-yl)piperidin-4-yl]-1,4-diazepan-1-yl}pyridine-2-carboxamide | 155, * | 14% | HRMS (ESI+) calculated for C23H37N5O2: 415.294726, found 415.296206. HPLC: Rf 3.62 min, 100% purity. |
| 184 | 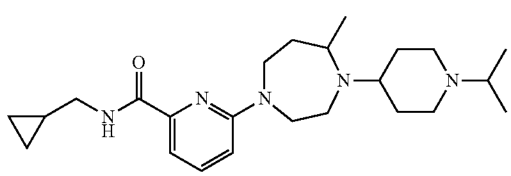 [SMILES: CC(C)N1CCC(N2CCN(c3cccc(C(=O)NCC4CC4)n3)CCC2C)CC1] | N-(Cyclopropylmethyl)-6-{5-methyl-4-[1-(propan-2-yl)piperidin-4-yl]-1,4-diazepan-1-yl}pyridine-2-carboxamide | 156, * | 17% | HRMS (ESI+) calculated for C24H39N5O: 413.315461, found 413.315271. HPLC: Rf 3.85 min, 98.5% purity. |

* Commercially available

Example 185

6-{4-[3-Fluoro-1-(propan-2-yl)piperidin-4-yl]-1,4-diazepan-1-yl}-N-(pyridin-3-ylmethyl)pyridine-2-carboxamide

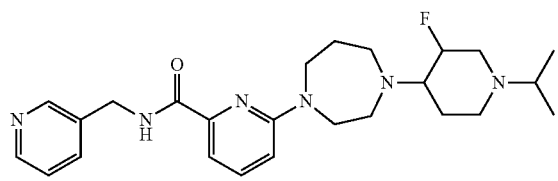 [SMILES: CC(C)N1CCC(N2CCCN(c3cccc(C(=O)NCc4cccnc4)n3)CC2)C(F)C1]

Intermediate 43 (224 mg, 0.90 mmol) was dissolved in dioxane (3 mL) and NaOtBu (111 mg, 1.15 mmol), Pd$_2$(dba)$_3$ (30.1 mg, 0.03 mmol), Xantphos (53.7 mg, 0.07 mmol) and Intermediate 183 (200 mg, 0.82 mmol) were added. The reaction mixture was heated at 100° C. for 3 d. The solvents were removed in vacuo and the residue was dissolved in DCM, filtered and concentrated in vacuo. The residue was purified by reverse phase HPLC to give the title compound (5.61 mg, 1%) as a light yellow solid. HRMS (ESI+) calculated for C25H35FN6O: 454.285638. found 454.287278. HPLC: Rf 3.07 min, 99.7% purity.

Example 186

6-{5,5-Dihydrogenio-4-[1-(propan-2-yl)piperidin-4-yl]-1,4-diazepan-1-yl}-N-(pyridin-4-yl)pyridine-2-carboxamide

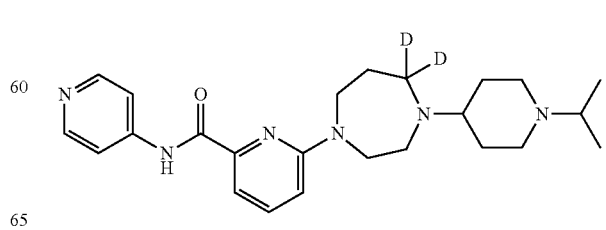

Intermediate 173 (150 mg, 0.54 mmol), Intermediate 159 (123 mg, 0.54 mmol), BINAP (33.6 mg, 0.05 mmol), palladium acetate (8.50 mg, 0.04 mmol) and Cs₂CO₃ (264 mg, 0.81 mmol) were dissolved in dioxane (2 mL) and heated at 100° C. for 4 d. The reaction mixture was filtered and concentrated in vacuo. The residue was purified by reverse phase HPLC to give the title compound (14.1 mg, 6%) as a light yellow gum. HRMS (ESI+) calculated for C24H32[2H]2N6O: 424.29506. found 424.29411. HPLC: Rf 3.43 min, 98.5% purity.

Examples 187-202

Examples 187-202 were prepared similarly to Example 186, by Buchwald-Hartwig reactions with Intermediates 173 and 174; see Table 22 below.

TABLE 22

Buchwald-Hartwig reactions of Intermediates 173 and 174

| Ex | Structure | Name | Ints | Yield | HRMS (ESI⁺), HPLC |
|---|---|---|---|---|---|
| 187 | 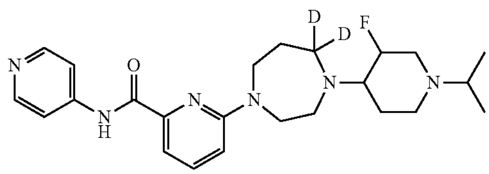 [SMILES: [2H]C1([2H])CCN(c2cccc(C(=O)Nc3ccncc3)n2)CCN1C1CCN(C(C)C)CC1F] | 6-{4-[3-Fluoro-1-(propan-2-yl)piperidin-4-yl]-5,5-dihydrogenio-1,4-diazepan-1-yl}-N-(pyridin-4-yl)pyridine-2-carboxamide | 173, 182 | 6% | HRMS (ESI+) calculated for C24H31[2H]2FN6O: 442.285638, found 442.283958. HPLC: Rf 3.42 min, 98.2% purity. |
| 188 | 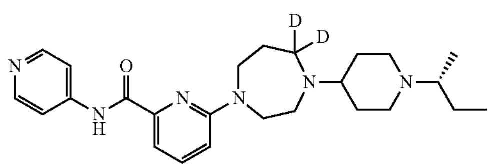 [SMILES: [2H]C1([2H])CCN(c2cccc(C(=O)Nc3ccncc3)n2)CCN1C1CCN([C@H](C)CC)CC1] | 6-(4-{1-[(2R)-Butan-2-yl]piperidin-4-yl}-5,5-dihydrogenio-1,4-diazepan-1-yl)-N-(pyridin-4-yl)pyridine-2-carboxamide | 173, 164 | 16% | HRMS (ESI+) calculated for C25H34[2H]2N6O: 438.31071, found 438.31053. HPLC: Rf 3.54 min, 99.6% purity. |
| 189 | 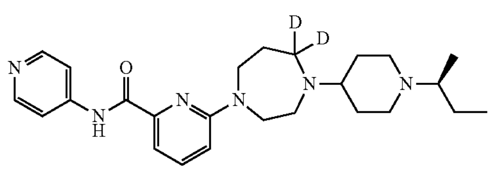 [SMILES: [2H]C1([2H])CCN(c2cccc(C(=O)Nc3ccncc3)n2)CCN1C1CCN([C@@H](C)CC)CC1] | 6-(4-{1-[(2S)-Butan-2-yl]piperidin-4-yl}-5,5-dihydrogenio-1,4-diazepan-1-yl)-N-(pyridin-4-yl)pyridine-2-carboxamide | 173, 165 | 6% | HRMS (ESI+) calculated for C25H34[2H]2N6O: 438.31071, found 438.3094. HPLC: Rf 3.54 min, 100% purity. |
| 190 | 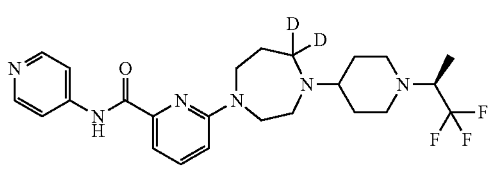 [SMILES: [2H]C1([2H])CCN(c2cccc(C(=O)Nc3ccncc3)n2)CCN1C1CCN([C@@H](C)C(F)(F)F)CC1] | 6-(5,5-Dihydrogenio-4-{1-[(2S)-1,1,1-trifluoropropan-2-yl]piperidin-4-yl}-1,4-diazepan-1-yl)-N-(pyridin-4-yl)pyridine-2-carboxamide | 173, 166 | 16% | HRMS (ESI+) calculated for C24H29[2H]2F3N6O: 478.266794, found 478.264634. HPLC: Rf 4.35 min, 100% purity. |
| 191 | 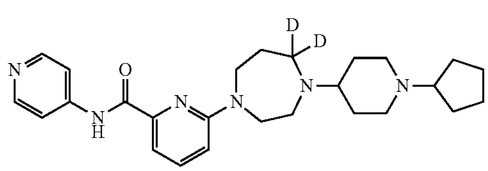 [SMILES: [2H]C1([2H])CCN(c2cccc(C(=O)Nc3ccncc3)n2)CCN1C1CCN(C2CCCC2)CC1] | 6-[4-(1-Cyclopentylpiperidin-4-yl)-5,5-dihydrogenio-1,4-diazepan-1-yl]-N-(pyridin-4-yl)pyridine-2-carboxamide | 173, 167 | 2% | HRMS (ESI+) calculated for C26H34[2H]2N6O: 450.31071, found 450.31108. HPLC: Rf 3.60 min, 100% purity. |
| 192 | 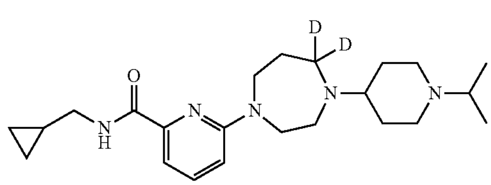 [SMILES: [2H]C1([2H])CCN(c2cccc(C(=O)NCC3CC3)n2)CCN1C1CCN(C(C)C)CC1] | N-(Cyclopropylmethyl)-6-{5,5-dihydrogenio-4-[1-(propan-2-yl)piperidin-4-yl]-1,4-diazepan-1-yl}pyridine-2-carboxamide | 174, 159 | 1% | LCMS (ES⁺): 402.5 [MH]⁺. HPLC: Rf 3.75 min, 99.5% purity. |
| 193 | 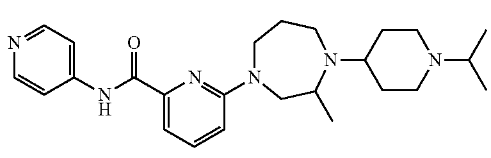 [SMILES: CC(C)N1CCC(N2CCCN(c3cccc(C(=O)Nc4ccncc4)n3)CC2C)CC1] | 6-{3-Methyl-4-[1-(propan-2-yl)piperidin-4-yl]-1,4-diazepan-1-yl}-N-(pyridin-4-yl)pyridine-2-carboxamide | 173, 168 | 6% | HRMS (ESI+) calculated for C25H36N6O: 436.29506, found 436.29695. HPLC: Rf 3.54 min, 100% purity. |

TABLE 22-continued

Buchwald-Hartwig reactions of Intermediates 173 and 174

| Ex | Structure | Name | Ints | Yield | HRMS (ESI+), HPLC |
|---|---|---|---|---|---|
| 194 | 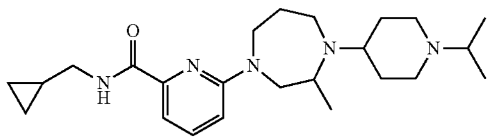 [SMILES: CC(C)N1CCC(N2CCCN(c3cccc(C(=O)NCC4CC4)n3)CC2C)CC1] | N-(Cyclopropylmethyl)-6-{3-methyl-4-[1-(propan-2-yl)piperidin-4-yl]-1,4-diazepan-1-yl}pyridine-2-carboxamide | 174, 168 | 3% | HRMS (ESI+) calculated for C24H39N5O: 413.315461, found 413.316781. HPLC: Rf 4.05 min, 100% purity. |
| 195 | 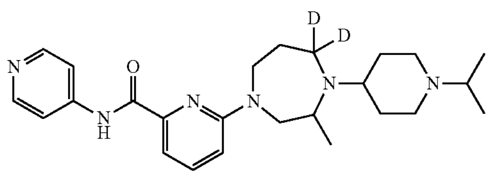 [SMILES: [2H]C1([2H])CCN(c2cccc(C(=O)Nc3ccncc3)n2)CC(C)N1C1CCN(C(C)C)CC1] | 6-{5,5-Dihydrogenio-3-methyl-4-[1-(propan-2-yl)piperidin-4-yl]-1,4-diazepan-1-yl}-N-(pyridin-4-yl)pyridine-2-carboxamide | 173, 169 | 10% | HRMS (ESI+) calculated for C25H34[2H]2N6O: 438.31071, found 438.30995. HPLC: Rf 3.53 min, 98.9% purity. |
| 196 | 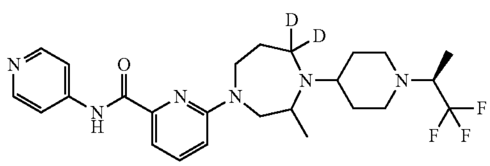 [SMILES: [2H]C1([2H])CCN(c2cccc(C(=O)Nc3ccncc3)n2)CC(C)N1C1CCN([C@@H](C)C(F)(F)F)CC1] | 6-(5,5-Dihydrogenio-3-methyl-4-{1-[(2S)-1,1,1-trifluoropropan-2-yl]piperidin-4-yl}-1,4-diazepan-1-yl)-N-(pyridin-4-yl)pyridine-2-carboxamide | 173, 170 | 1% | HRMS (ESI+) calculated for C25H31[2H]2F3N6O: 492.282444, found 492.281754. HPLC: Rf 4.41 min, 96.2% purity. |
| 197 | 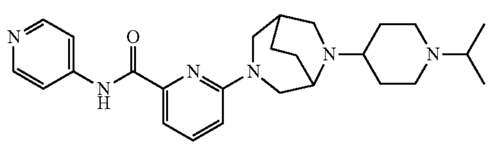 [SMILES: CC(C)N1CCC(N2CC3CCC2CN(c2cccc(C(=O)Nc4ccncc4)n2)C3)CC1] | 6-{6-[1-(Propan-2-yl)piperidin-4-yl]-3,6-diazabicyclo[3.2.2]nonan-3-yl}-N-(pyridin-4-yl)pyridine-2-carboxamide | 173, 172 | 7% | HRMS (ESI+) calculated for C26H36N6O: 448.29506, found 448.29647. HPLC: Rf 3.62 min, 100% purity. |
| 198 | 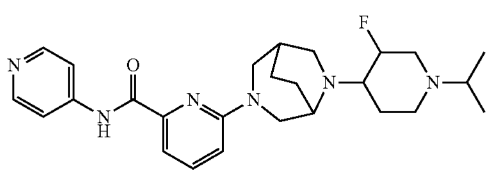 [SMILES: CC(C)N1CCC(N2CC3CCC2CN(c2cccc(C(=O)Nc4ccncc4)n2)C3)C(F)C1] | 6-{6-[3-Fluoro-1-(propan-2-yl)piperidin-4-yl]-3,6-diazabicyclo[3.2.2]nonan-3-yl}-N-(pyridin-4-yl)pyridine-2-carboxamide | 173, 188 | 1% | HRMS (ESI+) calculated for C26H35FN6O: 466.285638, found 466.287348. HPLC: Rf 3.50 min, 99.7% purity. |
| 199 | 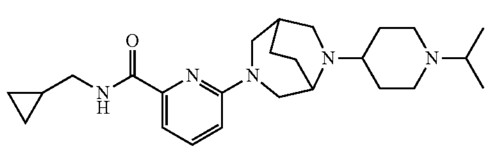 [SMILES: CC(C)N1CCC(N2CC3CCC2CN(c2cccc(C(=O)NCC4CC4)n2)C3)CC1] | N-(Cyclopropylmethyl)-6-{6-[1-(propan-2-yl)piperidin-4-yl]-3,6-diaza-bicyclo[3.2.2]nonan-3-yl}pyridine-2-carboxamide trihydrochloride | 174, 172 | 15% | HRMS (ESI+) calculated for C25H39N5O: 425.315461, found 425.314961. HPLC: Rf 3.85 min, 97.5% purity. |
| 200 | 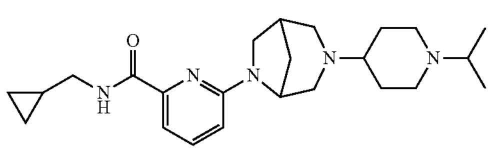 [SMILES: CC(C)N1CCC(N2CC3CC(C2)N(c2cccc(C(=O)NCC4CC4)n2)C3)CC1] | N-(Cyclopropylmethyl)-6-{3-[1-(propan-2-yl)piperidin-4-yl]-3,6-diaza-bicyclo[3.2.1]octan-6-yl}pyridine-2-carboxamide | 174 | 32% | HRMS (ESI+) calculated for C24H37N5O: 411.299811, found 411.298381. HPLC: Rf 3.64 min, 99.2% purity. |
| 201 | 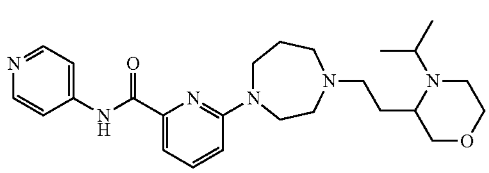 [SMILES: CC(C)N1CCOCC1CCN1CCCN(c2cccc(C(=O)Nc3ccncc3)n2)CC1] | 6-(4-{2-[4-(Propan-2-yl)morpholin-3-yl]ethyl}-1,4-diazepan-1-yl)-N-(pyridin-4-yl)pyridine-2-carboxamide | 173, 243 | 15% | HRMS (ESI+) calculated for C25H36N6O2: 452.289974, found 452.291804. HPLC: Rf 3.50 min, 99.3% purity. |
| 202 | 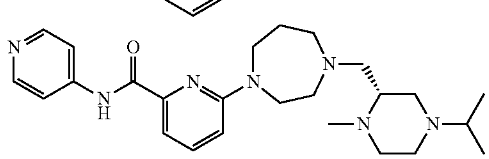 | 6-(4-{[(2R)-1-Methyl-4-(propan-2-yl)piperazin-2-yl]methyl}-1,4-diazepan-1-yl)-N-(pyridin-4-yl)pyridine-2-carboxamide | 173, 249 | 2% | HRMS (ESI+) calculated for C25H37N7O: 451.305959, found 451.307619. HPLC: Rf 3.59 min, 99.5% purity. |

Example 203

6-(4-{1-[(2-Chloro-4-fluorophenyl)methyl]piperidin-4-yl}-5,5-dihydrogenio-1,4-diazepan-1-yl)-N-(pyridin-4-yl)pyridine-2-carboxamide

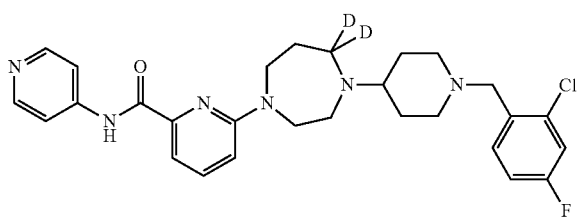 [SMILES: [2H]C1([2H])CCN(c2cccc(C(=O)Nc3ccncc3)n2)CCN1C1CCN(Cc2ccc(F)cc2Cl)CC1]

Intermediate 175 (200 mg, 0.52 mmol) was dissolved in DCM (30 mL) and 2-chloro-4-fluorobenzaldehyde (166 mg, 1.05 mmol) and NaBH(OAc)$_3$ (554 mg, 2.61 mmol) were added. The reaction mixture was stirred for 18 h, diluted with DCM (30 mL), washed with sat aq Na$_2$CO$_3$ (30 mL), dried (MgSO$_4$) and concentrated in vacuo. The residue was purified by reverse phase HPLC to give the title compound (69.7 mg, 25%) as a pale yellow solid. HRMS (ESI+) calculated for C28H30[2H]2ClFN6O: 524.246666. found 524.245956. HPLC: Rf 3.93 min, 99.3% purity.

Examples 204-209

Examples 204-209 were prepared similarly to Example 203, by reacting Intermediates 175, 185, 191 and 273 with the appropriate aldehyde; see Table 23 below.

TABLE 23

Reductive alkylation reactions with Intermediates 175, 185, 191 and 273

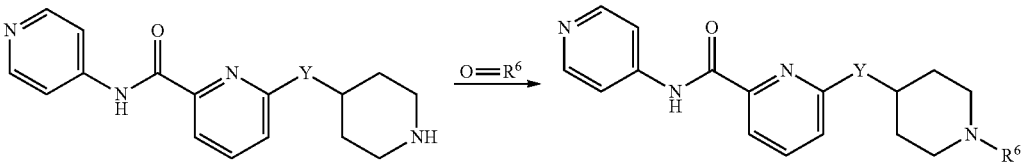

| Ex | Structure | Name | Int | Yield | HRMS (ESI⁺), HPLC |
|---|---|---|---|---|---|
| 204 | 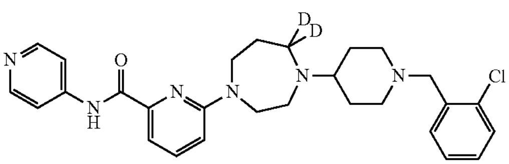 [SMILES: [2H]C1([2H])CCN(c2cccc(C(=O)Nc3ccncc3)n2)CCN1C1CCN(Cc2ccccc2Cl)CC1] | 6-(4-{1-[(2-Chlorophenyl)methyl]piperidin-4-yl}-5,5-dihydrogenio-1,4-diazepan-1-yl)-N-(pyridin-4-yl)pyridine-2-carboxamide | 175 | 18% | HRMS (ESI+) calculated for C28H31[2H]2ClN6O: 506.256087, found 506.256187. HPLC: Rf 3.86 min, 98.9% purity. |
| 205 | 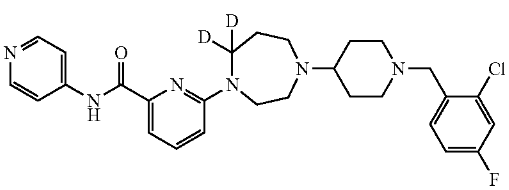 [SMILES: [2H]C1([2H])CCN(C2CCN(Cc3ccc(F)cc3Cl)CC2)CCN1c1cccc(C(=O)Nc2ccncc2)n1] | 6-(4-{1-[(2-Chloro-4-fluorophenyl)methyl]piperidin-4-yl}-7,7-dihydrogenio-1,4-diazepan-1-yl)-N-(pyridin-4-yl)pyridine-2-carboxamide | 273 | 17% | HRMS (ESI+) calculated for C28H30[2H]2ClFN6O: 524.246666, found 524.246206. HPLC: Rf 3.95 min, 99.5% purity. |
| 206 | 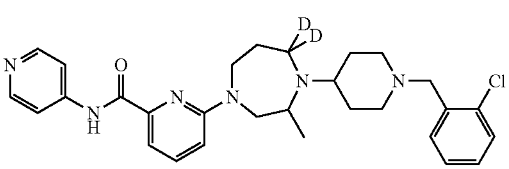 [SMILES: [2H]C1([2H])CCN(c2cccc(C(=O)Nc3ccncc3)n2)CC(C)N1C1CCN(Cc2ccccc2Cl)CC1] | 6-(4-{1-[(2-Chlorophenyl)methyl]piperidin-4-yl}-5,5-dihydrogenio-3-methyl-1,4-diazepan-1-yl)-N-(pyridin-4-yl)pyridine-2-carboxamide | 185 | 27% | HRMS (ESI+) calculated for C29H33[2H]2ClN6O: 520.271738, found 520.271778. HPLC: Rf 3.94 min, 100% purity. |
| 207 | 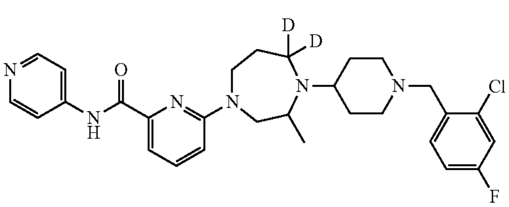 [SMILES: [2H]C1([2H])CCN(c2cccc(C(=O)Nc3ccncc3)n2)CC(C)N1C1CCN(Cc2ccc(F)cc2Cl)CC1] | 6-(4-{1-[(2-Chloro-4-fluorophenyl)methyl]piperidin-4-yl}-5,5-dihydrogenio-3-methyl-1,4-diazepan-1-yl)-N-(pyridin-4-yl)pyridine-2-carboxamide | 185 | 8% | HRMS (ESI+) calculated for C29H32[2H]2ClFN6O: 538.262316, found 538.261216. HPLC: Rf 4.01 min, 99.1% purity. |
| 208 | 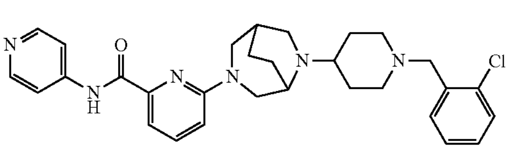 [SMILES: O=C(Nc1ccncc1)c1cccc(N2CC3CCC(C2)N(C2CCN(Cc4ccccc4Cl)CC2)C3)n1] | 6-(6-{1-[(2-Chlorophenyl)methyl]piperidin-4-yl}-3,6-diazabicyclo[3.2.2]nonan-3-yl)-N-(pyridin-4-yl)pyridine-2-carboxamide | 191 | 6% | HRMS (ESI+) calculated for C30H35ClN6O: 530.256087, found 530.256037. HPLC: Rf 3.98 min, 99.8% purity. |

TABLE 23-continued

Reductive alkylation reactions with Intermediates 175, 185, 191 and 273

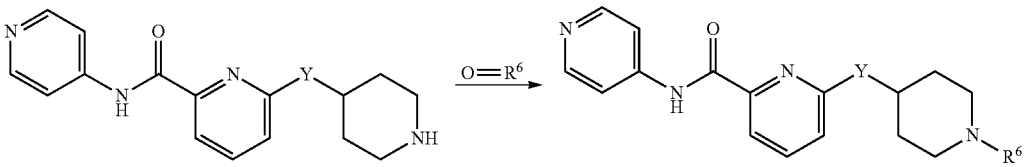

| Ex | Structure | Name | Int | Yield | HRMS (ESI+), HPLC |
|---|---|---|---|---|---|
| 209 | 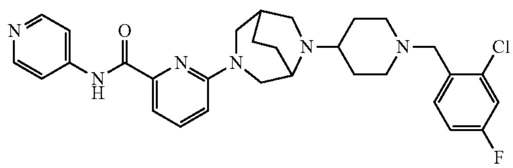 [SMILES: O=C(Nc1ccncc1)c1cccc(N2CC3CCC(C2)N(C2CCN(Cc4ccc(F)cc4Cl)CC2)C3)n1] | 6-(6-{1-[(2-Chloro-4-methyl]piperidin-4-yl}-3,6-diazabicyclo[3.2.2]nonan-3-yl)-N-(pyridin-4-yl)pyridine-2-carboxamide | 191 | 7% | HRMS (ESI+) calculated for C30H34ClFN6O: 548.246666, found 548.246636. HPLC: Rf 4.07 min, 100% purity. |

Example 210

6-{4-[3-Fluoro-1-(propan-2-yl)piperidin-4-yl]-1,4-diazepan-1-yl}-N-(pyridin-4-yl)pyridine-2-carboxamide

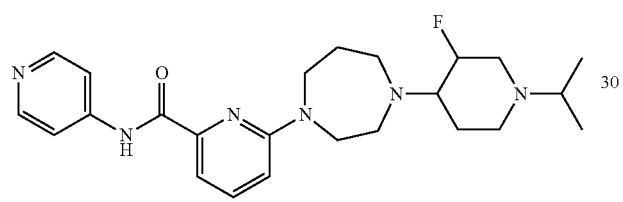

Example 210 was prepared similarly to Example 203, using Intermediate 125 instead of Intermediate 175 and acetone instead of 2-chloro-4-fluorobenzaldehyde, to give the title compound (22%) as a colourless gum. HRMS (ESI+) calculated for C24H33FN6O: 440.269988. found 440.271298. HPLC: Rf 3.40 min, 100% purity.

Examples 211-214

Examples 211-214 were prepared similarly to Example 210, by reacting Intermediates 126, 176 and 177 with the appropriate ketone; see Table 24 below.

TABLE 24

Reductive alkylation reactions with Intermediates 126, 176 and 177

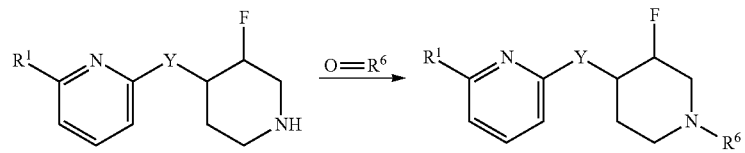

| Ex | Structure | Name | Ints | Yield | HRMS (ESI+), HPLC |
|---|---|---|---|---|---|
| 211 | 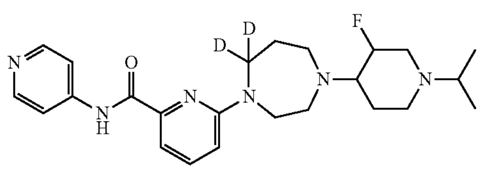 [SMILES: [2H]C1([2H])CCN(C2CCN(C(C)C)CC2F)CCN1c1cccc(C(=O)Nc2ccncc2)n1] | 6-{4-[3-Fluoro-1-(propan-2-yl)piperidin-4-yl]-7,7-dihydrogenio-1,4-diazepan-1-yl}-N-(pyridin-4-yl)pyridine-2-carboxamide | 176 | 21% | HRMS (ESI+) calculated for C24H31[2H]2FN6O: 442.285638, found 442.284838. HPLC: Rf 3.86 min, 98.2% purity. |
| 212 | 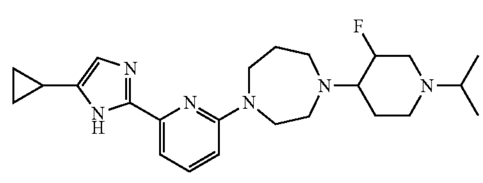 [SMILES: CC(C)N1CCC(N2CCCN(c3cccc(-c4ncc(C5CC5)[nH]4)n3)CC2)C(F)C1] | 1-[6-(4-Cyclopropyl-1H-imidazol-2-yl)pyridin-2-yl]-4-[3-fluoro-1-(propan-2-yl)piperidin-4-yl]-1,4-diazepane | 126 | 30% | HRMS (ESI+) calculated for C24H35FN6: 427.298, found 427.29803. HPLC: Rf 3.58 min, 99.1% purity. |

TABLE 24-continued

Reductive alkylation reactions with Intermediates 126, 176 and 177

| Ex | Structure | Name | Ints | Yield | HRMS (ESI+), HPLC |
|---|---|---|---|---|---|
| 213 | 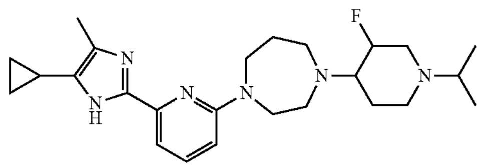 [SMILES: Cc1nc(-c2cccc(N3CCCN(C4CCN(C(C)C)CC4F)CC3)n2)[nH]c1C1CC1] | 1-[6-(4-Cyclopropyl-5-methyl-1H-imidazol-2-yl)pyridin-2-yl]-4-[3-fluoro-1-(propan-2-yl)piperidin-4-yl]-1,4-diazepane | 177 | 15% | HRMS (ESI+) calculated for C25H37FN6: 441.31365, found 441.3136. HPLC: Rf 3.71 min, 98.4% purity. |
| 214 | 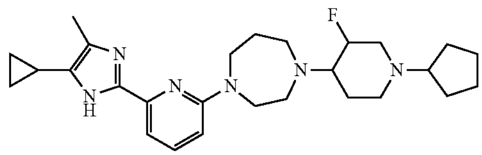 [SMILES: Cc1nc(-c2cccc(N3CCCN(C4CCN(C5CCCC5)CC4F)CC3)n2)[nH]c1C1CC1] | 1-(1-Cyclopentyl-3-fluoro-piperidin-4-yl)-4-[6-(4-cyclopropyl-5-methyl-1H-imidazol-2-yl)pyridin-2-yl]-1,4-diazepane | 177 | 8% | HRMS (ESI+) calculated for C27H39FN6: 467.3293, found 467.3287. HPLC: Rf 3.81 min, 99.3% purity. |

Example 215

6-{4-[2-Methyl-1-(propan-2-yl)piperidin-4-yl]-1,4-diazepan-1-yl}-N-(pyridin-3-ylmethyl)pyridine-2-carboxamide

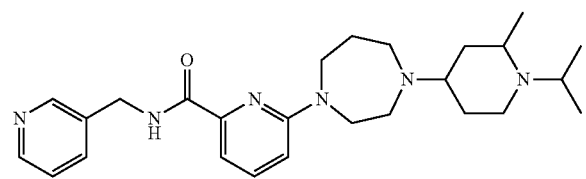 [SMILES: CC(C)N1CCC(N2CCCN(c3cccc(C(=O)NCc4cccnc4)n3)CC2)CC1C]

Example 215 was prepared similarly to Example 203, using Intermediate 127 instead of Intermediate 175 and acetone instead of 2-chloro-4-fluorobenzaldehyde, to give the title compound (1%) as a white solid. HRMS (ESI+) calculated for C26H38N6O: 450.31071. found 450.31244. HPLC: Rf 3.24 min, 100% purity.

Example 216

N-(Cyclopropylmethyl)-6-{4-[(3R)-3-hydroxy-1-(propan-2-yl)piperidin-4-yl]-1,4-diazepan-1-yl}pyridine-2-carboxamide

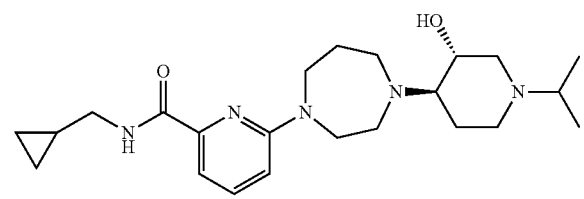 [SMILES: CC(C)N1CC[C@@H](N2CCCN(c3cccc(C(=O)NCC4CC4)n3)CC2)[C@H](O)C1]

Example 216 was prepared similarly to Example 203, using Intermediate 128 instead of Intermediate 175 and acetone instead of 2-chloro-4-fluorobenzaldehyde, to give the title compound (14%) as a white solid. HRMS (ESI+) calculated for C23H37N5O2: 415.294726. found 415.295486. HPLC: Rf 3.58 min, 100% purity.

Example 217

N-(Cyclopropylmethyl)-6-{10-[1-(propan-2-yl)piperidin-4-yl]-3,10-diazabicyclo[4.3.1]decan-3-yl}pyridine-2-carboxamide

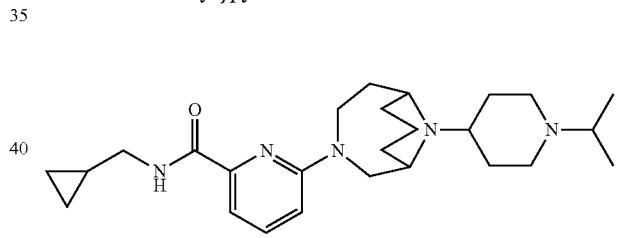

Example 217 was prepared similarly to Example 63, using Intermediate 192 instead of Intermediate 81, to give the title compound (11%) as a colourless gum. HRMS (ESI+) calculated for C26H41N5O: 439.331111. found 439.333241. HPLC: Rf 4.18 min, 98.9% purity.

Example 218

6-(10-{1-[(2-Chlorophenyl)methyl]piperidin-4-yl}-3,10-diazabicyclo[4.3.1]decan-3-yl)-N-(pyridin-4-yl)pyridine-2-carboxamide

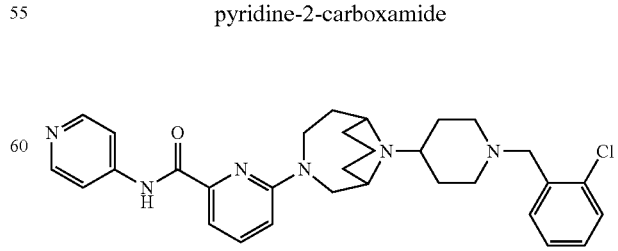

Example 218 was prepared similarly to Example 217, using Intermediate 193 instead of Intermediate 192 and Intermediate 25 instead of 1-(propan-2-yl)piperidin-4-one, to give the title compound (23%) as a yellow solid. HRMS (ESI+) calculated for C31H37ClN6O: 544.271738. found 544.271478. HPLC: Rf 4.08 min, 99.4% purity.

Example 219

1-(6-{4-[1-(Propan-2-yl)piperidin-4-yl]-1,4-diazepan-1-yl}pyridin-2-yl)butan-1-one

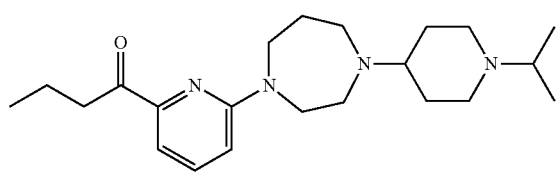 [SMILES: CCCC(=O)c1cccc(N2CCCN(C3CCN(C(C)C)CC3)CC2)n1]

Intermediate 184 (100 mg, 0.26 mmol) was dissolved in THF (3 mL) and propylmagnesium bromide (1.28 mL, 2 M in Et₂O, 2.57 mmol) was added. The reaction mixture was stirred for 18 h and concentrated in vacuo. The residue was dissolved in DCM (20 mL), washed with sat aq Na₂CO₃ (15 mL), dried (MgSO₄) and concentrated in vacuo. The residue was purified by reverse phase HPLC to give the title compound (20.2 mg, 21%) as a yellow gum. HRMS (ESI+) calculated for C22H36N4O: 372.288912. found 372.290132. HPLC: Rf 4.18 min, 99.2% purity.

Example 220

2-Phenyl-1-(6-{4-[1-(propan-2-yl)piperidin-4-yl]-1,4-diazepan-1-yl}pyridin-2-yl)ethan-1-one

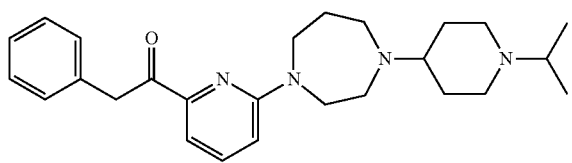 [SMILES: CC(C)N1CCC(N2CCCN(c3cccc(C(=O)Cc4ccccc4)n3)CC2)CC1]

Intermediate 184 (342 mg, 0.88 mmol) was dissolved in THF (8 mL) and benzylmagnesium chloride (8.78 mL, 1 M in Et₂O, 8.78 mmol) was added. The reaction mixture was stirred for 18 h and the solvents were removed in vacuo. The residue was dissolved in DCM (20 mL), washed with sat aq Na₂CO₃ (15 mL), dried (MgSO₄) and concentrated in vacuo. The residue was purified by column chromatography and reverse phase HPLC to give the title compound (2.83 mg, 1%) as a yellow gum. HRMS (ESI+) calculated for C26H36N4O: 420.288912. found 420.290762. HPLC: Rf 4.50 min, 99.6% purity.

Example 221

6-({1-[1-(Propan-2-yl)azepan-4-yl]piperidin-4-yl}oxy)-N-(pyridin-4-yl)pyridine-2-carboxamide

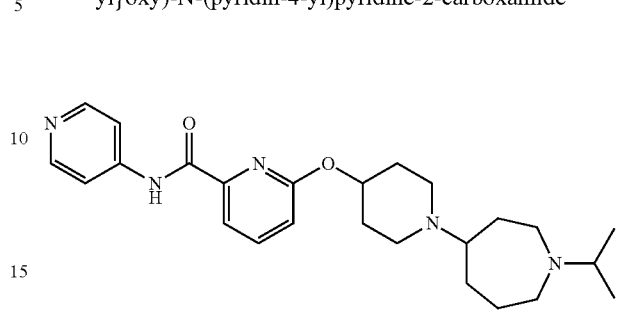

Intermediate 200 (102 mg, 0.26 mmol) was dissolved in DCM (3 mL) and acetone (19.0 µL, 0.26 mmol) and NaBH(OAc)₃ (273 mg, 1.29 mmol) were added. The reaction mixture was stirred for 2 d, diluted with DCM (30 mL) and quenched with sat aq Na₂CO₃ (20 mL). The aq fraction was extracted with DCM (2×15 mL) and the combined organic fractions were dried (MgSO₄) and concentrated in vacuo. The residue was purified by reverse phase HPLC to give the title compound (0.86 mg, 1%) as a colourless gum. HRMS (ESI+) calculated for C25H35N5O2: 437.279075. found 437.279315. HPLC: Rf 3.45 min, 95.6% purity.

Example 222

6-({1-[1-(Propan-2-yl)piperidin-4-yl]piperidin-3-yl}amino)-N-(pyridin-4-yl)pyridine-2-carboxamide

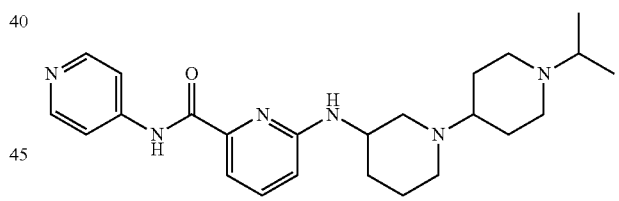

Intermediate 201 (54.0 mg, 0.14 mmol) was dissolved in DCM (4 mL) and TFA (1 mL) was added. The reaction mixture was stirred for 2 h. The solvents were removed in vacuo and the residue partitioned between DCM (20 mL) and 1 M aq NaOH (20 mL). The aq fraction was basified to pH 14 with NaOH and extracted with DCM (3×50 mL). The combined organic fractions were dried (MgSO₄) and concentrated in vacuo. The residue was dissolved in DCM (5 mL) and 1-(propan-2-yl)piperidin-4-one (40.0 µL, 0.27 mmol) and NaBH(OAc)₃ (57.0 mg, 0.30 mmol) were added. The reaction mixture was stirred for 4 d. Further 1-(propan-2-yl)piperidin-4-one (40.0 µL, 0.27 mmol) and NaBH(OAc)₃ (57.0 mg, 0.30 mmol) were added. The reaction mixture was stirred for 1 d. The reaction mixture was diluted with DCM (10 mL) and quenched with water (5 mL). The organic fraction was washed with sat aq Na₂CO₃ (5 mL), dried (MgSO₄) and concentrated in vacuo. The residue was purified by column chromatography and reverse phase HPLC to give the title compound (2.33 mg, 4%) as a white gum. LCMS (ES+): 423.2 [MH]+. HPLC: Rf 3.49 min, 99.2% purity.

Example 223

(3R)-1-[6-(4-Cyclopropyl-1H-imidazol-2-yl)pyridin-2-yl]-N-{[1-(propan-2-yl)piperidin-4-yl]methyl}pyrrolidin-3-amine

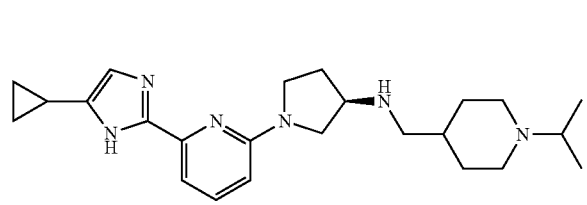 [SMILES: CC(C)N1CCC(CN[C@@H]2CCN(c3cccc(-c4ncc(C5CC5)[nH]4)n3)C2)CC1]

Intermediate 206 (75.0 mg, 0.18 mmol) was dissolved in THF (5 mL), the reaction mixture was cooled to 0° C. and LiAlH$_4$ (0.71 mL, 2.4 M in THF, 1.77 mmol) was added. The reaction mixture was heated at reflux for 5 h and cooled to 0° C. The reaction mixture was diluted with Et$_2$O (20 mL) and quenched with water (0.40 mL) and 1 M aq NaOH (0.20 mL). MgSO$_4$ was added and the reaction was stirred for 15 min, filtered and concentrated in vacuo. The residue was purified by column chromatography and reverse phase HPLC to give the title compound (8.39 mg, 12%) as a beige solid. HRMS (ESI+) calculated for C24H36N6: 409.30742. found 409.30701. HPLC: Rf 3.61 min, 99.4% purity.

Example 224

(3R)—N-{[(3S)-1-Cyclopentylpyrrolidin-3-yl]methyl}-1-[6-(4-cyclopropyl-5-methyl-1H-imidazol-2-yl)pyridin-2-yl]pyrrolidin-3-amine

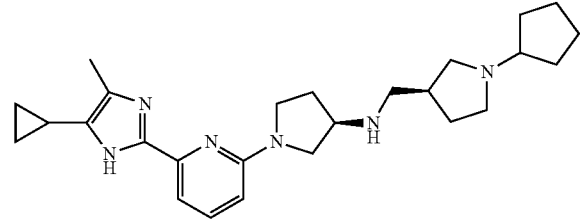 [SMILES: Cc1nc(-c2cccc(N3CC[C@@H](NC[C@@H]4CCN(C5CCCC5)C4)C3)n2)[nH]c1C1CC1]

Example 224 was prepared similarly to Example 223, using Intermediate 210 instead of Intermediate 206, to give the title compound (22.1 mg, 44%) as a white solid. HRMS (ESI+) calculated for C26H38N6: 435.32307. found 435.32275. HPLC: Rf 3.58 min, 98.4% purity.

Example 225

(3R)—N-{[(3R)-1-Cyclopentylpyrrolidin-3-yl]methyl}-1-[6-(4-cyclopropyl-5-methyl-1H-imidazol-2-yl)pyridin-2-yl]pyrrolidin-3-amine

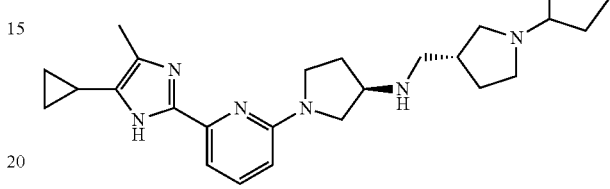

Example 225 was prepared similarly to Example 223, using Intermediate 211 instead of Intermediate 206, to give the title compound (30.3 mg, 46%) as a white solid. HRMS (ESI+) calculated for C26H38N6: 435.32307. found 435.32291. HPLC: Rf 3.57 min, 98.4% purity.

Example 226

6-[(3R)-3-({[(3S)-1-Cyclopentylpyrrolidin-3-yl]methyl}amino)pyrrolidin-1-yl]-N-(pyridin-4-yl)pyridine-2-carboxamide

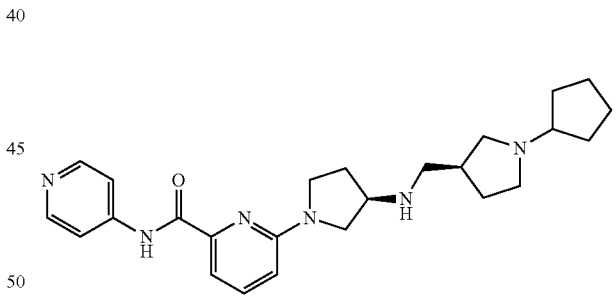

Intermediate 213 (300 mg, 0.82 mmol) was dissolved in DCM (10.0 mL), cyclopentanone (72.3 mg, 0.86 mmol) and NaBH(OAc)$_3$ (347 mg, 1.64 mmol) were added and the reaction mixture was stirred overnight. The reaction mixture was diluted with DCM (10 mL) and quenched with water (5 mL). The organic fraction was washed with sat aq Na$_2$CO$_3$ (5 mL), dried (MgSO$_4$) and concentrated in vacuo. The residue was purified by column chromatography and reverse phase HPLC to give the title compound as a white solid (98.9 mg, 28%). HRMS (ESI+) calculated for C25H34N6O: 435.28669. found 435.28659. HPLC: Rf 3.26 min, 100% purity.

Example 227

6-[(3R)-3-({[(3R)-1-Cyclopentylpyrrolidin-3-yl]methyl}amino)pyrrolidin-1-yl]-N-(pyridin-4-yl)pyridine-2-carboxamide

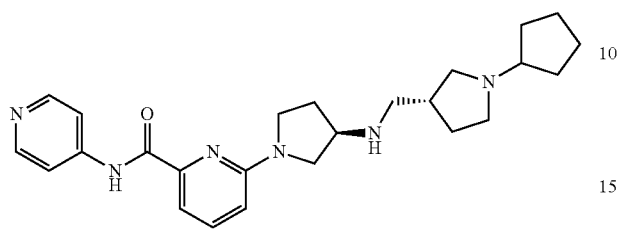

Example 227 was prepared similarly to Example 226, using Intermediate 214 instead of Intermediate 213, to give the title compound (6%) as a light yellow solid. HRMS (ESI+) calculated for C25H34N6O: 435.28669. found 435.28711. HPLC: Rf 3.27 min, 100% purity.

Example 228

6-[(3R)-3-{[(1-Cyclopentylpiperidin-4-yl)methyl]amino}pyrrolidin-1-yl]-N-(pyridin-4-yl)pyridine-2-carboxamide

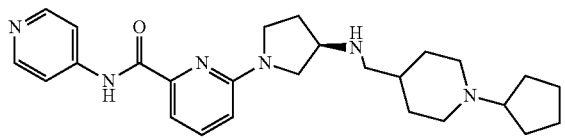 [SMILES: O=C(Nc1ccncc1)c1cccc(N2CC[C@@H](NCC3CCN(C4CCCC4)CC3)C2)n1]

Intermediate 215 was dissolved in DCM (10 mL) and cyclopentanone (170 mg, 2.02 mmol) and NaBH(OAc)$_3$ (779 mg, 3.68 mmol) were added. The reaction mixture was stirred overnight, diluted with DCM (25 mL) and quenched with water (10 mL). The organic fraction was washed with sat aq Na$_2$CO$_3$ (510 mL), dried (MgSO$_4$) and concentrated in vacuo. The residue was purified by column chromatography and reverse phase HPLC to give the title compound (10.9 mg, 1%) as a white solid. HRMS (ESI+) calculated for C26H36N6O: 449.30234. found 449.30127. HPLC: Rf 3.25 min, 99.8% purity.

Example 229

[(1-Cyclopentylpyrrolidin-3-yl)methyl](2-{[6-(5-cyclopropyl-1H-imidazol-2-yl)pyridin-2-yl]amino}ethyl)amine

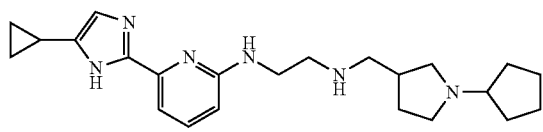 [SMILES: c1cc(NCCNCC2CCN(C3CCCC3)C2)nc(-c2ncc(C3CC3)[nH]2)c1]

Intermediate 225 (150 mg, 0.37 mmol) was dissolved in THF (5 mL) at 0° C. and LiAlH$_4$ (1.00 mL, 2.4 M in THF, 2.40 mmol) was added dropwise. The reaction mixture was heated at 67° C. for 18 h. The reaction mixture was cooled to −5° C. and quenched with water (98 μL), 15% aq NaOH (98 μL) and water (300 μL). The residue was extracted with EtOAc (7×10 mL) and the combined organic fractions were dried (MgSO$_4$) and concentrated in vacuo. The residue was purified by reverse phase HPLC and column chromatography to give the title compound (4.07 mg, 3%) as a light yellow gum. LCMS (ES+): 395.2 [MH]+. HPLC: Rf 3.70 min, 99.6% purity.

Example 230

1-Cyclopentyl-N-(2-{[6-(5-cyclopropyl-1H-imidazol-2-yl)pyridin-2-yl]amino}ethyl)piperidin-3-amine

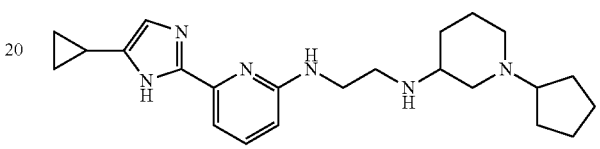

Intermediate 228 (226 mg, 0.53 mmol) was dissolved in DCM (4 mL), TFA (1 mL) was added and the reaction mixture was stirred for 3 h. The solvents were removed in vacuo and the residue was de-salted using a MP-TsOH SPE cartridge, eluting with 7 N ammonia in MeOH. Half of the residue was dissolved in DCM (5 mL) and cyclopentanone (19.8 μL, 0.22 mmol) and NaBH(OAc)$_3$ (85.7 mg, 0.40 mmol) were added. The reaction mixture was stirred overnight, diluted with DCM (10 mL) and quenched with water (5 mL). The organic fraction was washed with sat aq Na$_2$CO$_3$ (5 mL), dried (MgSO$_4$) and concentrated in vacuo. The residue was purified by column chromatography and reverse phase HPLC to give the crude title compound (13.2 mg, 17%) as a white solid HRMS (ESI+) calculated for C23H34N6: 395.29177. found 395.29117. HPLC: Rf 3.63 min, 98.2% purity.

Example 231

N-{2-[(1-Cyclopentylpiperidin-3-yl)amino]ethyl}-6-(5-cyclopropyl-4-methyl-1H-imidazol-2-yl)pyridin-2-amine

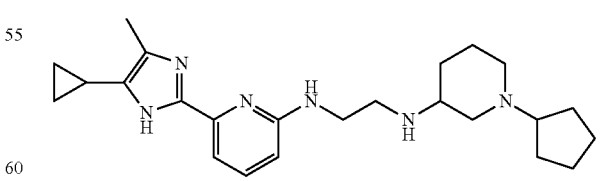

Example 231 was prepared similarly to Example 230, using Intermediate 229 instead of Intermediate 228, to give the title compound (22%) as a white solid. HRMS (ESI+) calculated for C24H36N6: 409.30742. found 409.30695. HPLC: Rf 3.81 min, 96.7% purity.

Example 232

1-Cyclopentyl-N-(2-{[6-(5-cyclopropyl-4-methyl-1H-imidazol-2-yl)pyridin-2-yl]amino}ethyl)piperidin-4-amine

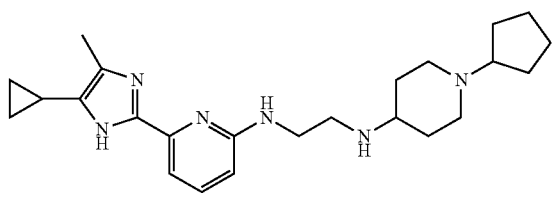 [SMILES: Cc1nc(-c2cccc(NCCNC3CCN(C4CCCC4)CC3)n2)[nH]c1C1CC1]

Example 232 was prepared similarly to Example 231, using Intermediate 230 instead of Intermediate 229, to give the title compound (11%) as a white solid. HRMS (ESI+) calculated for C24H36N6: 409.30742. found 409.30737. HPLC: Rf 3.78 min, 98.4% purity.

Example 233

N-{2-[(1-Cyclopentylpyrrolidin-3-yl)amino]ethyl}-6-(5-cyclopropyl-1H-imidazol-2-yl)pyridin-2-amine

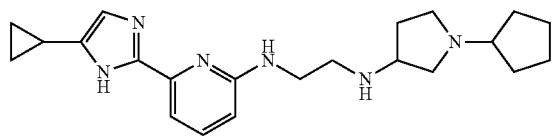 [SMILES: c1cc(NCCNC2CCN(C3CCCC3)C2)nc(-c2ncc(C3CC3)[nH]2)c1]

Example 233 was prepared similarly to Example 230, using Intermediate 231 instead of Intermediate 228, to give the title compound (11%) as an off-white solid. HRMS (ESI+) calculated for C22H32N6: 381.27612. found 381.27554. HPLC: Rf 3.74 min, 98.5% purity.

Example 234

6-[(2-{[1-(Propan-2-yl)azepan-4-yl]amino}ethyl)amino]-N-(pyridin-4-yl)pyridine-2-carboxamide

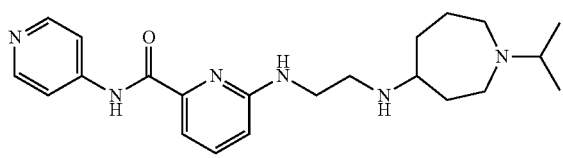

Example 234 was prepared similarly to Example 230, using Intermediate 232 instead of Intermediate 228 and acetone instead of cyclopentanone, to give the title compound (18%) as a colourless gum. HRMS (ESI+) calculated for C22H32N6O: 396.26376. found 396.26423. HPLC: Rf 3.35 min, 95.1% purity.

Example 235

1-[(2R)-Butan-2-yl]-N-(2-{[6-(4-ethyl-1H-imidazol-2-yl)pyridin-2-yl]amino}ethyl)piperidin-4-amine

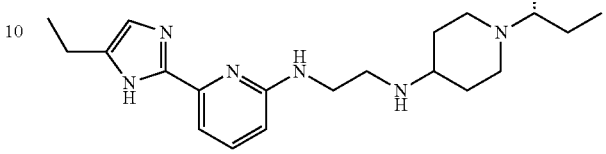

Intermediate 217 (168 mg, 0.73 mmol) was dissolved in DCM (3 mL) and (R)-1-sec-butyl-piperidin-4-one (169 mg, 1.09 mmol) and NaBH(OAc)3 (308 mg, 1.45 mmol) were added. The reaction mixture was stirred overnight, diluted with DCM (10 mL) and quenched with water (5 mL). The organic fraction was washed with sat aq Na2CO3 (5 mL), dried (MgSO4) and concentrated in vacuo. The residue was purified by reverse phase HPLC to give the title compound (66.7 mg, 25%) as a white solid. HRMS (ESI+) calculated for C21H34N6: 371.29177. found 371.29163. HPLC: Rf 3.52 min, 99.5% purity.

Example 236

N-(2-{[6-(5-Cyclopropyl-4-methyl-1H-imidazol-2-yl)pyridin-2-yl]amino}ethyl)-1-(propan-2-yl)piperidin-4-amine

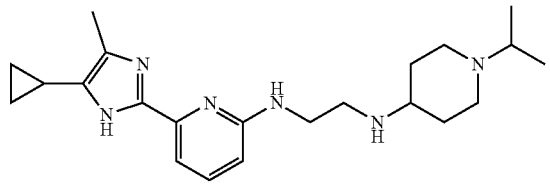 [SMILES: Cc1nc(-c2cccc(NCCNC3CCN(C(C)C)CC3)n2)[nH]c1C1CC1]

Example 236 was prepared similarly to Example 235, using Intermediate 218 instead of Intermediate 217 and 1-(propan-2-yl)piperidin-4-one instead of (R)-1-sec-butyl-piperidin-4-one, to give the title compound (9%) as a white solid. HRMS (ESI+) calculated for C22H34N6: 383.29177. found 383.29147. HPLC: Rf 3.60 min, 97.2% purity.

Example 237

N-(2-{[3-(Cyclopentylamino)propyl]amino}ethyl)-6-(5-cyclopropyl-1H-imidazol-2-yl)pyridin-2-amine

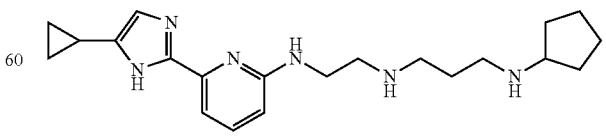

Example 237 was prepared similarly to Example 229, using Intermediate 235 instead of Intermediate 225, to give the title compound (17%) as a pale yellow gum. HRMS

Example 238

6-[Methyl(2-{methyl[1-(propan-2-yl)azepan-4-yl]amino}ethyl)amino]-N-(pyridin-4-yl)pyridine-2-carboxamide

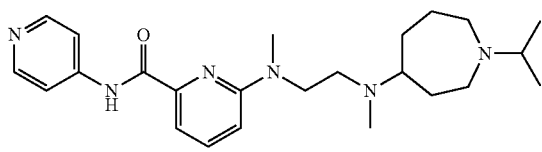 [SMILES: CC(C)N1CCCC(N(C)CCN(C)c2cccc(C(=O)Nc3ccncc3)n2)CC1]

Intermediate 220 (163 mg, 0.64 mmol) was dissolved in DCM (10 mL) and Intermediate 236 (299 mg, 1.93 mmol) and NaBH(OAc)$_3$ (880 mg, 3.21 mmol) were added. The reaction mixture was stirred for 3 d, diluted with DCM (20 mL) and quenched with sat aq Na$_2$CO$_3$ (20 mL). The aq fraction was extracted with DCM (2×15 mL) and the combined organic fractions were dried (MgSO$_4$) and concentrated in vacuo. The residue was purified by reverse phase HPLC to give the title compound (2.49 mg, 1%) as a colourless gum. HRMS (ESI+) calculated for C24H36N6O: 424.29506. found 424.29622. HPLC: Rf 3.43 min, 100% purity.

Example 239

6-[(3-{[1-(Propan-2-yl)piperidin-4-yl]amino}propyl)amino]-N-(pyridin-4-yl)pyridine-2-carboxamide

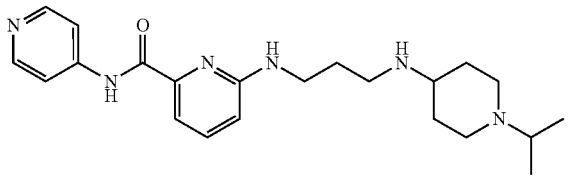 [SMILES: CC(C)N1CCC(NCCCNc2cccc(C(=O)Nc3ccncc3)n2)CC1]

Example 239 was prepared similarly to Example 238, using Intermediate 221 instead of Intermediate 220 and 1-(propan-2-yl)piperidin-4-one instead of Intermediate 236, to give the title compound (1%) as a yellow solid. HRMS (ESI+) calculated for C22H32N6O: 396.26376. found 396.26402. HPLC: Rf 3.38 min, 98.3% purity.

Example 240

6-(4-{1-[(2-Methylphenyl)methyl]azepan-4-yl}piperazin-1-yl)-N-(pyridin-4-yl)pyridine-2-carboxamide

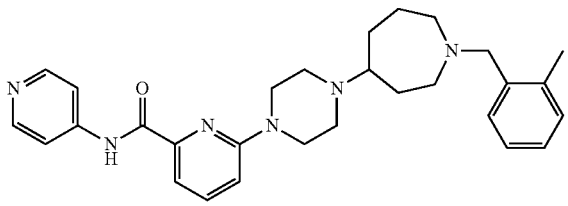 [SMILES: Cc1ccccc1CN1CCCC(N2CCN(c3cccc(C(=O)Nc4ccncc4)n3)CC2)CC1]

Intermediate 238 (250 mg, 0.30 mmol) was dissolved in MeCN (20 mL) and K$_2$CO$_3$ (220 mg, 1.58 mmol) and 2-methylbenzyl bromide (50.0 mg, 0.29 mmol) were added. The reaction mixture was heated at 50° C. for 3 h and the solvents were removed in vacuo. The residue was partitioned between DCM (100 mL) and water (50 mL), the organic fraction was washed with brine (50 mL), dried (MgSO$_4$) and the solvents were removed in vacuo. The residue was purified by reverse phase HPLC to give the title compound (0.050 g, 38%) as a light yellow gum. HRMS (ESI+) calculated for C29H36N6O: 484.29506. found 484.29613. HPLC: Rf 3.86 min, 98.9% purity.

Example 241

6-(4-{1-[(2-Chloro-4-fluorophenyl)methyl]azepan-4-yl}piperazin-1-yl)-N-(pyridin-4-yl)pyridine-2-carboxamide

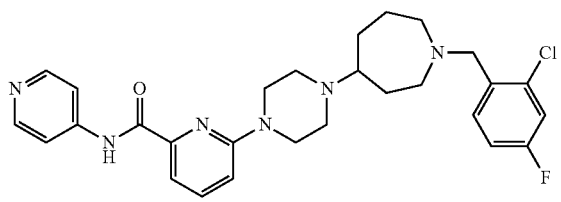 [SMILES: O=C(Nc1ccncc1)c1cccc(N2CCN(C3CCCN(Cc4ccc(F)cc4Cl)CC3)CC2)n1]

Intermediate 238 (50.0 mg, 0.53 mmol) was dissolved in DCM (20 mL) and 2-chloro-4-fluorobenzaldehyde (170 mg, 1.05 mmol) and NaBH(OAc)$_3$ (0.56 g, 2.63 mmol) were added. The reaction mixture was stirred for 96 h, diluted with DCM (50 mL), washed with sat aq Na$_2$CO$_3$ (75 mL), brine (50 mL), dried (MgSO$_4$) and concentrated in vacuo. The residue was purified by reverse phase HPLC to give the title compound (0.060 g, 23%) as a yellow gum. HRMS (ESI+) calculated for C28H32ClFN6O: 522.231016. found 522.233146. HPLC: Rf 3.91 min, 100% purity.

Example 242

6-{4-[1-(Propan-2-yl)azepan-4-yl]piperazin-1-yl}-N-(pyridin-4-yl)pyridine-2-carboxamide

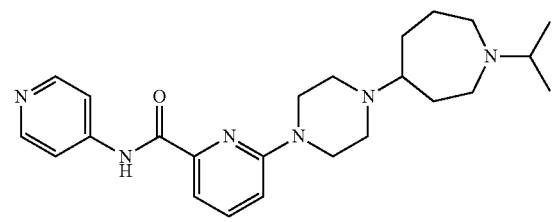 [SMILES: CC(C)N1CCCC(N2CCN(c3cccc(C(=O)Nc4ccncc4)n3)CC2)CC1]

Intermediate 237 (71.0 mg, 0.15 mmol) was dissolved in DCM (10 mL), TFA (1 mL) was added and the reaction mixture was stirred for 18 h. The solvents were removed in vacuo, the residue was dissolved in DCM (10 mL), and acetone (17.2 mg, 0.30 mmol) and NaBH(OAc)$_3$ (157 mg, 0.74 mmol) were added. The reaction mixture was stirred for 7 h, diluted with DCM (20 mL), washed with sat aq Na$_2$CO$_3$ (25 mL), dried (MgSO$_4$) and concentrated in vacuo. The residue was purified by reverse phase HPLC to give the title compound (12.4 mg, 20%) as a light yellow gum. HRMS (ESI+) calculated for $C_{24}H_{34}N_6O$: 422.27941. found 422.28141. HPLC: Rf 3.35 min, 97.4% purity.

Example 243

4-{4-[6-(5-Cyclopropyl-4-methyl-1H-imidazol-2-yl)pyridin-2-yl]piperazin-1-yl}-1-(propan-2-yl)azepane

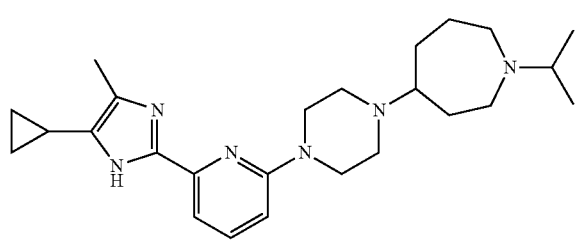 [SMILES: Cc1nc(-c2cccc(N3CCN(C4CCCN(C(C)C)CC4)CC3)n2)[nH]c1C1CC1]

Example 243 was prepared similarly to Example 242, using Intermediate 240 instead of Intermediate 237, to give the title compound (49%) as a white solid. HRMS (ESI+) calculated for C25H38N6: 423.32307. found 423.32147. HPLC: Rf 3.67 min, 99.6% purity.

Example 244

6-(4-{[(2R)-4-(Propan-2-yl)morpholin-2-yl]methyl}-1,4-diazepan-1-yl)-N-(pyridin-4-yl)pyridine-2-carboxamide

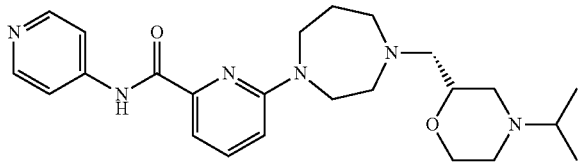

Example 244 was prepared similarly to Example 242, using Intermediate 252 instead of Intermediate 237, to give the title compound (15%) as a white solid. HRMS (ESI+) calculated for C24H34N6O2: 438.274324. found 438.275684. HPLC: Rf 3.51 min, 99.1% purity.

Example 245

1-Cyclopentyl-4-{4-[6-(5-cyclopropyl-4-methyl-1H-imidazol-2-yl)pyridin-2-yl]piperazin-1-yl}azepane

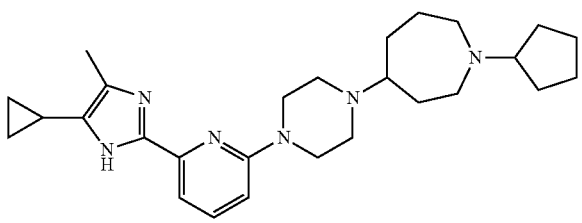 [SMILES: Cc1nc(-c2cccc(N3CCN(C4CCCN(C5CCCC5)CC4)CC3)n2)[nH]c1C1CC1]

Example 245 was prepared similarly to Example 243, using cyclopentanone instead of acetone, to give the title compound (28%) as a white solid. HRMS (ESI+) calculated for C27H40N6: 449.33872. found 449.33856. HPLC: Rf 3.80 min, 99.4% purity.

Example 246

1-Cyclopentyl-N-(2-{[6-(5-cyclopropyl-4-methyl-1H-imidazol-2-yl)pyridin-2-yl]amino}ethyl)azepan-4-amine

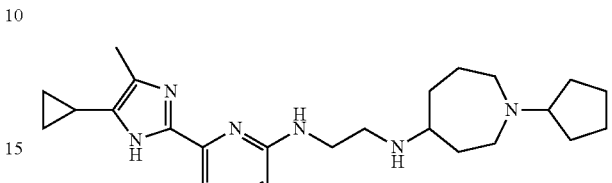

Example 246 was prepared similarly to Example 245, using Intermediate 233 instead of Intermediate 240, to give the title compound (12%) as a white solid. HRMS (ESI+) calculated for C25H38N6: 423.32307. found 423.32214. HPLC: Rf 3.78 min, 98.1% purity.

Example 247

{[(3S)-1-Cyclopentylpyrrolidin-3-yl]methyl}(2-{[6-(5-cyclopropyl-4-methyl-1H-imidazol-2-yl)pyridin-2-yl]amino}ethyl)amine

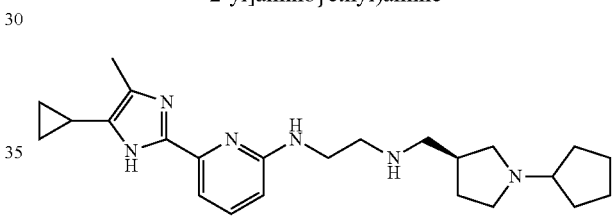

Example 247 was prepared similarly to Example 223, using Intermediate 227 instead of Intermediate 206, to give the title compound (8.77 mg, 8%) as a white solid. HRMS (ESI+) calculated for C24H36N6: 409.30742. found 409.30582. HPLC: Rf 3.50 min, 98.2% purity.

Example 248

6-(4-{[(2-Chlorophenyl)methyl]amino}piperidin-1-yl)-N-(cyclopropylmethyl)pyridine-2-carboxamide

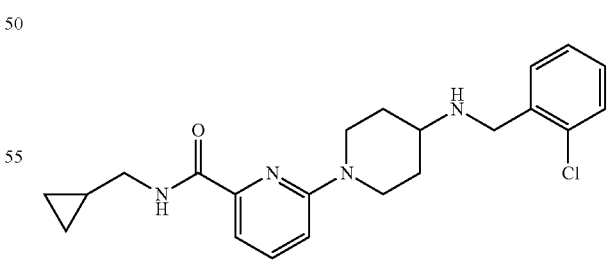

Intermediate 203 (427 mg, 1.38 mmol) and 2-chlorobenzaldehyde (193 mg, 1.38 mmol) were dissolved in DCM (10 mL) and NaBH(OAc)$_3$ (1.46 g, 6.88 mmol) was added. The reaction mixture was stirred for 16 h and quenched with sat aq Na$_2$CO$_3$ (5 mL). The reaction mixture was diluted with a DCM (20 mL), washed with sat aq Na$_2$CO$_3$ solution (3×15 mL), brine (15 mL), dried (MgSO$_4$) and concentrated in

Example 249

6-(4-{[1-(Propan-2-yl)piperidin-4-yl]amino}piperidin-1-yl)-N-(pyridin-4-yl)pyridine-2-carboxamide

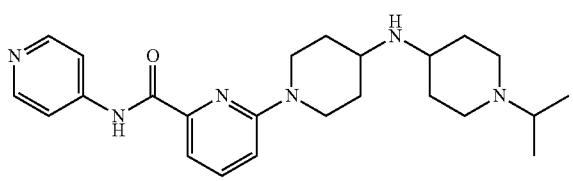 [SMILES: CC(C)N1CCC(NC2CCN(c3cccc(C(=O)Nc4ccncc4)n3)CC2)CC1]

Intermediate 274 (254 mg, 0.64 mmol) was dissolved in DCM (8 mL), TFA (2 mL) was added and the reaction mixture was stirred overnight. The solvents were removed in vacuo and the residue partitioned between DCM (20 mL) and 1M aq NaOH (10 mL). The aq fraction was basified to pH 14 with NaOH and extracted with DCM (3×50 mL). The combined organic fractions were dried (MgSO$_4$) and the solvents were removed in vacuo. The residue was dissolved in DCM (6 mL) and 1-(propan-2-yl)piperidin-4-one (78.0 μL, 0.53 mmol) and NaBH(OAc)$_3$ (111 mg, 0.50 mmol) were added. The reaction mixture was stirred for 3 d. Further 1-(propan-2-yl)piperidin-4-one (78.0 μL, 0.53 mmol) and NaBH(OAc)$_3$ (111 mg, 0.50 mmol) were added and the reaction mixture was stirred overnight. The reaction mixture was diluted with DCM (10 mL), quenched with water (5 mL) and the organic fraction was washed with sat aq Na$_2$CO$_3$ (5 mL), dried (MgSO$_4$) and concentrated in vacuo. The residue was purified by column chromatography and reverse phase HPLC to give the title compound (22.0 mg, 11%) as a white solid. HRMS (ESI+) calculated for C24H34N6O: 422.27941. found 422.28129. HPLC: Rf 3.53 min, 100% purity.

Example 250

N-Butyl-6-(4-{[4-(propan-2-yl)morpholin-2-yl]methyl}-1,4-diazepan-1-yl)pyridine-2-carboxamide

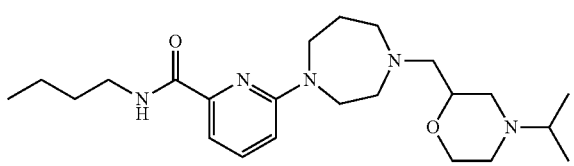 [SMILES: CCCCNC(=O)c1cccc(N2CCCN(CC3CN(C(C)C)CCO3)CC2)n1]

Example 250 was prepared similarly to Example 242 using Intermediate 239 instead of Intermediate 237, to give the title compound (19%) as a colourless gum. HRMS (ESI+) calculated for C23H39N5O2: 417.310376. found 417.312286. HPLC: Rf 3.99 min, 100% purity.

Example 251

6-{4-[(2-Chloro-4-fluorophenyl)methyl]-1,4-diazepan-1-yl}-N-(pyridin-4-yl)pyridine-2-carboxamide

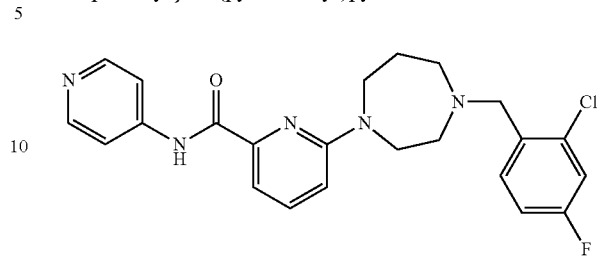

Intermediate 83 (256 mg, 0.86 mmol) was dissolved in DCM (15 mL), 2-chloro-4-fluorobenzaldehyde (149 mg, 0.94 mmol) and NaBH(OAc)$_3$ (907 mg, 4.28 mmol) were added and the reaction mixture was stirred for 18 h. The reaction mixture was diluted with DCM (30 mL), washed with sat aq Na$_2$CO$_3$ (35 mL), dried (MgSO$_4$) and concentrated in vacuo. The residue was purified by reverse phase HPLC to give the title compound (116 mg, 31%) as a light yellow gum. HRMS (ESI+) calculated for C23H23ClFN5O: 439.157516. found 439.157156. HPLC: Rf 4.40 min, 100% purity.

Example 252

N-(Cyclopropylmethyl)-6-{4-[3-(1,2,3,4-tetrahydroisoquinolin-2-yl)propyl]-1,4-diazepan-1-yl}pyridine-2-carboxamide

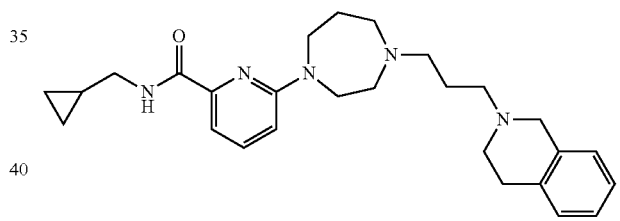

Intermediate 81 (100 mg, 0.36 mmol), K$_2$CO$_3$ (75.6 mg, 0.55 mmol) and Intermediate 244 (98.2 mg, 0.36 mmol) were dissolved in MeCN (2 mL) and heated at 70° C. for 18 h. The reaction mixture was filtered, washing with DCM (20 mL) and concentrated in vacuo. The residue was purified by reverse phase HPLC to give the title compound (28.4 mg, 17%) as a yellow gum. HRMS (ESI+) calculated for C27H37N5O: 447.299811. found 447.298621. HPLC: Rf 4.18 min, 97.5% purity.

Example 253

N-(Cyclopropylmethyl)-6-{4-[3-(3,3-difluoropyrrolidin-1-yl)propyl]-1,4-diazepan-1-yl}pyridine-2-carboxamide

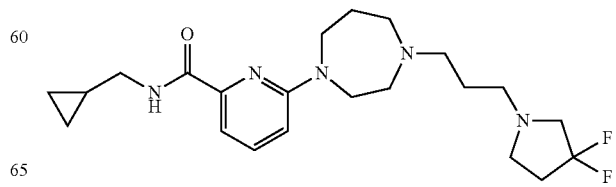

Example 253 was prepared similarly to Example 252, using Intermediate 245 instead of Intermediate 244, to give the title compound as a colourless gum (15.3 mg, 10%). HRMS (ESI+) calculated for C22H33F2N5O: 421.265317. found 421.265627. HPLC: Rf 3.85 min, 98.8% purity.

Example 254

6-{4-[2-Hydroxy-3-(propan-2-ylamino)propyl]-1,4-diazepan-1-yl}-N-(pyridin-3-ylmethyl)pyridine-2-carboxamide

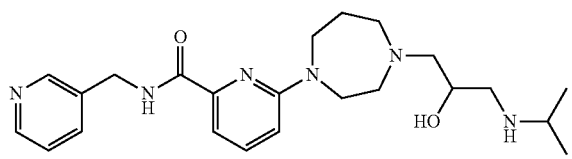 [SMILES: CC(C)NCC(O)CN1CCCN(c2cccc(C(=O)NCc3cccnc3)n2)CC1]

Intermediate 246 (206 mg, 0.51 mmol) was dissolved in IPA (10 mL), isopropylamine (151 mg, 2.55 mmol) was added and the reaction mixture was heated at reflux for 3 h. The reaction mixture was concentrated in vacuo and purified by column chromatography to give the title compound (192 mg, 88%) as a white solid. HRMS (ESI+) calculated for C23H34N6O2: 426.274324. found 426.276264. HPLC: Rf 2.98 min, 98.3% purity.

Example 255

1-[6-(4-Cyclopropyl-1H-imidazol-2-yl)pyridin-2-yl]-4-[4-(pyrrolidin-1-yl)cyclohexyl]-1,4-diazepane

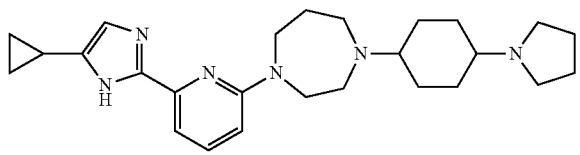 [SMILES: c1cc(-c2ncc(C3CC3)[nH]2)nc(N2CCCN(C3CCC(N4CCCC4)CC3)CC2)c1]

Intermediate 106 (520 mg, 1.37 mmol) and 4-(pyrrolidin-1-yl)cyclohexan-1-one (687 mg, 4.11 mmol) were dissolved in DCM (10 mL) and NaBH(OAc)3 (1.02 g, 4.80 mmol) was added. The reaction mixture was stirred overnight, poured into 1 M aq Na2CO3 (25 mL) and extracted with DCM (3×25 mL). The combined organic fractions were dried (MgSO4) and concentrated in vacuo. The residue was purified by column chromatography and reverse phase HPLC to give the title compound (31.0 mg, 5%) as a white solid. HRMS (ESI+) calculated for C26H38N6: 435.32307. found 435.32434. HPLC: Rf 3.68 min, 99.7% purity.

Example 256

6-[4-(4-tert-Butylcyclohexyl)-1,4-diazepan-1-yl]-N-(pyridin-3-ylmethyl)pyridine-2-carboxamide

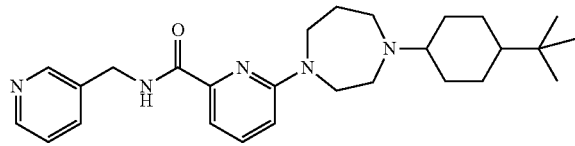 [SMILES: CC(C)(C)C1CCC(N2CCCN(c3cccc(C(=O)NCc4cccnc4)n3)CC2)CC1]

Intermediate 134 (100 mg, 0.28 mmol), 3-(aminomethyl)-pyridine (45.1 mg, 0.42 mmol), HBTU (106 mg, 0.28 mmol) and DIPEA (108 mg, 0.83 mmol) were dissolved in DMF (2 mL) and stirred for 4 h. The solvents were removed in vacuo and the residue purified by reverse phase HPLC to give the title compound (2.87 mg, 2%) as a colourless gum. HRMS (ESI+) calculated for C27H39N5O: 449.315461. found 449.316351. HPLC: Rf 4.77 min, 99.2% purity.

Example 257

N-(Pyridin-4-yl)-6-(4-{4-[2-(trifluoromethyl)pyrrolidin-1-yl]cyclohexyl}-1,4-diazepan-1-yl)pyridine-2-carboxamide

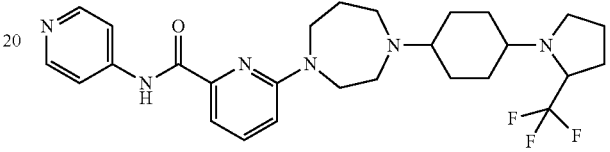

Intermediate 83 (100 mg, 0.34 mmol), 4-(2-trifluoromethyl-pyrrolidin-1-yl)-cyclohexanone (98.9 mg, 0.42 mmol) and NaBH(OAc)3 (356 mg, 1.68 mmol) were stirred for 7 d. The reaction mixture was diluted with DCM (15 mL), washed with sat aq Na2CO3 (25 mL), brine (20 mL), dried (MgSO4) and concentrated in vacuo. The residue was purified by reverse phase HPLC to give the title compound (5.67 mg, 3%) as a light yellow gum. HRMS (ESI+) calculated for C27H35F3N6O: 516.282444. found 516.281974. HPLC: Rf 4.11 min, 99.2% purity.

Example 258

6-[4-(3-{[(2-Chlorophenyl)methyl]amino}propyl)-1,4-diazepan-1-yl]-N-(cyclopropylmethyl)pyridine-2-carboxamide

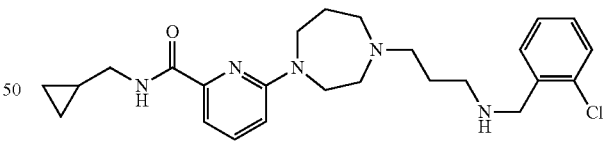

Intermediate 253 (200 mg, 0.43 mmol) and hydrazine monohydrate (27.8 mg, 0.87 mmol) were dissolved in EtOH (20 mL) and the reaction mixture was stirred for 6 h. The solvents were removed in vacuo and 2-chlorobenzaldehyde (122 mg, 0.87 mmol), DCM (10 mL) and NaBH(OAc)3 (459 mg, 2.17 mmol) were added. The reaction mixture was stirred for 18 h. The reaction mixture was diluted with DCM (50 mL), washed with sat aq Na2CO3 (40 mL), brine (30 mL), dried (MgSO4) and concentrated in vacuo. The residue was purified by reverse phase HPLC to the title compound (13.2 mg, 7%) as a colourless gum. HRMS (ESI+) calculated for C25H34ClN5O: 455.245188. found 455.245878. HPLC: Rf 4.36 min, 99.1% purity.

Example 259

6-(4-{1-[(2-Chlorophenyl)methyl]piperidin-4-yl}-1,4-diazepan-1-yl)pyridine-2-carbonitrile

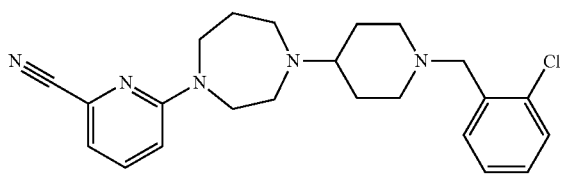 [SMILES: N#Cc1cccc(N2CCCN(C3CCN(Cc4ccccc4Cl)CC3)CC2)n1]

Example 136 (50.0 mg, 0.12 mmol) was dissolved in THF (1 mL), the reaction mixture was cooled to −5° C. and trifluoroacetic anhydride (19.8 μL, 0.14 mmol) and Et₃N (39.0 μL, 0.28 mmol) were added. The reaction mixture was stirred for 5 h, concentrated in vacuo, diluted with DCM (20 mL), washed with sat aq Na₂CO₃ (10 mL), dried (MgSO₄) and concentrated in vacuo. The residue was purified by reverse phase HPLC to give the title compound (12.4 mg, 26%) as a yellow solid. HRMS (ESI+) calculated for C23H28ClN5: 409.203324. found 409.203394. HPLC: Rf 4.32 min, 98.1% purity.

Example 260

[6-(4-{1-[(2-Chlorophenyl)methyl]piperidin-4-yl}-1,4-diazepan-1-yl)pyridin-2-yl]methanol

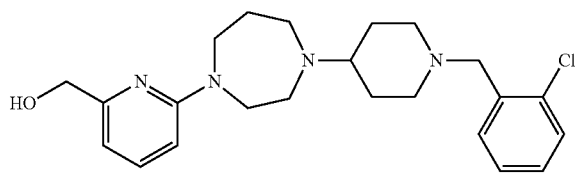 [SMILES: OCc1cccc(N2CCCN(C3CCN(Cc4ccccc4Cl)CC3)CC2)n1]

Intermediate 133 (190 mg, 0.43 mmol) was dissolved in MeOH (5 mL) and the reaction mixture was cooled to 0° C. NaBH₄ (64.9 mg, 1.72 mmol) was added and the reaction mixture was stirred at 60° C. for 2 d. Further NaBH₄ (64.9 mg, 1.72 mmol) was added and the reaction mixture was stirred at 60° C. for 3 d. The solvents were removed in vacuo and the residue was partitioned between DCM (25 mL) and sat aq Na₂CO₃ (20 mL). The organic fraction was dried (MgSO₄) and concentrated in vacuo. The residue was purified by reverse phase HPLC to give the title compound (31.4 mg, 18%) as an off-white solid. HRMS (ESI+) calculated for C23H31ClN4O: 414.218639. found 414.218919. HPLC: Rf 3.37 min, 100% purity.

Example 261

1-{1-[(2-Chlorophenyl)methyl]piperidin-4-yl}-4-(pyridin-2-yl)-1,4-diazepane

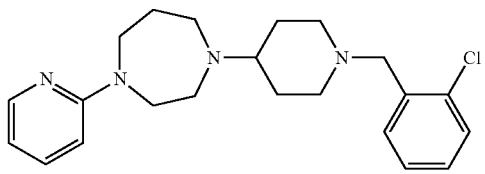 [SMILES: Clc1ccccc1CN1CCC(N2CCCN(c3ccccn3)CC2)CC1]

Intermediate 258 (361 mg, 1.39 mmol) was dissolved in DCM (15 mL), 2-chlorobenzaldehyde (343 μL, 3.05 mmol) and NaBH(OAc)₃ (1.18 g, 5.55 mmol) were added and the reaction mixture was stirred for 18 h. The reaction mixture was diluted with DCM (30 mL) and quenched with water (15 mL). The organic fraction was washed with sat aq Na₂CO₃ (15 mL), dried (MgSO₄) and concentrated in vacuo. The residue was purified by column chromatography and reverse phase HPLC to give the title compound (49.4 mg, 9%) as a colourless gum. HRMS (ESI+) calculated for C22H29ClN4: 384.208075. found 384.208755. HPLC: Rf 3.34 min, 99.2% purity.

Examples 262-264

Examples 262-264 were prepared similarly to Example 261, using Intermediates 259-261 instead of Intermediate 258; see Table 25 below.

TABLE 25

Reductive alkylation reactions of Intermediates 259-261

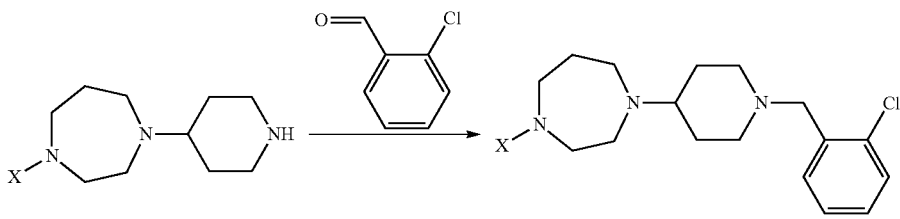

| Ex | Structure | Name | Ints | Yield | HRMS (ESI⁺), HPLC |
|---|---|---|---|---|---|
| 262 | 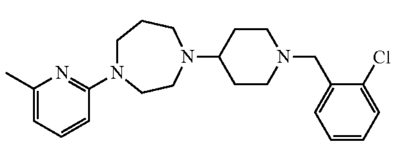 [SMILES: Cc1cccc(N2CCCN(C3CCN(Cc4ccccc4Cl)CC3)CC2)n1] | 1-{1-[(2-Chlorophenyl)methyl]piperidin-4-yl}-4-(6-methylpyridin-2-yl)-1,4-diazepane | 259 | 24% | HRMS (ESI+) calculated for C23H31ClN4: 398.223725, found 398.223905. HPLC: Rf 3.47 min, 100% purity. |

TABLE 25-continued

Reductive alkylation reactions of Intermediates 259-261

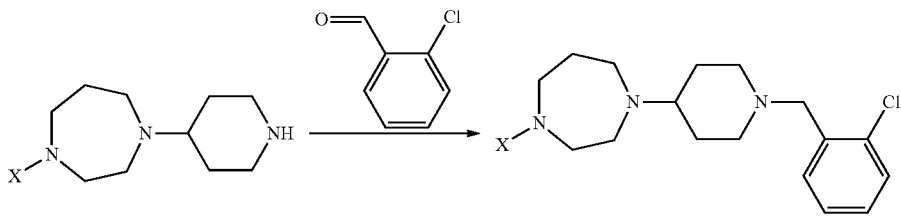

| Ex | Structure | Name | Ints | Yield | HRMS (ESI+), HPLC |
|----|-----------|------|------|-------|-------------------|
| 263 | 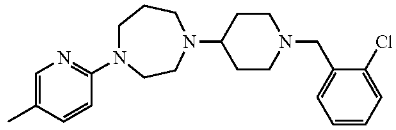 [SMILES: Cc1ccc(N2CCCN(C3CCN(Cc4ccccc4Cl)CC3)CC2)nc1] | 1-{1-[(2-Chlorophenyl)methyl]piperidin-4-yl}-4-(5-methylpyridin-2-yl)-1,4-diazepane | 260 | 35% | HRMS (ESI+) calculated for C23H31ClN4: 398.223725, found 398.224045. HPLC: Rf 3.50 min, 100% purity. |
| 264 | 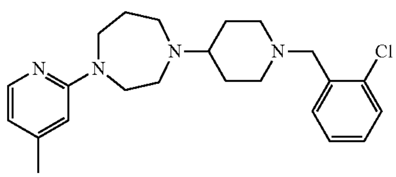 [SMILES: Cc1ccnc(N2CCCN(C3CCN(Cc4ccccc4Cl)CC3)CC2)c1] | 1-{1-[(2-Chlorophenyl)methyl]piperidin-4-yl}-4-(4-methylpyridin-2-yl)-1,4-diazepane | 261 | 21% | HRMS (ESI+) calculated for C23H31ClN4: 398.223725, found 398.224295. HPLC: Rf 3.44 min, 99.1% purity. |

Example 265

2-(4-{1-[(2-Chlorophenyl)methyl]piperidin-4-yl}-1,4-diazepan-1-yl)-N-(cyclopropylmethyl)-1,3-thiazole-4-carboxamide

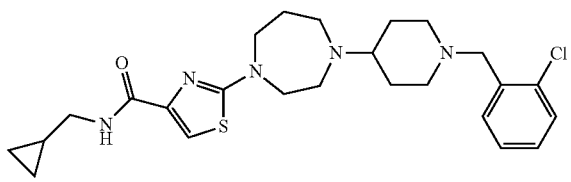 [SMILES: O=C(NCC1CC1)c1csc(N2CCCN(C3CCN(Cc4ccccc4Cl)CC3)CC2)n1]

Intermediate 264 (100 mg, 0.38 mmol) and Intermediate 263 (589 mg, 1.91 mmol) were dissolved in DMA (2 mL) and the reaction mixture was heated using a microwave (180° C., absorption high) for 20 min. The reaction mixture was partitioned between DCM (40 mL) and sat aq $Na_2CO_3$ (20 mL). The organic fraction was washed with brine (20 mL), dried ($MgSO_4$) and concentrated in vacuo. The residue was dissolved in DCM, stirred with isocyanate resin, for 3 h and filtered. The solvents were removed in vacuo and the residue was purified by column chromatography and reverse phase HPLC to give the title compound (20.4 mg, 11%) as an off-white solid. HRMS (ESI+) calculated for C25H34ClN5OS: 487.217259. found 487.217919. HPLC: Rf 4.14 min, 99.5% purity.

Example 266

2-(4-{1-[(2-Chlorophenyl)methyl]piperidin-4-yl}-1,4-diazepan-1-yl)-N-[3-(1H-imidazol-1-yl)propyl]-6-methylpyrimidine-4-carboxamide

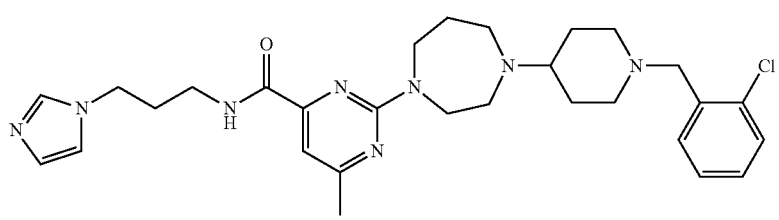 [SMILES: Cc1cc(C(=O)NCCCn2ccnc2)nc(N2CCCN(C3CCN(Cc4ccccc4Cl)CC3)CC2)n1]

Example 266 was prepared similarly to Example 265, using Intermediate 265 instead of Intermediate 264, to give the title compound (2%) as a yellow gum. HRMS (ESI+) calculated for C29H39ClN8O: 550.293536. found 550.293396. HPLC: Rf 3.70 min, 100% purity.

Example 267

1-{1-[(2-Chlorophenyl)methyl]piperidin-4-yl}-4-(1,3-thiazol-2-yl)-1,4-diazepane

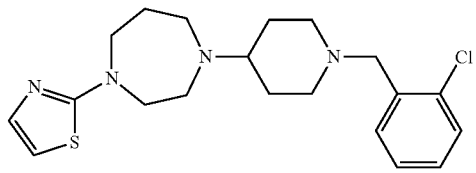 [SMILES: Clc1ccccc1CN1CCC(N2CCCN(c3nccs3)CC2)CC1]

2-Bromothiazole (234 mg, 1.43 mmol) was dissolved in dioxane (2 mL) and sodium tert-butoxide (175 mg, 1.82 mmol), Pd$_2$(dba)$_3$ (47.6 mg, 0.05 mmol), Xantphos (84.9 mg, 0.10 mmol) and Intermediate 263 (400 mg, 1.30 mmol) were added. The reaction mixture was heated at 106° C. for 3 d and the solvents were removed in vacuo. The residue was dissolved in DCM, filtered and concentrated in vacuo. The residue was purified by column chromatography and reverse phase HPLC to give the title compound (39.7 mg, 8%) as a yellow gum. HRMS (ESI+) calculated for C20H27ClN4S: 390.164495. found 390.164375. HPLC: Rf 3.38 min, 99.3% purity.

Example 268

6-(4-{1-[(2-Chlorophenyl)methyl]piperidin-4-yl}-1,4-diazepan-1-yl)-N-(cyclopropylmethyl)-4-methylpyridine-2-carboxamide

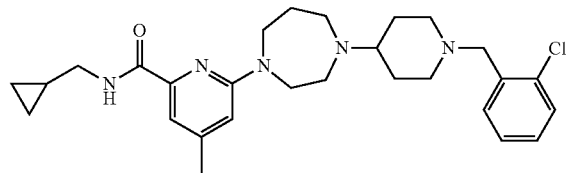 [SMILES: Cc1cc(C(=O)NCC2CC2)nc(N2CCCN(C3CCN(Cc4ccccc4Cl)CC3)CC2)c1]

Example 268 was prepared similarly to Example 267, using Intermediate 266 instead of 2-bromothiazole, to give the title compound (4%) as a yellow gum. HRMS (ESI+) calculated for C28H38ClN5O: 495.276489. found 495.277109. HPLC: Rf 4.51 min, 100% purity.

Example 269

2-(4-{1-[(2-chlorophenyl)methyl]piperidin-4-yl}-1,4-diazepan-1-yl)-N-(cyclopropylmethyl)pyridine-4-carboxamide

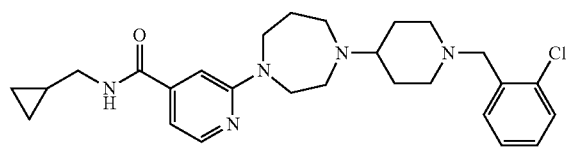 [SMILES: O=C(NCC1CC1)c1ccnc(N2CCCN(C3CCN(Cc4ccccc4Cl)CC3)CC2)c1]

Example 269 was prepared similarly to Example 132, using Intermediate 269 instead of Intermediate 119, to give the title compound (12%) as an off-white solid. HRMS (ESI+) calculated for C27H36ClN5O: 481.260839. found 481.262979. HPLC: Rf 3.84 min, 98.8% purity.

Example 270

6-(4-{1-[(2-Chlorophenyl)methyl]piperidin-4-yl}-1,4-diazepan-1-yl)-N-(cyclopropylmethyl)-5-methoxy-pyridine-2-carboxamide

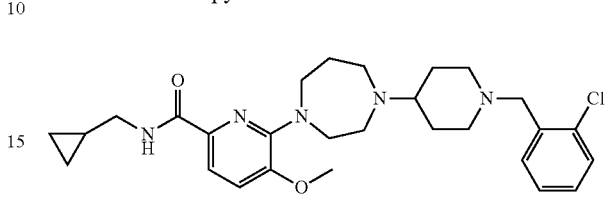

Example 270 was prepared similarly to Example 132, using Intermediate 272 instead of Intermediate 119, to give the title compound (6%) as a colourless gum. HRMS (ESI+) calculated for C28H38ClN5O2: 511.271403. found 511.273083. HPLC: Rf 4.37 mM, 100% purity.

Biological Tests

CXCR4 Functional Calcium Assay

The functional activity of test compounds was routinely tested by measuring the ability of compounds to antagonize CXCR4 activity in a dose dependent manner, using a calcium flux Fluorescent Imaging Plate Reader FLIPR assay.

Human CXCR4 transfected HEK293 cells were cultured in Dulbecco's modified Eagles medium containing 4.5 g/L glucose, L-glutamine, pyruvate, 50 µg/mL Geneticin and 250 µg/mL hygromycin B and maintained at 37° C. in a humidified, 5% CO$_2$ controlled atmosphere. Subcultivations were performed every 2-3 d.

At confluence the cells were lifted using Ca$^{2+}$ and Mg$^{2+}$ free PBS/0.02% (w/v) EDTA, spun at 1000 rpm for 3 min and resuspended at 2.5×10$^5$ cells/mL. Cells were plated into a 384 well, poly-d-lysine coated, black with clear bottomed plate (Becton Dickinson) at 7500 cells/well. The plates were incubated overnight at 37° C. under 5% CO$_2$. On the day of the experiment the cells were washed with incubation Buffer (HBSS containing 2.5 mM probenecid, 0.1% w/v BSA and 10 mM HEPES, pH 7.4 at 37° C.). After washing, the cells were loaded with Fluo-4 AM dye (Molecular probes) at 2 µM containing 0.48 µg/mL pluronic acid for 60 mM at 37° C. under 5% CO$_2$. After thorough washing with incubation buffer the cells were preincubated for 10 mM at 37° C. before use.

A combined agonist/antagonist protocol was used to measure changes in intracellular calcium concentration. Compound (antagonist) was added to the cell plate using a Fluorometric Imaging Plate Reader (FLIPR) (Molecular Devices, Sunnyvale, Calif., USA). Basal fluorescence was recorded every second for 10 seconds prior to compound addition (10 µl) and fluorescence recorded every second for 1 min then every 6 seconds for a further 1 min. SDF1α (EC$_{50}$ concentration) was then added using the FLIPR and fluorescence recorded as described above. Curve-fitting and parameter estimation were carried out using GraphPad Prism 4.0 (GraphPad Software Inc., San Diego, Calif.).

All of the exemplified compounds of the invention were found to be highly potent inhibitors of CXCR4 (See Table 26).

TABLE 26

CXCR4 functional activity
(A: <20 nM, B: 20-100 nM, C: 100-500 nM, D: 500-1000 nM)

| Example | CXCR4 fKi |
|---|---|
| 1 | C |
| 2 | C |
| 3 | C |
| 4 | C |
| 5 | B |
| 6 | C |
| 7 | B |
| 8 | C |
| 9 | C |
| 10 | C |
| 11 | C |
| 12 | C |
| 13 | C |
| 14 | B |
| 15 | C |
| 16 | C |
| 17 | D |
| 18 | C |
| 19 | C |
| 20 | C |
| 21 | C |
| 22 | C |
| 23 | A |
| 24 | B |
| 25 | C |
| 26 | B |
| 27 | B |
| 28 | A |
| 29 | B |
| 30 | A |
| 31 | A |
| 32 | A |
| 33 | B |
| 34 | A |
| 35 | C |
| 36 | A |
| 37 | C |
| 38 | B |
| 39 | B |
| 40 | A |
| 41 | B |
| 42 | B |
| 43 | B |
| 44 | B |
| 45 | B |
| 46 | B |
| 47 | A |
| 48 | C |
| 49 | C |
| 50 | C |
| 51 | B |
| 52 | B |
| 53 | B |
| 54 | A |
| 55 | B |
| 56 | A |
| 57 | B |
| 58 | C |
| 59 | C |
| 60 | D |
| 61 | C |
| 62 | D |
| 63 | A |
| 64 | B |
| 65 | A |
| 66 | B |
| 67 | D |
| 68 | C |
| 69 | C |
| 70 | B |
| 71 | D |
| 72 | B |
| 73 | B |
| 74 | C |
| 75 | C |

TABLE 26-continued

CXCR4 functional activity
(A: <20 nM, B: 20-100 nM, C: 100-500 nM, D: 500-1000 nM)

| Example | CXCR4 fKi |
|---|---|
| 76 | B |
| 77 | B |
| 78 | A |
| 79 | A |
| 80 | A |
| 81 | A |
| 82 | A |
| 83 | A |
| 84 | A |
| 85 | B |
| 86 | A |
| 87 | A |
| 88 | A |
| 89 | B |
| 90 | B |
| 91 | C |
| 92 | B |
| 93 | B |
| 94 | C |
| 95 | C |
| 96 | B |
| 97 | C |
| 98 | B |
| 99 | B |
| 100 | B |
| 101 | C |
| 102 | D |
| 103 | C |
| 104 | D |
| 105 | D |
| 106 | A |
| 107 | B |
| 108 | A |
| 109 | B |
| 110 | B |
| 111 | A |
| 112 | D |
| 113 | C |
| 114 | C |
| 115 | C |
| 116 | A |
| 117 | C |
| 118 | B |
| 119 | A |
| 120 | B |
| 121 | A |
| 122 | A |
| 123 | A |
| 124 | B |
| 125 | C |
| 126 | D |
| 127 | B |
| 128 | C |
| 129 | D |
| 130 | C |
| 131 | C |
| 132 | B |
| 133 | B |
| 134 | C |
| 135 | A |
| 136 | C |
| 137 | B |
| 138 | D |
| 139 | C |
| 140 | D |
| 141 | A |
| 142 | B |
| 143 | C |
| 144 | C |
| 145 | A |
| 146 | C |
| 147 | B |
| 148 | B |
| 149 | A |
| 150 | B |

TABLE 26-continued

CXCR4 functional activity
(A: <20 nM, B: 20-100 nM, C: 100-500 nM, D: 500-1000 nM)

| Example | CXCR4 fKi |
|---|---|
| 151 | C |
| 152 | C |
| 153 | D |
| 154 | C |
| 155 | C |
| 156 | B |
| 157 | C |
| 158 | D |
| 159 | D |
| 160 | C |
| 161 | C |
| 162 | C |
| 163 | C |
| 164 | B |
| 165 | C |
| 166 | C |
| 167 | B |
| 168 | C |
| 169 | D |
| 170 | C |
| 171 | D |
| 172 | C |
| 173 | D |
| 174 | C |
| 175 | A |
| 176 | A |
| 177 | A |
| 178 | B |
| 179 | A |
| 180 | A |
| 181 | B |
| 182 | B |
| 183 | C |
| 184 | B |
| 185 | C |
| 186 | A |
| 187 | B |
| 188 | A |
| 189 | A |
| 190 | A |
| 191 | A |
| 192 | B |
| 193 | A |
| 194 | B |
| 195 | A |
| 196 | B |
| 197 | B |
| 198 | C |
| 199 | D |
| 200 | D |
| 201 | C |
| 202 | D |
| 203 | A |
| 204 | A |
| 205 | A |
| 206 | A |
| 207 | A |
| 208 | C |
| 209 | C |
| 210 | A |
| 211 | B |
| 212 | C |
| 213 | B |
| 214 | C |
| 215 | B |
| 216 | C |
| 217 | C |
| 218 | C |
| 219 | C |
| 220 | B |
| 221 | C |
| 222 | D |
| 223 | D |
| 224 | A |
| 225 | A |
| 226 | A |
| 227 | A |
| 228 | A |
| 229 | C |
| 230 | C |
| 231 | C |
| 232 | C |
| 233 | D |
| 234 | C |
| 235 | C |
| 236 | C |
| 237 | C |
| 238 | C |
| 239 | C |
| 240 | B |
| 241 | B |
| 242 | C |
| 243 | C |
| 244 | B |
| 245 | B |
| 246 | B |
| 247 | B |
| 248 | D |
| 249 | C |
| 250 | B |
| 251 | C |
| 252 | D |
| 253 | D |
| 254 | C |
| 255 | C |
| 256 | B |
| 257 | D |
| 258 | C |
| 259 | D |
| 260 | D |
| 261 | C |
| 262 | D |
| 263 | C |
| 264 | C |
| 265 | D |
| 266 | C |
| 267 | C |
| 268 | C |
| 269 | C |
| 270 | C |

Efficacy in HIV In Vitro Assays

Example 30 has demonstrated potent activity in two in vitro assays indicating potential utility of test compounds for treatment of HIV.

Example 30 was tested in an HIV attachment assay, which detects compounds that block HIV-1IIIB (CXCR4-tropic) virus attachment to cells.

The CXCR4-tropic HIV-1 attachment assay uses MAGI-CCR5 cells that naturally express CXCR4 which were engineered to express high levels of CD4 and CCR5 and to contain one copy of the HIV-1 LTR promoter driving expression of the β-galactosidase gene upon HIV-1 Tat transactivation. Cells are incubated with Example 30 and the CXCR4-tropic virus HIV-1$_{IIIB}$ for 3 hours before washing to remove drug and unbound virus. Fresh media is added and the plates are incubated for 48 hours after which antiviral efficacy is measured as the inhibition of β-galactosidase reporter expression and cytotoxicity is monitored by MTS staining.

FIG. 1 shows the effect of Example 30 in the CXCR4-tropic HIV-1 attachment assay. More specifically, FIG. 1 shows that Example 30 inhibits attachment of CXCR4-tropic HIV-1, with an IC50 of 40 nM.

Example 30 was also tested in an HIV antiviral assay that detects compounds that block HIV-1IIIB (CXCR4-tropic)

replication via targets in the viral life cycle. The anti-viral assay uses MAGI-CCR5 cells that naturally express CXCR4 which were engineered to express high levels of CD4 and CCR5 and to contain one copy of the HIV-1 LTR promoter driving expression of the β-galactosidase gene upon HIV 1 Tat transactivation. Cells are incubated with Example 30 and the CXCR4-tropic virus HIV-1IIIB for 48 hours after which antiviral efficacy is measured as the inhibition of β-galactosidase reporter expression and cytotoxicity is monitored by MTS staining.

FIG. 2 shows the effect of Example 30 in the HIV anti-viral assay. More specifically, FIG. 2 shows that Example 30 inhibited HIV-1 antiviral activity, with an IC50 of 30 nM.

In Vivo Efficacy

The study investigated the ability of Example 30 alone and in combination with G-CSF to induce in vivo mobilization of white blood cells in C57BL/6 mice, as well as hematopoietic progenitors from bone marrow to peripheral blood as assessed by the evaluation of the frequency of colony forming cell colonies (CFC). Peripheral blood samples from each test group were collected 1 hour post injection. The white blood cell count (WBC) was determined from the peripheral blood collected for each individual mouse. Clonogenic progenitors of the multipotential (CFU-GEMM) lineages were assessed. Peripheral blood cells were added to MethoCult® 3434 in triplicate cultures for plating (0.5–3×10$^5$ cells/dish). Cultures were incubated for 8 days at 37° C., 5% CO$_2$ in humidified incubators. CFU-GEMM colony number was enumerated microscopically using an inverted microscope from appropriately plated culture dishes.

FIG. 3 shows a significant increase in circulating white blood cells (WBC) 1 hour after treatment with Example 30 when compared to mice in the vehicle control group. Treatment with G-CSF also resulted in an increase in circulating WBC compared to the vehicle group. There was a significant increase in WBC with Example 30 in combination with G-CSF after 1 hour when compared to mice treated with G-CSF alone.

Figure 4:
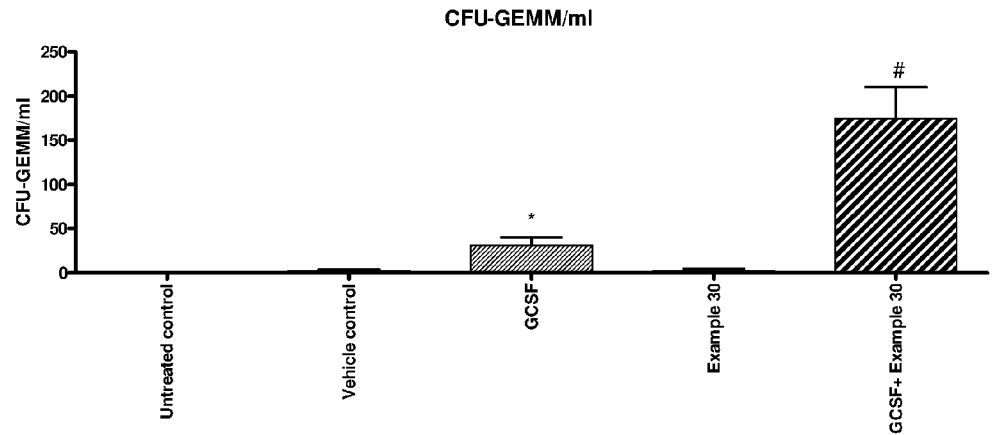

FIG. 4 shows the evaluation of hematopoietic progenitors following treatment with Example 30 and/or G-CSF. In particular, FIG. 4 shows a significant increase in multipotential mixed hematopoietic progenitors (CFU-GEMM/ml) one hour after treatment with Example 30 in combination with G-CSF when compared to G-CSF treatment alone. The results shown in FIGS. 3 and 4 support the utility of Example 30 and the compounds of the invention generally in stem cell apheresis, particularly therapeutic uses of stem cell apheresis.

The invention claimed is:

1. A compound of formula (I) or a pharmaceutically acceptable salt thereof:

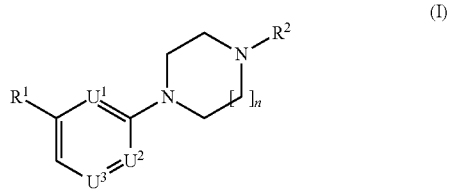

(I)

wherein:
R$^1$ is selected from C$_{1-4}$-alkyl, cyano, —COR$^3$, —CONR$^3$R$^4$, and heteroaryl, wherein
(a) said heteroaryl is optionally substituted with one more substituents independently selected from halogen, hydroxy, cyano, nitro, C$_{1-6}$-alkyl, C$_{3-5}$-cycloalkyl, C$_{1-4}$-alkoxy, fluoro-C$_{1-6}$-alkyl, fluoro-C$_{1-4}$-alkoxy, C$_{1-4}$-alkoxy-C$_{1-4}$-alkyl, fluoro-C$_{1-4}$-alkoxy-C$_{1-4}$-alkyl, C$_{6-10}$-aryl, heteroaryl, —NR$^{5A}$R$^{5B}$, —C$_{1-4}$-alkyl-NR$^{5A}$R$^{5B}$, —NR$^4$C(O)O—C$_{1-4}$-alkyl, —NR$^4$C(O)—C$_{1-4}$-alkyl, —NR$^4$C(O)O-fluoro-C$_{1-4}$-alkyl, —NR$^4$C(O)-fluoro-C$_{1-4}$-alkyl, —NR$^4$C(O)NR$^{5A}$R$^{5B}$, —C(O)NR$^{5A}$R$^{5B}$, —C(O)R$^4$, —C(O)OR$^4$, —NR$^4$S(O)$_2$—C$_{1-4}$-alkyl, and —NR$^4$S(O)$_2$-fluoro-C$_{1-4}$-alkyl, and (b) said C$_{1-4}$-alkyl is optionally substituted with one or more substituents independently selected from fluorine, hydroxyl, and C$_{1-4}$-alkoxy;

U$^1$, U$^2$ and U$^3$ are each independently —C(H)= or —N= so as to form a 6-membered heteroaryl ring, the heteroaryl ring having a configuration selected from (a), (b), (c), (d), and (f), wherein (a) is U$^1$ is —N= and U$^2$ and U$^3$ are each —C(H)=; (b) is U$^1$ and U$^2$ are each —N= and U$^3$ is —C(H)=; (c) is U$^2$ is —N= and U$^1$ and U$^3$ are each —C(H)=; (d) U$^3$ is —N= and U$^1$ and U$^2$ are each —C(H)=; and (f) is U$^1$ and U$^3$ are each —N= and U$^2$ is —C(H)=;

wherein the heteroaryl ring is optionally substituted with one more substituents independently selected from halogen, cyano, nitro, C$_{1-4}$-alkyl, C$_{1-4}$-alkoxy, fluoro-C$_{1-4}$-alkyl, and fluoro-C$_{1-4}$-alkoxy, and wherein

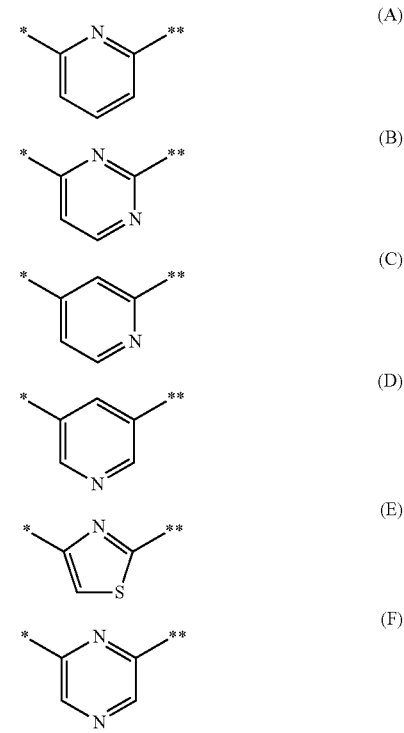

n is 1, so as to form a piperazine ring, or n is 2, so as to form a homopiperazine ring, wherein either ring is optionally substituted with one more substituents independently selected from fluorine, hydroxyl, C$_{1-4}$-alkyl, a divalent C$_{1-4}$-alkylene radical which forms a bridge between ring carbons of said homopiperazine or piperazine, C$_{1-4}$-alkoxy, fluoro-C$_{1-4}$-alkyl, a divalent fluoro-C$_{1-4}$-alkylene radical which forms a bridge between ring carbons of said homopiperazine or piperazine and fluoro-C$_{1-4}$-alkoxy;

(H)

(J)

(K)

(M)

$R^2$ is selected from radicals of formulae (N)-(R) inclusive, any of which is optionally substituted with one or more substituents independently selected from fluorine, hydroxyl, $C_{1-4}$-alkyl, $C_{1-4}$-alkoxy, fluoro-$C_{1-4}$-alkyl, and fluoro-$C_{1-4}$-alkoxy, wherein the bond marked * is attached to the piperazine or homopiperazine ring:

(N)

(O)

(P)

(Q)

(R)

and o and p are each independently 1 or 2, and W is O or $NR^9$;

$R^3$ is selected from hydrogen, $C_{1-6}$-alkyl, $C_{3-5}$-cycloalkyl, $C_{3-5}$-cycloalkyl-$C_{1-4}$-alkyl, heterocyclyl, heterocyclyl-$C_{1-4}$-alkyl, $C_{6-10}$-aryl, heteroaryl, $C_{6-10}$-aryl-$C_{1-4}$-alkyl, and heteroaryl-$C_{1-4}$-alkyl, wherein
(i) said $C_{1-6}$-alkyl, $C_{3-5}$-cycloalkyl, heterocyclyl or the heterocyclyl part of said heterocyclyl-$C_{1-4}$-alkyl, or the $C_{1-6}$-alkyl part of said heterocyclyl-$C_{1-4}$-alkyl, $C_{6-10}$-aryl-$C_{1-4}$-alkyl or heteroaryl-$C_{1-4}$-alkyl, is optionally substituted with one or more substituents independently selected from fluorine, hydroxy, cyano, $C_{1-4}$-alkoxy, and —$NR^{5A}R^{5B}$, and
(ii) said $C_{6-10}$-aryl or heteroaryl, or the $C_{6-10}$-aryl part of said $C_{6-10}$-aryl-$C_{1-4}$-alkyl or the heteroaryl part of said heteroaryl-$C_{1-4}$-alkyl, is optionally substituted with one more substituents independently selected from halogen, hydroxy, cyano, nitro, $C_{1-4}$-alkyl, $C_{1-4}$-alkoxy, fluoro-$C_{1-4}$-alkyl, fluoro-$C_{1-4}$-alkoxy, $C_{1-4}$-alkoxy-$C_{1-4}$-alkyl, fluoro-$C_{1-4}$-alkoxy-$C_{1-4}$-alkyl, —$NR^{5A}R^{5B}$, —$C_{1-4}$-alkyl-$NR^{5A}R^{5B}$, —$NR^4C(O)$O—$C_{1-4}$alkyl, —$NR^4C(O)$—$C_{1-4}$alkyl, —$NR^4C(O)$O-fluoro-$C_{1-4}$alkyl, —$NR^4C(O)$-fluoro-$C_{1-4}$alkyl, —$NR^4C(O)NR^{5A}R^{5B}$, —$C(O)NR^{5A}R^{5B}$, —$C(O)R^4$, —$C(O)OR^4$, —$NR^4S(O)_2$—$C_{1-4}$alkyl, and —$NR^4S(O)_2$-fluoro-$C_{1-4}$alkyl;

$R^4$, $R^{5A}$ and $R^{5B}$ are each independently selected from hydrogen, $C_{1-4}$-alkyl, and fluoro-$C_{1-4}$-alkyl, or $R^{5A}$ and $R^{5B}$ together with the nitrogen atom to which they are bound, form a 4- to 7-membered saturated heterocyclic ring or a heteroaryl ring, said ring being optionally substituted with one or more substituents independently selected from fluorine, hydroxyl, $C_{1-4}$-alkyl, fluoro-$C_{1-4}$-alkyl, and $C_{1-4}$-alkoxy, or $R^3$ and $R^4$, together with the nitrogen atom to which they are bound, form a 4- to 7-membered saturated heterocyclic ring or a heteroaryl ring, said ring being optionally substituted with one or more substituents independently selected from fluorine, hydroxyl, $C_{1-4}$-alkyl, fluoro-$C_{1-4}$-alkyl, and $C_{1-4}$-alkoxy; and $R^6$ is selected from $C_{1-6}$-alkyl, $C_{3-5}$-cycloalkyl, $C_{3-5}$-cycloalkyl-$C_{1-4}$-alkyl, heterocyclyl, heterocyclyl-$C_{1-4}$-alkyl, $C_{6-10}$-aryl-$C_{1-4}$-alkyl, and $C_{6-10}$-aryl, wherein
(iii) said $C_{1-6}$-alkyl, $C_{3-5}$-cycloalkyl, heterocyclyl, or the $C_{1-6}$-alkyl part of said heterocyclyl-$C_{1-4}$-alkyl or $C_{6-10}$-aryl-$C_{1-4}$-alkyl, or the heterocyclyl part of said heterocyclyl-$C_{1-4}$-alkyl is optionally substituted with one or more substituents independently selected from fluorine, hydroxyl, and $C_{1-4}$-alkoxy, and
(iv) said $C_{6-10}$-aryl or the $C_{6-10}$-aryl part of said $C_{6-10}$-aryl-$C_{1-4}$-alkyl is optionally substituted with one more substituents independently selected from halogen, hydroxy, cyano, nitro, $C_{1-4}$-alkyl, $C_{1-4}$-alkoxy, fluoro-$C_{1-4}$-alkyl, fluoro-$C_{1-4}$-alkoxy, $C_{1-4}$-alkoxy-$C_{1-4}$-alkyl, and fluoro-$C_{1-4}$-alkoxy-$C_{1-4}$-alkyl;

$R^7$ is selected from $C_{1-6}$-alkyl, $C_{3-5}$-cycloalkyl, $C_{3-5}$-cycloalkyl-$C_{1-4}$-alkyl, heterocyclyl, heterocyclyl-$C_{1-4}$-alkyl, $C_{6-10}$-aryl-$C_{1-4}$-alkyl, $C_{6-10}$-aryl, and —$NR^{10A}R^{10B}$, wherein
(v) said $C_{1-6}$-alkyl, $C_{3-5}$-cycloalkyl, heterocyclyl, or the $C_{1-6}$-alkyl part of said heterocyclyl-$C_{1-4}$-alkyl or $C_{6-10}$-aryl-$C_{1-4}$-alkyl, or the heterocyclyl part of said heterocyclyl-$C_{1-4}$-alkyl is optionally substituted with one or more substituents independently selected from fluorine, hydroxyl, and $C_{1-4}$-alkoxy, and
(vi) said $C_{6-10}$-aryl or the $C_{6-10}$-aryl part of said $C_{6-10}$-aryl-$C_{1-4}$-alkyl is optionally substituted with one more substituents independently selected from halogen, hydroxy, cyano, nitro, $C_{1-4}$-alkyl, $C_{1-4}$-alkoxy, fluoro-$C_{1-4}$-alkyl, fluoro-$C_{1-4}$-alkoxy, $C_{1-4}$-alkoxy-$C_{1-4}$-alkyl, and fluoro-$C_{1-4}$-alkoxy-$C_{1-4}$-alkyl;

$R^9$ is selected from hydrogen, $C_{3-5}$-cycloalkyl, $C_{1-6}$-alkyl, and $C_{6-10}$-aryl-$C_{1-4}$-alkyl wherein any alkyl residue or cycloalkyl or $C_{6-10}$-aryl ring system is optionally substituted with one or more substituents independently selected from halogen, hydroxyl, and $C_{1-4}$-alkyl; and $R^{10A}$ and $R^{10B}$ are each independently selected from hydrogen and $C_{1-6}$-alkyl, wherein said $C_{1-6}$-alkyl is optionally substituted with one or more substituents independently selected from fluorine, hydroxyl, and $C_{1-4}$-alkoxy, or $R^{10A}$ and $R^{10B}$, together with the nitrogen atom to which they are bound, form a 4- to 7-membered saturated heterocyclic ring or a heteroaryl ring, optionally substituted with one or more substituents independently selected from fluorine, hydroxyl, $C_{1-4}$-alkyl, fluoro-$C_{1-4}$-alkyl, and $C_{1-4}$-alkoxy; provided that when n=1, then $R^2$ is not piperidine wherein p=1, and o=2.

2. A compound as claimed in claim 1 wherein $R^1$ is $CONR^3R^4$ or heteroaryl wherein said heteroaryl is optionally substituted with one more substituents independently selected from halogen, cyano, $C_{1-6}$-alkyl, $C_{3-5}$-cycloalkyl, $C_{1-4}$-alkoxy, fluoro-$C_{1-6}$-alkyl, fluoro-$C_{1-4}$-alkoxy, and heteroaryl.

3. A compound as claimed in claim 1 wherein $R^1$ is heteroaryl selected from benzoxazolyl, indolyl, azaindolyl, imidazolyl, benzimidazolyl, oxazolyl, oxadiazolyl, and tetrazolyl, any of which being optionally substituted with one more substituents independently selected from halogen, hydroxy, cyano, nitro, $C_{1-6}$-alkyl, $C_{3-5}$-cycloalkyl, $C_{1-4}$-alkoxy, fluoro-$C_{1-6}$-alkyl, fluoro-$C_{1-4}$-alkoxy, $C_{1-4}$-alkoxy-$C_{1-4}$-alkyl, fluoro-$C_{1-4}$-alkoxy-$C_{1-4}$-alkyl, $C_{6-10}$-aryl, heteroaryl, —$NR^{5A}R^{5B}$, —$C_{1-4}$-alkyl-$NR^{5A}R^{5B}$, —$NR^4C(O)$O—$C_{1-4}$-alkyl, —$NR^4C(O)$—$C_{1-4}$-alkyl, —$NR^4C(O)O$-fluoro-$C_{1-4}$-alkyl, —$NR^4C(O)$-fluoro-$C_{1-4}$-alkyl, —$NR^4C(O)NR^{5A}R^{5B}$, —$C(O)NR^{5A}R^{5B}$, —$C(O)R^4$, —$C(O)OR^4$, —$NR^4S(O)_2$—$C_{1-4}$-alkyl, and —$NR^4S(O)_2$-fluoro-$C_{1-4}$-alkyl.

4. A compound as claimed in claim 1 wherein $R^1$ is $CONR^3R^4$ wherein $R^4$ is hydrogen or methyl.

5. A compound as claimed in claim 4 wherein $R^3$ is selected from tetrahydropyranyl, isopropylmethyl, tetrahydropyranylmethyl, imidazolylethyl, methoxyethyl, N-methylimidazolylmethyl, tetrahydrofuranylmethyl, 1-fluoroethyl, oxazolylmethyl, pyridylmethyl, 2,2-difluoromethyl, tetrahydrofuranyl, methyl, ethyl, n- or iso-propyl, n-sec- or tert-butyl, cyclopropyl, hydroxyethyl, cyanoethyl, phenyl, chlorophenyl, methoxyphenyl, methylphenyl, hydroxyphenyl, thiazoloylmethyl, indolyl, methoxypropyl, tetrahydroisoquinolinyl, furylmethyl, pyridylethyl, thiazolyl, and cyclopropylmethyl.

6. A compound according to claim 4 wherein $R^3$ is pyridyl optionally substituted with one or more substituents selected from halogen, $C_{1-4}$-alkyl, $C_{1-4}$-alkoxy, and fluoro-$C_{1-4}$-alkyl.

7. A compound according to claim 4 where $R^3$ is 4-pyridyl optionally substituted with one or more methyl group.

8. A compound as claimed in claim 1, wherein n is 2 so as to form a homopiperazine ring, the homopiperazine ring being optionally substituted with one more substituents independently selected from fluorine, hydroxyl, $C_{1-4}$-alkyl, a divalent $C_{1-4}$-alkylene radical which forms a bridge between ring carbons of said homopiperazine, $C_{1-4}$-alkoxy, fluoro-$C_{1-4}$-alkyl or a divalent fluoro-$C_{1-4}$-alkylene radical which forms a bridge between ring carbons of said homopiperazine and fluoro-$C_{1-4}$-alkoxy.

9. A compound as claimed in claim 1, wherein n is 1 so as to form a piperazine ring, the piperazine ring being optionally substituted with one more substituents independently selected from fluorine, hydroxyl, $C_{1-4}$-alkyl, a divalent $C_{1-4}$-alkylene radical which forms a bridge between ring carbons of said piperazine, $C_{1-4}$-alkoxy, fluoro-$C_{1-4}$-alkyl or a divalent fluoro-$C_{1-4}$-alkylene radical which forms a bridge between ring carbons of said piperazine, and fluoro-$C_{1-4}$-alkoxy.

10. A compound as claimed in claim 8 wherein $R^2$ is a 4-piperidine radical of formula (N) wherein o is 2 and p is 1, a 4-azepine radical of formula (N) wherein o is 2 and p is 2, a 1,4-cyclohexyl radical of formula (R) or a —$CH_2$morpholin-3-yl radical of formula (Q) wherein W is O, said 4-piperidine, 4-azepine, 1,4-cyclohexyl and —$CH_2$ morpholin-3-yl radicals being optionally substituted with one more substituents independently selected from fluorine, hydroxyl, $C_{1-4}$-alkyl, $C_{1-4}$-alkoxy, fluoro-$C_{1-4}$-alkyl, and fluoro-$C_{1-4}$-alkoxy.

11. A compound as claimed in claim 9 wherein $R^2$ is a 4-azepine radical of formula (N) wherein o is 2 and p is 2, a 1,4-cyclohexyl radical of formula (R) or a —$CH_2$morpholin-3-yl radical of formula (Q) wherein W is O, said a 4-azepine, 1,4-cyclohexyl and —$CH_2$morpholin-3-yl radicals being optionally substituted with one more substituents independently selected from fluorine, hydroxyl, $C_{1-4}$-alkyl, $C_{1-4}$-alkoxy, fluoro-$C_{1-4}$-alkyl, and fluoro-$C_{1-4}$-alkoxy.

12. A compound as claimed in claim 1, wherein $R^6$ is selected from $C_{1-6}$-alkyl, $C_{1-6}$ fluoroalkyl, $C_{1-2}$-alkoxy-$C_{1-4}$alkyl, $C_{3-5}$ cycloalkyl, $C_{3-5}$ fluorocycloalkyl, benzyl, alpha methyl-benzyl, and benzyl or alpha methyl-benzyl either of which being optionally ring-substituted by one or two substituents selected from halogen, $C_{1-4}$-alkyl, and $C_{1-4}$-alkoxy.

13. A compound having formula (IA):

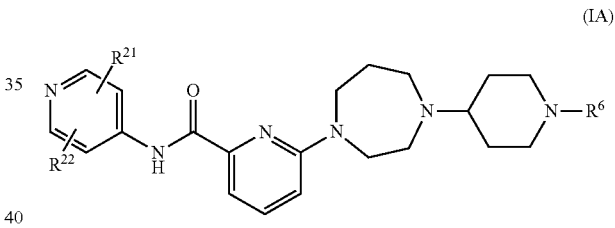

(IA)

wherein $R^6$ is selected from $C_{1-6}$-alkyl, $C_{3-5}$-cycloalkyl, $C_{3-5}$-cycloalkyl-$C_{1-4}$-alkyl, heterocyclyl, heterocyclyl-$C_{1-4}$-alkyl, $C_{6-10}$-aryl-$C_{1-4}$-alkyl, and $C_{6-10}$-aryl, wherein (i) said $C_{1-6}$-alkyl, $C_{3-5}$-cycloalkyl, heterocyclyl, or the $C_{1-6}$-alkyl part of said heterocyclyl-$C_{1-4}$-alkyl or $C_{6-10}$-aryl-$C_{1-4}$-alkyl, or the heterocyclyl part of said heterocyclyl-$C_{1-4}$-alkyl is optionally substituted with one or more substituents independently selected from fluorine, hydroxyl, and $C_{1-4}$-alkoxy, and (ii) said $C_{6-10}$-aryl or the $C_{6-10}$-aryl part of said $C_{6-10}$-aryl-$C_{1-4}$-alkyl is optionally substituted with one more substituents independently selected from halogen, hydroxy, cyano, nitro, $C_{1-4}$-alkyl, $C_{1-4}$-alkoxy, fluoro-$C_{1-4}$-alkyl, fluoro-$C_{1-4}$-alkoxy, $C_{1-4}$-alkoxy-$C_{1-4}$-alkyl, and fluoro-$C_{1-4}$-alkoxy-$C_{1-4}$-alkyl; and $R^{21}$ and $R^{22}$ are independently selected from hydrogen, halogen, $C_{1-6}$-alkyl, $C_{1-6}$ fluoroalkyl, $C_{1-4}$-alkoxy, $C_{1-2}$-alkoxy-$C_{1-4}$alkyl, $C_{3-5}$ cycloalkyl, $C_{3-5}$ fluorocycloalkyl, benzyl, alpha methyl-benzyl, and benzyl or alpha methyl-benzyl either of which being optionally ring-substituted by one or two substituents selected from halogen, $C_{1-4}$-alkyl, and $C_{1-4}$-alkoxy.

14. A compound as claimed in claim 13 wherein $R^{21}$ and $R^{22}$ are independently selected from hydrogen and methyl, and $R^6$ is isopropyl.

15. A pharmaceutical composition comprising a compound as claimed in claim 1, together with one or more pharmaceutically acceptable carriers and/or excipients.

16. The pharmaceutical composition of claim 15, the compound having formula (IA):

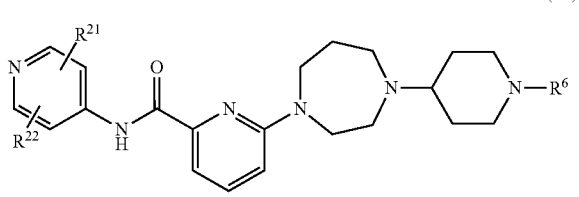

(IA)

wherein $R^6$ is selected from $C_{1-6}$-alkyl, $C_{3-5}$-cycloalkyl, $C_{3-5}$-cycloalkyl-$C_{1-4}$-alkyl, heterocyclyl, heterocyclyl-$C_{1-4}$-alkyl, $C_{6-10}$-aryl-$C_{1-4}$-alkyl, and $C_{6-10}$-aryl, wherein
(i) said $C_{1-6}$-alkyl, $C_{3-5}$-cycloalkyl, heterocyclyl, or the $C_{1-6}$-alkyl part of said heterocyclyl-$C_{1-4}$-alkyl or $C_{6-10}$-aryl-$C_{1-4}$-alkyl, or the heterocyclyl part of said heterocyclyl-$C_{1-4}$-alkyl is optionally substituted with one or more substituents independently selected from fluorine, hydroxyl, and $C_{1-4}$-alkoxy, and
(ii) said $C_{6-10}$-aryl or the $C_{6-10}$-aryl part of said $C_{6-10}$-aryl-$C_{1-4}$-alkyl is optionally substituted with one more substituents independently selected from halogen, hydroxy, cyano, nitro, $C_{1-4}$-alkyl, $C_{1-4}$-alkoxy, fluoro-$C_{1-4}$-alkyl, fluoro-$C_{1-4}$-alkoxy, $C_{1-4}$-alkoxy-$C_{1-4}$-alkyl, and fluoro-$C_{1-4}$-alkoxy-$C_{1-4}$-alkyl; and $R^{21}$ and $R^{22}$ are independently selected from hydrogen, halogen, $C_{1-6}$-alkyl, $C_{1-6}$ fluoroalkyl, $C_{1-4}$-alkoxy, $C_{1-2}$-alkoxy-$C_{1-4}$alkyl, $C_{3-5}$ cycloalkyl, $C_{3-5}$ fluorocycloalkyl, benzyl, alpha methyl-benzyl, and benzyl or alpha methyl-benzyl either of which being optionally ring-substituted by one or two substituents selected from halogen, $C_{1-4}$-alkyl, and $C_{1-4}$-alkoxy.

17. The pharmaceutical composition of claim 16, wherein $R^{21}$ and $R^{22}$ are independently selected from hydrogen and methyl, and $R^6$ is isopropyl.

* * * * *